(12) United States Patent
Kling et al.

(10) Patent No.: US 8,436,034 B2
(45) Date of Patent: *May 7, 2013

(54) CARBOXAMIDE COMPOUNDS AND THEIR USE AS CALPAIN INHIBITORS

(75) Inventors: Andreas Kling, Ludwigshafen (DE); Wilfried Hornberger, Ludwigshafen (DE); Helmut Mack, Ludwigshafen (DE); Achim Moeller, Ludwigshafen (DE); Volker Nimmrich, Ludwigshafen (DE); Dietmar Seeman, Ludwigshafen (DE); Wilfried Lubisch, Ludwigshafen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/990,652

(22) PCT Filed: Dec. 28, 2007

(86) PCT No.: PCT/EP2007/064617
§ 371 (c)(1), (2), (4) Date: Aug. 9, 2010

(87) PCT Pub. No.: WO2008/080969
PCT Pub. Date: Jul. 10, 2008

(65) Prior Publication Data
US 2010/0298326 A1    Nov. 25, 2010

(30) Foreign Application Priority Data
Dec. 29, 2006    (EP) ..................... 06127369

(51) Int. Cl.
*A61K 31/4155*    (2006.01)
*A61K 31/4178*    (2006.01)
*C07D 403/04*    (2006.01)

(52) U.S. Cl.
USPC ...... 514/397; 514/406; 548/314.7; 548/364.1

(58) Field of Classification Search ......................... None
See application file for complete search history.

(56) References Cited

U.S. PATENT DOCUMENTS

| 5,665,681 | A | * | 9/1997 | Seckinger et al. ............ 504/246 |
| 6,482,832 | B1 | | 11/2002 | Lubisch et al. |
| 6,562,827 | B1 | | 5/2003 | Lubisch et al. |
| 6,630,493 | B1 | * | 10/2003 | Lubisch et al. ............... 514/354 |

(Continued)

FOREIGN PATENT DOCUMENTS

| WO | WO 98/16512 | 4/1998 |
| WO | WO 98/25899 | 6/1998 |

(Continued)

OTHER PUBLICATIONS

Wu and Farrelly, Toxicology 236:1-6, 2007.*

(Continued)

*Primary Examiner* — Yong Chu
(74) *Attorney, Agent, or Firm* — Lisa V. Mueller; Michael Best & Friedrich LLP

(57) ABSTRACT

The present invention relates to novel carboxamide compounds and their use for the manufacture of a medicament. The carboxamide compounds are inhibitors of calpain (calcium dependant cysteine proteases). The invention therefore also relates to the use of these carboxamide compounds for treating a disorder associated with an elevated calpain activity.

The carboxamide compounds are compounds of the general formula I

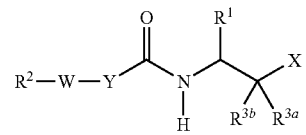

in which $R^1$, $R^2$, $R^{3a}$, $R^{3b}$, W, Y and X have the meanings mentioned in the claims and the description, the tautomers thereof and the pharmaceutically suitable salts thereof. In particular, the compounds have the general formula I-A.a' and I-A.a"

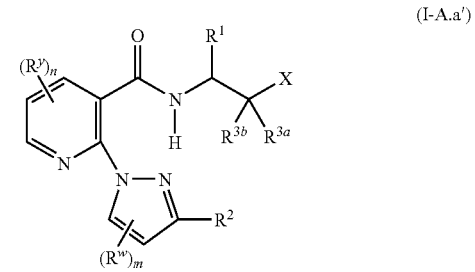

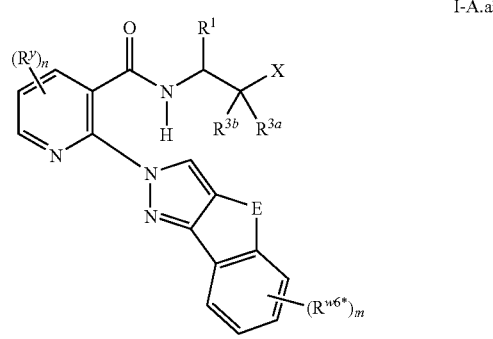

in which m, E, $R^1$, $R^{3a}$, $R^{3b}$, $R^2$, $R^y$, $R^w$ and $R^{w6*}$ have the meanings mentioned in the claims, n is 0, 1 or 2, the tautomers thereof and the pharmaceutically suitable salts thereof.

13 Claims, No Drawings

U.S. PATENT DOCUMENTS

| | | | | |
|---|---|---|---|---|
| 7,728,012 B2 * | 6/2010 | Kling et al. | ................... | 514/341 |
| 7,799,809 B2 * | 9/2010 | Kling et al. | ................... | 514/341 |
| 2011/0059968 A1 * | 3/2011 | Hornberger et al. | ........ | 514/235.5 |

FOREIGN PATENT DOCUMENTS

| | | |
|---|---|---|
| WO | WO 99/17775 | 4/1999 |
| WO | WO 99/54293 | 10/1999 |
| WO | WO 99/54294 | 10/1999 |
| WO | WO 99/54304 | 10/1999 |
| WO | WO 99/54305 | 10/1999 |
| WO | WO 99/54310 | 10/1999 |
| WO | WO 99/54320 | 10/1999 |
| WO | WO 99/61423 | 12/1999 |
| WO | WO 03/080182 | 10/2003 |

OTHER PUBLICATIONS

Neffe et al., Current Opinion in Drug Discovery & Development "Developments in the Design and Synthesis of Calpain Inhibitors", 2005 8(6) pp. 684-700, XP0009072341.

Barrett et al., Life Sciences, "Effect of Substrate on Ca2+-Concentration Required for Activity of the Ca2+-Dependent Proteinases, u- and m-Calpain", vol. 48, pp. 1659-1669, (1991).

Bartus et al., Neurological Research, "Calpain as a Novel Target for Treating Acute Neurodegenerative Disorders", 1995, vol. 17, pp. 249-258.

Carragher, Current Pharmaceutical Design, "Calpain Inhibition: A Therapeutic Strategy Targeting Multiple Disease States", 2006, 12, pp. 615-638.

Cuzzocrea et al., American Journal of Pathology, "Calpain Inhibitor I Reduces the Development of Acute and Chronic Inflammation", vol. 157, No. 6, Dec. 2000, pp. 2065-2079.

Edelstein et al., Proc. Nat. Acad. Sci. USA, "The Role of Cysteine Proteases in Hypoxia-Induced Rat Renal Proximal Tubular Injury", vol. 92, Aug. 1995, pp. 7662-7666.

Fehrentz et al., Centre CNRS-INSERM de Pharmacologie-Endocrinologie, Rue de la Cardonille, B.P. 5055, F-34033 Montpellier Cedex, "An Efficient Synthesis of Optically Active a-(t-Butoxycarbonylamino)-aldehydes from a-Amino Acids", pp. 676-678, (1983).

Higaki et al., Neuron "Inhibition of B-Amylois Fomation Identifies Proteolytic Precursors and Subcellular Site of Catabolism", vol. 14, Mar. 1995, pp. 651-659.

Higuchi et al., The Journal of Biological Chemistry, "Distinct Mechanistic Roles of Calpain and Caspase Activation in Neurodegeneration as Revealed in Mice Overexpressing Their Specific Inhibitors", 2005, vol. 280, No. 15, pp. 15229-15237.

Kunz et al., International Association for the Study of Pin, "The Calpain Inhibitor MDL 28170 Prevents Inflammation-Induced Neurofilament Light Chain Breakdown in the Spinal Cord and Reduces Thermal Hyperalgesis", 2004, 110, pp. 409-418.

Hassen et al., Journal of Neuroimmunology, "A Novel Calpain Inhibitor for the Treatment of Acute Experimental Autoimmune Encephalomyelitis", 2006, 180, pp. 135-146.

O'Donnell, The Journal of Neuroscience, "Human Innumodeficiency Virus (HIV)-Induced Neurotoxicity: Roles for the NMDA Receptor Subtypes 2A and 2B and the Calcium-Activated Protease Calpain by a CSF-Derived HIV-1 Strain", Jan. 18, 2006, 26(3), pp. 981-990.

Park et al., The Journal of Neuroscience, "The Generation of a 17 kDa Neurotoxic Fragment: An Alternative Mechanism by Which Tau Mediates B-Amyloid-Induced Neurodegeneration", Jun. 1, 2005, 25(22), pp. 5365-5375.

Patrick et al., Nature, "Conversion of p35 to p25 Deregulates Cdk5 Activity and Promotes Neurodegeneration", Dec. 9, 1999, vol. 402, pp. 615-622.

Saatman et al., Proc. Natl. Acad. Sci. USA, "Calpain Inhibitor AK295 Attenuates Motor and Cognitive Deficits Following Experimental Brain Injury in the Rat", Apr. 1996, vol. 93, pp. 3428-3433.

Saez et al., Drug Discovery Today, "The Therapeutic Potential of the Calpain Family: New Aspects", Oct. 2006, vol. 11, Nos. 19/20, pp. 917-923.

Hong et al., Stroke, "Neuroprotection With a Calpain Inhibitor in a Model fo Focal Cerebral Ischemia", Mar. 1994, vol. 25, No. 3, pp. 663-669.

Shiba et al., International Journal of Oncology, "Mechanism of Growth Inhibition of MCF-7 by a Cell Permeable Calpin Inhibitor", 1994.

Suzuki et al., Biol. Chem. Hoppe-Seyler "Calpain: Novel Family Members, Activation, and Physiological Funcation", Sep. 1995, vol. 376, pp. 523-529.

Teranishi et al., Biochemical and Biophysical Research Communications, "Calpain is involved in the HIV Replication from the Latently Infected OM10.0 Cells", 2003, 303, pp. 940-946.

Wang et al., Brain, "Calpain Inhibition Protects Against Taxol-induced Sensory Neuropathy", 2004, 127, pp. 671-679.

Yuen et al., Drugs of the Future, "Calpain Inhibitors: Novel Neuroprotectants and Potential Anticataract Agents", 1998, 23(7), pp. 741-749.

Wang et al., TIPS, "Calpain Inhibition: an Overview of its Therapeutic Potential", Nov. 1994, vol. 15, pp. 412-419.

Watanabe et al., Cytokine, "Selective Release of a Processed Form of Interleukin 1a", Nov. 1994, vol. 6, No. 6, pp. 597-601.

Yoshida et al., Japanese Circulation Journal, "Calpain is Implicated in Rat Myocardial Injury After Ischemia or Reperfusion", Jan. 1995, vol. 59, pp. 40-48.

Monaco, E.A., III, "Recent evidence regarding a role for CdkS dysregulation in Alzheimer's Disease," 2004, Bentham Science Publishers, Ltd., pp. 2-7.

* cited by examiner

CARBOXAMIDE COMPOUNDS AND THEIR USE AS CALPAIN INHIBITORS

CROSS-REFERENCE TO RELATED APPLICATIONS

This is a U.S. national stage entry of International Patent Application No. PCT/EP2007/064617, filed Dec. 28, 2007, which claims priority to European Patent Application No. 06127369.4, filed on Dec. 29, 2006, the contents of all of which are herein fully incorporated by reference.

The present invention relates to novel carboxamide compounds and their use for the manufacture of a medicament. The carboxamide compounds are inhibitors of calpain (calcium dependant cysteine proteases). The invention therefore also relates to the use of these carboxamide compounds for treating a disorder associated with an elevated calpain activity.

Calpains are intracellular, proteolytic enzymes from the cysteine protease group and are found in many cells. The enzyme calpain is activated by elevated calcium concentration, with a distinction being made between calpain I or µ-calpain, which is activated by µ-molar concentrations of calcium ions, and calpain II or m-calpain, which is activated by m-molar concentrations of calcium ions. Currently, further calpain isoenzymes are also postulated (M. E. Saez et al.; Drug Discovery Today 2006, 11 (19/20), pp. 917-923; K. Suzuki et al., Biol. Chem. Hoppe-Seyler, 1995, 376 (9), pp. 523-9).

Calpains play an important role in various physiological processes. These processes include the cleavage of different regulatory proteins such as protein kinase C, cytoskeletal proteins such as MAP 2 and spectrin, and muscle proteins, protein degradation in rheumatoid arthritis, proteins in the activation of platelets, neuropeptide metabolism, proteins in mitosis, and others which are listed in: M. J. Barrett et al., Life Sci. 1991, 48, pp. 1659-69; K. Wang et al., Trends in Pharmacol. Sci. 1994, 15, pp. 412-419.

Elevated calpain levels have been measured in various pathophysiological processes, for example: ischemias of the heart (e.g. myocardial infarction), the kidney or the central nervous system (e.g. stroke), inflammations, muscular dystrophies, cataracts of the eyes, diabetes, HIV disorders, injuries to the central nervous system (e.g. brain trauma), Alzheimer's, Huntington's, Parkinson's diseases, multiple sclerosis etc. (see K. K. Wang, above). It is assumed that there is a connection between these diseases and generally or persistently elevated intracellular calcium levels. This results in calcium-dependent processes becoming hyperactivated and no longer being subject to normal physiological control. A corresponding hyperactivation of calpains can also trigger pathophysiological processes.

For this reason, it was postulated that inhibitors of calpain could be of use for treating these diseases. This postulate was confirmed by a variety of investigations. Thus, Seung-Chyul Hong et al., Stroke 1994, 25 (3), pp. 663-669, and R. T. Bartus et al., Neurological Res. 1995, 17, pp. 249-258, have demonstrated that calpain inhibitors have a neuroprotective effect in acute neurodegenerative impairments or ischemias such as occur after cerebral stroke. K. E. Saatman et al., Proc. Natl. Acad. Sci. USA, 1996, 93, pp. 3428-3433 describe that following experimental brain traumas, calpain inhibitors also improved recovery from the memory performance deficits and neuromotor impairments. C. L. Edelstein et al., Proc. Natl. Acad. Sci. USA, 1995, 92, pp. 7662-6, found that calpain inhibitors have a protective effect on hypoxia-damaged kidneys. Yoshida, Ken Ischi et al., Jap. Circ. J. 1995, 59 (1), pp. 40-48, pointed out that calpain inhibitors had favorable effects following cardiac damage which was produced by ischemia or reperfusion.

It has been shown in recent years that both the function and the metabolism of a number of important proteins involved in the development of Alzheimer's disease are modulated by calpain. Various external influences such as, for example, excitotoxins, oxidative stress or else the action of amyloid protein lead to hyperactivation of calpain in the nerve cell, causing, as cascade, a dysregulation of the CNS-specific kinase cdk5 and subsequently a hyperphosphorylation of the so-called tau protein. Whereas the actual task of the tau protein consists of stabilizing the microtubules and thus the cytoskeleton, phosphorylated tau is no longer able to fulfil this function; the cytoskeleton collapses, axonal transport of matter is impaired and thus eventually the nerve cell degenerates (G. Patrick et al., Nature 1999, 402, pp. 615-622; E. A. Monaco et al.; Curr. Alzheimer Res. 2004, 1 (1), pp. 33-38). Accumulation of phosphorylated tau additionally leads to the formation of so-called neurofibrillary tangles (NFTs) which, together with the well-known amyloid plaques, represent an important feature of Alzheimer's disease. Similar changes in the tau protein, generally referred to as tauopathies are also observed in other (neuro)degenerative disorders such as, for example, following stroke, inflammations of the brain, Parkinsonism, in normal-pressure hydrocephalus and Creutzfeldt-Jakob disease.

It has been possible to demonstrate the involvement of calpain in neurodegenerative processes in transgenic mice with the aid of appropriate inhibitors (Higuchi et al.; J. Biol. Chem. 2005, 280 (15), pp. 15229-15237). It was possible with the aid of a calpain inhibitor to reduce markedly the clinical signs of acute autoimmune encephalomyelitis in a mouse model of multiple sclerosis (F. Mokhtarian et al.; J. Neuroimmunology 2006, Vol. 180, pp. 135-146). It has further been shown that calpain inhibitors on the one hand block the Aβ-induced degeneration of neurons (Park et al.; J. Neurosci. 2005, 25, pp. 5365-5375), and in addition reduce the release of the β-amyloid precursor protein (β APP) (J. Higaki et al., Neuron, 1995, 14, pp. 651-659). With this background, calpain inhibitors having sufficient CNS availability represent a novel therapeutic principle for the treatment of neurodegenerative disorders in general and in particular also of Alzheimer's disease.

The release of interleukin-Iα is likewise inhibited by calpain inhibitors (N. Watanabe et al., Cytokine 1994, 6(6), pp. 597-601). It has additionally been found that calpain inhibitors show cytotoxic effects on tumor cells (E. Shiba et al. 20th Meeting Int. Ass. Breast Cancer Res., Sendai Jp, 1994, 25.-28. Sep., Int. J. Oncol. S(Suppl.), 1994, 381).

The involvement of calpain in HIV disorders has only recently been shown. Thus, it has been demonstrated that the HIV-induced neurotoxicity is mediated by calpain (O'Donnell et al.; J. Neurosci. 2006, 26 (3), pp. 981-990). Calpain involvement in the replication of the HIV virus has also been shown (Teranishi et al.; Biochem. Biophys. Res. Comm. 2003, 303 (3), pp. 940-946).

Recent investigations indicate that calpain plays a part in so-called nociception, the perception of pain. Calpain inhibitors showed a distinctly beneficial effect in various preclinically relevant models of pain, e.g. in the thermally induced hyperalgesia in rats (Kunz et al.; Pain 2004, 110, pp. 409-418), in Taxol-induced neuropathy (Wang et al.; Brain 2004, 127, pp. 671-679) and in acute and chronic inflammatory processes (Cuzzocrea et al.; American Journal of Pathololgy 2000, 157 (6), pp. 2065-2079).

Further possible applications of calpain inhibitors are detailed in: M. E. Saez et al.; Drug Discovery Today 2006, 11 (19/20), pp. 917-923; N, O. Carragher, Curr. Pharm. Design 2006, 12, pp. 615-638; K. K. Wang et al.; Drugs of the Future 1998, 23 (7), pp. 741-749; and Trends in Pharmacol. Sci., 1994, 15, pp. 412-419.

With the calpain inhibitors described to date a general distinction is made between irreversible and reversible inhibitors, and peptide and non-peptide inhibitors.

Irreversible inhibitors are usually alkylating substances. They have the disadvantage that they firstly react unselectively and/or are unstable in the body. Thus, corresponding inhibitors often show unwanted side effects such as toxicity, and application thereof is therefore markedly restricted. The irreversible inhibitors include for example epoxides such as E64, α-halo ketones, and disulfides.

A large number of known reversible calpain inhibitors are peptide aldehydes which are derived in particular from di- or tripeptides such as, for example, Z-Val-Phe-H (MDL 28170). Derivatives and prodrugs structurally derived from aldehydes are also described, especially corresponding acetals and hemiacetals (e.g. hydroxytetrahydrofurans, hydroxyoxazolindines, hydroxymorpholines and the like), but also imines or hydrazones. However, under physiological conditions, peptide aldehydes and related compounds usually have the disadvantage that, owing to their reactivity, they are frequently unstable, are rapidly metabolized and are prone to unspecific reactions which may likewise cause toxic effects (J. A. Fehrentz and B. Castro, *Synthesis* 1983, pp. 676-78).

In recent years, a number of non-peptide carboxamides having a β-keto function in the amine moiety and inhibiting calpain have been described. Thus, WO-98/16512 describes 3-amino-2-oxo carboxylic acid derivatives whose amino group is amidated with a 4-piperidinecarboxylic acid compound. WO-99/17775 describes similar compounds which are amidated with a quinolinecarboxylic acid. WO-98/25883, WO-98/25899 and WO-99/54294 describe 3-amino-2-oxo carboxylic acid derivatives whose amino group is amidated with a substituted benzoic acid. WO-99/61423 describes 3-amino-2-oxo carboxylic acid derivatives whose amino group is amidated with an aromatic carboxylic acid carrying a tetrahydroquinoline/isoquinoline and 2,3-dihydroindole/isoindole residue. Similar compounds in which the aromatic carboxylic acid residue carries a heterocycloalkyl radical or (hetero)aryl radical which is optionally connected via a linker are described in WO-99/54320, WO-99/54310, WO-99/54304 and WO-99/54305. WO-99/54293 describes benzamides of 4-amino-3-oxo carboxylic acid derivatives. WO-03/080182 describes the use of the aforementioned amides for the treatment of pulmonary diseases. The nonpeptide calpain inhibitors mentioned therein also have a number of disadvantages, in particular a low or absent selectivity in respect of related cysteine proteases, such as various cathepsins, likewise possibly leading to unwanted side effects.

The present invention is thus based on the object of providing compounds which inhibit, in particular selectively, calpain even at low serum concentrations. The compounds were intended in particular to display a high selectivity in relation to the inhibition of calpain, i.e. inhibit other cystein proteases, e.g. cathepsin, not at all or only at higher concentrations.

This object and further objects are achieved by the carboxamide compounds of the general formula I described below, the pharmaceutically suitable salts, the prodrugs and the tautomers thereof:

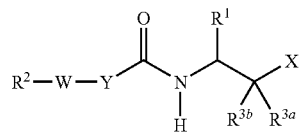

in which
$R^1$ is hydrogen, $C_1$-$C_{10}$-alkyl, $C_2$-$C_{10}$-alkenyl, $C_2$-$C_{10}$-alkynyl, where the last 3 radicals mentioned may be partly or completely halogenated and/or have 1, 2 or 3 substituents $R^{1a}$,
$C_3$-$C_7$-cycloalkyl, $C_3$-$C_7$-cycloalkyl-$C_1$-$C_4$-alkyl, where a $CH_2$ group in the cycloalkyl moiety of the last two radicals mentioned may be replaced by O, NH, or S, or two adjacent C atoms may form a double bond, where the cycloalkyl moiety may further have 1, 2, 3 or 4 radicals $R^{1b}$,
aryl, hetaryl, aryl-$C_1$-$C_6$-alkyl, aryl-$C_2$-$C_6$-alkenyl, hetaryl-$C_1$-$C_4$-alkyl or hetaryl-$C_2$-$C_6$-alkenyl, where aryl and hetaryl in the last 6 radicals mentioned may be unsubstituted or carry 1, 2, 3 or 4 identical or different radicals $R^{1c}$; where
   $R^{1a}$ is selected independently of one another from OH, SH, COOH, CN, $OCH_2COOH$, $C_1$-$C_6$-alkoxy, $C_1$-$C_6$-halolkoxy, $C_3$-$C_7$-cycloalkyloxy, $C_1$-$C_6$-haloalkylthio, $COOR^{a1}$, $CONR^{a2}R^{a3}$, $SO_2NR^{a2}R^{a3}$, —$NR^{a2}$—$SO_2$—$R^{a4}$, $NR^{a2}$—$CO$—$R^{a5}$, $SO_2$—$R^{a4}$, $NR^{a6}R^{a7}$,
   $R^{1b}$ is selected independently of one another from OH, SH, COOH, CN, $OCH_2COOH$, halogen, phenyl which optionally has 1, 2 or 3 substituents $R^{1d}$, or $C_1$-$C_6$-alkyl, $C_1$-$C_6$-alkoxy, $C_1$-$C_6$-alkylthio, where the alkyl moieties in the last 3 substituents mentioned may be partly or completely halogenated and/or have 1, 2 or 3 substituents $R^{1a}$,
   $COOR^{b1}$, $CONR^{b2}R^{b3}$, $SO_2NR^{b2}R^{b3}$, $NR^{b2}$—$SO_2$—$R^{b4}$, $NR^{b2}$—$CO$—$R^{b5}$, $SO_2$—$R^{b4}$, $NR^{b6}R^{b7}$, in addition two $R^{1b}$ radicals may together form a $C_1$-$C_4$-alkylene group, or 2 $R^{1b}$ radicals bonded to adjacent C atoms of cycloalkyl may form together with the carbon atoms to which they are bonded also a benzene ring,
   $R^{1c}$ is selected independently of one another from OH, SH, halogen, $NO_2$, $NH_2$, CN, $CF_3$, $CHF_2$, $CH_2F$, O—$CF_3$, O—$CHF_2$, O—$CH_2F$, COOH, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the alkyl moieties in the last 4 substituents mentioned may be partly or completely halogenated and/or have 1, 2 or 3 substituents $R^{1a}$,
   $C_3$-$C_7$-cycloalkyl, $C_3$-$C_7$-cycloalkyl-$C_1$-$C_4$-alkyl, $C_3$-$C_7$-cycloalkyloxy, where the cycloalkyl moiety of the last three radicals mentioned may have 1, 2, 3 or 4 $R^{1b}$ radicals,
   aryl, hetaryl, O-aryl, O—$CH_2$-aryl, where the last three radicals mentioned are unsubstituted in the aryl moiety or may carry 1, 2, 3 or 4 $R^{1d}$ radicals,
   $COOR^{c1}$, $CONR^{c2}R^{c3}$, $SO_2NR^{c2}R^{c3}$, $NR^{c2}$—$SO_2$—$R^{c4}$,
   $NR^{c2}$—$CO$—$R^{c5}$, $SO_2$—$R^{c4}$,
   —$(CH_2)_p$—$NR^{c6}R^{c7}$ with p=0, 1, 2, 3, 4, 5 or 6 and O—$(CH_2)_q$—$NR^{c6}R^{c7}$ with q=2, 3, 4, 5 or 6; where
   $R^{a1}$, $R^{b1}$ and $R^{c1}$ are independently of one another H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, $R^{a2}$, $R^{b2}$ and $R^{c2}$ are independently of one another H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, and $R^{a3}$, $R^{b3}$ and $R^{c3}$ are independently of one another H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, or the two radicals $R^{a2}$ and $R^{a3}$, or $R^{b2}$ and $R^{b3}$ or $R^{c2}$ and $R^{c3}$ form together with the N atom a 3 to 7-membered, optionally substituted nitrogen heterocycle which may optionally have 1, 2 or 3 further different or identical heteroatoms from the group of O, N, S as ring members, $R^{a4}$, $R^{b4}$ and $R^{c4}$ are independently of one another $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, and $R^{a5}$, $R^{b5}$ and $R^{c5}$ have independently of one another one of the meanings mentioned for $R^{a1}$, $R^{b1}$ and $R^{c1}$;

$R^{a6}$, $R^{b6}$ and $R^{c6}$ are independently of one another H, $C_1$-$C_6$-alkyl, $C_1$-$C_6$-alkoxy, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, CO—$C_1$-$C_6$-alkyl, CO—O—$C_1$-$C_6$-alkyl, $SO_2$—$C_1$-$C_6$-alkyl, aryl, hetaryl, O-aryl, $OCH_2$-aryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO—O-aryl, CO—O-hetaryl, CO—O-(aryl-$C_1$-$C_4$-alkyl), CO—O-(hetaryl-$C_1$-$C_4$-alkyl), $SO_2$-aryl, $SO_2$-hetaryl, $SO_2$-(aryl-$C_1$-$C_4$-alkyl) or $SO_2$-(hetaryl-$C_1$-$C_4$-alkyl), where aryl and hetaryl in the last 18 radicals mentioned are unsubstituted or have 1, 2 or 3 substituents $R^{1d}$, and $R^{a7}$, $R^{b7}$ and $R^{c7}$ are independently of one another H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, or the two radicals $R^{a6}$ and $R^{a7}$, or $R^{b6}$ and $R^{b7}$ or $R^{c6}$ and $R^{c7}$ form together with the N atom a 3 to 7-membered, optionally substituted nitrogen heterocycle which may optionally have 1, 2 or 3 further different or identical heteroatoms from the group of O, N and S as ring members, or two radicals $R^{1b}$ and $R^{1c}$ bonded to adjacent C atoms form together with the C atoms to which they are bonded a 4, 5, 6 or 7-membered, optionally substituted carbocycle or an optionally substituted heterocycle which has 1, 2 or 3 different or identical heteroatoms from the group of O, N and S as ring members;

$R^{1d}$ is selected from halogen, OH, SH, $NO_2$, COOH, C(O)$NH_2$, CHO, CN, $NH_2$, $OCH_2COOH$, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NHCHO, NH—C(O)$C_1$-$C_6$-alkyl, and $SO_2$—$C_1$-$C_6$-alkyl;

$R^2$ is hydrogen, $C_1$-$C_{10}$-alkyl, $C_1$-$C_{10}$-alkoxy, $C_2$-$C_{10}$-alkenyl, $C_2$-$C_{10}$-alkynyl, where the last 4 radicals mentioned may be partly or completely halogenated and/or have 1, 2 or 3 substituents $R^{2a}$, $C_3$-$C_7$-cycloalkyl, $C_3$-$C_7$-cycloalkyl-$C_1$-$C_4$-alkyl, where a $CH_2$ group in the cycloalkyl moiety of the last two radicals mentioned may be replaced by O, NH, or S, or two adjacent C atoms may form a double bond, where the cycloalkyl moiety may additionally have 1, 2, 3 or 4 $R^{2b}$ radicals;

aryl, O-aryl, O—$CH_2$-aryl, hetaryl, aryl-$C_1$-$C_6$-alkyl, aryl-$C_2$-$C_6$-alkenyl, hetaryl-$C_1$-$C_4$-alkyl or hetaryl-$C_2$-$C_6$-alkenyl, where aryl and hetaryl in the last 8 radicals mentioned may be unsubstituted or carry 1, 2, 3 or 4 identical or different $R^{2c}$ radicals; where $R^{2a}$ has one of the meanings indicated for $R^{1a}$,
$R^{2b}$ has one of the meanings indicated for $R^{1b}$, and
$R^{2c}$ has one of the meanings indicated for $R^{1c}$;
$R^{3a}$ and $R^{3b}$ are independently of one another hydroxy or $C_1$-$C_4$-alkoxy, or together with the carbon atom to which they are bonded are C=O;

X is hydrogen or a radical of the formulae C(=O)—O—$R^{x1}$, C(=O)—$NR^{x2}R^{x3}$, C(=O)—N($R^{x4}$)—($C_1$-$C_6$-alkylene)-$NR^{x2}R^{x3}$ or C(=O)—N($R^{x4}$)$NR^{x2}R^{x3}$, in which $R^{x1}$ is hydrogen, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, where alkyl, alkenyl, alkoxy, alkynyl, cycloalkyl, heterocycloalkyl in the last 6 radicals mentioned are unsubstituted or have 1, 2 or 3 substituents $R^{xa}$, or aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{xd}$, $R^{x2}$ is H, OH, CN, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_3$-$C_7$-heterocycloalkyl-$C_1$-$C_4$-alkyl, $C_1$-$C_6$-alkoxy-$C_1$-$C_4$-alkyl, CO—$C_1$-$C_6$-alkyl, CO—O—$C_1$-$C_6$-alkyl, $SO_2$—$C_1$-$C_6$-alkyl, O—$C_1$-$C_6$-alkyl, where alkyl, alkoxy, alkenyl, alkynyl, cycloalkyl, heterocycloalkyl in the last 10 radicals mentioned are unsubstituted or have 1, 2 or 3 substituents $R^{xa}$, aryl, O-aryl, O—$CH_2$-aryl, hetaryl, O—$CH_2$-hetaryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO—O-aryl, CO—O-hetaryl, CO—O-(aryl-$C_1$-$C_4$-alkyl), CO—O-(hetaryl-$C_1$-$C_4$-alkyl), $SO_2$-aryl, $SO_2$-hetaryl, $SO_2$-(aryl-$C_1$-$C_4$-alkyl) or $SO_2$-(hetaryl- $C_1$-$C_4$-alkyl), where aryl and hetaryl in the last 19 radicals mentioned are unsubstituted or have 1, 2 or 3 substituents $R^{xd}$, and $R^{x3}$ is H, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, where alkyl, alkenyl, alkoxy, alkynyl, cycloalkyl, heterocycloalkyl in the last 6 radicals mentioned are unsubstituted or have 1, 2 or 3 substituents $R^{xa}$, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{xd}$, or the two radicals $R^{x2}$ and $R^{x3}$ form together with the N atom a 3 to 7-membered nitrogen heterocycle which may optionally have 1, 2 or 3 further different or identical heteroatoms from the group of O, N, S as ring members, and which may have 1, 2 or 3 substituents $R^{xb}$, $R^{x4}$ is H, OH, CN, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, CO—$C_1$-$C_6$-alkyl, CO—O—$C_1$-$C_6$-alkyl, $SO_2$—$C_1$-$C_6$-alkyl, where alkyl, alkenyl, alkoxy, alkynyl, cycloalkyl, heterocycloalkyl in the last 9 radicals mentioned are unsubstituted or have 1, 2 or 3 substituents $R^{xa}$, aryl, O-aryl, O—$CH_2$-aryl, hetaryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO—O-aryl, CO—O-hetaryl, CO—O-(aryl-$C_1$-$C_4$-alkyl), CO—O-(hetaryl-$C_1$-$C_4$-alkyl), $SO_2$-aryl, $SO_2$-hetaryl, $SO_2$-(aryl-$C_1$-$C_4$-alkyl) or $SO_2$-(hetaryl-$C_1$-$C_4$-alkyl), where aryl and hetaryl in the last 18 radicals mentioned are unsubstituted or have 1, 2 or 3 substituents $R^{xd}$, and where $R^{xa}$ has one of the meanings indicated for $R^{1a}$, $R^{xb}$ has one of the meanings indicated for $R^{1b}$, and $R^{xd}$ has one of the meanings indicated for $R^{1d}$;

Y is a divalent, aromatic or 6-membered heteroaromatic radical which has 1 or 2 nitrogen atoms as ring members and which optionally has 1 or 2 identical or different substituents $R^y$:

$R^y$ is selected independently of one another from OH, SH, halogen, $NO_2$, $NH_2$, CN, $CF_3$, $CHF_2$, $CH_2F$, O—$CF_3$, O—$CHF_2$, O—$CH_2F$, COOH, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the last 4 radicals mentioned may be partly or completely halogenated and/or have 1, 2 or 3 substituents $R^{ya}$, $C_3$-$C_7$-cycloalkyl, $C_3$-$C_7$-cycloalkyl-$C_1$-$C_4$-alkyl, $C_3$-$C_7$-cycloalkyl-O, where the cycloalkyl moiety in the last three radicals mentioned may have 1, 2, 3 or 4 $R^{yb}$ radicals, aryl, O-aryl, $CH_2$-aryl, O—$CH_2$-aryl, where the last 4 radicals mentioned are unsubstituted in the aryl moiety or may carry 1, 2, 3 or 4 radicals $R^{yd}$, $COOR^{y1}$, $CONR^{y2}R^{y3}$, $SO_2NR^{y2}R^{y3}$, —NH—$SO_2$—$R^{y4}$, NH—CO—$R^{y5}$, $SO_2$—$R^{y4}$, —$(CH_2)_p$—$NR^{y6}R^{y7}$ with p=0, 1, 2, 3, 4, 5 or 6 and O—$(CH_2)_q$—$NR^{y6}R^{y7}$ with q=2, 3, 4, 5 or 6;

or two $R^y$ radicals bonded to adjacent C atoms form together with the C atoms to which they are bonded a 4, 5, 6 or 7-membered, optionally substituted carbocycle or an optionally substituted heterocycle which has 1, 2 or 3 different or identical heteroatoms from the group of O, N, S as ring members, where $R^{ya}$ has one of the meanings indicated for $R^{1a}$,
$R^{yb}$ has one of the meanings indicated for $R^{1b}$,
$R^{yd}$ has one of the meanings indicated for $R^{1d}$,
$R^{y1}$ has one of the meanings indicated for $R^{c1}$,
$R^{y2}$ has one of the meanings indicated for $R^{c2}$,
$R^{y3}$ has one of the meanings indicated for $R^{c3}$,
$R^{y4}$ has one of the meanings indicated for $R^{c4}$,
$R^{y5}$ has one of the meanings indicated for $R^{c5}$,
$R^{y6}$ has one of the meanings indicated for $R^{c6}$, and
$R^{y7}$ has one of the meanings indicated for $R^{c7}$;

W is a radical of the formulae W1 or W2 which is linked via nitrogen:

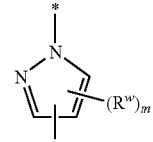

(W1)

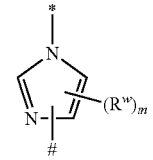

(W2)

in which

* means the linkage to Y, and # means the linkage to $R^2$, m is 0, 1 or 2, and $R^w$ is selected from OH, SH, halogen, $NO_2$, $NH_2$, CN, $CF_3$, $CHF_2$, $CH_2F$, O—$CF_3$, O—$CHF_2$, O—$CH_2F$, COOH, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the last 4 radicals mentioned may be partly or completely halogenated and/or have 1, 2 or 3 substituents $R^{wa}$, $C_3$-$C_7$-cycloalkyl, $C_3$-$C_7$-cycloalkyl-$C_1$-$C_4$-alkyl, $C_3$-$C_7$-cycloalkyloxy, where the cycloalkyl moiety of the last three radicals mentioned may have 1, 2, 3 or 4 radicals $R^{wb}$, aryl, O-aryl, O—$CH_2$-aryl, hetaryl, where the last four radicals mentioned are unsubstituted in the aryl moiety or may carry 1, 2, 3 or 4 radicals $R^{wd}$, $COOR^{w1}$, $CONR^{w2}R^{w3}$, $SO_2NR^{w2}R^{w3}$, $NR^{w2}$—$SO_2$—$R^{w4}$, $NR^{w2}$—CO—$R^{w5}$, $SO_2$—$R^{w4}$, —$(CH_2)_p$—$NR^{w6}R^{w7}$ with p=0, 1, 2, 3, 4, 5 or 6 and O—$(CH_2)_q$—$NR^{w6}R^{w7}$ with q=2, 3, 4, 5 or 6;

or two $R^w$ radicals bonded to adjacent C atoms form together with the C atoms to which they are bonded a 4, 5, 6 or 7-membered, optionally substituted carbocycle or an optionally substituted heterocycle which has 1, 2 or 3 different or identical heteroatoms from the group of O, N, S as ring members, where $R^{wa}$ has one of the meanings indicated for $R^{1a}$,
$R^{wb}$ has one of the meanings indicated for $R^{1b}$,
$R^{wd}$ has one of the meanings indicated for $R^{1d}$,
$R^{w1}$ has one of the meanings indicated for $R^{c1}$,
$R^{w2}$ has one of the meanings indicated for $R^{c2}$,
$R^{w3}$ has one of the meanings indicated for $R^{c3}$,
$R^{w4}$ has one of the meanings indicated for $R^{c4}$,
$R^{w5}$ has one of the meanings indicated for $R^{c5}$,
$R^{w6}$ has one of the meanings indicated for $R^{c6}$,
$R^{w7}$ has one of the meanings indicated for $R^{c7}$, or W forms together with $R^2$ a bi- or tricyclic radical of the formulae W3, W4, W5, W6, W7 or W8 which is linked via nitrogen:

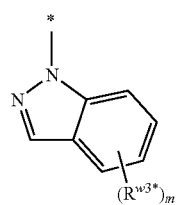
(W3)

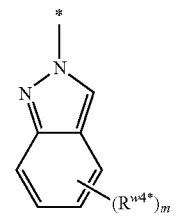
(W4)

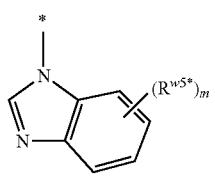
(W5)

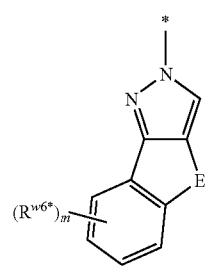
(W6)

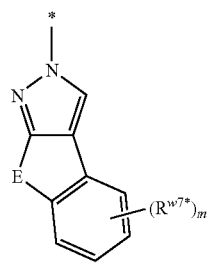
(W7)

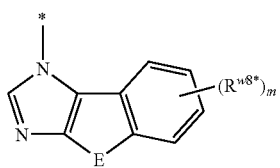
(W8)

in which

* means the linkage to Y, m is 0, 1 or 2, and $R^{w3*}$, $R^{w4*}$, $R^{w5*}$, $R^{w6*}$, $R^{w7*}$ and $R^{w8*}$ have independently of one another one of the meanings indicated for $R^w$, E has one of the following meanings: —$CR_E^2R_E^3$—, —$CHR_E^2$—$CHR_E^3$, $CH_2$—$CH_2$—$CH_2$—, —CO—, —CO—$NR_E^1$—, —$NR_E^1$—CO—, —O—, —$CH_2$—O—, —O—$CH_2$—,
—S—, —S—$CH_2$—, —$CH_2$—S—, —SO—, $CH_2$—SO—, —SO—$CH_2$—, —$SO_2$—, —$CH_2$—$SO_2$—, —$SO_2$—$CH_2$—, —$NR_E^1$—, —$NR_E^1$—$CH_2$—, —$CH_2$—$NR_E^1$—, —$SO_2$—$NR_E^1$—, —$NR_E^1$—$SO_2$—, —CO—O—, —O—CO—, —C(=$CR_E^2R_E^3$)—, —$CR_E^2$=$CR_E^3$—, $R_E^1$ is H, $C_1$-$C_6$-alkyl, $C_1$-$C_6$-haloalkyl, $C_1$-$C_6$-alkyl which has 1, 2 or 3 substituents $R_E^{1a}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, CO—$C_1$-$C_6$-alkyl, CO—O—$C_1$-$C_6$-alkyl, $SO_2$—$C_1$-$C_6$-alkyl, aryl, hetaryl, aryl-$C_1$-$C_4$-alkyl, hetaryl-$C_1$-$C_4$-alkyl, CO-aryl, CO-hetaryl, CO-(aryl-$C_1$-$C_4$-alkyl), CO-(hetaryl-$C_1$-$C_4$-alkyl), CO—O—aryl, CO—O-hetaryl, CO—O-(aryl-$C_1$-$C_4$-alkyl), CO—O-(hetaryl-$C_1$-$C_4$-alkyl), $SO_2$-aryl, $SO_2$-hetaryl, $SO_2$-(aryl-$C_1$-$C_4$-alkyl) or $SO_2$-(hetaryl-$C_1$-$C_4$-alkyl), where aryl and hetaryl in the last 16 radicals mentioned are unsubstituted or have 1, 2 or 3 substituents $R_E^{1d}$, and $R_E^2$, $R_E^3$ are independently of one another selected from hydrogen, $C_1$-$C_6$-alkyl, $C_1$-$C_6$-alkoxy, $C_2$-$C_6$-alkenyl, $C_2$-$C_6$-alkynyl, where the last 4 radicals mentioned may be partly or completely halogenated and/or have 1, 2 or 3 substituents $R_E^{1a}$,
$C_3$-$C_7$-cycloalkyl, $C_3$-$C_7$-cycloalkyl-$C_1$-$C_4$-alkyl, $C_3$-$C_7$-cycloalkyl-O, where a $CH_2$ group in the cycloalkyl moiety of the last three radicals mentioned may be replaced by O, NH, or S, or two adjacent C atoms may form a double bond, where the cycloalkyl moiety may further have 1, 2, 3 or 4 $R_E^{1b}$ radicals,
aryl, hetaryl, aryl-$C_1$-$C_6$-alkyl, or hetaryl-$C_1$-$C_4$-alkyl, where aryl and hetaryl in the last 4 radicals mentioned may be unsubstituted or carry 1, 2, 3 or 4 identical or different radicals $R_E^{1d}$; and where $R_E^{1a}$ has one of the meanings indicated for $R^{1a}$, $R_E^{1b}$ has one of the meanings indicated for $R^{1b}$, and $R_E^{1d}$ has one of the meanings indicated for $R^{1d}$.

The present invention therefore relates to the carboxamide compounds of the general formula I, their tautomers, the pharmaceutically suitable salts of the carboxamide compounds I, the prodrugs of I and the pharmaceutically suitable salts of the prodrugs or tautomers of I.

The carboxamide compounds of the invention of the formula I, their salts, their prodrugs and their tautomers effectively inhibit calpain even at low concentrations. They are additionally distinguished by a high selectivity in relation to the inhibition of the calpain compared with other cysteine proteases such as cathepsin B, cathepsin K, cathepsin L and cathepsin S.

The carboxamide compounds of the invention of the formula I, their salts, their prodrugs and their tautomers are therefore particularly suitable for treating disorders and conditions in creatures, especially human creatures, which are associated with an elevated calpain activity.

The invention therefore also relates to the use of carboxamide compounds of the formula I, their tautomers and their pharmaceutically suitable salts for the manufacture of a medicament, in particular of a medicament which is suitable for the treatment of a disorder or a condition which is associated with an elevated calpain activity.

The invention further relates to a medicament, in particular a medicament which is suitable for the treatment of a disorder or a condition which is associated with an elevated calpain activity. The medicament comprises at least one carboxamide compound of the formula I, as described herein, a tautomer or a pharmaceutically suitable salt of the compound I or of the tautomer or a prodrug of I, or a salt or tautomer of said prodrug.

The carboxamide compounds of the formula I may be in the form of β-keto compounds, i.e. the radicals $R^{3a}$ and $R^{3b}$ in the compounds of the formula I form together with the carbon atom to which they are bonded a carbonyl group as shown in the formula on the left in Scheme A. The compounds of the invention may also be in the form of a hydrate, i.e. the radicals $R^{3a}$ and $R^{3b}$ are each OH, as shown in the formula on the right in Scheme A. $R^1$, $R^2$, W, X and Y in Scheme A have the aforementioned meanings.

Scheme A:

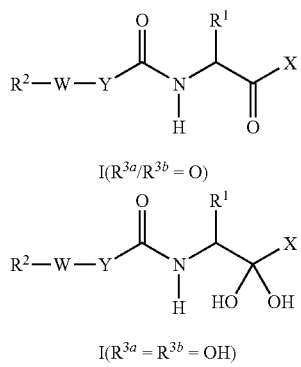

In the presence of water, especially under physiological conditions, usually both the β-keto form and the hydrate form are present in a mixture.

Where only the β-keto form is indicated in the following formulae and descriptions, this is intended to include also the hydrate and mixtures thereof with the β-keto form unless indicated otherwise. Hydrates and β-keto forms are equally suitable as calpain inhibitors.

The carboxamide compounds of the invention of the formula I are also able to form tautomers when $R^{3a}$ and $R^{3b}$ form a carbonyl group together with the carbon atom to which they are bonded. The tautomers are equally suitable as calpain inhibitors. Particular examples of tautomers to be mentioned are the compounds of the formula I-T:

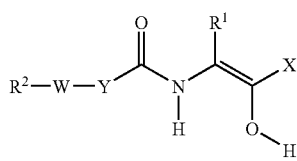

$R^1$, $R^2$, W, X and Y in formula I-T have the aforementioned meanings.

The carboxamide compounds of the invention of the formula I can also form hemiacetals, hemiketals, acetals or ketals with alkanols. These compounds are equally suitable as calpain inhibitors as they are prodrugs of the compounds I, where $CR^{3a}R^{3b}$ is a carbonyl group (i.e. C=O) or $C(OH)_2$. Accordingly, compounds where one or both radicals $R^{3a}$ and $R^{3b}$ are a radical derived from an alkanol, and especially $C_1$-$C_6$-alkoxy, can also be used according to the invention.

The term prodrug, as used herein and in the claims refers to a compound which is transformed under metabolic conditions into a compound of the formula I. Apart from the aforementioned hemiacetals, hemiketals, acetals and ketals prodrugs of the compounds I include the compounds of the formula I, wherein $R^{3a}$ and $R^{3b}$ together form a group O-Alk-O, S-Alk-O or S-Alk-S, where Alk is linear $C_2$-$C_5$-alkandiyl, which may be unsubstituted or substituted with 1, 2, 3 or 4 radicals selected from $C_1$-$C_4$-alkyl or halogen, examples for such groups including $O(CH_2)_2O$, $O(CH_2)_5O$, $O(CH_2)_4O$, $S(CH_2)_2O$, $S(CH_2)_5O$, $S(CH_2)_4O$, etc. Further prodrugs or the compounds I include the compounds of the formula I, wherein $R^{3a}$ and $R^{3b}$ together with the carbon atom form a group C=$NR^3$, where $R^3$ is selected from H, $C_1$-$C_6$-alkyl, $C_1$-$C_6$-alkoxy, $C_2$-$C_6$-alkenyl, $C_3$-$C_6$-cycloalkyl, $C_3$-$C_6$-cycloalkyl-$C_1$-$C_4$-alkyl, $C3_2$-$C_6$-alkenyloxy, $C_3$-$C_6$-cycloalkyloxy, $C_3$-$C_6$-cycloalkyl-$C_1$-$C_4$-alkyloxy. Under metabolic conditions, the aforementioned prodrugs are transformed into the corresponding β-keto compounds of the formula I ($CR^{3a}R^{3b}$ is C=O) or into the hydrates thereof ($CR^{3a}R^{3b}$ is $C(OH)_2$). Therefore, said prodrugs and their pharmaceutically acceptable salts are also part of the invention.

It is equally possible to use pharmaceutically suitable salts of the carboxamide compounds of the formula I of their tautomers or of their prodrugs, especially acid addition salts with physiologically tolerated organic or inorganic acids. Examples of suitable physiologically tolerated organic and inorganic acids are hydrochloric acid, hydrobromic acid, phosphoric acid, nitric acid, sulfuric acid, organic sulfonic acids having 1 to 12 carbon atoms, e.g. $C_1$-$C_4$-alkylsulfonic acids such as methanesulfonic acid, cycloaliphatic sulfonic acids such as S-(+)-10-camphorsulfonic acids, and aromatic sulfonic acids such as benzenesulfonic acid and toluenesulfonic acid, di- and tricarboxylic acids and hydroxy carboxylic acids having 2 to 10 carbon atoms, such as oxalic acid, malonic acid, maleic acid, fumaric acid, mucic acid, lactic acid, tartaric acid, citric acid, glycolic acid and adipic acid, as well as cis- and trans-cinnamic acid, furan-2-carboxylic acid and benzoic acid. Further suitable acids are described in Fortschritte der Arzneimittelforschung, Volume 10, pages 224 et seq., Birkhäuser Verlag, Basel and Stuttgart, 1966. The physiologically tolerated salts of the compounds of the formula I may be in the form of mono-, di-, tri- or tetrasalts, meaning that they may comprise 1, 2, 3 or 4 of the aforementioned acid molecules per molecule of the formula I. The acid molecules may be present in their acidic form or as anion.

The compounds of the invention may be in the form of a mixture of diastereomers, or of a mixture of diastereomers in which one of the two diastereomers is enriched, or of essentially diastereomerically pure compounds (diastereomeric excess de>90%). The compounds are preferably in the form of essentially diastereomerically pure compounds (diastereomeric excess de>90%). The compounds I of the invention may furthermore be in the form of a mixture of enantiomers (for example as racemate), of a mixture of enantiomers in which one of the two enantiomers is enriched, or essentially in enantiomerically pure compounds (enantiomeric excess ee>90%). However, the compounds of the invention are frequently prone to racemization in relation to the stereochemistry of the carbon atom which carries the radical $R^1$, so that mixtures are frequently obtained in relation to this carbon atom, or compounds which exhibit a uniform stereochemistry in relation to this C atom form mixtures under physiological conditions. However, in relation to other stereocenters and the occurrence, associated therewith, of enantiomers and diastereomers, it is preferred to employ the compounds enantiomerically pure or diastereomerically pure.

In the context of the present description, unless stated otherwise, the terms "alkyl", "alkoxy", "alkylthio", "haloalkyl", "haloalkoxy", "haloalkylthio", "alkenyl", "alkynyl", "alkylene" and radicals derived therefrom always include both unbranched and branched "alkyl", "alkoxy", "alkylthio", "haloalkyl", "haloalkoxy", "haloalkylthio", "alkenyl", "alkynyl" and "alkylene", respectively.

The prefix $C_n$-$C_m$- indicates the respective number of carbons in the hydrocarbon unit. Unless indicated otherwise, halogenated substituents preferably have one to five identical or different halogen atoms, especially fluorine atoms or chlorine atoms. $C_0$-Alkylene or $(CH_2)_0$ or similar expressions in the context of the description designate, unless indicated otherwise, a single bond.

The term "halogen" designates in each case, fluorine, bromine, chlorine or iodine, specifically fluorine, chlorine or bromine.

Examples of other meanings are:

Alkyl, and the alkyl moieties for example in alkoxy, alkylthio, arylalkyl, hetarylalkyl, cycloalkylalkyl or alkoxyalkyl: saturated, straight-chain or branched hydrocarbon radicals having one or more C atoms, e.g. 1 to 4, 1 to 6 or 1 to 10 carbon atoms, e.g. $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl. In one embodiment of the invention, alkyl stands for small alkyl groups such as $C_1$-$C_4$-alkyl. In another embodiment of the invention, alkyl stands for larger alkyl groups such as $C_5$-$C_{10}$-alkyl.

Haloalkyl: an alkyl radical having ordinarily 1 to 6 or 1 to 4 C atoms as mentioned above, whose hydrogen atoms are partly or completely replaced by halogen atoms such as fluorine, chlorine, bromine and/or iodine, e.g. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl.

Cycloalkyl, and the cycloalkyl moieties for example in cycloalkoxy or cycloalkyl-$C_1$-$C_6$-alkyl: monocyclic, saturated hydrocarbon groups having three or more C atoms, e.g. 3 to 7 carbon ring members, such as cyclopropyl, cyclobutyl, cyclopentyl, cyclohexyl.

Alkenyl, and alkenyl moieties for example in aryl-($C_2$-$C_6$)-alkenyl: monounsaturated, straight-chain or branched hydrocarbon radicals having two or more C atoms, e.g. 2 to 4, 2 to 6 or 2 to 10 carbon atoms and one double bond in any position, e.g. $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl.

Alkynyl: straight-chain or branched hydrocarbon groups having two or more C atoms, e.g. 2 to 4, 2 to 6 or 2 to 10 carbon atoms and one or two triple bonds in any position but nonadjacent, e.g. $C_2$-$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl.

Alkoxy or alkoxy moieties for example in alkoxyalkyl:

Alkyl as defined above having preferably 1 to 6 or 1 to 4 C atoms, which is linked via an O atom: e.g. methoxy, ethoxy, n-propoxy, 1-methylethoxy, butoxy, 1-methylpropoxy, 2-methylpropoxy or 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

Haloalkoxy: alkoxy as described above, in which the hydrogen atoms of these groups are partly or completely replaced by halogen atoms, i.e. for example $C_1$-$C_6$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, specifically chloromethoxy, fluoromethoxy, difluoromethoxy, trifluoromethoxy, 2-fluoroethoxy, 2-chloroethoxy or 2,2,2-trifluoroethoxy.

Alkoxyalkyl: an alkyl radical ordinarily having 1 to 4 C atoms, in which one hydrogen atom is replaced by an alkoxy radical ordinarily having 1 to 6 or 1 to 4 C atoms. Examples thereof are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl, etc.

Alkylthio: alkyl as defined above preferably having 1 to 6 or 1 to 4 C atoms, which is linked via an S atom, e.g. methylthio, ethylthio, n-propylthio and the like.

Haloalkylthio: haloalkyl as defined above preferably having 1 to 6 or 1 to 4 C atoms, which is linked via an S atom, e.g. fluoromethylthio, difluoromethylthio, trifluoromethylthio, 2-fluoroethylthio, 2,2-difluoroethylthio, 2,2,2-trifluoroethylthio, pentafluoroethylthio, 2-fluoropropylthio, 3-fluoropropylthio, 2,2-difluoropropylthio, 2,3-difluoropropylthio, and heptafluoropropylthio.

Aryl: a mono-, bi- or tricyclic aromatic hydrocarbon radical such as phenyl or naphthyl, especially phenyl.

Heterocyclyl: a heterocyclic radical which may be saturated, partly unsaturated or aromatic and which ordinarily has 3, 4, 5, 6, 7 or 8 ring atoms, where ordinarily 1, 2, 3 or 4, in particular 1, 2 or 3, of the ring atoms are heteroatoms such as N, S or O, besides carbon atoms as ring members. Examples of saturated heterocycles are in particular:

Heterocycloalkyl: i.e. a saturated heterocyclic radical which ordinarily has 3, 4, 5, 6 or 7 ring atoms, where ordinarily 1, 2 or 3 of the ring atoms are heteroatoms such as N, S or O, besides carbon atoms as ring members. These include for example:

C-bonded, 3-4-membered saturated rings such as
2-oxiranyl, 2-oxetanyl, 3-oxetanyl, 2-aziridinyl, 3-thiethanyl, 1-azetidinyl, 2-azetidinyl.

C-bonded, 5-membered saturated rings such as
tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl.

C-bonded, 6-membered saturated rings such as:
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl.

N-bonded, 5-membered saturated rings such as:
tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl.

N-bonded, 6-membered saturated rings such as:
piperidin-1-yl, hexahydropyrimidin-1-yl, hexahydropyrazin-1-yl, hexahydro-pyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl.

Unsaturated heterocyclic radicals which ordinarily have 4, 5, 6 or 7 ring atoms, where ordinarily 1, 2 or 3 of the ring atoms are heteroatoms such as N, S or O, besides carbon atoms as ring members. These include for example:

C-bonded, 5-membered, partially unsaturated rings such as:
2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H- pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl.

C-bonded, 6-membered, partially unsaturated rings such as:

2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydro-pyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4- dihydropyrimidin-2-yl, 3,4-dihydropyrimidin-4-yl, 3,4-dihydropyrimidin-5-yl or 3,4-dihydropyrimidin-6-yl.

N-bonded, 5-membered, partially unsaturated rings such as:
2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl.

N-bonded, 6-membered, partially unsaturated rings such as:
1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

Hetaryl: a 5- or 6-membered aromatic heterocyclic radical which ordinarily has 1, 2, 3 or 4 nitrogen atoms or a heteroatom selected from oxygen and sulfur and, if appropriate, 1, 2 or 3 nitrogen atoms as ring members besides carbon atoms as ring members: for example C-bonded, 5-membered heteroaromatic radicals having 1, 2, 3 or 4 nitrogen atoms or a heteroatom selected from oxygen and sulfur and, if appropriate, having 1, 2 or 3 nitrogen atoms as ring members, such as:
2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl.

C-bonded, 6-membered heteroaromatic radicals having 1, 2, 3 or 4 nitrogen atoms as ring members, such as:
pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl.

N-bonded, 5-membered heteroaromatic radicals having 1, 2, 3 or 4 nitrogen atoms as ring members, such as:
pyrrol-1-yl, pyrazol-1-yl, imidazol-1-yl, 1,2,3-triazol-1-yl, 1,2,4-triazol-1-yl, tetrazol-1-yl.

Heterocyclyl also includes bicyclic heterocycles which have one of the aforementioned 5- or 6-membered heterocyclic rings and a further saturated, unsaturated or aromatic carbocycle fused thereto, for example a benzene, cyclohexane, cyclohexene or cyclohexadiene ring, or a further 5- or 6-membered heterocyclic ring fused thereto, where the latter may likewise be saturated, unsaturated or aromatic. These include for example quinolinyl, isoquinolinyl, indolyl, indolizynyl, isoindolyl, indazolyl, benzofuryl, benzothienyl, benzo[b]thiazolyl, benzoxazolyl, benzthiazolyl and benzimidazolyl. Examples of 5- to 6-membered heteroaromatic compounds comprising a fused benzene ring include dihydroindolyl, dihydroindolizynyl, dihydroisoindolyl, dihydroquinolinyl, dihydroisoquinolinyl, chromenyl and chromanyl.

Arylalkyl: an aryl radical as defined above which is linked via an alkylene group, in particular via a methylene, 1,1-ethylene or 1,2-ethylene group, e.g. benzyl, 1-phenylethyl and 2-phenylethyl.

Arylalkenyl: an aryl radical as defined above, which is linked via an alkenylene group, in particular via a 1,1-ethenyl, 1,2-ethenyl or 1,3-propenyl group, e.g. 2-phenylethen-1-yl and 1-phenylethen-1-yl.

Cycloalkoxy: a cycloalkyl radical as defined above which is linked via an oxygen atom, e.g. cyclopropyloxy, cyclobutyloxy, cyclopentyloxy or cyclohexyloxy.

Cycloalkylalkyl: a cycloalkyl radical as defined above which is linked via an alkylene group, in particular via a methylene, 1,1-ethylene or 1,2-ethylene group, e.g. cyclopropylmethyl, cyclobutylmethyl, cyclopentylmethyl or cyclohexylmethyl.

Heterocyclylalkyl and hetarylalkyl: a heterocyclyl or hetaryl radical as defined above which is linked via an alkylene group, in particular via a methylene, 1,1-ethylene or 1,2-ethylene group.

The expression "optionally substituted" means in the context of the present invention that the respective moiety is substituted or has 1, 2 or 3, in particular 1, substituents which are selected from halogen, $C_1$-$C_4$-alkyl, OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2$NH—$C_1$-$C_6$-alkyl, CON—($C_1$-$C_6$-alkyl)$_2$, $SO_2$N—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2$NH-phenyl, CONH-hetaryl, $SO_2$NH-hetaryl, $SO_2$-phenyl, NH—$SO_2$-phenyl, NH—CO-phenyl, NH—$SO_2$-hetaryl and NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

In relation to their use as calpain inhibitors, the variables $R^1$, $R^2$, W, X and Y preferably have the following meanings, where these represent, both considered on their own and in combination with one other, special configurations of the compounds of the formula I:

$R^1$ $C_1$-$C_{10}$-alkyl, preferably $C_3$-$C_8$-alkyl, which may be partly or completely halogenated and/or have 1, 2 or 3 substituents $R^{1a}$, in particular unsubstituted $C_1$-$C_{10}$-alkyl, specifically unsubstituted $C_3$-$C_8$-alkyl,
$C_3$-$C_7$-cycloalkyl-$C_1$-$C_4$-alkyl, specifically $C_3$-$C_7$-cycloalkylmethyl, 1-($C_3$-$C_7$-cycloalkyl)ethyl or 2-($C_3$-$C_7$-cycloalkyl)ethyl, where the cycloalkyl moiety may have 1, 2, 3 or 4 radicals $R^{1b}$, very specifically cyclohexylmethyl, phenyl-$C_1$-$C_4$-alkyl and hetaryl-$C_1$-$C_4$-alkyl, in particular benzyl, 1-phenylethyl, 2-phenylethyl, hetarylmethyl, 1-hetarylethyl, 2-hetarylethyl such as thienylmethyl, pyridinylmethyl, where phenyl and hetaryl in the last radicals mentioned may be unsubstituted or carry 1, 2, 3 or 4 identical or different radicals $R^{1c}$.

In this connection, $R^{1a}$, $R^{1b}$ and $R^{1c}$ where present have the aforementioned meanings. In particular:

$R^{1a}$ is $C_1$-$C_4$-alkoxy or $C_1$-$C_4$-haloalkoxy;

$R^{1b}$ is halogen, $C_1$-$C_4$-alkyl, $C_1$-$C_4$-haloalkyl, $C_1$-$C_4$-alkoxy or $C_1$-$C_4$-haloalkoxy; and $R^{1c}$ is halogen, $C_1$-$C_4$-alkyl, OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2NH$-phenyl, CONH-hetaryl, $SO_2NH$-hetaryl, $SO_2$-phenyl, NH—$SO_2$-phenyl, NH—CO-phenyl, NH—$SO_2$-hetaryl, NH—CO-hetaryl where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy, —($CH_2$)$_p$—$NR^{c6}R^{c7}$ with p=0, 1, 2, 3, 4, 5 or 6, in particular 0, and —O—($CH_2$)$_q$—$NR^{c6}R^{c7}$ with q=2, 3, 4, 5 or 6, in particular 2, where $R^{c6}$, $R^{c7}$ are independently of one another hydrogen or $C_1$-$C_6$-alkyl, or together with the nitrogen atom to which they are bonded, are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy. $R^{1c}$ is in particular halogen, $C_1$-$C_4$-alkyl, $C_1$-$C_4$-alkoxy or $C_1$-$C_4$-haloalkoxy.

$R^2$ one of the aforementioned radicals different from hydrogen, in particular:

$C_1$-$C_{10}$-alkyl which may be partly or completely halogenated and/or carry 1, 2 or 3 substituents $R^{2a}$, aryl or hetaryl, where aryl and hetaryl in the last 2 radicals mentioned may be unsubstituted or carry 1, 2, 3 or 4 identical or different radicals $R^{2c}$, aryl-$C_1$-$C_6$-alkyl, aryl-$C_2$-$C_6$-alkenyl or hetaryl-$C_1$-$C_4$-alkyl, where aryl and hetaryl in the last 3 radicals mentioned may be unsubstituted or carry 1, 2, 3 or 4 identical or different radicals $R^{2c}$.

Preferred among these are those compounds of the general formula I in which $R^2$ is selected from aryl and hetaryl, specifically from phenyl, thienyl and pyridyl, where aryl and hetaryl (or phenyl, thienyl and pyridyl) may be unsubstituted or carry 1, 2, 3 or 4, in particular 1 or 2, identical or different radicals $R^{2c}$.

In this connection, $R^{2a}$, $R^{2b}$ and $R^{2c}$ where present have the aforementioned meanings. In particular:

$R^{2a}$ is OH, CN, $CF_3$, O—$CF_3$, COOH, O—$CH_2$—COOH, $C_1$-$C_6$-alkoxy, $C_1$-$C_6$-alkylthio, COO—$C_1$-$C_6$-alkyl, $CONH_2$, CONH—$C_1$-$C_6$-alkyl, $SO_2NH$—$C_1$-$C_6$-alkyl, CONH-phenyl, $SO_2NH$-phenyl, CONH-hetaryl, $SO_2NH$-hetaryl, CON—($C_1$-$C_6$-alkyl)$_2$, $SO_2N$—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, $SO_2$-phenyl, NH—$SO_2$-phenyl, NH—CO-phenyl, NH—$SO_2$-hetaryl, NH—CO-hetaryl, $NR^{a6}R^{a7}$, where $R^{a6}$, $R^{a7}$ are independently of one another hydrogen or $C_1$-$C_6$-alkyl, or together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy;

$R^{2b}$ is halogen, $C_1$-$C_4$-alkyl, OH, CN, $CF_3$, O—$CF_3$, COOH, O—$CH_2$—COOH, $C_1$-$C_6$-alkoxy, $C_1$-$C_6$-alkylthio, COO—$C_1$-$C_6$-alkyl, $CONH_2$, CONH—$C_1$-$C_6$-alkyl, $SO_2NH$—$C_1$-$C_6$-alkyl, CONH-phenyl, $SO_2NH$-phenyl, CONH-hetaryl, $SO_2NH$-hetaryl, CON—($C_1$-$C_6$-alkyl)$_2$, $SO_2N$—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, $SO_2$-phenyl, NH—$SO_2$-phenyl, NH—CO-phenyl, NH—$SO_2$-hetaryl, NH—CO-hetaryl or $NR^{b6}R^{b7}$, where $R^{b6}$, $R^{b7}$ are independently of one another hydrogen or $C_1$-$C_6$-alkyl, or together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy; and $R^{2c}$ is halogen, $C_1$-$C_4$-alkyl, OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2NH$-phenyl, CONH-hetaryl, $SO_2NH$-hetaryl, $SO_2$-phenyl, NH—$SO_2$-phenyl, NH—CO-phenyl, NH—$SO_2$-hetaryl, NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy, —($CH_2$)$_p$—$NR^{c6}R^{c7}$ with p=0, 1, 2, 3, 4, 5 or 6, in particular 0, and —O—($CH_2$)$_q$—$NR^{c6}R^{c7}$ with q=2, 3, 4, 5 or 6, in particular 2, where $R^{c6}$, $R^{c7}$ are independently of one another hydrogen or $C_1$-$C_6$-alkyl, or together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy.

$R^{3a}$, $R^{3b}$ in particular OH or the group $CR^{3a}R^{3b}$ is a carbonyl group.

W a radical of the formulae W1 or W2 or the group W—$R^2$ is a radical of the formula W6.

In the formulae W1 and W2, $R^2$ is preferably bonded to the carbon in position 3 or 4, as shown in the following formulae W1a, W1b and W2a:

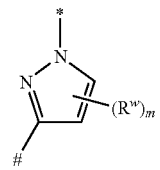

W1a

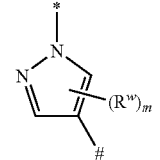

W1b

W2a

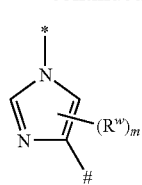

In the formulae W1a, W1b and W2a, the meanings of *, #, m and $R^w$ are those mentioned above. In particular, m is 0 or 1 and specifically 0. Where m is 1, $R^w$ is preferably selected from halogen, $C_1$-$C_6$-alkyl, $C_1$-$C_6$-alkyl which is substituted by 1, 2 or 3 substituents $R^{wa}$, or OH, SH, CN, $CF_3$, O—$CF_3$, COOH, O—$CH_2$—COOH, $C_1$-$C_6$-alkoxy, $C_3$-$C_7$-cycloalkyl, COO—$C_1$-$C_6$-alkyl, $CONH_2$, CONH—$C_1$-$C_6$-alkyl, $SO_2$NH—$C_1$-$C_6$-alkyl, CON—($C_1$-$C_6$-alkyl)$_2$, $SO_2$N—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2$NH-phenyl, CONH-hetaryl, $SO_2$NH-hetaryl, $SO_2$-phenyl, NH—$SO_2$-phenyl, NH—CO-phenyl, NH—$SO_2$-hetaryl, NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy. $R^w$ is in particular selected from OH, F, Cl, CN, $CF_3$, $C_1$-$C_6$-alkyl which is unsubstituted or may have 1, 2 or 3 substituents $R^{wa}$, or $C_1$-$C_6$-haloalkyl, $C_1$-$C_6$-alkoxy, $C_1$-$C_6$-haloalkoxy and $C_3$-$C_7$-cycloalkyl. In this connection, $R^{wa}$ has the aforementioned meanings and is in particular $C_1$-$C_4$-alkoxy or $C_1$-$C_4$-haloalkoxy. $R^w$ is particularly preferably selected from F, Cl, CN, $CF_3$, $CH_3$, $C_2H_5$ and $OCH_3$.

Where the group W—$R^2$ is a radical of the formula W6, m is preferably 0 or 1 and specifically 0. Where m is 1, $R^{w6*}$ is preferably selected from halogen, $C_1$-$C_6$-alkyl, $C_1$-$C_6$-alkyl which is substituted by 1, 2 or 3 substituents $R^{wa}$, or OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2$NH—$C_1$-$C_6$-alkyl, CON—($C_1$-$C_6$-alkyl)$_2$, $SO_2$N—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2$NH-phenyl, CONH-hetaryl, $SO_2$NH-hetaryl, $SO_2$-phenyl, NH—$SO_2$-phenyl, NH—CO-phenyl, NH—$SO_2$-hetaryl, NH—CO-hetaryl where phenyl and hetaryl in the last 11 radicals mentioned are unsubstituted or may have 1, 2 or 3 substituents which are selected from halogen, $C_1$-$C_4$-alkyl, $C_1$-$C_4$-alkoxy and $C_1$-$C_4$-haloalkoxy. $R^{w6*}$ is in particular selected from OH, F, Cl, CN, $CF_3$, $C_1$-$C_6$-alkyl which is unsubstituted or may have 1, 2 or 3 substituents $R^{wa}$, or $C_1$-$C_6$-haloalkyl, $C_1$-$C_6$-alkoxy, $C_1$-$C_6$-haloalkoxy and $C_3$-$C_7$-cycloalkyl. In this connection, $R^{wa}$ has the aforementioned meanings and is in particular $C_1$-$C_4$-alkoxy or $C_1$-$C_4$-haloalkoxy. E in W6 preferably has one of the following meanings: $CH_2$, $CH_2CH_2$, CO, CO—NH, O, CH=CH, $CH_2$O, $OCH_2$, $SO_2$, $SO_2NR_E^1$ or $NR_E^1SO_2$, and is in particular $CH_2$, $CH_2CH_2$, O, CH=CH, $CH_2$O, $OCH_2$, $SO_2$, $SO_2NR_E^1$ or $NR_E^1SO_2$. In this connection, $R_E^1$ has one of the aforementioned meanings and is in particular hydrogen or $C_1$-$C_4$-alkyl.

Compounds of the formula I which are particularly preferred among the compounds of the invention of the general formula I are those in which W is a radical W1a, and particularly preferred among these are those in which m is 0 or 1 and specifically 0.

Compounds of the formula I which are particularly preferred among the compounds of the invention of the general formula I are those in which W—$R^2$ is a radical W6, and particularly preferred among these are those in which m is 0 or 1 and specifically 0.

X is a radical C(=O)—$NR^{x2}R^{x3}$ in which $R^{x2}$ and $R^{x3}$ have one of the aforementioned meanings. Compounds preferred among these are those in which:

$R^{x2}$ is H, OH, CN, $C_1$-$C_6$-alkyl, $C_1$-$C_6$-haloalkyl, $C_1$-$C_6$-alkyl which has 1, 2 or 3 substituents $R^{xa}$, or $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, hetaryl, aryl-$C_1$-$C_4$-alkyl or hetaryl-$C_1$-$C_4$-alkyl, where aryl and hetaryl in the last 4 radicals mentioned are unsubstituted or have 1, 2 or 3 substituents $R^{xd}$. In particular, $R^{x2}$ is hydrogen, $C_1$-$C_6$-alkyl, $C_1$-$C_6$-haloalkyl, $C_1$-$C_6$-alkyl which has 1 or 2 substituents $R^{xa}$, $C_3$-$C_7$-cycloalkyl-$C_1$-$C_4$-alkyl, $C_3$-$C_7$-heterocycloalkyl-$C_1$-$C_4$-alkyl, aryl, hetaryl, aryl-$C_1$-$C_4$-alkyl or hetaryl-$C_1$-$C_4$-alkyl. $R^{x2}$ is very particularly preferably hydrogen.

$R^{x3}$ is H, $C_1$-$C_6$-alkyl, $C_1$-$C_6$-haloalkyl or $C_1$-$C_6$-alkyl which has 1, 2 or 3 substituents $R^{xa}$. In particular, $R^{x3}$ is hydrogen, $C_1$-$C_6$-alkyl, $C_1$-$C_6$-haloalkyl, $C_1$-$C_6$-alkyl which has 1 or 2 substituents $R^{xa}$. $R^{x3}$ is very particularly preferably hydrogen.

Compounds of the formula I which are likewise preferred are those in which the group $NR^{x2}R^{x3}$ is a nitrogen heterocycle of the following formulae:

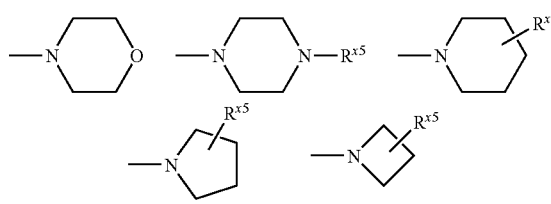

in which $R^{x5}$ is hydrogen or has the meaning indicated for $R^{xb}$. In particular, $R^{x5}$ is $C_1$-$C_6$-alkyl, $C_1$-$C_6$-haloalkyl, $C_1$-$C_6$-alkyl which has 1, 2 or 3 substituents $R^{xa}$, or $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl-$C_1$-$C_4$-alkyl or hetaryl-$C_1$-$C_4$-alkyl, where aryl and hetaryl in the last 2 radicals mentioned are unsubstituted or have 1, 2 or 3 substituents $R^{xd}$, or COO—$C_1$-$C_6$-alkyl, $CONH_2$, CONH—$C_1$-$C_6$-alkyl, $SO_2$NH—$C_1$-$C_6$-alkyl, CON—($C_1$-$C_6$-alkyl)$_2$, $SO_2$N—($C_1$-$C_6$-alkyl)$_2$, NH—$SO_2$—$C_1$-$C_6$-alkyl, CONH-phenyl, $SO_2$NH-phenyl, CONH-hetaryl, $SO_2$NH-hetaryl, where phenyl and hetaryl in the last 4 radicals mentioned are unsubstituted or may have 1, 2 or 3 substituents which are selected from the halogen, $C_1$-$C_4$-alkyl, $C_1$-$C_4$-haloalkyl, $C_1$-$C_4$-alkoxy and $C_1$-$C_4$-haloalkoxy. In particular, $R^{x5}$ is hydrogen or $C_1$-$C_4$-alkyl.

In a particularly preferred embodiment of the invention, X is C(O)—$NH_2$.

In another embodiment of the invention, X is hydrogen.

In another embodiment of the invention, X is C(O)$OR^{x1}$ in which $R^{x1}$ has the aforementioned meanings. In particular, $R^1$ is $C_1$-$C_6$-Alkyl, $C_1$-$C_6$-haloalkyl, $C_1$-$C_6$-alkyl which has 1, 2 or 3 substituents $R^{xa}$, or $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, hetaryl, aryl-$C_1$-$C_4$-alkyl or hetaryl-$C_1$-$C_4$-alkyl stands, where aryl and hetaryl in the last 4 radicals mentioned are unsubstituted or have 1, 2 or 3 substituents $R^{xd}$.

In this connection, $R^{xa}$ has the aforementioned meanings and is in particular $C_1$-$C_4$-alkoxy or $C_1$-$C_4$-haloalkoxy. In this connection, $R^{xd}$ has the aforementioned meanings and is preferably F, Cl, OH, COOH, C(O)NH$_2$, CN, NH$_2$, OCH$_2$COOH, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, CO—$C_1$-$C_4$-alkyl, CO—O—$C_1$-$C_4$-alkyl, NH—$C_1$-$C_4$-alkyl, NH—C(O)$C_1$-$C_4$-alkyl or SO$_2$—$C_1$-$C_4$-alkyl.

Y a divalent, 6-membered heteroaromatic radical which has 1 or 2 nitrogen atoms as ring members and which is preferably selected from pyridinediyl and pyrimidinediyl and which optionally has 1 or 2 identical or different substituents $R^y$. Y is in particular pyridinediyl which is unsubstituted or has 1 or 2 identical or different substituents $R^y$. Y is in particular unsubstituted or has one substituent $R^y$.

W is preferably bonded to a C atom of Y which is located in the position ortho to the C atom of Y which is connected to the carbonyl group. Accordingly, Y is preferably selected from pyridine-2,3-diyl, pyridine-3,4-diyl and pyrimidine-5,6-diyl. A nitrogen atom is preferably present at the other position ortho to the C atom of Y to which W is bonded.

Where $R^y$ is present, $R^y$ is preferably selected from OH, F, Cl, NH$_2$, CN, CF$_3$, CHF$_2$, O—CF$_3$, O—CHF$_2$, O—CH$_2$F, $C_1$-$C_6$-alkyl, $C_3$-$C_7$-cycloalkyl, $C_1$-$C_6$-alkylamino, $C_1$-$C_6$-dialkylamino, pyrrolidinyl, piperidinyl, morpholinyl, imidazolyl, $C_1$-$C_4$-alkoxy, $C_1$-$C_4$-alkoxy-$C_1$-$C_4$-alkyl, CONR$^{y2}$R$^{y3}$, SO$_2$NR$^{y2}$R$^{y3}$, NH—SO$_2$—R$^{y4}$, —(CH$_2$)$_p$—NR$^{y6}$R$^{y7}$, NH—CO—R$^{y5}$, in which p is 0, 1, 2, 3, 4, or 5, and in which R$^{y2}$, R$^{y3}$, R$^{y4}$, R$^{y5}$, R$^{y6}$, R$^{y7}$ have the aforementioned meanings, preferably the meanings mentioned as preferred below, and are in particular H and $C_1$-$C_6$-alkyl, phenyl, benzyl and O-benzyl, where the phenyl ring in the last 3 groups mentioned may have 1, 2 or 3 substituents selected from halogen, OH, SH, NO$_2$, COOH, C(O)NH$_2$, CHO, CN, NH$_2$, OCH$_2$COOH, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NHCHO, NH—C(O)$C_1$-$C_6$-alkyl, and SO$_2$—$C_1$-$C_6$-alkyl.

In particular, $R^y$ is OH, F, Cl, NH$_2$, CN, CF$_3$, CHF$_2$, O—CF$_3$, O—CHF$_2$, O—CH$_2$F, $C_1$-$C_6$-alkyl, $C_3$-$C_7$-cycloalkyl, $C_1$-$C_6$-alkylamino, $C_1$-$C_6$-dialkylamino, pyrrolidinyl, piperidinyl, morpholinyl, imidazolyl, $C_1$-$C_4$-alkoxy, $C_1$-$C_4$-alkoxy-$C_1$-$C_4$-alkyl, CONH—$C_1$-$C_6$-alkyl, SO$_2$N($C_1$-$C_6$-alkyl)$_2$, NH—SO$_2$—$C_1$-$C_6$-alkyl, NH—CO—$C_1$-$C_6$-alkyl, (CH$_2$)$_p$—N($C_1$-$C_6$-alkyl)$_2$, in which p is 2, 3 or 4.

$R^y$ is particularly preferably F, Cl, CN, CF$_3$, CHF$_2$, O—CF$_3$, O—CHF$_2$, O—CH$_2$F or $C_1$-$C_3$-alkyl.

Otherwise, the radicals $R^{x4}$, $R^{ya}$, $R^{wa}$, $R_E^{1a}$, $R^{yb}$, $R^{wb}$, $R_E^{1b}$, $R^{yd}$, $R^{wd}$, $R_E^{1d}$, $R^{a1}$, $R^{b1}$, $R^{c1}$, $R^{y1}$, $R^{w1}$, $R^{a2}$, $R^{b2}$, $R^{c2}$, $R^{y2}$, $R^{w2}$, $R^{a3}$, $R^{b3}$, $R^{c3}$, $R^{y3}$, $R^{w3}$, $R^{a4}$, $R^{b4}$, $R^{c4}$, $R^{y4}$, $R^{w4}$, $R^{a5}$, $R^{b5}$, $R^{c5}$, $R^{y5}$, $R^{w5}$, $R^{a6}$, $R^{b6}$, $R^{c6}$, $R^{y6}$, $R^{w6}$, $R^{a7}$, $R^{b7}$, $R^{c7}$, $R^{y7}$ and $R^{w7}$ have, unless otherwise indicated, independently of one another preferably one of the following meanings:

$R^{x4}$: hydrogen or $C_1$-$C_6$-alkyl.

$R^{ya}$, $R^{wa}$, $R_E^{1a}$ independently of one another: $C_1$-$C_4$-alkoxy or $C_1$-$C_4$-haloalkoxy.

$R^{yb}$, $R^{wb}$, $R_E^{1b}$ independently of one another: halogen, $C_1$-$C_4$-alkyl, $C_1$-$C_4$-haloalkyl, $C_1$-$C_4$-alkoxy or $C_1$-$C_4$-haloalkoxy.

$R^{yd}$, $R^{wd}$, $R_E^{1d}$ independently of one another: F, Cl, OH, COOH, C(O)NH$_2$, CN, NH$_2$, OCH$_2$COOH, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, CO—$C_1$-$C_4$-alkyl, CO—O—$C_1$-$C_4$-alkyl, NH—$C_1$-$C_4$-alkyl, NH—C(O)$C_1$-$C_4$-alkyl or SO$_2$—$C_1$-$C_4$-alkyl.

$R^{a1}$, $R^{b1}$, $R^{c1}$, $R^{y1}$, $R^{w1}$ independently of one another: hydrogen, $C_1$-$C_6$-alkyl, $C_1$-$C_6$-haloalkyl, phenyl, benzyl, hetaryl and hetarylmethyl, where phenyl and hetaryl in the last 4 radicals mentioned are unsubstituted or have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

$R^{a2}$, $R^{b2}$, $R^{c2}$, $R^{y2}$, $R^{w2}$ independently of one another: hydrogen, $C_1$-$C_6$-alkyl, phenyl, benzyl, hetaryl and hetarylmethyl, where phenyl and hetaryl in the last 4 radicals mentioned are unsubstituted or have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

$R^{a3}$, $R^{b3}$, $R^{c3}$, $R^{y3}$, $R^{w3}$ independently of one another: hydrogen or $C_1$-$C_6$-alkyl, or $R^{a2}$ with $R^{a3}$ (and likewise $R^{b2}$ with $R^{b3}$, $R^{c2}$ with $R^{c3}$, $R^{y2}$ with $R^{y3}$ and $R^{w2}$ with $R^{w3}$) together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy.

$R^{a4}$, $R^{b4}$, $R^{c4}$, $R^{y4}$, $R^{w4}$ independently of one another: hydrogen, $C_1$-$C_6$-alkyl, phenyl, benzyl, hetaryl and hetarylmethyl, where phenyl and hetaryl in the last 4 radicals mentioned are unsubstituted or have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

$R^{a5}$, $R^{b5}$, $R^{c5}$, $R^{y5}$, $R^{w5}$ independently of one another: hydrogen, $C_1$-$C_6$-alkyl, phenyl, benzyl, hetaryl and hetarylmethyl, where phenyl and hetaryl in the last 4 radicals mentioned are unsubstituted or have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

$R^{a6}$, $R^{b6}$, $R^{c6}$, $R^{y6}$, $R^{w6}$ independently of one another: hydrogen, $C_1$-$C_6$-alkyl, phenyl, benzyl, hetaryl and hetarylmethyl, where phenyl and hetaryl in the last 4 radicals mentioned are unsubstituted or have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

$R^{a7}$, $R^{b7}$, $R^{c7}$, $R^{y7}$, $R^{w7}$ independently of one another: hydrogen or $C_1$-$C_6$-alkyl, or $R^{a6}$ with $R^{a7}$ (and likewise $R^{b6}$ with $R^{b7}$, $R^{c6}$ with $R^{c7}$, $R^{y6}$ with $R^{y7}$ and $R^{w6}$ with $R^{w7}$) together with the nitrogen atom to which they are bonded are a morpholine, piperidine, pyrrolidine, azetidine or piperazine residue, where the last 5 radicals mentioned are unsubstituted or may carry 1, 2, 3 or 4 radicals selected from $C_1$-$C_4$-alkyl, $C_1$-$C_4$-haloalkyl, $C_1$-$C_4$-alkoxy or $C_1$-$C_4$-haloalkoxy.

Compounds preferred among the carboxamide compounds of the invention of the formula I are those which correspond to the general formula I-A,

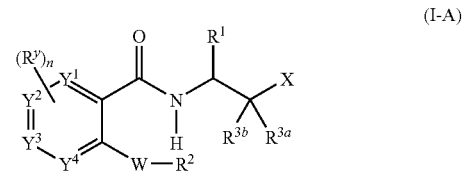

(I-A)

in which X, W, R¹, R², $R^{3a}$, $R^{3b}$, $R^y$ have the aforementioned meanings, in particular the meanings mentioned as preferred, n is 0, 1 or 2, in particular 0 or 1, one of the variables Y¹, Y², Y³ and Y⁴ is a nitrogen atom and the remaining variables Y¹, Y², Y³ or Y⁴ are CH (or C—$R^y$ if n is different from 0). Also preferred are the tautomers of I-A, the pharmaceutically suitable salts thereof and the tautomers thereof.

Compounds in turn preferred among the carboxamide compounds of the invention of the formula I-A are those which correspond to the general formulae I-A' or I-A",

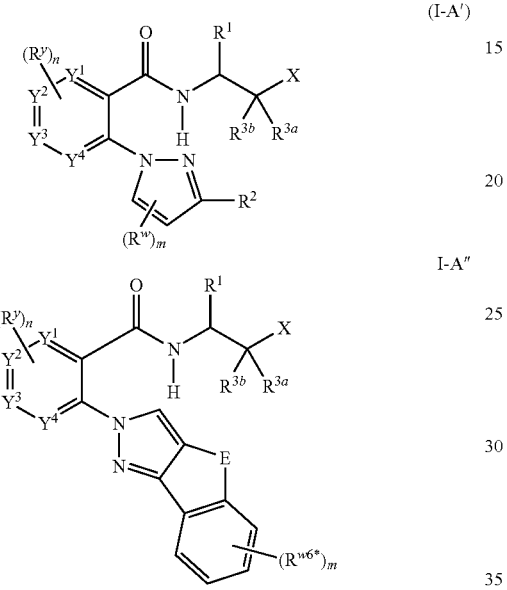

in which m, X, E, R¹, R², $R^{3a}$, $R^{3b}$, $R^y$, $R^w$ and $R^{w6}$ have the aforementioned meanings, in particular the meanings mentioned as preferred, n is 0, 1 or 2, in particular 0 or 1, one of the variables Y¹, Y², Y³ and Y⁴ is a nitrogen atom and the remaining variables Y¹, Y², Y³ or Y⁴ are CH (or C—$R^y$ if n is different from 0). Also preferred are the tautomers of I-A' and I-A", the pharmaceutically suitable salts thereof and the tautomers thereof.

Compounds preferred in turn among the carboxamide compounds of the invention of the formula I-A are those which correspond to the general formula I-A.a,

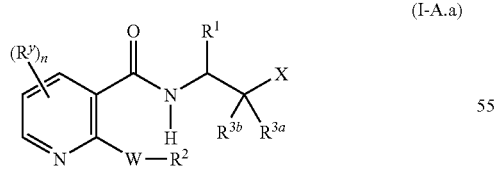

in which X, W, R¹, R², $R^{3a}$, $R^{3b}$, $R^y$ have the aforementioned meanings, especially those mentioned as preferred, and n is 0, 1 or 2, in particular 0 or 1. Also preferred are the tautomers of I-A.a, the pharmaceutically acceptable salts thereof and the tautomers thereof.

Compounds in turn preferred among the carboxamide compounds of the invention of the formula I-A.a are those which correspond to the general formulae I-A.a' or I-A.a",

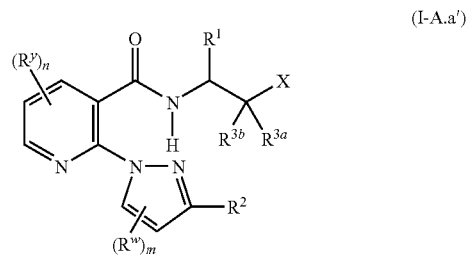

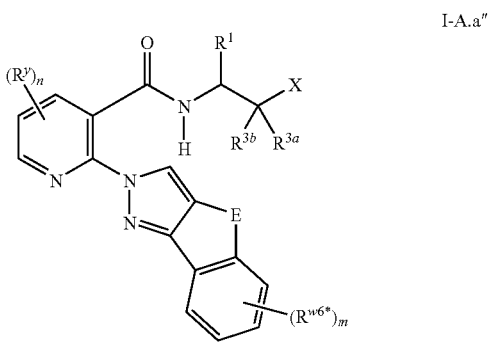

in which m, E, R¹, $R^{3a}$, $R^{3b}$, R², $R^y$, $R^w$ and $R^{w6}$ have the aforementioned meanings, especially those mentioned as preferred, and n is 0, 1 or 2, in particular 0 or 1. Also preferred are the tautomers of I-A.a' and I-A.a", the pharmaceutically suitable salts thereof and the tautomers thereof.

The compounds of the general formula I-A.a which are indicated in Tables 1 to 20 below and in which $CR^{3a}R^{3b}$ is a carbonyl function or a $C(OH)_2$ group, and their tautomers, prodrugs and pharmaceutically acceptable salts, represent per se preferred embodiments of the present invention. The meanings for R¹, R² and W indicated in Table A below represent embodiments of the invention which are likewise preferred independently of one another and especially in combination.

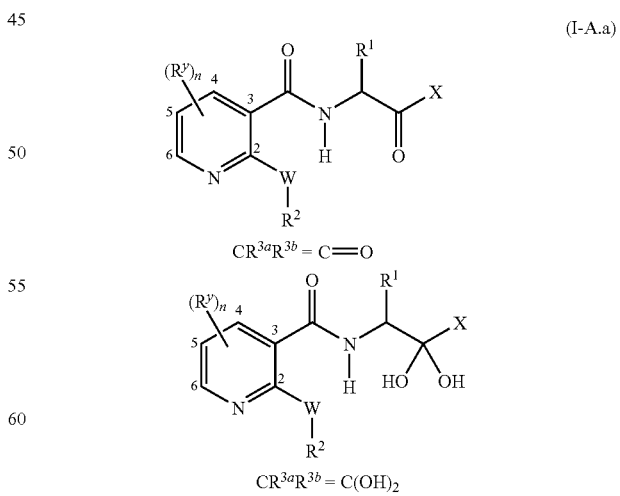

Table 1

Compounds of the formula I-A.a in which the group $C(R^{3a}R^{3b})$ is C=O, X is carbamoyl, n=0, i.e. $(R^y)_n$ is absent, and the combination of R¹, R² and W for a compound in each case corresponds to one line of Table A.

Table 2
Compounds of the formula I-A.a in which the group $C(R^{3a}R^{3b})$ is C=O, X is carbamoyl, $(R^y)_n$ is 5-F, and the combination of R¹, R² and W for a compound in each case corresponds to one line of Table A.

Table 3
Compounds of the formula I-A.a in which the group $C(R^{3a}R^{3b})$ is C=O, X is carbamoyl, $(R^y)_n$ is 5-Cl, and the combination of R¹, R² and W for a compound in each case corresponds to one line of Table A.

Table 4
Compounds of the formula I-A.a in which the group $C(R^{3a}R^{3b})$ is C=O, X is carbamoyl, $(R^y)_n$ is 5-CN, and the combination of R¹, R² and W for a compound in each case corresponds to one line of Table A.

Table 5
Compounds of the formula I-A.a in which the group $C(R^{3a}R^{3b})$ is C=O, X is carbamoyl, $(R^y)_n$ is 5-CH₃, and the combination of R¹, R² and W for a compound in each case corresponds to one line of Table A.

Table 6
Compounds of the formula I-A.a in which the group $C(R^{3a}R^{3b})$ is C=O, X is —C(O)NHCH₃, n=0, i.e. $(R^y)_n$ is absent, and the combination of R¹, R² and W for a compound in each case corresponds to one line of Table A.

Table 7
Compounds of the formula I-A.a in which the group $C(R^{3a}R^{3b})$ is C=O, X is —C(O)NHCH₃, $(R^y)_n$ is 5-F, and the combination of R¹, R² and W for a compound in each case corresponds to one line of Table A.

Table 8
Compounds of the formula I-A.a in which the group $C(R^{3a}R^{3b})$ is C=O, X is —C(O)NHCH₃, $(R^y)_n$ is 5-Cl, and the combination of R¹, R² and W for a compound in each case corresponds to one line of Table A.

Table 9
Compounds of the formula I-A.a in which the group $C(R^{3a}R^{3b})$ is C=O, X is —C(O)NHCH₃, $(R^y)_n$ is 5-CN, and the combination of R¹, R² and W for a compound in each case corresponds to one line of Table A.

Table 10
Compounds of the formula I-A.a in which the group $C(R^{3a}R^{3b})$ is C=O, X is —C(O)NHCH₃, $(R^y)_n$ is 5-CH₃, and the combination of R¹, R² and W for a compound in each case corresponds to one line of Table A.

Table 11
Compounds of the formula I-A.a in which the group $C(R^{3a}R^{3b})$ is C(OH)₂, X is carbamoyl, n=0, i.e. $(R^y)_n$ is absent, and the combination of R¹, R² and W for a compound in each case corresponds to one line of Table A.

Table 12
Compounds of the formula I-A.a in which the group $C(R^{3a}R^{3b})$ is C(OH)₂, X is carbamoyl, $(R^y)_n$ is 5-F, and the combination of R¹, R² and W for a compound in each case corresponds to one line of Table A.

Table 13
Compounds of the formula I-A.a in which the group $C(R^{3a}R^{3b})$ is C(OH)₂, X is carbamoyl, $(R^y)_n$ is 5-Cl, and the combination of R¹, R² and W for a compound in each case corresponds to one line of Table A.

Table 14
Compounds of the formula I-A.a in which the group $C(R^{3a}R^{3b})$ is C(OH)₂, X is carbamoyl, $(R^y)_n$ is 5-CN, and the combination of R¹, R² and W for a compound in each case corresponds to one line of Table A.

Table 15
Compounds of the formula I-A.a in which the group $C(R^{3a}R^{3b})$ is C(OH)₂, X is carbamoyl, $(R^y)_n$ is 5-CH₃, and the combination of R¹, R² and W for a compound in each case corresponds to one line of Table A.

Table 16
Compounds of the formula I-A.a in which the group $C(R^{3a}R^{3b})$ is C(OH)₂, X is —C(O)NHCH₃, n=0, i.e. $(R^y)_n$ is absent, and the combination of R¹, R² and W for a compound in each case corresponds to one line of Table A.

Table 17
Compounds of the formula I-A.a in which the group $C(R^{3a}R^{3b})$ is C(OH)₂, X is —C(O)NHCH₃, $(R^y)_n$ is 5-F, and the combination of R¹, R² and W for a compound in each case corresponds to one line of Table A.

Table 18
Compounds of the formula I-A.a in which the group $C(R^{3a}R^{3b})$ is C(OH)₂, X is —C(O)NHCH₃, $(R^y)_n$ is 5-Cl, and the combination of R¹, R² and W for a compound in each case corresponds to one line of Table A.

Table 19
Compounds of the formula I-A.a in which the group $C(R^{3a}R^{3b})$ is C(OH)₂, X is —C(O)NHCH₃, $(R^y)_n$ is 5-CN, and the combination of R¹, R² and W for a compound in each case corresponds to one line of Table A.

Table 20
Compounds of the formula I-A.a in which the group $C(R^{3a}R^{3b})$ is C(OH)₂, X is —C(O)NHCH₃, $(R^y)_n$ is 5-CH₃, and the combination of R¹, R² and W for a compound in each case corresponds to one line of Table A.

TABLE A

| No. | R¹ | R² | W |
|---|---|---|---|
| A-1 | n-Butyl | Phenyl | W1a (m = 0) |
| A-2 | n-Butyl | 2-Methylphenyl | W1a (m = 0) |
| A-3 | n-Butyl | 2-Methoxyphenyl | W1a (m = 0) |
| A-4 | n-Butyl | 2-Chlorophenyl | W1a (m = 0) |
| A-5 | n-Butyl | 2-Fluorophenyl | W1a (m = 0) |
| A-6 | n-Butyl | 2-Trifluoromethylphenyl | W1a (m = 0) |
| A-7 | n-Butyl | 3-Methylphenyl | W1a (m = 0) |
| A-8 | n-Butyl | 3-Methoxyphenyl | W1a (m = 0) |
| A-9 | n-Butyl | 3-Chlorophenyl | W1a (m = 0) |
| A-10 | n-Butyl | 3-Fluorophenyl | W1a (m = 0) |
| A-11 | n-Butyl | 3-Trifluoromethyl | W1a (m = 0) |
| A-12 | n-Butyl | 3-[(Phenylmethyl)oxy]phenyl | W1a (m = 0) |
| A-13 | n-Butyl | 3-Morpholin-4-ylphenyl | W1a (m = 0) |
| A-14 | n-Butyl | 3-(Morpholin-4-ylmethyl)phenyl | W1a (m = 0) |
| A-15 | n-Butyl | 3-Pyrrolidin-1-ylphenyl | W1a (m = 0) |
| A-16 | n-Butyl | 4-Methylphenyl | W1a (m = 0) |

TABLE A-continued

| No. | R¹ | R² | W |
|---|---|---|---|
| A-17 | n-Butyl | 4-(1-Methylethyl)phenyl | W1a (m = 0) |
| A-18 | n-Butyl | 4-Methoxyphenyl | W1a (m = 0) |
| A-19 | n-Butyl | 4-Chlorophenyl | W1a (m = 0) |
| A-20 | n-Butyl | 4-Fluorophenyl | W1a (m = 0) |
| A-21 | n-Butyl | 4-Trifluoromethylphenyl | W1a (m = 0) |
| A-22 | n-Butyl | 4-Diethylaminophenyl | W1a (m = 0) |
| A-23 | n-Butyl | 4-[(Diethylamino)methyl]phenyl | W1a (m = 0) |
| A-24 | n-Butyl | 4-Cyanophenyl | W1a (m = 0) |
| A-25 | n-Butyl | 4-(Piperidin-1-yl)phenyl | W1a (m = 0) |
| A-26 | n-Butyl | 4-(4-Methylpiperazin-1-yl)phenyl | W1a (m = 0) |
| A-27 | n-Butyl | 4-Pyrrolidin-1-ylphenyl | W1a (m = 0) |
| A-28 | n-Butyl | 4-(1H-Imidazol-1-yl)phenyl | W1a (m = 0) |
| A-29 | n-Butyl | 4-Morpholin-4-ylphenyl | W1a (m = 0) |
| A-30 | n-Butyl | 4-(Morpholin-4-ylmethyl)phenyl | W1a (m = 0) |
| A-31 | n-Butyl | 2,4-Difluorophenyl | W1a (m = 0) |
| A-32 | n-Butyl | 2,6-Difluorophenyl | W1a (m = 0) |
| A-33 | n-Butyl | 3,5-Difluorophenyl | W1a (m = 0) |
| A-34 | n-Butyl | 2,4-Dichlorophenyl | W1a (m = 0) |
| A-35 | n-Butyl | 2,6-Dichlorophenyl | W1a (m = 0) |
| A-36 | n-Butyl | 3,5-Dichlorophenyl | W1a (m = 0) |
| A-37 | n-Butyl | 2-Chloro-4-fluorophenyl | W1a (m = 0) |
| A-38 | n-Butyl | 2-Chloro-4-morpholin-4-ylphenyl | W1a (m = 0) |
| A-39 | n-Butyl | 2-Fluoro-4-morpholin-4-ylphenyl | W1a (m = 0) |
| A-40 | n-Butyl | Pyridin-2-yl | W1a (m = 0) |
| A-41 | n-Butyl | Pyridin-4-yl | W1a (m = 0) |
| A-42 | n-Butyl | Thien-2-yl | W1a (m = 0) |
| A-43 | n-Butyl | 2,3-Dihydrobenzo[b]furan-5-yl | W1a (m = 0) |
| A-44 | Isobutyl | Phenyl | W1a (m = 0) |
| A-45 | Isobutyl | 2-Methylphenyl | W1a (m = 0) |
| A-46 | Isobutyl | 2-Methoxyphenyl | W1a (m = 0) |
| A-47 | Isobutyl | 2-Chlorophenyl | W1a (m = 0) |
| A-48 | Isobutyl | 2-Fluorophenyl | W1a (m = 0) |
| A-49 | Isobutyl | 2-Trifluoromethylphenyl | W1a (m = 0) |
| A-50 | Isobutyl | 3-Methylphenyl | W1a (m = 0) |
| A-51 | Isobutyl | 3-Methoxyphenyl | W1a (m = 0) |
| A-52 | Isobutyl | 3-Chlorophenyl | W1a (m = 0) |
| A-53 | Isobutyl | 3-Fluorophenyl | W1a (m = 0) |
| A-54 | Isobutyl | 3-Trifluoromethyl | W1a (m = 0) |
| A-55 | Isobutyl | 3-[(Phenylmethyl)oxy]phenyl | W1a (m = 0) |
| A-56 | Isobutyl | 3-Morpholin-4-ylphenyl | W1a (m = 0) |
| A-57 | Isobutyl | 3-(Morpholin-4-ylmethyl)phenyl | W1a (m = 0) |
| A-58 | Isobutyl | 3-Pyrrolidin-1-ylphenyl | W1a (m = 0) |
| A-59 | Isobutyl | 4-Methylphenyl | W1a (m = 0) |
| A-60 | Isobutyl | 4-(1-Methylethyl)phenyl | W1a (m = 0) |
| A-61 | Isobutyl | 4-Methoxyphenyl | W1a (m = 0) |
| A-62 | Isobutyl | 4-Chlorophenyl | W1a (m = 0) |
| A-63 | Isobutyl | 4-Fluorophenyl | W1a (m = 0) |
| A-64 | Isobutyl | 4-Trifluoromethylphenyl | W1a (m = 0) |
| A-65 | Isobutyl | 4-Diethylaminophenyl | W1a (m = 0) |
| A-66 | Isobutyl | 4-[(Diethylamino)methyl]phenyl | W1a (m = 0) |
| A-67 | Isobutyl | 4-Cyanophenyl | W1a (m = 0) |
| A-68 | Isobutyl | 4-(Piperidin-1-yl)phenyl | W1a (m = 0) |
| A-69 | Isobutyl | 4-(4-Methylpiperazin-1-yl)phenyl | W1a (m = 0) |
| A-70 | Isobutyl | 4-Pyrrolidin-1-ylphenyl | W1a (m = 0) |
| A-71 | Isobutyl | 4-(1H-Imidazol-1-yl)phenyl | W1a (m = 0) |
| A-72 | Isobutyl | 4-Morpholin-4-ylphenyl | W1a (m = 0) |
| A-73 | Isobutyl | 4-(Morpholin-4-ylmethyl)phenyl | W1a (m = 0) |
| A-74 | Isobutyl | 2,4-Difluorophenyl | W1a (m = 0) |
| A-75 | Isobutyl | 2,6-Difluorophenyl | W1a (m = 0) |
| A-76 | Isobutyl | 3,5-Difluorophenyl | W1a (m = 0) |
| A-77 | Isobutyl | 2,4-Dichlorophenyl | W1a (m = 0) |
| A-78 | Isobutyl | 2,6-Dichlorophenyl | W1a (m = 0) |
| A-79 | Isobutyl | 3,5-Dichlorophenyl | W1a (m = 0) |
| A-80 | Isobutyl | 2-Chloro-4-fluorophenyl | W1a (m = 0) |
| A-81 | Isobutyl | 2-Chloro-4-morpholin-4-ylphenyl | W1a (m = 0) |
| A-82 | Isobutyl | 2-Fluoro-4-morpholin-4-ylphenyl | W1a (m = 0) |
| A-83 | Isobutyl | Pyridin-2-yl | W1a (m = 0) |
| A-84 | Isobutyl | Pyridin-4-yl | W1a (m = 0) |
| A-85 | Isobutyl | Thien-2-yl | W1a (m = 0) |
| A-86 | Isobutyl | 2,3-Dihydrobenzo[b]furan-5-yl | W1a (m = 0) |
| A-87 | Benzyl | Phenyl | W1a (m = 0) |
| A-88 | Benzyl | 2-Methylphenyl | W1a (m = 0) |
| A-89 | Benzyl | 2-Methoxyphenyl | W1a (m = 0) |
| A-90 | Benzyl | 2-Chlorophenyl | W1a (m = 0) |
| A-91 | Benzyl | 2-Fluorophenyl | W1a (m = 0) |
| A-92 | Benzyl | 2-Trifluoromethylphenyl | W1a (m = 0) |
| A-93 | Benzyl | 3-Methylphenyl | W1a (m = 0) |
| A-94 | Benzyl | 3-Methoxyphenyl | W1a (m = 0) |

TABLE A-continued

| No. | R¹ | R² | W |
|---|---|---|---|
| A-95 | Benzyl | 3-Chlorophenyl | W1a (m = 0) |
| A-96 | Benzyl | 3-Fluorophenyl | W1a (m = 0) |
| A-97 | Benzyl | 3-Trifluoromethyl | W1a (m = 0) |
| A-98 | Benzyl | 3-[(Phenylmethyl)oxy]phenyl | W1a (m = 0) |
| A-99 | Benzyl | 3-Morpholin-4-ylphenyl | W1a (m = 0) |
| A-100 | Benzyl | 3-(Morpholin-4-ylmethyl)phenyl | W1a (m = 0) |
| A-101 | Benzyl | 3-Pyrrolidin-1-ylphenyl | W1a (m = 0) |
| A-102 | Benzyl | 4-Methylphenyl | W1a (m = 0) |
| A-103 | Benzyl | 4-(1-Methylethyl)phenyl | W1a (m = 0) |
| A-104 | Benzyl | 4-Methoxyphenyl | W1a (m = 0) |
| A-105 | Benzyl | 4-Chlorophenyl | W1a (m = 0) |
| A-106 | Benzyl | 4-Fluorophenyl | W1a (m = 0) |
| A-107 | Benzyl | 4-Trifluoromethylphenyl | W1a (m = 0) |
| A-108 | Benzyl | 4-Diethylaminophenyl | W1a (m = 0) |
| A-109 | Benzyl | 4-[(Diethylamino)methyl]phenyl | W1a (m = 0) |
| A-110 | Benzyl | 4-Cyanophenyl | W1a (m = 0) |
| A-111 | Benzyl | 4-(Piperidin-1-yl)phenyl | W1a (m = 0) |
| A-112 | Benzyl | 4-(4-Methylpiperazin-1-yl)phenyl | W1a (m = 0) |
| A-113 | Benzyl | 4-Pyrrolidin-1-ylphenyl | W1a (m = 0) |
| A-114 | Benzyl | 4-(1H-Imidazol-1-yl)phenyl | W1a (m = 0) |
| A-115 | Benzyl | 4-Morpholin-4-ylphenyl | W1a (m = 0) |
| A-116 | Benzyl | 4-(Morpholin-4-ylmethyl)phenyl | W1a (m = 0) |
| A-117 | Benzyl | 2,4-Difluorophenyl | W1a (m = 0) |
| A-118 | Benzyl | 2,6-Difluorophenyl | W1a (m = 0) |
| A-119 | Benzyl | 3,5-Difluorophenyl | W1a (m = 0) |
| A-120 | Benzyl | 2,4-Dichlorophenyl | W1a (m = 0) |
| A-121 | Benzyl | 2,6-Dichlorophenyl | W1a (m = 0) |
| A-122 | Benzyl | 3,5-Dichlorophenyl | W1a (m = 0) |
| A-123 | Benzyl | 2-Chloro-4-fluorophenyl | W1a (m = 0) |
| A-124 | Benzyl | 2-Chloro-4-morpholin-4-ylphenyl | W1a (m = 0) |
| A-125 | Benzyl | 2-Fluoro-4-morpholin-4-ylphenyl | W1a (m = 0) |
| A-126 | Benzyl | Pyridin-2-yl | W1a (m = 0) |
| A-127 | Benzyl | Pyridin-4-yl | W1a (m = 0) |
| A-128 | Benzyl | Thien-2-yl | W1a (m = 0) |
| A-129 | Benzyl | 2,3-Dihydrobenzo[b]furan-5-yl | W1a (m = 0) |
| A-130 | 4-Chlorobenzyl | Phenyl | W1a (m = 0) |
| A-131 | 4-Chlorobenzyl | 2-Methylphenyl | W1a (m = 0) |
| A-132 | 4-Chlorobenzyl | 2-Methoxyphenyl | W1a (m = 0) |
| A-133 | 4-Chlorobenzyl | 2-Chlorophenyl | W1a (m = 0) |
| A-134 | 4-Chlorobenzyl | 2-Fluorophenyl | W1a (m = 0) |
| A-135 | 4-Chlorobenzyl | 2-Trifluoromethylphenyl | W1a (m = 0) |
| A-136 | 4-Chlorobenzyl | 3-Methylphenyl | W1a (m = 0) |
| A-137 | 4-Chlorobenzyl | 3-Methoxyphenyl | W1a (m = 0) |
| A-138 | 4-Chlorobenzyl | 3-Chlorophenyl | W1a (m = 0) |
| A-139 | 4-Chlorobenzyl | 3-Fluorophenyl | W1a (m = 0) |
| A-140 | 4-Chlorobenzyl | 3-Trifluoromethyl | W1a (m = 0) |
| A-141 | 4-Chlorobenzyl | 3-[(Phenylmethyl)oxy]phenyl | W1a (m = 0) |
| A-142 | 4-Chlorobenzyl | 3-Morpholin-4-ylphenyl | W1a (m = 0) |
| A-143 | 4-Chlorobenzyl | 3-(Morpholin-4-ylmethyl)phenyl | W1a (m = 0) |
| A-144 | 4-Chlorobenzyl | 3-Pyrrolidin-1-ylphenyl | W1a (m = 0) |
| A-145 | 4-Chlorobenzyl | 4-Methylphenyl | W1a (m = 0) |
| A-146 | 4-Chlorobenzyl | 4-(1-Methylethyl)phenyl | W1a (m = 0) |
| A-147 | 4-Chlorobenzyl | 4-Methoxyphenyl | W1a (m = 0) |
| A-148 | 4-Chlorobenzyl | 4-Chlorophenyl | W1a (m = 0) |
| A-149 | 4-Chlorobenzyl | 4-Fluorophenyl | W1a (m = 0) |
| A-150 | 4-Chlorobenzyl | 4-Trifluoromethylphenyl | W1a (m = 0) |
| A-151 | 4-Chlorobenzyl | 4-Diethylaminophenyl | W1a (m = 0) |
| A-152 | 4-Chlorobenzyl | 4-[(Diethylamino)methyl]phenyl | W1a (m = 0) |
| A-153 | 4-Chlorobenzyl | 4-Cyanophenyl | W1a (m = 0) |
| A-154 | 4-Chlorobenzyl | 4-(Piperidin-1-yl)phenyl | W1a (m = 0) |
| A-155 | 4-Chlorobenzyl | 4-(4-Methylpiperazin-1-yl)phenyl | W1a (m = 0) |
| A-156 | 4-Chlorobenzyl | 4-Pyrrolidin-1-ylphenyl | W1a (m = 0) |
| A-157 | 4-Chlorobenzyl | 4-(1H-Imidazol-1-yl)phenyl | W1a (m = 0) |
| A-158 | 4-Chlorobenzyl | 4-Morpholin-4-ylphenyl | W1a (m = 0) |
| A-159 | 4-Chlorobenzyl | 4-(Morpholin-4-ylmethyl)phenyl | W1a (m = 0) |
| A-160 | 4-Chlorobenzyl | 2,4-Difluorophenyl | W1a (m = 0) |
| A-161 | 4-Chlorobenzyl | 2,6-Difluorophenyl | W1a (m = 0) |
| A-162 | 4-Chlorobenzyl | 3,5-Difluorophenyl | W1a (m = 0) |
| A-163 | 4-Chlorobenzyl | 2,4-Dichlorophenyl | W1a (m = 0) |
| A-164 | 4-Chlorobenzyl | 2,6-Dichlorophenyl | W1a (m = 0) |
| A-165 | 4-Chlorobenzyl | 3,5-Dichlorophenyl | W1a (m = 0) |
| A-166 | 4-Chlorobenzyl | 2-Chloro-4-fluorophenyl | W1a (m = 0) |
| A-167 | 4-Chlorobenzyl | 2-Chloro-4-morpholin-4-ylphenyl | W1a (m = 0) |
| A-168 | 4-Chlorobenzyl | 2-Fluoro-4-morpholin-4-ylphenyl | W1a (m = 0) |
| A-169 | 4-Chlorobenzyl | Pyridin-2-yl | W1a (m = 0) |
| A-170 | 4-Chlorobenzyl | Pyridin-4-yl | W1a (m = 0) |
| A-171 | 4-Chlorobenzyl | Thien-2-yl | W1a (m = 0) |
| A-172 | 4-Chlorobenzyl | 2,3-Dihydrobenzo[b]furan-5-yl | W1a (m = 0) |

TABLE A-continued

| No. | R¹ | R² | W |
|---|---|---|---|
| A-173 | 4-Methoxybenzyl | Phenyl | W1a (m = 0) |
| A-174 | 4-Methoxybenzyl | 2-Methylphenyl | W1a (m = 0) |
| A-175 | 4-Methoxybenzyl | 2-Methoxyphenyl | W1a (m = 0) |
| A-176 | 4-Methoxybenzyl | 2-Chlorophenyl | W1a (m = 0) |
| A-177 | 4-Methoxybenzyl | 2-Fluorophenyl | W1a (m = 0) |
| A-178 | 4-Methoxybenzyl | 2-Trifluoromethylphenyl | W1a (m = 0) |
| A-179 | 4-Methoxybenzyl | 3-Methylphenyl | W1a (m = 0) |
| A-180 | 4-Methoxybenzyl | 3-Methoxyphenyl | W1a (m = 0) |
| A-181 | 4-Methoxybenzyl | 3-Chlorophenyl | W1a (m = 0) |
| A-182 | 4-Methoxybenzyl | 3-Fluorophenyl | W1a (m = 0) |
| A-183 | 4-Methoxybenzyl | 3-Trifluoromethyl | W1a (m = 0) |
| A-184 | 4-Methoxybenzyl | 3-[(Phenylmethyl)oxy]phenyl | W1a (m = 0) |
| A-185 | 4-Methoxybenzyl | 3-Morpholin-4-ylphenyl | W1a (m = 0) |
| A-186 | 4-Methoxybenzyl | 3-(Morpholin-4-ylmethyl)phenyl | W1a (m = 0) |
| A-187 | 4-Methoxybenzyl | 3-Pyrrolidin-1-ylphenyl | W1a (m = 0) |
| A-188 | 4-Methoxybenzyl | 4-Methylphenyl | W1a (m = 0) |
| A-189 | 4-Methoxybenzyl | 4-(1-Methylethyl)phenyl | W1a (m = 0) |
| A-190 | 4-Methoxybenzyl | 4-Methoxyphenyl | W1a (m = 0) |
| A-191 | 4-Methoxybenzyl | 4-Chlorophenyl | W1a (m = 0) |
| A-192 | 4-Methoxybenzyl | 4-Fluorophenyl | W1a (m = 0) |
| A-193 | 4-Methoxybenzyl | 4-Trifluoromethylphenyl | W1a (m = 0) |
| A-194 | 4-Methoxybenzyl | 4-Diethylaminophenyl | W1a (m = 0) |
| A-195 | 4-Methoxybenzyl | 4-[(Diethylamino)methyl]phenyl | W1a (m = 0) |
| A-196 | 4-Methoxybenzyl | 4-Cyanophenyl | W1a (m = 0) |
| A-197 | 4-Methoxybenzyl | 4-(Piperidin-1-yl)phenyl | W1a (m = 0) |
| A-198 | 4-Methoxybenzyl | 4-(4-Methylpiperazin-1-yl)phenyl | W1a (m = 0) |
| A-199 | 4-Methoxybenzyl | 4-Pyrrolidin-1-ylphenyl | W1a (m = 0) |
| A-200 | 4-Methoxybenzyl | 4-(1H-Imidazol-1-yl)phenyl | W1a (m = 0) |
| A-201 | 4-Methoxybenzyl | 4-Morpholin-4-ylphenyl | W1a (m = 0) |
| A-202 | 4-Methoxybenzyl | 4-(Morpholin-4-ylmethyl)phenyl | W1a (m = 0) |
| A-203 | 4-Methoxybenzyl | 2,4-Difluorophenyl | W1a (m = 0) |
| A-204 | 4-Methoxybenzyl | 2,6-Difluorophenyl | W1a (m = 0) |
| A-205 | 4-Methoxybenzyl | 3,5-Difluorophenyl | W1a (m = 0) |
| A-206 | 4-Methoxybenzyl | 2,4-Dichlorophenyl | W1a (m = 0) |
| A-207 | 4-Methoxybenzyl | 2,6-Dichlorophenyl | W1a (m = 0) |
| A-208 | 4-Methoxybenzyl | 3,5-Dichlorophenyl | W1a (m = 0) |
| A-209 | 4-Methoxybenzyl | 2-Chloro-4-fluorophenyl | W1a (m = 0) |
| A-210 | 4-Methoxybenzyl | 2-Chloro-4-morpholin-4-ylphenyl | W1a (m = 0) |
| A-211 | 4-Methoxybenzyl | 2-Fluoro-4-morpholin-4-ylphenyl | W1a (m = 0) |
| A-212 | 4-Methoxybenzyl | Pyridin-2-yl | W1a (m = 0) |
| A-213 | 4-Methoxybenzyl | Pyridin-4-yl | W1a (m = 0) |
| A-214 | 4-Methoxybenzyl | Thien-2-yl | W1a (m = 0) |
| A-215 | 4-Methoxybenzyl | 2,3-Dihydrobenzo[b]furan-5-yl | W1a (m = 0) |
| A-216 | Cyclohexylmethyl | Phenyl | W1a (m = 0) |
| A-217 | Cyclohexylmethyl | 2-Methylphenyl | W1a (m = 0) |
| A-218 | Cyclohexylmethyl | 2-Methoxyphenyl | W1a (m = 0) |
| A-219 | Cyclohexylmethyl | 2-Chlorophenyl | W1a (m = 0) |
| A-220 | Cyclohexylmethyl | 2-Fluorophenyl | W1a (m = 0) |
| A-221 | Cyclohexylmethyl | 2-Trifluoromethylphenyl | W1a (m = 0) |
| A-222 | Cyclohexylmethyl | 3-Methylphenyl | W1a (m = 0) |
| A-223 | Cyclohexylmethyl | 3-Methoxyphenyl | W1a (m = 0) |
| A-224 | Cyclohexylmethyl | 3-Chlorophenyl | W1a (m = 0) |
| A-225 | Cyclohexylmethyl | 3-Fluorophenyl | W1a (m = 0) |
| A-226 | Cyclohexylmethyl | 3-Trifluoromethyl | W1a (m = 0) |
| A-227 | Cyclohexylmethyl | 3-[(Phenylmethyl)oxy]phenyl | W1a (m = 0) |
| A-228 | Cyclohexylmethyl | 3-Morpholin-4-ylphenyl | W1a (m = 0) |
| A-229 | Cyclohexylmethyl | 3-(Morpholin-4-ylmethyl)phenyl | W1a (m = 0) |
| A-230 | Cyclohexylmethyl | 3-Pyrrolidin-1-ylphenyl | W1a (m = 0) |
| A-231 | Cyclohexylmethyl | 4-Methylphenyl | W1a (m = 0) |
| A-232 | Cyclohexylmethyl | 4-(1-Methylethyl)phenyl | W1a (m = 0) |
| A-233 | Cyclohexylmethyl | 4-Methoxyphenyl | W1a (m = 0) |
| A-234 | Cyclohexylmethyl | 4-Chlorophenyl | W1a (m = 0) |
| A-235 | Cyclohexylmethyl | 4-Fluorophenyl | W1a (m = 0) |
| A-236 | Cyclohexylmethyl | 4-Trifluoromethylphenyl | W1a (m = 0) |
| A-237 | Cyclohexylmethyl | 4-Diethylaminophenyl | W1a (m = 0) |
| A-238 | Cyclohexylmethyl | 4-[(Diethylamino)methyl]phenyl | W1a (m = 0) |
| A-239 | Cyclohexylmethyl | 4-Cyanophenyl | W1a (m = 0) |
| A-240 | Cyclohexylmethyl | 4-(Piperidin-1-yl)phenyl | W1a (m = 0) |
| A-241 | Cyclohexylmethyl | 4-(4-Methylpiperazin-1-yl)phenyl | W1a (m = 0) |
| A-242 | Cyclohexylmethyl | 4-Pyrrolidin-1-ylphenyl | W1a (m = 0) |
| A-243 | Cyclohexylmethyl | 4-(1H-Imidazol-1-yl)phenyl | W1a (m = 0) |
| A-244 | Cyclohexylmethyl | 4-Morpholin-4-ylphenyl | W1a (m = 0) |
| A-245 | Cyclohexylmethyl | 4-(Morpholin-4-ylmethyl)phenyl | W1a (m = 0) |
| A-246 | Cyclohexylmethyl | 2,4-Difluorophenyl | W1a (m = 0) |
| A-247 | Cyclohexylmethyl | 2,6-Difluorophenyl | W1a (m = 0) |
| A-248 | Cyclohexylmethyl | 3,5-Difluorophenyl | W1a (m = 0) |
| A-249 | Cyclohexylmethyl | 2,4-Dichlorophenyl | W1a (m = 0) |
| A-250 | Cyclohexylmethyl | 2,6-Dichlorophenyl | W1a (m = 0) |

TABLE A-continued

| No. | R¹ | R² | W |
|---|---|---|---|
| A-251 | Cyclohexylmethyl | 3,5-Dichlorophenyl | W1a (m = 0) |
| A-252 | Cyclohexylmethyl | 2-Chloro-4-fluorophenyl | W1a (m = 0) |
| A-253 | Cyclohexylmethyl | 2-Chloro-4-morpholin-4-ylphenyl | W1a (m = 0) |
| A-254 | Cyclohexylmethyl | 2-Fluoro-4-morpholin-4-ylphenyl | W1a (m = 0) |
| A-255 | Cyclohexylmethyl | Pyridin-2-yl | W1a (m = 0) |
| A-256 | Cyclohexylmethyl | Pyridin-4-yl | W1a (m = 0) |
| A-257 | Cyclohexylmethyl | Thien-2-yl | W1a (m = 0) |
| A-258 | Cyclohexylmethyl | 2,3-Dihydrobenzo[b]furan-5-yl | W1a (m = 0) |
| A-259 | 2-Thienylmethyl | Phenyl | W1a (m = 0) |
| A-260 | 2-Thienylmethyl | 2-Methylphenyl | W1a (m = 0) |
| A-261 | 2-Thienylmethyl | 2-Methoxyphenyl | W1a (m = 0) |
| A-262 | 2-Thienylmethyl | 2-Chlorophenyl | W1a (m = 0) |
| A-263 | 2-Thienylmethyl | 2-Fluorophenyl | W1a (m = 0) |
| A-264 | 2-Thienylmethyl | 2-Trifluoromethylphenyl | W1a (m = 0) |
| A-265 | 2-Thienylmethyl | 3-Methylphenyl | W1a (m = 0) |
| A-266 | 2-Thienylmethyl | 3-Methoxyphenyl | W1a (m = 0) |
| A-267 | 2-Thienylmethyl | 3-Chlorophenyl | W1a (m = 0) |
| A-268 | 2-Thienylmethyl | 3-Fluorophenyl | W1a (m = 0) |
| A-269 | 2-Thienylmethyl | 3-Trifluoromethyl | W1a (m = 0) |
| A-270 | 2-Thienylmethyl | 3-[(Phenylmethyl)oxy]phenyl | W1a (m = 0) |
| A-271 | 2-Thienylmethyl | 3-Morpholin-4-ylphenyl | W1a (m = 0) |
| A-272 | 2-Thienylmethyl | 3-(Morpholin-4-ylmethyl)phenyl | W1a (m = 0) |
| A-273 | 2-Thienylmethyl | 3-Pyrrolidin-1-ylphenyl | W1a (m = 0) |
| A-274 | 2-Thienylmethyl | 4-Methylphenyl | W1a (m = 0) |
| A-275 | 2-Thienylmethyl | 4-(1-Methylethyl)phenyl | W1a (m = 0) |
| A-276 | 2-Thienylmethyl | 4-Methoxyphenyl | W1a (m = 0) |
| A-277 | 2-Thienylmethyl | 4-Chlorophenyl | W1a (m = 0) |
| A-278 | 2-Thienylmethyl | 4-Fluorophenyl | W1a (m = 0) |
| A-279 | 2-Thienylmethyl | 4-Trifluoromethylphenyl | W1a (m = 0) |
| A-280 | 2-Thienylmethyl | 4-Diethylaminophenyl | W1a (m = 0) |
| A-281 | 2-Thienylmethyl | 4-[(Diethylamino)methyl]phenyl | W1a (m = 0) |
| A-282 | 2-Thienylmethyl | 4-Cyanophenyl | W1a (m = 0) |
| A-283 | 2-Thienylmethyl | 4-(Piperidin-1-yl)phenyl | W1a (m = 0) |
| A-284 | 2-Thienylmethyl | 4-(4-Methylpiperazin-1-yl)phenyl | W1a (m = 0) |
| A-285 | 2-Thienylmethyl | 4-Pyrrolidin-1-ylphenyl | W1a (m = 0) |
| A-286 | 2-Thienylmethyl | 4-(1H-Imidazol-1-yl)phenyl | W1a (m = 0) |
| A-287 | 2-Thienylmethyl | 4-Morpholin-4-ylphenyl | W1a (m = 0) |
| A-288 | 2-Thienylmethyl | 4-(Morpholin-4-ylmethyl)phenyl | W1a (m = 0) |
| A-289 | 2-Thienylmethyl | 2,4-Difluorophenyl | W1a (m = 0) |
| A-290 | 2-Thienylmethyl | 2,6-Difluorophenyl | W1a (m = 0) |
| A-291 | 2-Thienylmethyl | 3,5-Difluorophenyl | W1a (m = 0) |
| A-292 | 2-Thienylmethyl | 2,4-Dichlorophenyl | W1a (m = 0) |
| A-293 | 2-Thienylmethyl | 2,6-Dichlorophenyl | W1a (m = 0) |
| A-294 | 2-Thienylmethyl | 3,5-Dichlorophenyl | W1a (m = 0) |
| A-295 | 2-Thienylmethyl | 2-Chloro-4-fluorophenyl | W1a (m = 0) |
| A-296 | 2-Thienylmethyl | 2-Chloro-4-morpholin-4-ylphenyl | W1a (m = 0) |
| A-297 | 2-Thienylmethyl | 2-Fluoro-4-morpholin-4-ylphenyl | W1a (m = 0) |
| A-298 | 2-Thienylmethyl | Pyridin-2-yl | W1a (m = 0) |
| A-299 | 2-Thienylmethyl | Pyridin-4-yl | W1a (m = 0) |
| A-300 | 2-Thienylmethyl | Thien-2-yl | W1a (m = 0) |
| A-301 | 2-Thienylmethyl | 2,3-Dihydrobenzo[b]furan-5-yl | W1a (m = 0) |
| A-302 | Pyridin-3-ylmethyl | Phenyl | W1a (m = 0) |
| A-303 | Pyridin-3-ylmethyl | 2-Methylphenyl | W1a (m = 0) |
| A-304 | Pyridin-3-ylmethyl | 2-Methoxyphenyl | W1a (m = 0) |
| A-305 | Pyridin-3-ylmethyl | 2-Chlorophenyl | W1a (m = 0) |
| A-306 | Pyridin-3-ylmethyl | 2-Fluorophenyl | W1a (m = 0) |
| A-307 | Pyridin-3-ylmethyl | 2-Trifluoromethylphenyl | W1a (m = 0) |
| A-308 | Pyridin-3-ylmethyl | 3-Methylphenyl | W1a (m = 0) |
| A-309 | Pyridin-3-ylmethyl | 3-Methoxyphenyl | W1a (m = 0) |
| A-310 | Pyridin-3-ylmethyl | 3-Chlorophenyl | W1a (m = 0) |
| A-311 | Pyridin-3-ylmethyl | 3-Fluorophenyl | W1a (m = 0) |
| A-312 | Pyridin-3-ylmethyl | 3-Trifluoromethyl | W1a (m = 0) |
| A-313 | Pyridin-3-ylmethyl | 3-[(Phenylmethyl)oxy]phenyl | W1a (m = 0) |
| A-314 | Pyridin-3-ylmethyl | 3-Morpholin-4-ylphenyl | W1a (m = 0) |
| A-315 | Pyridin-3-ylmethyl | 3-(Morpholin-4-ylmethyl)phenyl | W1a (m = 0) |
| A-316 | Pyridin-3-ylmethyl | 3-Pyrrolidin-1-ylphenyl | W1a (m = 0) |
| A-317 | Pyridin-3-ylmethyl | 4-Methylphenyl | W1a (m = 0) |
| A-318 | Pyridin-3-ylmethyl | 4-(1-Methylethyl)phenyl | W1a (m = 0) |
| A-319 | Pyridin-3-ylmethyl | 4-Methoxyphenyl | W1a (m = 0) |
| A-320 | Pyridin-3-ylmethyl | 4-Chlorophenyl | W1a (m = 0) |
| A-321 | Pyridin-3-ylmethyl | 4-Fluorophenyl | W1a (m = 0) |
| A-322 | Pyridin-3-ylmethyl | 4-Trifluoromethylphenyl | W1a (m = 0) |
| A-323 | Pyridin-3-ylmethyl | 4-Diethylaminophenyl | W1a (m = 0) |
| A-324 | Pyridin-3-ylmethyl | 4-[(Diethylamino)methyl]phenyl | W1a (m = 0) |
| A-325 | Pyridin-3-ylmethyl | 4-Cyanophenyl | W1a (m = 0) |
| A-326 | Pyridin-3-ylmethyl | 4-(Piperidin-1-yl)phenyl | W1a (m = 0) |
| A-327 | Pyridin-3-ylmethyl | 4-(4-Methylpiperazin-1-yl)phenyl | W1a (m = 0) |
| A-328 | Pyridin-3-ylmethyl | 4-Pyrrolidin-1-ylphenyl | W1a (m = 0) |

TABLE A-continued

| No. | R¹ | R² | W |
|---|---|---|---|
| A-329 | Pyridin-3-ylmethyl | 4-(1H-Imidazol-1-yl)phenyl | W1a (m = 0) |
| A-330 | Pyridin-3-ylmethyl | 4-Morpholin-4-ylphenyl | W1a (m = 0) |
| A-331 | Pyridin-3-ylmethyl | 4-(Morpholin-4-ylmethyl)phenyl | W1a (m = 0) |
| A-332 | Pyridin-3-ylmethyl | 2,4-Difluorophenyl | W1a (m = 0) |
| A-333 | Pyridin-3-ylmethyl | 2,6-Difluorophenyl | W1a (m = 0) |
| A-334 | Pyridin-3-ylmethyl | 3,5-Difluorophenyl | W1a (m = 0) |
| A-335 | Pyridin-3-ylmethyl | 2,4-Dichlorophenyl | W1a (m = 0) |
| A-336 | Pyridin-3-ylmethyl | 2,6-Dichlorophenyl | W1a (m = 0) |
| A-337 | Pyridin-3-ylmethyl | 3,5-Dichlorophenyl | W1a (m = 0) |
| A-338 | Pyridin-3-ylmethyl | 2-Chloro-4-fluorophenyl | W1a (m = 0) |
| A-339 | Pyridin-3-ylmethyl | 2-Chloro-4-morpholin-4-ylphenyl | W1a (m = 0) |
| A-340 | Pyridin-3-ylmethyl | 2-Fluoro-4-morpholin-4-ylphenyl | W1a (m = 0) |
| A-341 | Pyridin-3-ylmethyl | Pyridin-2-yl | W1a (m = 0) |
| A-342 | Pyridin-3-ylmethyl | Pyridin-4-yl | W1a (m = 0) |
| A-343 | Pyridin-3-ylmethyl | Thien-2-yl | W1a (m = 0) |
| A-344 | Pyridin-3-ylmethyl | 2,3-Dihydrobenzo[b]furan-5-yl | W1a (m = 0) |
| A-345 | n-Butyl | Phenyl | W1b (m = 0) |
| A-346 | n-Butyl | 2-Methylphenyl | W1b (m = 0) |
| A-347 | n-Butyl | 2-Methoxyphenyl | W1b (m = 0) |
| A-348 | n-Butyl | 2-Chlorophenyl | W1b (m = 0) |
| A-349 | n-Butyl | 2-Fluorophenyl | W1b (m = 0) |
| A-350 | n-Butyl | 2-Trifluoromethylphenyl | W1b (m = 0) |
| A-351 | n-Butyl | 3-Methylphenyl | W1b (m = 0) |
| A-352 | n-Butyl | 3-Methoxyphenyl | W1b (m = 0) |
| A-353 | n-Butyl | 3-Chlorophenyl | W1b (m = 0) |
| A-354 | n-Butyl | 3-Fluorophenyl | W1b (m = 0) |
| A-355 | n-Butyl | 3-Trifluoromethyl | W1b (m = 0) |
| A-356 | n-Butyl | 3-[(Phenylmethyl)oxy]phenyl | W1b (m = 0) |
| A-357 | n-Butyl | 3-Morpholin-4-ylphenyl | W1b (m = 0) |
| A-358 | n-Butyl | 3-(Morpholin-4-ylmethyl)phenyl | W1b (m = 0) |
| A-359 | n-Butyl | 3-Pyrrolidin-1-ylphenyl | W1b (m = 0) |
| A-360 | n-Butyl | 4-Methylphenyl | W1b (m = 0) |
| A-361 | n-Butyl | 4-(1-Methylethyl)phenyl | W1b (m = 0) |
| A-362 | n-Butyl | 4-Methoxyphenyl | W1b (m = 0) |
| A-363 | n-Butyl | 4-Chlorophenyl | W1b (m = 0) |
| A-364 | n-Butyl | 4-Fluorophenyl | W1b (m = 0) |
| A-365 | n-Butyl | 4-Trifluoromethylphenyl | W1b (m = 0) |
| A-366 | n-Butyl | 4-Diethylaminophenyl | W1b (m = 0) |
| A-367 | n-Butyl | 4-[(Diethylamino)methyl]phenyl | W1b (m = 0) |
| A-368 | n-Butyl | 4-Cyanophenyl | W1b (m = 0) |
| A-369 | n-Butyl | 4-(Piperidin-1-yl)phenyl | W1b (m = 0) |
| A-370 | n-Butyl | 4-(4-Methylpiperazin-1-yl)phenyl | W1b (m = 0) |
| A-371 | n-Butyl | 4-Pyrrolidin-1-ylphenyl | W1b (m = 0) |
| A-372 | n-Butyl | 4-(1H-Imidazol-1-yl)phenyl | W1b (m = 0) |
| A-373 | n-Butyl | 4-Morpholin-4-ylphenyl | W1b (m = 0) |
| A-374 | n-Butyl | 4-(Morpholin-4-ylmethyl)phenyl | W1b (m = 0) |
| A-375 | n-Butyl | 2,4-Difluorophenyl | W1b (m = 0) |
| A-376 | n-Butyl | 2,6-Difluorophenyl | W1b (m = 0) |
| A-377 | n-Butyl | 3,5-Difluorophenyl | W1b (m = 0) |
| A-378 | n-Butyl | 2,4-Dichlorophenyl | W1b (m = 0) |
| A-379 | n-Butyl | 2,6-Dichlorophenyl | W1b (m = 0) |
| A-380 | n-Butyl | 3,5-Dichlorophenyl | W1b (m = 0) |
| A-381 | n-Butyl | 2-Chloro-4-fluorophenyl | W1b (m = 0) |
| A-382 | n-Butyl | 2-Chloro-4-morpholin-4-ylphenyl | W1b (m = 0) |
| A-383 | n-Butyl | 2-Fluoro-4-morpholin-4-ylphenyl | W1b (m = 0) |
| A-384 | n-Butyl | Pyridin-2-yl | W1b (m = 0) |
| A-385 | n-Butyl | Pyridin-4-yl | W1b (m = 0) |
| A-386 | n-Butyl | Thien-2-yl | W1b (m = 0) |
| A-387 | n-Butyl | 2,3-Dihydrobenzo[b]furan-5-yl | W1b (m = 0) |
| A-388 | Isobutyl | Phenyl | W1b (m = 0) |
| A-389 | Isobutyl | 2-Methylphenyl | W1b (m = 0) |
| A-390 | Isobutyl | 2-Methoxyphenyl | W1b (m = 0) |
| A-391 | Isobutyl | 2-Chlorophenyl | W1b (m = 0) |
| A-392 | Isobutyl | 2-Fluorophenyl | W1b (m = 0) |
| A-393 | Isobutyl | 2-Trifluoromethylphenyl | W1b (m = 0) |
| A-394 | Isobutyl | 3-Methylphenyl | W1b (m = 0) |
| A-395 | Isobutyl | 3-Methoxyphenyl | W1b (m = 0) |
| A-396 | Isobutyl | 3-Chlorophenyl | W1b (m = 0) |
| A-397 | Isobutyl | 3-Fluorophenyl | W1b (m = 0) |
| A-398 | Isobutyl | 3-Trifluoromethyl | W1b (m = 0) |
| A-399 | Isobutyl | 3-[(Phenylmethyl)oxy]phenyl | W1b (m = 0) |
| A-400 | Isobutyl | 3-Morpholin-4-ylphenyl | W1b (m = 0) |
| A-401 | Isobutyl | 3-(Morpholin-4-ylmethyl)phenyl | W1b (m = 0) |
| A-402 | Isobutyl | 3-Pyrrolidin-1-ylphenyl | W1b (m = 0) |
| A-403 | Isobutyl | 4-Methylphenyl | W1b (m = 0) |
| A-404 | Isobutyl | 4-(1-Methylethyl)phenyl | W1b (m = 0) |
| A-405 | Isobutyl | 4-Methoxyphenyl | W1b (m = 0) |
| A-406 | Isobutyl | 4-Chlorophenyl | W1b (m = 0) |

TABLE A-continued

| No. | R¹ | R² | W |
|---|---|---|---|
| A-407 | Isobutyl | 4-Fluorophenyl | W1b (m = 0) |
| A-408 | Isobutyl | 4-Trifluoromethylphenyl | W1b (m = 0) |
| A-409 | Isobutyl | 4-Diethylaminophenyl | W1b (m = 0) |
| A-410 | Isobutyl | 4-[(Diethylamino)methyl]phenyl | W1b (m = 0) |
| A-411 | Isobutyl | 4-Cyanophenyl | W1b (m = 0) |
| A-412 | Isobutyl | 4-(Piperidin-1-yl)phenyl | W1b (m = 0) |
| A-413 | Isobutyl | 4-(4-Methylpiperazin-1-yl)phenyl | W1b (m = 0) |
| A-414 | Isobutyl | 4-Pyrrolidin-1-ylphenyl | W1b (m = 0) |
| A-415 | Isobutyl | 4-(1H-Imidazol-1-yl)phenyl | W1b (m = 0) |
| A-416 | Isobutyl | 4-Morpholin-4-ylphenyl | W1b (m = 0) |
| A-417 | Isobutyl | 4-(Morpholin-4-ylmethyl)phenyl | W1b (m = 0) |
| A-418 | Isobutyl | 2,4-Difluorophenyl | W1b (m = 0) |
| A-419 | Isobutyl | 2,6-Difluorophenyl | W1b (m = 0) |
| A-420 | Isobutyl | 3,5-Difluorophenyl | W1b (m = 0) |
| A-421 | Isobutyl | 2,4-Dichlorophenyl | W1b (m = 0) |
| A-422 | Isobutyl | 2,6-Dichlorophenyl | W1b (m = 0) |
| A-423 | Isobutyl | 3,5-Dichlorophenyl | W1b (m = 0) |
| A-424 | Isobutyl | 2-Chloro-4-fluorophenyl | W1b (m = 0) |
| A-425 | Isobutyl | 2-Chloro-4-morpholin-4-ylphenyl | W1b (m = 0) |
| A-426 | Isobutyl | 2-Fluoro-4-morpholin-4-ylphenyl | W1b (m = 0) |
| A-427 | Isobutyl | Pyridin-2-yl | W1b (m = 0) |
| A-428 | Isobutyl | Pyridin-4-yl | W1b (m = 0) |
| A-429 | Isobutyl | Thien-2-yl | W1b (m = 0) |
| A-430 | Isobutyl | 2,3-Dihydrobenzo[b]furan-5-yl | W1b (m = 0) |
| A-431 | Benzyl | Phenyl | W1b (m = 0) |
| A-432 | Benzyl | 2-Methylphenyl | W1b (m = 0) |
| A-433 | Benzyl | 2-Methoxyphenyl | W1b (m = 0) |
| A-434 | Benzyl | 2-Chlorophenyl | W1b (m = 0) |
| A-435 | Benzyl | 2-Fluorophenyl | W1b (m = 0) |
| A-436 | Benzyl | 2-Trifluoromethylphenyl | W1b (m = 0) |
| A-437 | Benzyl | 3-Methylphenyl | W1b (m = 0) |
| A-438 | Benzyl | 3-Methoxyphenyl | W1b (m = 0) |
| A-439 | Benzyl | 3-Chlorophenyl | W1b (m = 0) |
| A-440 | Benzyl | 3-Fluorophenyl | W1b (m = 0) |
| A-441 | Benzyl | 3-Trifluoromethyl | W1b (m = 0) |
| A-442 | Benzyl | 3-[(Phenylmethyl)oxy]phenyl | W1b (m = 0) |
| A-443 | Benzyl | 3-Morpholin-4-ylphenyl | W1b (m = 0) |
| A-444 | Benzyl | 3-(Morpholin-4-ylmethyl)phenyl | W1b (m = 0) |
| A-445 | Benzyl | 3-Pyrrolidin-1-ylphenyl | W1b (m = 0) |
| A-446 | Benzyl | 4-Methylphenyl | W1b (m = 0) |
| A-447 | Benzyl | 4-(1-Methylethyl)phenyl | W1b (m = 0) |
| A-448 | Benzyl | 4-Methoxyphenyl | W1b (m = 0) |
| A-449 | Benzyl | 4-Chlorophenyl | W1b (m = 0) |
| A-450 | Benzyl | 4-Fluorophenyl | W1b (m = 0) |
| A-451 | Benzyl | 4-Trifluoromethylphenyl | W1b (m = 0) |
| A-452 | Benzyl | 4-Diethylaminophenyl | W1b (m = 0) |
| A-453 | Benzyl | 4-[(Diethylamino)methyl]phenyl | W1b (m = 0) |
| A-454 | Benzyl | 4-Cyanophenyl | W1b (m = 0) |
| A-455 | Benzyl | 4-(Piperidin-1-yl)phenyl | W1b (m = 0) |
| A-456 | Benzyl | 4-(4-Methylpiperazin-1-yl)phenyl | W1b (m = 0) |
| A-457 | Benzyl | 4-Pyrrolidin-1-ylphenyl | W1b (m = 0) |
| A-458 | Benzyl | 4-(1H-Imidazol-1-yl)phenyl | W1b (m = 0) |
| A-459 | Benzyl | 4-Morpholin-4-ylphenyl | W1b (m = 0) |
| A-460 | Benzyl | 4-(Morpholin-4-ylmethyl)phenyl | W1b (m = 0) |
| A-461 | Benzyl | 2,4-Difluorophenyl | W1b (m = 0) |
| A-462 | Benzyl | 2,6-Difluorophenyl | W1b (m = 0) |
| A-463 | Benzyl | 3,5-Difluorophenyl | W1b (m = 0) |
| A-464 | Benzyl | 2,4-Dichlorophenyl | W1b (m = 0) |
| A-465 | Benzyl | 2,6-Dichlorophenyl | W1b (m = 0) |
| A-466 | Benzyl | 3,5-Dichlorophenyl | W1b (m = 0) |
| A-467 | Benzyl | 2-Chloro-4-fluorophenyl | W1b (m = 0) |
| A-468 | Benzyl | 2-Chloro-4-morpholin-4-ylphenyl | W1b (m = 0) |
| A-469 | Benzyl | 2-Fluoro-4-morpholin-4-ylphenyl | W1b (m = 0) |
| A-470 | Benzyl | Pyridin-2-yl | W1b (m = 0) |
| A-471 | Benzyl | Pyridin-4-yl | W1b (m = 0) |
| A-472 | Benzyl | Thien-2-yl | W1b (m = 0) |
| A-473 | Benzyl | 2,3-Dihydrobenzo[b]furan-5-yl | W1b (m = 0) |
| A-474 | 4-Chlorobenzyl | Phenyl | W1b (m = 0) |
| A-475 | 4-Chlorobenzyl | 2-Methylphenyl | W1b (m = 0) |
| A-476 | 4-Chlorobenzyl | 2-Methoxyphenyl | W1b (m = 0) |
| A-477 | 4-Chlorobenzyl | 2-Chlorophenyl | W1b (m = 0) |
| A-478 | 4-Chlorobenzyl | 2-Fluorophenyl | W1b (m = 0) |
| A-479 | 4-Chlorobenzyl | 2-Trifluoromethylphenyl | W1b (m = 0) |
| A-480 | 4-Chlorobenzyl | 3-Methylphenyl | W1b (m = 0) |
| A-481 | 4-Chlorobenzyl | 3-Methoxyphenyl | W1b (m = 0) |
| A-482 | 4-Chlorobenzyl | 3-Chlorophenyl | W1b (m = 0) |
| A-483 | 4-Chlorobenzyl | 3-Fluorophenyl | W1b (m = 0) |
| A-484 | 4-Chlorobenzyl | 3-Trifluoromethyl | W1b (m = 0) |

TABLE A-continued

| No. | R¹ | R² | W |
|---|---|---|---|
| A-485 | 4-Chlorobenzyl | 3-[(Phenylmethyl)oxy]phenyl | W1b (m = 0) |
| A-486 | 4-Chlorobenzyl | 3-Morpholin-4-ylphenyl | W1b (m = 0) |
| A-487 | 4-Chlorobenzyl | 3-(Morpholin-4-ylmethyl)phenyl | W1b (m = 0) |
| A-488 | 4-Chlorobenzyl | 3-Pyrrolidin-1-ylphenyl | W1b (m = 0) |
| A-489 | 4-Chlorobenzyl | 4-Methylphenyl | W1b (m = 0) |
| A-490 | 4-Chlorobenzyl | 4-(1-Methylethyl)phenyl | W1b (m = 0) |
| A-491 | 4-Chlorobenzyl | 4-Methoxyphenyl | W1b (m = 0) |
| A-492 | 4-Chlorobenzyl | 4-Chlorophenyl | W1b (m = 0) |
| A-493 | 4-Chlorobenzyl | 4-Fluorophenyl | W1b (m = 0) |
| A-494 | 4-Chlorobenzyl | 4-Trifluoromethylphenyl | W1b (m = 0) |
| A-495 | 4-Chlorobenzyl | 4-Diethylaminophenyl | W1b (m = 0) |
| A-496 | 4-Chlorobenzyl | 4-[(Diethylamino)methyl]phenyl | W1b (m = 0) |
| A-497 | 4-Chlorobenzyl | 4-Cyanophenyl | W1b (m = 0) |
| A-498 | 4-Chlorobenzyl | 4-(Piperidin-1-yl)phenyl | W1b (m = 0) |
| A-499 | 4-Chlorobenzyl | 4-(4-Methylpiperazin-1-yl)phenyl | W1b (m = 0) |
| A-500 | 4-Chlorobenzyl | 4-Pyrrolidin-1-ylphenyl | W1b (m = 0) |
| A-501 | 4-Chlorobenzyl | 4-(1H-Imidazol-1-yl)phenyl | W1b (m = 0) |
| A-502 | 4-Chlorobenzyl | 4-Morpholin-4-ylphenyl | W1b (m = 0) |
| A-503 | 4-Chlorobenzyl | 4-(Morpholin-4-ylmethyl)phenyl | W1b (m = 0) |
| A-504 | 4-Chlorobenzyl | 2,4-Difluorophenyl | W1b (m = 0) |
| A-505 | 4-Chlorobenzyl | 2,6-Difluorophenyl | W1b (m = 0) |
| A-506 | 4-Chlorobenzyl | 3,5-Difluorophenyl | W1b (m = 0) |
| A-507 | 4-Chlorobenzyl | 2,4-Dichlorophenyl | W1b (m = 0) |
| A-508 | 4-Chlorobenzyl | 2,6-Dichlorophenyl | W1b (m = 0) |
| A-509 | 4-Chlorobenzyl | 3,5-Dichlorophenyl | W1b (m = 0) |
| A-510 | 4-Chlorobenzyl | 2-Chloro-4-fluorophenyl | W1b (m = 0) |
| A-511 | 4-Chlorobenzyl | 2-Chloro-4-morpholin-4-ylphenyl | W1b (m = 0) |
| A-512 | 4-Chlorobenzyl | 2-Fluoro-4-morpholin-4-ylphenyl | W1b (m = 0) |
| A-513 | 4-Chlorobenzyl | Pyridin-2-yl | W1b (m = 0) |
| A-514 | 4-Chlorobenzyl | Pyridin-4-yl | W1b (m = 0) |
| A-515 | 4-Chlorobenzyl | Thien-2-yl | W1b (m = 0) |
| A-516 | 4-Chlorobenzyl | 2,3-Dihydrobenzo[b]furan-5-yl | W1b (m = 0) |
| A-517 | 4-Methoxybenzyl | Phenyl | W1b (m = 0) |
| A-518 | 4-Methoxybenzyl | 2-Methylphenyl | W1b (m = 0) |
| A-519 | 4-Methoxybenzyl | 2-Methoxyphenyl | W1b (m = 0) |
| A-520 | 4-Methoxybenzyl | 2-Chlorophenyl | W1b (m = 0) |
| A-521 | 4-Methoxybenzyl | 2-Fluorophenyl | W1b (m = 0) |
| A-522 | 4-Methoxybenzyl | 2-Trifluoromethylphenyl | W1b (m = 0) |
| A-523 | 4-Methoxybenzyl | 3-Methylphenyl | W1b (m = 0) |
| A-524 | 4-Methoxybenzyl | 3-Methoxyphenyl | W1b (m = 0) |
| A-525 | 4-Methoxybenzyl | 3-Chlorophenyl | W1b (m = 0) |
| A-526 | 4-Methoxybenzyl | 3-Fluorophenyl | W1b (m = 0) |
| A-527 | 4-Methoxybenzyl | 3-Trifluoromethyl | W1b (m = 0) |
| A-528 | 4-Methoxybenzyl | 3-[(Phenylmethyl)oxy]phenyl | W1b (m = 0) |
| A-529 | 4-Methoxybenzyl | 3-Morpholin-4-ylphenyl | W1b (m = 0) |
| A-530 | 4-Methoxybenzyl | 3-(Morpholin-4-ylmethyl)phenyl | W1b (m = 0) |
| A-531 | 4-Methoxybenzyl | 3-Pyrrolidin-1-ylphenyl | W1b (m = 0) |
| A-532 | 4-Methoxybenzyl | 4-Methylphenyl | W1b (m = 0) |
| A-533 | 4-Methoxybenzyl | 4-(1-Methylethyl)phenyl | W1b (m = 0) |
| A-534 | 4-Methoxybenzyl | 4-Methoxyphenyl | W1b (m = 0) |
| A-535 | 4-Methoxybenzyl | 4-Chlorophenyl | W1b (m = 0) |
| A-536 | 4-Methoxybenzyl | 4-Fluorophenyl | W1b (m = 0) |
| A-537 | 4-Methoxybenzyl | 4-Trifluoromethylphenyl | W1b (m = 0) |
| A-538 | 4-Methoxybenzyl | 4-Diethylaminophenyl | W1b (m = 0) |
| A-539 | 4-Methoxybenzyl | 4-[(Diethylamino)methyl]phenyl | W1b (m = 0) |
| A-540 | 4-Methoxybenzyl | 4-Cyanophenyl | W1b (m = 0) |
| A-541 | 4-Methoxybenzyl | 4-(Piperidin-1-yl)phenyl | W1b (m = 0) |
| A-542 | 4-Methoxybenzyl | 4-(4-Methylpiperazin-1-yl)phenyl | W1b (m = 0) |
| A-543 | 4-Methoxybenzyl | 4-Pyrrolidin-1-ylphenyl | W1b (m = 0) |
| A-544 | 4-Methoxybenzyl | 4-(1H-Imidazol-1-yl)phenyl | W1b (m = 0) |
| A-545 | 4-Methoxybenzyl | 4-Morpholin-4-ylphenyl | W1b (m = 0) |
| A-546 | 4-Methoxybenzyl | 4-(Morpholin-4-ylmethyl)phenyl | W1b (m = 0) |
| A-547 | 4-Methoxybenzyl | 2,4-Difluorophenyl | W1b (m = 0) |
| A-548 | 4-Methoxybenzyl | 2,6-Difluorophenyl | W1b (m = 0) |
| A-549 | 4-Methoxybenzyl | 3,5-Difluorophenyl | W1b (m = 0) |
| A-550 | 4-Methoxybenzyl | 2,4-Dichlorophenyl | W1b (m = 0) |
| A-551 | 4-Methoxybenzyl | 2,6-Dichlorophenyl | W1b (m = 0) |
| A-552 | 4-Methoxybenzyl | 3,5-Dichlorophenyl | W1b (m = 0) |
| A-553 | 4-Methoxybenzyl | 2-Chloro-4-fluorophenyl | W1b (m = 0) |
| A-554 | 4-Methoxybenzyl | 2-Chloro-4-morpholin-4-ylphenyl | W1b (m = 0) |
| A-555 | 4-Methoxybenzyl | 2-Fluoro-4-morpholin-4-ylphenyl | W1b (m = 0) |
| A-556 | 4-Methoxybenzyl | Pyridin-2-yl | W1b (m = 0) |
| A-557 | 4-Methoxybenzyl | Pyridin-4-yl | W1b (m = 0) |
| A-558 | 4-Methoxybenzyl | Thien-2-yl | W1b (m = 0) |
| A-559 | 4-Methoxybenzyl | 2,3-Dihydrobenzo[b]furan-5-yl | W1b (m = 0) |
| A-560 | Cyclohexylmethyl | Phenyl | W1b (m = 0) |
| A-561 | Cyclohexylmethyl | 2-Methylphenyl | W1b (m = 0) |
| A-562 | Cyclohexylmethyl | 2-Methoxyphenyl | W1b (m = 0) |

TABLE A-continued

| No. | R¹ | R² | W |
|---|---|---|---|
| A-563 | Cyclohexylmethyl | 2-Chlorophenyl | W1b (m = 0) |
| A-564 | Cyclohexylmethyl | 2-Fluorophenyl | W1b (m = 0) |
| A-565 | Cyclohexylmethyl | 2-Trifluoromethylphenyl | W1b (m = 0) |
| A-566 | Cyclohexylmethyl | 3-Methylphenyl | W1b (m = 0) |
| A-567 | Cyclohexylmethyl | 3-Methoxyphenyl | W1b (m = 0) |
| A-568 | Cyclohexylmethyl | 3-Chlorophenyl | W1b (m = 0) |
| A-569 | Cyclohexylmethyl | 3-Fluorophenyl | W1b (m = 0) |
| A-570 | Cyclohexylmethyl | 3-Trifluoromethyl | W1b (m = 0) |
| A-571 | Cyclohexylmethyl | 3-[(Phenylmethyl)oxy]phenyl | W1b (m = 0) |
| A-572 | Cyclohexylmethyl | 3-Morpholin-4-ylphenyl | W1b (m = 0) |
| A-573 | Cyclohexylmethyl | 3-(Morpholin-4-ylmethyl)phenyl | W1b (m = 0) |
| A-574 | Cyclohexylmethyl | 3-Pyrrolidin-1-ylphenyl | W1b (m = 0) |
| A-575 | Cyclohexylmethyl | 4-Methylphenyl | W1b (m = 0) |
| A-576 | Cyclohexylmethyl | 4-(1-Methylethyl)phenyl | W1b (m = 0) |
| A-577 | Cyclohexylmethyl | 4-Methoxyphenyl | W1b (m = 0) |
| A-578 | Cyclohexylmethyl | 4-Chlorophenyl | W1b (m = 0) |
| A-579 | Cyclohexylmethyl | 4-Fluorophenyl | W1b (m = 0) |
| A-580 | Cyclohexylmethyl | 4-Trifluoromethylphenyl | W1b (m = 0) |
| A-581 | Cyclohexylmethyl | 4-Diethylaminophenyl | W1b (m = 0) |
| A-582 | Cyclohexylmethyl | 4-[(Diethylamino)methyl]phenyl | W1b (m = 0) |
| A-583 | Cyclohexylmethyl | 4-Cyanophenyl | W1b (m = 0) |
| A-584 | Cyclohexylmethyl | 4-(Piperidin-1-yl)phenyl | W1b (m = 0) |
| A-585 | Cyclohexylmethyl | 4-(4-Methylpiperazin-1-yl)phenyl | W1b (m = 0) |
| A-586 | Cyclohexylmethyl | 4-Pyrrolidin-1-ylphenyl | W1b (m = 0) |
| A-587 | Cyclohexylmethyl | 4-(1H-Imidazol-1-yl)phenyl | W1b (m = 0) |
| A-588 | Cyclohexylmethyl | 4-Morpholin-4-ylphenyl | W1b (m = 0) |
| A-589 | Cyclohexylmethyl | 4-(Morpholin-4-ylmethyl)phenyl | W1b (m = 0) |
| A-590 | Cyclohexylmethyl | 2,4-Difluorophenyl | W1b (m = 0) |
| A-591 | Cyclohexylmethyl | 2,6-Difluorophenyl | W1b (m = 0) |
| A-592 | Cyclohexylmethyl | 3,5-Difluorophenyl | W1b (m = 0) |
| A-593 | Cyclohexylmethyl | 2,4-Dichlorophenyl | W1b (m = 0) |
| A-594 | Cyclohexylmethyl | 2,6-Dichlorophenyl | W1b (m = 0) |
| A-595 | Cyclohexylmethyl | 3,5-Dichlorophenyl | W1b (m = 0) |
| A-596 | Cyclohexylmethyl | 2-Chloro-4-fluorophenyl | W1b (m = 0) |
| A-597 | Cyclohexylmethyl | 2-Chloro-4-morpholin-4-ylphenyl | W1b (m = 0) |
| A-598 | Cyclohexylmethyl | 2-Fluoro-4-morpholin-4-ylphenyl | W1b (m = 0) |
| A-599 | Cyclohexylmethyl | Pyridin-2-yl | W1b (m = 0) |
| A-600 | Cyclohexylmethyl | Pyridin-4-yl | W1b (m = 0) |
| A-601 | Cyclohexylmethyl | Thien-2-yl | W1b (m = 0) |
| A-602 | Cyclohexylmethyl | 2,3-Dihydrobenzo[b]furan-5-yl | W1b (m = 0) |
| A-603 | 2-Thienylmethyl | Phenyl | W1b (m = 0) |
| A-604 | 2-Thienylmethyl | 2-Methyl phenyl | W1b (m = 0) |
| A-605 | 2-Thienylmethyl | 2-Methoxyphenyl | W1b (m = 0) |
| A-606 | 2-Thienylmethyl | 2-Chlorophenyl | W1b (m = 0) |
| A-607 | 2-Thienylmethyl | 2-Fluorophenyl | W1b (m = 0) |
| A-608 | 2-Thienylmethyl | 2-Trifluoromethylphenyl | W1b (m = 0) |
| A-609 | 2-Thienylmethyl | 3-Methylphenyl | W1b (m = 0) |
| A-610 | 2-Thienylmethyl | 3-Methoxyphenyl | W1b (m = 0) |
| A-611 | 2-Thienylmethyl | 3-Chlorophenyl | W1b (m = 0) |
| A-612 | 2-Thienylmethyl | 3-Fluorophenyl | W1b (m = 0) |
| A-613 | 2-Thienylmethyl | 3-Trifluoromethyl | W1b (m = 0) |
| A-614 | 2-Thienylmethyl | 3-[(Phenylmethyl)oxy]phenyl | W1b (m = 0) |
| A-615 | 2-Thienylmethyl | 3-Morpholin-4-ylphenyl | W1b (m = 0) |
| A-616 | 2-Thienylmethyl | 3-(Morpholin-4-ylmethyl)phenyl | W1b (m = 0) |
| A-617 | 2-Thienylmethyl | 3-Pyrrolidin-1-ylphenyl | W1b (m = 0) |
| A-618 | 2-Thienylmethyl | 4-Methyiphenyl | W1b (m = 0) |
| A-619 | 2-Thienylmethyl | 4-(1-Methylethyl)phenyl | W1b (m = 0) |
| A-620 | 2-Thienylmethyl | 4-Methoxyphenyl | W1b (m = 0) |
| A-621 | 2-Thienylmethyl | 4-Chlorophenyl | W1b (m = 0) |
| A-622 | 2-Thienylmethyl | 4-Fluorophenyl | W1b (m = 0) |
| A-623 | 2-Thienylmethyl | 4-Trifluoromethylphenyl | W1b (m = 0) |
| A-624 | 2-Thienylmethyl | 4-Diethylaminophenyl | W1b (m = 0) |
| A-625 | 2-Thienylmethyl | 4-[(Diethylamino)methyl]phenyl | W1b (m = 0) |
| A-626 | 2-Thienylmethyl | 4-Cyanophenyl | W1b (m = 0) |
| A-627 | 2-Thienylmethyl | 4-(Piperidin-1-yl)phenyl | Wlb (m = 0) |
| A-628 | 2-Thienylmethyl | 4-(4-Methylpiperazin-1-yl)phenyl | W1b (m = 0) |
| A-629 | 2-Thienylmethyl | 4-Pyrrolidin-i-ylphenyl | W1b (m = 0) |
| A-630 | 2-Thienylmethyl | 4-(1H-Imidazol-1-yl)phenyl | W1b (m = 0) |
| A-631 | 2-Thienylmethyl | 4-Morpholin-4-ylphenyl | W1b (m = 0) |
| A-632 | 2-Thienylmethyl | 4-(Morpholin-4-ylmethyl)phenyl | W1b (m = 0) |
| A-633 | 2-Thienylmethyl | 2,4-Difluorophenyl | W1b (m = 0) |
| A-634 | 2-Thienylmethyl | 2,6-Difluorophenyl | W1b (m = 0) |
| A-635 | 2-Thienylmethyl | 3,5-Difluorophenyl | W1b (m = 0) |
| A-636 | 2-Thienylmethyl | 2,4-Dichlorophenyl | W1b (m = 0) |
| A-637 | 2-Thienylmethyl | 2,6-Dichlorophenyl | W1b (m = 0) |
| A-638 | 2-Thienylmethyl | 3,5-Dichlorophenyl | W1b (m = 0) |
| A-639 | 2-Thienylmethyl | 2-Chloro-4-fluorophenyl | W1b (m = 0) |
| A-640 | 2-Thienylmethyl | 2-Chloro-4-morpholin-4-ylphenyl | W1b (m = 0) |

TABLE A-continued

| No. | R¹ | R² | W |
|---|---|---|---|
| A-641 | 2-Thienylmethyl | 2-Fluoro-4-morpholin-4-ylphenyl | W1b (m = 0) |
| A-642 | 2-Thienylmethyl | Pyridin-2-yl | W1b (m = 0) |
| A-643 | 2-Thienylmethyl | Pyridin-4-yl | W1b (m = 0) |
| A-644 | 2-Thienylmethyl | Thien-2-yl | W1b (m = 0) |
| A-645 | 2-Thienylmethyl | 2,3-Dihydrobenzo[b]furan-5-yl | W1b (m = 0) |
| A-646 | Pyridin-3-ylmethyl | Phenyl | W1b (m = 0) |
| A-647 | Pyridin-3-ylmethyl | 2-Methylphenyl | W1b (m = 0) |
| A-648 | Pyridin-3-ylmethyl | 2-Methoxyphenyl | W1b (m = 0) |
| A-649 | Pyridin-3-ylmethyl | 2-Chlorophenyl | W1b (m = 0) |
| A-650 | Pyridin-3-ylmethyl | 2-Fluorophenyl | W1b (m = 0) |
| A-651 | Pyridin-3-ylmethyl | 2-Trifluoromethylphenyl | W1b (m = 0) |
| A-652 | Pyridin-3-ylmethyl | 3-Methylphenyl | W1b (m = 0) |
| A-653 | Pyridin-3-ylmethyl | 3-Methoxyphenyl | W1b (m = 0) |
| A-654 | Pyridin-3-ylmethyl | 3-Chlorophenyl | W1b (m = 0) |
| A-655 | Pyridin-3-ylmethyl | 3-Fluorophenyl | W1b (m = 0) |
| A-656 | Pyridin-3-ylmethyl | 3-Trifluoromethyl | W1b (m = 0) |
| A-657 | Pyridin-3-ylmethyl | 3-[(Phenylmethyl)oxy]phenyl | W1b (m = 0) |
| A-658 | Pyridin-3-ylmethyl | 3-Morpholin-4-ylphenyl | W1b (m = 0) |
| A-659 | Pyridin-3-ylmethyl | 3-(Morpholin-4-ylmethyl)phenyl | W1b (m = 0) |
| A-660 | Pyridin-3-ylmethyl | 3-Pyrrolidin-1-ylphenyl | W1b (m = 0) |
| A-661 | Pyridin-3-ylmethyl | 4-Methylphenyl | W1b (m = 0) |
| A-662 | Pyridin-3-ylmethyl | 4-(1-Methylethyl)phenyl | W1b (m = 0) |
| A-663 | Pyridin-3-ylmethyl | 4-Methoxyphenyl | W1b (m = 0) |
| A-664 | Pyridin-3-ylmethyl | 4-Chlorophenyl | W1b (m = 0) |
| A-665 | Pyridin-3-ylmethyl | 4-Fluorophenyl | W1b (m = 0) |
| A-666 | Pyridin-3-ylmethyl | 4-Trifluoromethylphenyl | W1b (m = 0) |
| A-667 | Pyridin-3-ylmethyl | 4-Diethylaminophenyl | W1b (m = 0) |
| A-668 | Pyridin-3-ylmethyl | 4-[(Diethylamino)methyl]phenyl | W1b (m = 0) |
| A-669 | Pyridin-3-ylmethyl | 4-Cyanophenyl | W1b (m = 0) |
| A-670 | Pyridin-3-ylmethyl | 4-(Piperidin-1-yl)phenyl | W1b (m = 0) |
| A-671 | Pyridin-3-ylmethyl | 4-(4-Methylpiperazin-1-yl)phenyl | W1b (m = 0) |
| A-672 | Pyridin-3-ylmethyl | 4-Pyrrolidin-1-ylphenyl | W1b (m = 0) |
| A-673 | Pyridin-3-ylmethyl | 4-(1H-Imidazol-1-yl)phenyl | W1b (m = 0) |
| A-674 | Pyridin-3-ylmethyl | 4-Morpholin-4-ylphenyl | W1b (m = 0) |
| A-675 | Pyridin-3-ylmethyl | 4-(Morpholin-4-ylmethyl)phenyl | W1b (m = 0) |
| A-676 | Pyridin-3-ylmethyl | 2,4-Difluorophenyl | W1b (m = 0) |
| A-677 | Pyridin-3-ylmethyl | 2,6-Difluorophenyl | W1b (m = 0) |
| A-678 | Pyridin-3-ylmethyl | 3,5-Difluorophenyl | W1b (m = 0) |
| A-679 | Pyridin-3-ylmethyl | 2,4-Dichlorophenyl | W1b (m = 0) |
| A-680 | Pyridin-3-ylmethyl | 2,6-Dichlorophenyl | W1b (m = 0) |
| A-681 | Pyridin-3-ylmethyl | 3,5-Dichlorophenyl | W1b (m = 0) |
| A-682 | Pyridin-3-ylmethyl | 2-Chloro-4-fluorophenyl | W1b (m = 0) |
| A-683 | Pyridin-3-ylmethyl | 2-Chloro-4-morpholin-4-ylphenyl | W1b (m = 0) |
| A-684 | Pyridin-3-ylmethyl | 2-Fluoro-4-morpholin-4-ylphenyl | W1b (m = 0) |
| A-685 | Pyridin-3-ylmethyl | Pyridin-2-yl | W1b (m = 0) |
| A-686 | Pyridin-3-ylmethyl | Pyridin-4-yl | W1b (m = 0) |
| A-687 | Pyridin-3-ylmethyl | Thien-2-yl | W1b (m = 0) |
| A-688 | Pyridin-3-ylmethyl | 2,3-Dihydrobenzo[b]furan-5-yl | W1b (m = 0) |
| A-689 | n-Butyl | Phenyl | W2a (m = 0) |
| A-690 | n-Butyl | 2-Methylphenyl | W2a (m = 0) |
| A-691 | n-Butyl | 2-Methoxyphenyl | W2a (m = 0) |
| A-692 | n-Butyl | 2-Chlorophenyl | W2a (m = 0) |
| A-693 | n-Butyl | 2-Fluorophenyl | W2a (m = 0) |
| A-694 | n-Butyl | 2-Trifluoromethylphenyl | W2a (m = 0) |
| A-695 | n-Butyl | 3-Methylphenyl | W2a (m = 0) |
| A-696 | n-Butyl | 3-Methoxyphenyl | W2a (m = 0) |
| A-697 | n-Butyl | 3-Chlorophenyl | W2a (m = 0) |
| A-698 | n-Butyl | 3-Fluorophenyl | W2a (m = 0) |
| A-699 | n-Butyl | 3-Trifluoromethyl | W2a (m = 0) |
| A-700 | n-Butyl | 3-[(Phenylmethyl)oxy]phenyl | W2a (m = 0) |
| A-701 | n-Butyl | 3-Morpholin-4-ylphenyl | W2a (m = 0) |
| A-702 | n-Butyl | 3-(Morpholin-4-ylmethyl)phenyl | W2a (m = 0) |
| A-703 | n-Butyl | 3-Pyrrolidin-1-ylphenyl | W2a (m = 0) |
| A-704 | n-Butyl | 4-Methylphenyl | W2a (m = 0) |
| A-705 | n-Butyl | 4-(1-Methylethyl)phenyl | W2a (m = 0) |
| A-706 | n-Butyl | 4-Methoxyphenyl | W2a (m = 0) |
| A-707 | n-Butyl | 4-Chlorophenyl | W2a (m = 0) |
| A-708 | n-Butyl | 4-Fluorophenyl | W2a (m = 0) |
| A-709 | n-Butyl | 4-Trifluoromethylphenyl | W2a (m = 0) |
| A-710 | n-Butyl | 4-Diethylaminophenyl | W2a (m = 0) |
| A-711 | n-Butyl | 4-[(Diethylamino)methyl]phenyl | W2a (m = 0) |
| A-712 | n-Butyl | 4-Cyanophenyl | W2a (m = 0) |
| A-713 | n-Butyl | 4-(Piperidin-1-yl)phenyl | W2a (m = 0) |
| A-714 | n-Butyl | 4-(4-Methylpiperazin-1-yl)phenyl | W2a (m = 0) |
| A-715 | n-Butyl | 4-Pyrrolidin-1-ylphenyl | W2a (m = 0) |
| A-716 | n-Butyl | 4-(1H-Imidazol-1-yl)phenyl | W2a (m = 0) |
| A-717 | n-Butyl | 4-Morpholin-4-ylphenyl | W2a (m = 0) |
| A-718 | n-Butyl | 4-(Morpholin-4-ylmethyl)phenyl | W2a (m = 0) |

TABLE A-continued

| No. | R¹ | R² | W |
|---|---|---|---|
| A-719 | n-Butyl | 2,4-Difluorophenyl | W2a (m = 0) |
| A-720 | n-Butyl | 2,6-Difluorophenyl | W2a (m = 0) |
| A-721 | n-Butyl | 3,5-Difluorophenyl | W2a (m = 0) |
| A-722 | n-Butyl | 2,4-Dichlorophenyl | W2a (m = 0) |
| A-723 | n-Butyl | 2,6-Dichlorophenyl | W2a (m = 0) |
| A-724 | n-Butyl | 3,5-Dichlorophenyl | W2a (m = 0) |
| A-725 | n-Butyl | 2-Chloro-4-fluorophenyl | W2a (m = 0) |
| A-726 | n-Butyl | 2-Chloro-4-morpholin-4-ylphenyl | W2a (m = 0) |
| A-727 | n-Butyl | 2-Fluoro-4-morpholin-4-ylphenyl | W2a (m = 0) |
| A-728 | n-Butyl | Pyridin-2-yl | W2a (m = 0) |
| A-729 | n-Butyl | Pyridin-4-yl | W2a (m = 0) |
| A-730 | n-Butyl | Thien-2-yl | W2a (m = 0) |
| A-731 | n-Butyl | 2,3-Dihydrobenzo[b]furan-5-yl | W2a (m = 0) |
| A-732 | Isobutyl | Phenyl | W2a (m = 0) |
| A-733 | Isobutyl | 2-Methylphenyl | W2a (m = 0) |
| A-734 | Isobutyl | 2-Methoxyphenyl | W2a (m = 0) |
| A-735 | Isobutyl | 2-Chlorophenyl | W2a (m = 0) |
| A-736 | Isobutyl | 2-Fluorophenyl | W2a (m = 0) |
| A-737 | Isobutyl | 2-Trifluoromethylphenyl | W2a (m = 0) |
| A-738 | Isobutyl | 3-Methylphenyl | W2a (m = 0) |
| A-739 | Isobutyl | 3-Methoxyphenyl | W2a (m = 0) |
| A-740 | Isobutyl | 3-Chlorophenyl | W2a (m = 0) |
| A-741 | Isobutyl | 3-Fluorophenyl | W2a (m = 0) |
| A-742 | Isobutyl | 3-Trifluoromethyl | W2a (m = 0) |
| A-743 | Isobutyl | 3-[(Phenylmethyl)oxy]phenyl | W2a (m = 0) |
| A-744 | Isobutyl | 3-Morpholin-4-ylphenyl | W2a (m = 0) |
| A-745 | Isobutyl | 3-(Morpholin-4-ylmethyl)phenyl | W2a (m = 0) |
| A-746 | Isobutyl | 3-Pyrrolidin-1-ylphenyl | W2a (m = 0) |
| A-747 | Isobutyl | 4-Methylphenyl | W2a (m = 0) |
| A-748 | Isobutyl | 4-(1-Methylethyl)phenyl | W2a (m = 0) |
| A-749 | Isobutyl | 4-Methoxyphenyl | W2a (m = 0) |
| A-750 | Isobutyl | 4-Chlorophenyl | W2a (m = 0) |
| A-751 | Isobutyl | 4-Fluorophenyl | W2a (m = 0) |
| A-752 | Isobutyl | 4-Trifluoromethylphenyl | W2a (m = 0) |
| A-753 | Isobutyl | 4-Diethylaminophenyl | W2a (m = 0) |
| A-754 | Isobutyl | 4-[(Diethylamino)methyl]phenyl | W2a (m = 0) |
| A-755 | Isobutyl | 4-Cyanophenyl | W2a (m = 0) |
| A-756 | Isobutyl | 4-(Piperidin-1-yl)phenyl | W2a (m = 0) |
| A-757 | Isobutyl | 4-(4-Methylpiperazin-1-yl)phenyl | W2a (m = 0) |
| A-758 | Isobutyl | 4-Pyrrolidin-1-ylphenyl | W2a (m = 0) |
| A-759 | Isobutyl | 4-(1H-Imidazol-1-yl)phenyl | W2a (m = 0) |
| A-760 | Isobutyl | 4-Morpholin-4-ylphenyl | W2a (m = 0) |
| A-761 | Isobutyl | 4-(Morpholin-4-ylmethyl)phenyl | W2a (m = 0) |
| A-762 | Isobutyl | 2,4-Difluorophenyl | W2a (m = 0) |
| A-763 | Isobutyl | 2,6-Difluorophenyl | W2a (m = 0) |
| A-764 | Isobutyl | 3,5-Difluorophenyl | W2a (m = 0) |
| A-765 | Isobutyl | 2,4-Dichlorophenyl | W2a (m = 0) |
| A-766 | Isobutyl | 2,6-Dichlorophenyl | W2a (m = 0) |
| A-767 | Isobutyl | 3,5-Dichlorophenyl | W2a (m = 0) |
| A-768 | Isobutyl | 2-Chloro-4-fluorophenyl | W2a (m = 0) |
| A-769 | Isobutyl | 2-Chloro-4-morpholin-4-ylphenyl | W2a (m = 0) |
| A-770 | Isobutyl | 2-Fluoro-4-morpholin-4-ylphenyl | W2a (m = 0) |
| A-771 | Isobutyl | Pyridin-2-yl | W2a (m = 0) |
| A-772 | Isobutyl | Pyridin-4-yl | W2a (m = 0) |
| A-773 | Isobutyl | Thien-2-yl | W2a (m = 0) |
| A-774 | Isobutyl | 2,3-Dihydrobenzo[b]furan-5-yl | W2a (m = 0) |
| A-775 | Benzyl | Phenyl | W2a (m = 0) |
| A-776 | Benzyl | 2-Methylphenyl | W2a (m = 0) |
| A-777 | Benzyl | 2-Methoxyphenyl | W2a (m = 0) |
| A-778 | Benzyl | 2-Chlorophenyl | W2a (m = 0) |
| A-779 | Benzyl | 2-Fluorophenyl | W2a (m = 0) |
| A-780 | Benzyl | 2-Trifluoromethylphenyl | W2a (m = 0) |
| A-781 | Benzyl | 3-Methylphenyl | W2a (m = 0) |
| A-782 | Benzyl | 3-Methoxyphenyl | W2a (m = 0) |
| A-783 | Benzyl | 3-Chlorophenyl | W2a (m = 0) |
| A-784 | Benzyl | 3-Fluorophenyl | W2a (m = 0) |
| A-785 | Benzyl | 3-Trifluoromethyl | W2a (m = 0) |
| A-786 | Benzyl | 3-[(Phenylmethyl)oxy]phenyl | W2a (m = 0) |
| A-787 | Benzyl | 3-Morpholin-4-ylphenyl | W2a (m = 0) |
| A-788 | Benzyl | 3-(Morpholin-4-ylmethyl)phenyl | W2a (m = 0) |
| A-789 | Benzyl | 3-Pyrrolidin-1-ylphenyl | W2a (m = 0) |
| A-790 | Benzyl | 4-Methylphenyl | W2a (m = 0) |
| A-791 | Benzyl | 4-(1-Methylethyl)phenyl | W2a (m = 0) |
| A-792 | Benzyl | 4-Methoxyphenyl | W2a (m = 0) |
| A-793 | Benzyl | 4-Chlorophenyl | W2a (m = 0) |
| A-794 | Benzyl | 4-Fluorophenyl | W2a (m = 0) |
| A-795 | Benzyl | 4-Trifluoromethylphenyl | W2a (m = 0) |
| A-796 | Benzyl | 4-Diethylaminophenyl | W2a (m = 0) |

TABLE A-continued

| No. | R¹ | R² | W |
|---|---|---|---|
| A-797 | Benzyl | 4-[(Diethylamino)methyl]phenyl | W2a (m = 0) |
| A-798 | Benzyl | 4-Cyanophenyl | W2a (m = 0) |
| A-799 | Benzyl | 4-(Piperidin-1-yl)phenyl | W2a (m = 0) |
| A-800 | Benzyl | 4-(4-Methylpiperazin-1-yl)phenyl | W2a (m = 0) |
| A-801 | Benzyl | 4-Pyrrolidin-1-ylphenyl | W2a (m = 0) |
| A-802 | Benzyl | 4-(1H-Imidazol-1-yl)phenyl | W2a (m = 0) |
| A-803 | Benzyl | 4-Morpholin-4-ylphenyl | W2a (m = 0) |
| A-804 | Benzyl | 4-(Morpholin-4-ylmethyl)phenyl | W2a (m = 0) |
| A-805 | Benzyl | 2,4-Difluorophenyl | W2a (m = 0) |
| A-806 | Benzyl | 2,6-Difluorophenyl | W2a (m = 0) |
| A-807 | Benzyl | 3,5-Difluorophenyl | W2a (m = 0) |
| A-808 | Benzyl | 2,4-Dichlorophenyl | W2a (m = 0) |
| A-809 | Benzyl | 2,6-Dichlorophenyl | W2a (m = 0) |
| A-810 | Benzyl | 3,5-Dichlorophenyl | W2a (m = 0) |
| A-811 | Benzyl | 2-Chloro-4-fluorophenyl | W2a (m = 0) |
| A-812 | Benzyl | 2-Chloro-4-morpholin-4-ylphenyl | W2a (m = 0) |
| A-813 | Benzyl | 2-Fluoro-4-morpholin-4-ylphenyl | W2a (m = 0) |
| A-814 | Benzyl | Pyridin-2-yl | W2a (m = 0) |
| A-815 | Benzyl | Pyridin-4-yl | W2a (m = 0) |
| A-816 | Benzyl | Thien-2-yl | W2a (m = 0) |
| A-817 | Benzyl | 2,3-Dihydrobenzo[b]furan-5-yl | W2a (m = 0) |
| A-818 | 4-Chlorobenzyl | Phenyl | W2a (m = 0) |
| A-819 | 4-Chlorobenzyl | 2-Methylphenyl | W2a (m = 0) |
| A-820 | 4-Chlorobenzyl | 2-Methoxyphenyl | W2a (m = 0) |
| A-821 | 4-Chlorobenzyl | 2-Chlorophenyl | W2a (m = 0) |
| A-822 | 4-Chlorobenzyl | 2-Fluorophenyl | W2a (m = 0) |
| A-823 | 4-Chlorobenzyl | 2-Trifluoromethylphenyl | W2a (m = 0) |
| A-824 | 4-Chlorobenzyl | 3-Methylphenyl | W2a (m = 0) |
| A-825 | 4-Chlorobenzyl | 3-Methoxyphenyl | W2a (m = 0) |
| A-826 | 4-Chlorobenzyl | 3-Chlorophenyl | W2a (m = 0) |
| A-827 | 4-Chlorobenzyl | 3-Fluorophenyl | W2a (m = 0) |
| A-828 | 4-Chlorobenzyl | 3-Trifluoromethyl | W2a (m = 0) |
| A-829 | 4-Chlorobenzyl | 3-[(Phenylmethyl)oxy]phenyl | W2a (m = 0) |
| A-830 | 4-Chlorobenzyl | 3-Morpholin-4-ylphenyl | W2a (m = 0) |
| A-831 | 4-Chlorobenzyl | 3-(Morpholin-4-ylmethyl)phenyl | W2a (m = 0) |
| A-832 | 4-Chlorobenzyl | 3-Pyrrolidin-1-ylphenyl | W2a (m = 0) |
| A-833 | 4-Chlorobenzyl | 4-Methylphenyl | W2a (m = 0) |
| A-834 | 4-Chlorobenzyl | 4-(1-Methylethyl)phenyl | W2a (m = 0) |
| A-835 | 4-Chlorobenzyl | 4-Methoxyphenyl | W2a (m = 0) |
| A-836 | 4-Chlorobenzyl | 4-Chlorophenyl | W2a (m = 0) |
| A-837 | 4-Chlorobenzyl | 4-Fluorophenyl | W2a (m = 0) |
| A-838 | 4-Chlorobenzyl | 4-Trifluoromethylphenyl | W2a (m = 0) |
| A-839 | 4-Chlorobenzyl | 4-Diethylaminophenyl | W2a (m = 0) |
| A-840 | 4-Chlorobenzyl | 4-[(Diethylamino)methyl]phenyl | W2a (m = 0) |
| A-841 | 4-Chlorobenzyl | 4-Cyanophenyl | W2a (m = 0) |
| A-842 | 4-Chlorobenzyl | 4-(Piperidin-1-yl)phenyl | W2a (m = 0) |
| A-843 | 4-Chlorobenzyl | 4-(4-Methylpiperazin-1-yl)phenyl | W2a (m = 0) |
| A-844 | 4-Chlorobenzyl | 4-Pyrrolidin-1-ylphenyl | W2a (m = 0) |
| A-845 | 4-Chlorobenzyl | 4-(1H-Imidazol-1-yl)phenyl | W2a (m = 0) |
| A-846 | 4-Chlorobenzyl | 4-Morpholin-4-ylphenyl | W2a (m = 0) |
| A-847 | 4-Chlorobenzyl | 4-(Morpholin-4-ylmethyl)phenyl | W2a (m = 0) |
| A-848 | 4-Chlorobenzyl | 2,4-Difluorophenyl | W2a (m = 0) |
| A-849 | 4-Chlorobenzyl | 2,6-Difluorophenyl | W2a (m = 0) |
| A-850 | 4-Chlorobenzyl | 3,5-Difluorophenyl | W2a (m = 0) |
| A-851 | 4-Chlorobenzyl | 2,4-Dichlorophenyl | W2a (m = 0) |
| A-852 | 4-Chlorobenzyl | 2,6-Dichlorophenyl | W2a (m = 0) |
| A-853 | 4-Chlorobenzyl | 3,5-Dichlorophenyl | W2a (m = 0) |
| A-854 | 4-Chlorobenzyl | 2-Chloro-4-fluorophenyl | W2a (m = 0) |
| A-855 | 4-Chlorobenzyl | 2-Chloro-4-morpholin-4-ylphenyl | W2a (m = 0) |
| A-856 | 4-Chlorobenzyl | 2-Fluoro-4-morpholin-4-ylphenyl | W2a (m = 0) |
| A-857 | 4-Chlorobenzyl | Pyridin-2-yl | W2a (m = 0) |
| A-858 | 4-Chlorobenzyl | Pyridin-4-yl | W2a (m = 0) |
| A-859 | 4-Chlorobenzyl | Thien-2-yl | W2a (m = 0) |
| A-860 | 4-Chlorobenzyl | 2,3-Dihydrobenzo[b]furan-5-yl | W2a (m = 0) |
| A-861 | 4-Methoxybenzyl | Phenyl | W2a (m = 0) |
| A-862 | 4-Methoxybenzyl | 2-Methylphenyl | W2a (m = 0) |
| A-863 | 4-Methoxybenzyl | 2-Methoxyphenyl | W2a (m = 0) |
| A-864 | 4-Methoxybenzyl | 2-Chlorophenyl | W2a (m = 0) |
| A-865 | 4-Methoxybenzyl | 2-Fluorophenyl | W2a (m = 0) |
| A-866 | 4-Methoxybenzyl | 2-Trifluoromethylphenyl | W2a (m = 0) |
| A-867 | 4-Methoxybenzyl | 3-Methylphenyl | W2a (m = 0) |
| A-868 | 4-Methoxybenzyl | 3-Methoxyphenyl | W2a (m = 0) |
| A-869 | 4-Methoxybenzyl | 3-Chlorophenyl | W2a (m = 0) |
| A-870 | 4-Methoxybenzyl | 3-Fluorophenyl | W2a (m = 0) |
| A-871 | 4-Methoxybenzyl | 3-Trifluoromethyl | W2a (m = 0) |
| A-872 | 4-Methoxybenzyl | 3-[(Phenylmethyl)oxy]phenyl | W2a (m = 0) |
| A-873 | 4-Methoxybenzyl | 3-Morpholin-4-ylphenyl | W2a (m = 0) |
| A-874 | 4-Methoxybenzyl | 3-(Morpholin-4-ylmethyl)phenyl | W2a (m = 0) |

TABLE A-continued

| No. | R¹ | R² | W |
|---|---|---|---|
| A-875 | 4-Methoxybenzyl | 3-Pyrrolidin-1-ylphenyl | W2a (m = 0) |
| A-876 | 4-Methoxybenzyl | 4-Methylphenyl | W2a (m = 0) |
| A-877 | 4-Methoxybenzyl | 4-(1-Methylethyl)phenyl | W2a (m = 0) |
| A-878 | 4-Methoxybenzyl | 4-Methoxyphenyl | W2a (m = 0) |
| A-879 | 4-Methoxybenzyl | 4-Chlorophenyl | W2a (m = 0) |
| A-880 | 4-Methoxybenzyl | 4-Fluorophenyl | W2a (m = 0) |
| A-881 | 4-Methoxybenzyl | 4-Trifluoromethylphenyl | W2a (m = 0) |
| A-882 | 4-Methoxybenzyl | 4-Diethylaminophenyl | W2a (m = 0) |
| A-883 | 4-Methoxybenzyl | 4-[(Diethylamino)methyl]phenyl | W2a (m = 0) |
| A-884 | 4-Methoxybenzyl | 4-Cyanophenyl | W2a (m = 0) |
| A-885 | 4-Methoxybenzyl | 4-(Piperidin-1-yl)phenyl | W2a (m = 0) |
| A-886 | 4-Methoxybenzyl | 4-(4-Methylpiperazin-1-yl)phenyl | W2a (m = 0) |
| A-887 | 4-Methoxybenzyl | 4-Pyrrolidin-1-ylphenyl | W2a (m = 0) |
| A-888 | 4-Methoxybenzyl | 4-(1H-Imidazol-1-yl)phenyl | W2a (m = 0) |
| A-889 | 4-Methoxybenzyl | 4-Morpholin-4-ylphenyl | W2a (m = 0) |
| A-890 | 4-Methoxybenzyl | 4-(Morpholin-4-ylmethyl)phenyl | W2a (m = 0) |
| A-891 | 4-Methoxybenzyl | 2,4-Difluorophenyl | W2a (m = 0) |
| A-892 | 4-Methoxybenzyl | 2,6-Difluorophenyl | W2a (m = 0) |
| A-893 | 4-Methoxybenzyl | 3,5-Difluorophenyl | W2a (m = 0) |
| A-894 | 4-Methoxybenzyl | 2,4-Dichlorophenyl | W2a (m = 0) |
| A-895 | 4-Methoxybenzyl | 2,6-Dichlorophenyl | W2a (m = 0) |
| A-896 | 4-Methoxybenzyl | 3,5-Dichlorophenyl | W2a (m = 0) |
| A-897 | 4-Methoxybenzyl | 2-Chloro-4-fluorophenyl | W2a (m = 0) |
| A-898 | 4-Methoxybenzyl | 2-Chloro-4-morpholin-4-ylphenyl | W2a (m = 0) |
| A-899 | 4-Methoxybenzyl | 2-Fluoro-4-morpholin-4-ylphenyl | W2a (m = 0) |
| A-900 | 4-Methoxybenzyl | Pyridin-2-yl | W2a (m = 0) |
| A-901 | 4-Methoxybenzyl | Pyridin-4-yl | W2a (m = 0) |
| A-902 | 4-Methoxybenzyl | Thien-2-yl | W2a (m = 0) |
| A-903 | 4-Methoxybenzyl | 2,3-Dihydrobenzo[b]furan-5-yl | W2a (m = 0) |
| A-904 | Cyclohexylmethyl | Phenyl | W2a (m = 0) |
| A-905 | Cyclohexylmethyl | 2-Methylphenyl | W2a (m = 0) |
| A-906 | Cyclohexylmethyl | 2-Methoxyphenyl | W2a (m = 0) |
| A-907 | Cyclohexylmethyl | 2-Chlorophenyl | W2a (m = 0) |
| A-908 | Cyclohexylmethyl | 2-Fluorophenyl | W2a (m = 0) |
| A-909 | Cyclohexylmethyl | 2-Trifluoromethylphenyl | W2a (m = 0) |
| A-910 | Cyclohexylmethyl | 3-Methylphenyl | W2a (m = 0) |
| A-911 | Cyclohexylmethyl | 3-Methoxyphenyl | W2a (m = 0) |
| A-912 | Cyclohexylmethyl | 3-Chlorophenyl | W2a (m = 0) |
| A-913 | Cyclohexylmethyl | 3-Fluorophenyl | W2a (m = 0) |
| A-914 | Cyclohexylmethyl | 3-Trifluoromethyl | W2a (m = 0) |
| A-915 | Cyclohexylmethyl | 3-[(Phenylmethyl)oxy]phenyl | W2a (m = 0) |
| A-916 | Cyclohexylmethyl | 3-Morpholin-4-ylphenyl | W2a (m = 0) |
| A-917 | Cyclohexylmethyl | 3-(Morpholin-4-ylmethyl)phenyl | W2a (m = 0) |
| A-918 | Cyclohexylmethyl | 3-Pyrrolidin-1-ylphenyl | W2a (m = 0) |
| A-919 | Cyclohexylmethyl | 4-Methyl phenyl | W2a (m = 0) |
| A-920 | Cyclohexylmethyl | 4-(1-Methylethyl)phenyl | W2a (m = 0) |
| A-921 | Cyclohexylmethyl | 4-Methoxyphenyl | W2a (m = 0) |
| A-922 | Cyclohexylmethyl | 4-Chlorophenyl | W2a (m = 0) |
| A-923 | Cyclohexylmethyl | 4-Fluorophenyl | W2a (m = 0) |
| A-924 | Cyclohexylmethyl | 4-Trifluoromethylphenyl | W2a (m = 0) |
| A-925 | Cyclohexylmethyl | 4-Diethylaminophenyl | W2a (m = 0) |
| A-926 | Cyclohexylmethyl | 4-[(Diethylamino)methyl]phenyl | W2a (m = 0) |
| A-927 | Cyclohexylmethyl | 4-Cyanophenyl | W2a (m = 0) |
| A-928 | Cyclohexylmethyl | 4-(Piperidin-1-yl)phenyl | W2a (m = 0) |
| A-929 | Cyclohexylmethyl | 4-(4-Methylpiperazin-1-yl)phenyl | W2a (m = 0) |
| A-930 | Cyclohexylmethyl | 4-Pyrrolidin-1-ylphenyl | W2a (m = 0) |
| A-931 | Cyclohexylmethyl | 4-(1H-Imidazol-1-yl)phenyl | W2a (m = 0) |
| A-932 | Cyclohexylmethyl | 4-Morpholin-4-ylphenyl | W2a (m = 0) |
| A-933 | Cyclohexylmethyl | 4-(Morpholin-4-ylmethyl)phenyl | W2a (m = 0) |
| A-934 | Cyclohexylmethyl | 2,4-Difluorophenyl | W2a (m = 0) |
| A-935 | Cyclohexylmethyl | 2,6-Difluorophenyl | W2a (m = 0) |
| A-936 | Cyclohexylmethyl | 3,5-Difluorophenyl | W2a (m = 0) |
| A-937 | Cyclohexylmethyl | 2,4-Dichlorophenyl | W2a (m = 0) |
| A-938 | Cyclohexylmethyl | 2,6-Dichlorophenyl | W2a (m = 0) |
| A-939 | Cyclohexylmethyl | 3,5-Dichlorophenyl | W2a (m = 0) |
| A-940 | Cyclohexylmethyl | 2-Chloro-4-fluorophenyl | W2a (m = 0) |
| A-941 | Cyclohexylmethyl | 2-Chloro-4-morpholin-4-ylphenyl | W2a (m = 0) |
| A-942 | Cyclohexylmethyl | 2-Fluoro-4-morpholin-4-ylphenyl | W2a (m = 0) |
| A-943 | Cyclohexylmethyl | Pyridin-2-yl | W2a (m = 0) |
| A-944 | Cyclohexylmethyl | Pyridin-4-yl | W2a (m = 0) |
| A-945 | Cyclohexylmethyl | Thien-2-yl | W2a (m = 0) |
| A-946 | Cyclohexylmethyl | 2,3-Dihydrobenzo[b]furan-5-yl | W2a (m = 0) |
| A-947 | 2-Thienylmethyl | Phenyl | W2a (m = 0) |
| A-948 | 2-Thienylmethyl | 2-Methylphenyl | W2a (m = 0) |
| A-949 | 2-Thienylmethyl | 2-Methoxyphenyl | W2a (m = 0) |
| A-950 | 2-Thienylmethyl | 2-Chlorophenyl | W2a (m = 0) |
| A-951 | 2-Thienylmethyl | 2-Fluorophenyl | W2a (m = 0) |
| A-952 | 2-Thienylmethyl | 2-Trifluoromethylphenyl | W2a (m = 0) |

TABLE A-continued

| No. | R¹ | R² | W |
|---|---|---|---|
| A-953 | 2-Thienylmethyl | 3-Methylphenyl | W2a (m = 0) |
| A-954 | 2-Thienylmethyl | 3-Methoxyphenyl | W2a (m = 0) |
| A-955 | 2-Thienylmethyl | 3-Chlorophenyl | W2a (m = 0) |
| A-956 | 2-Thienylmethyl | 3-Fluorophenyl | W2a (m = 0) |
| A-957 | 2-Thienylmethyl | 3-Trifluoromethyl | W2a (m = 0) |
| A-958 | 2-Thienylmethyl | 3-[(Phenylmethyl)oxy]phenyl | W2a (m = 0) |
| A-959 | 2-Thienylmethyl | 3-Morpholin-4-ylphenyl | W2a (m = 0) |
| A-960 | 2-Thienylmethyl | 3-(Morpholin-4-ylmethyl)phenyl | W2a (m = 0) |
| A-961 | 2-Thienylmethyl | 3-Pyrrolidin-1-ylphenyl | W2a (m = 0) |
| A-962 | 2-Thienylmethyl | 4-Methylphenyl | W2a (m = 0) |
| A-963 | 2-Thienylmethyl | 4-(1-Methylethyl)phenyl | W2a (m = 0) |
| A-964 | 2-Thienylmethyl | 4-Methoxyphenyl | W2a (m = 0) |
| A-965 | 2-Thienylmethyl | 4-Chlorophenyl | W2a (m = 0) |
| A-966 | 2-Thienylmethyl | 4-Fluorophenyl | W2a (m = 0) |
| A-967 | 2-Thienylmethyl | 4-Trifluoromethylphenyl | W2a (m = 0) |
| A-968 | 2-Thienylmethyl | 4-Diethylaminophenyl | W2a (m = 0) |
| A-969 | 2-Thienylmethyl | 4-[(Diethylamino)methyl]phenyl | W2a (m = 0) |
| A-970 | 2-Thienylmethyl | 4-Cyanophenyl | W2a (m = 0) |
| A-971 | 2-Thienylmethyl | 4-(Piperidin-1-yl)phenyl | W2a (m = 0) |
| A-972 | 2-Thienylmethyl | 4-(4-Methylpiperazin-1-yl)phenyl | W2a (m = 0) |
| A-973 | 2-Thienylmethyl | 4-Pyrrolidin-1-ylphenyl | W2a (m = 0) |
| A-974 | 2-Thienylmethyl | 4-(1H-Imidazol-1-yl)phenyl | W2a (m = 0) |
| A-975 | 2-Thienylmethyl | 4-Morpholin-4-ylphenyl | W2a (m = 0) |
| A-976 | 2-Thienylmethyl | 4-(Morpholin-4-ylmethyl)phenyl | W2a (m = 0) |
| A-977 | 2-Thienylmethyl | 2,4-Difluorophenyl | W2a (m = 0) |
| A-978 | 2-Thienylmethyl | 2,6-Difluorophenyl | W2a (m = 0) |
| A-979 | 2-Thienylmethyl | 3,5-Difluorophenyl | W2a (m = 0) |
| A-980 | 2-Thienylmethyl | 2,4-Dichlorophenyl | W2a (m = 0) |
| A-981 | 2-Thienylmethyl | 2,6-Dichlorophenyl | W2a (m = 0) |
| A-982 | 2-Thienylmethyl | 3,5-Dichlorophenyl | W2a (m = 0) |
| A-983 | 2-Thienylmethyl | 2-Chloro-4-fluorophenyl | W2a (m = 0) |
| A-984 | 2-Thienylmethyl | 2-Chloro-4-morpholin-4-ylphenyl | W2a (m = 0) |
| A-985 | 2-Thienylmethyl | 2-Fluoro-4-morpholin-4-ylphenyl | W2a (m = 0) |
| A-986 | 2-Thienylmethyl | Pyridin-2-yl | W2a (m = 0) |
| A-987 | 2-Thienylmethyl | Pyridin-4-yl | W2a (m = 0) |
| A-988 | 2-Thienylmethyl | Thien-2-yl | W2a (m = 0) |
| A-989 | 2-Thienylmethyl | 2,3-Dihydrobenzo[b]furan-5-yl | W2a (m = 0) |
| A-990 | Pyridin-3-ylmethyl | Phenyl | W2a (m = 0) |
| A-991 | Pyridin-3-ylmethyl | 2-Methylphenyl | W2a (m = 0) |
| A-992 | Pyridin-3-ylmethyl | 2-Methoxyphenyl | W2a (m = 0) |
| A-993 | Pyridin-3-ylmethyl | 2-Chlorophenyl | W2a (m = 0) |
| A-994 | Pyridin-3-ylmethyl | 2-Fluorophenyl | W2a (m = 0) |
| A-995 | Pyridin-3-ylmethyl | 2-Trifluoromethylphenyl | W2a (m = 0) |
| A-996 | Pyridin-3-ylmethyl | 3-Methylphenyl | W2a (m = 0) |
| A-997 | Pyridin-3-ylmethyl | 3-Methoxyphenyl | W2a (m = 0) |
| A-998 | Pyridin-3-ylmethyl | 3-Chlorophenyl | W2a (m = 0) |
| A-999 | Pyridin-3-ylmethyl | 3-Fluorophenyl | W2a (m = 0) |
| A-1000 | Pyridin-3-ylmethyl | 3-Trifluoromethyl | W2a (m = 0) |
| A-1001 | Pyridin-3-ylmethyl | 3-[(Phenylmethyl)oxy]phenyl | W2a (m = 0) |
| A-1002 | Pyridin-3-ylmethyl | 3-Morpholin-4-ylphenyl | W2a (m = 0) |
| A-1003 | Pyridin-3-ylmethyl | 3-(Morpholin-4-ylmethyl)phenyl | W2a (m = 0) |
| A-1004 | Pyridin-3-ylmethyl | 3-Pyrrolidin-1-ylphenyl | W2a (m = 0) |
| A-1005 | Pyridin-3-ylmethyl | 4-Methylphenyl | W2a (m = 0) |
| A-1006 | Pyridin-3-ylmethyl | 4-(1-Methylethyl)phenyl | W2a (m = 0) |
| A-1007 | Pyridin-3-ylmethyl | 4-Methoxyphenyl | W2a (m = 0) |
| A-1008 | Pyridin-3-ylmethyl | 4-Chlorophenyl | W2a (m = 0) |
| A-1009 | Pyridin-3-ylmethyl | 4-Fluorophenyl | W2a (m = 0) |
| A-1010 | Pyridin-3-ylmethyl | 4-Trifluoromethylphenyl | W2a (m = 0) |
| A-1011 | Pyridin-3-ylmethyl | 4-Diethylaminophenyl | W2a (m = 0) |
| A-1012 | Pyridin-3-ylmethyl | 4-[(Diethylamino)methyl]phenyl | W2a (m = 0) |
| A-1013 | Pyridin-3-ylmethyl | 4-Cyanophenyl | W2a (m = 0) |
| A-1014 | Pyridin-3-ylmethyl | 4-(Piperidin-1-yl)phenyl | W2a (m = 0) |
| A-1015 | Pyridin-3-ylmethyl | 4-(4-Methylpiperazin-1-yl)phenyl | W2a (m = 0) |
| A-1016 | Pyridin-3-ylmethyl | 4-Pyrrolidin-1-ylphenyl | W2a (m = 0) |
| A-1017 | Pyridin-3-ylmethyl | 4-(1H-Imidazol-1-yl)phenyl | W2a (m = 0) |
| A-1018 | Pyridin-3-ylmethyl | 4-Morpholin-4-ylphenyl | W2a (m = 0) |
| A-1019 | Pyridin-3-ylmethyl | 4-(Morpholin-4-ylmethyl)phenyl | W2a (m = |
| A-1020 | Pyridin-3-ylmethyl | 2,4-Difluorophenyl | W2a (m = 0) |
| A-1021 | Pyridin-3-ylmethyl | 2,6-Difluorophenyl | W2a (m = 0) |
| A-1022 | Pyridin-3-ylmethyl | 3,5-Difluorophenyl | W2a (m = 0) |
| A-1023 | Pyridin-3-ylmethyl | 2,4-Dichlorophenyl | W2a (m = 0) |
| A-1024 | Pyridin-3-ylmethyl | 2,6-Dichlorophenyl | W2a (m = 0) |
| A-1025 | Pyridin-3-ylmethyl | 3,5-Dichlorophenyl | W2a (m = 0) |
| A-1026 | Pyridin-3-ylmethyl | 2-Chloro-4-fluorophenyl | W2a (m = 0) |
| A-1027 | Pyridin-3-ylmethyl | 2-Chloro-4-morpholin-4-ylphenyl | W2a (m = 0) |
| A-1028 | Pyridin-3-ylmethyl | 2-Fluoro-4-morpholin-4-ylphenyl | W2a (m = 0) |
| A-1029 | Pyridin-3-ylmethyl | Pyridin-2-yl | W2a (m = 0) |
| A-1030 | Pyridin-3-ylmethyl | Pyridin-4-yl | W2a (m = 0) |

TABLE A-continued

| No. | R¹ | R² | W |
|---|---|---|---|
| A-1031 | Pyridin-3-ylmethyl | Thien-2-yl | W2a (m = 0) |
| A-1032 | Pyridin-3-ylmethyl | 2,3-Dihydrobenzo[b]furan-5-yl | W2a (m = 0) |
| A-1033 | n-Butyl | 4,5-dihydro-2H-benzo[g]indazol-2-yl | |
| A-1034 | n-Butyl | 1H-Indazol-1-yl | |
| A-1035 | n-Butyl | 2H-Indazol-2-yl | |
| A-1036 | n-Butyl | Chromeno[4,3-c]pyrazol-2(4H)-yl | |
| A-1037 | Isobutyl | 4,5-dihydro-2H-benzo[g]indazol-2-yl | |
| A-1038 | Isobutyl | 1H-Indazol-1-yl | |
| A-1039 | Isobutyl | 2H-Indazol-2-yl | |
| A-1040 | Isobutyl | Chromeno[4,3-c]pyrazol-2(4H)-yl | |
| A-1041 | Benzyl | 4,5-dihydro-2H-benzo[g]indazol-2-yl | |
| A-1042 | Benzyl | 1H-Indazol-1-yl | |
| A-1043 | Benzyl | 2H-Indazol-2-yl | |
| A-1044 | Benzyl | Chromeno[4,3-c]pyrazol-2(4H)-yl | |
| A-1045 | 4-Chlorobenzyl | 4,5-dihydro-2H-benzo[g]indazol-2-yl | |
| A-1046 | 4-Chlorobenzyl | 1H-Indazol-1-yl | |
| A-1047 | 4-Chlorobenzyl | 2H-Indazol-2-yl | |
| A-1048 | 4-Chlorobenzyl | Chromeno[4,3-c]pyrazol-2(4H)-yl | |
| A-1049 | 4-Methoxybenzyl | 4,5-dihydro-2H-benzo[g]indazol-2-yl | |
| A-1050 | 4-Methoxybenzyl | 1H-Indazol-1-yl | |
| A-1051 | 4-Methoxybenzyl | 2H-Indazol-2-yl | |
| A-1052 | 4-Methoxybenzyl | Chromeno[4,3-c]pyrazol-2(4H)-yl | |
| A-1053 | Cyclohexylmethyl | 4,5-dihydro-2H-benzo[g]indazol-2-yl | |
| A-1054 | Cyclohexylmethyl | 1H-Indazol-1-yl | |
| A-1055 | Cyclohexylmethyl | 2H-Indazol-2-yl | |
| A-1056 | Cyclohexylmethyl | Chromeno[4,3-c]pyrazol-2(4H)-yl | |
| A-1057 | 2-Thienylmethyl | 4,5-dihydro-2H-benzo[g]indazol-2-yl | |
| A-1058 | 2-Thienylmethyl | 1H-Indazol-1-yl | |
| A-1059 | 2-Thienylmethyl | 2H-Indazol-2-yl | |
| A-1060 | 2-Thienylmethyl | Chromeno[4,3-c]pyrazol-2(4H)-yl | |
| A-1061 | Pyridin-3-ylmethyl | 4,5-dihydro-2H-benzo[g]indazol-2-yl | |
| A-1062 | Pyridin-3-ylmethyl | 1H-Indazol-1-yl | |
| A-1063 | Pyridin-3-ylmethyl | 2H-Indazol-2-yl | |
| A-1064 | Pyridin-3-ylmethyl | Chromeno[4,3-c]pyrazol-2(4H)-yl | |

The compounds of the invention of the general formula I and the starting materials used to prepare them can be prepared in analogy to known processes of organic chemistry as are described in standard works of organic chemistry, e.g. Houben-Weyl, "Methoden der Organischen Chemie", Thieme-Verlag, Stuttgart, Jerry March "Advanced Organic Chemistry", 5$^{th}$ edition, Wiley & Sons and the literature cited therein, and R. Larock, "Comprehensive Organic Transformations", 2$^{nd}$ edition, Weinheim, 1999 and the literature cited therein. The carboxamide compounds of the invention of the general formula I are advantageously prepared by the methods described below and/or in the experimental section.

The compounds of the formula I can be prepared in analogy to the schemes and methods described in WO 99/54305, pp. 6-10. An important access to compounds of the formula I is depicted in Scheme 1.

Scheme 1:

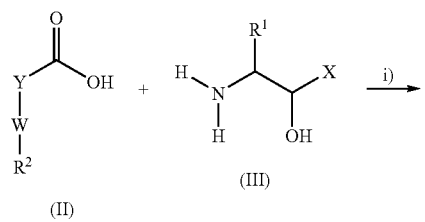

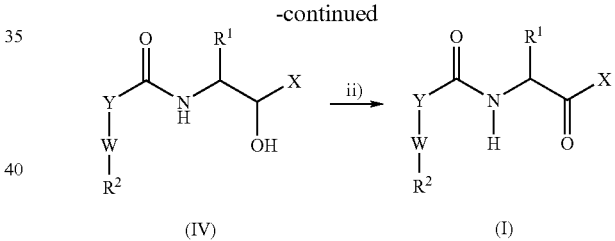

In Scheme 1, R¹, R², W, Y and X exhibit the aforementioned meanings.

In a first step i), a carboxylic acid II is converted by reaction with an amino alcohol III into a corresponding hydroxy amide IV. In this connection, conventional peptide coupling methods are ordinarily used, as are described for example in R. C. Larock, Comprehensive Organic Transformations, VCH Publisher, 1989, pages 972-976, or in Houben-Weyl, Methoden der organischen Chemie, 4$^{th}$ edition, E5, Chap. V. It may be advantageous firstly to activate the carboxylic acid II. For this purpose, for example, the carboxylic acid II is reacted with a carbodiimide such as dicyclohexylcarbodiimide (DCC) or 1-ethyl-3-(3-dimethylaminopropyl)carbodiimide (EDC) in the presence of hydroxybenzotriazole (HOBt), nitrophenol, pentafluorophenol, 2,4,5-trichlorophenol or N-hydroxysuccinimide, to obtain an activated ester IIa. It may further be advantageous to prepare the activated ester IIa in the presence of a base, for example a tertiary amine. The activated ester IIa is subsequently reacted with the amino alcohol of the formula III or its hydrohalide salt to give the hydroxy amide IV. The reaction normally takes place in anhydrous inert solvents such as chlorinated hydrocarbons, e.g. dichloromethane or dichloroethane, ethers, e.g. tetrahydrofuran or 1,4-dioxane or carboxamides, e.g. N,N-dimethylformamide, N,N-dimethylacetamide or N-methylpyrrolidone. Step i) is ordinarily carried out at temperatures in the range from −20° C. to +25° C.

Subsequently, in a second step ii), the hydroxy amide compound IV is oxidized to the carboxamide compound I of the invention. Various conventional oxidation reactions are suitable for this (see R. C. Larock, Comprehensive Organic Transformations, VCH Publisher, 1989, page 604 et seq.) such as, for example, swern oxidation and swern analogous oxidations (T. T. Tidwell, Synthesis 1990, pp. 857-870) or Pfitzner-Moffatt oxidation. Suitable oxidizing agents are dimethyl sulfoxide (DMSO) in combination with dicyclohexylcarbodiimide or 1-ethyl-3-(3-dimethylaminopropyl) carbodiimide, dimethyl sulfoxide in combination with the pyridine-SO$_3$ complex or dimethyl sulfoxide in combination with oxalyl chloride, sodium hypochloride/TEMPO (S. L. Harbenson et al., J. MED: Chem. 1994, 37, 2918-2929) or the Dess-Martin reagent (J. Org. Chem. 1983, 48, 4155). Depending on the oxidizing agent used, the oxidation of the hydroxy amide compound IV takes place at temperatures of from −50 to +25° C.

Compounds of the formula I in which X is —C(O)N (R$^{x4}$)—(C$_1$-C$_6$-alkylene)-NR$^{x2}$R$^{x3}$ or is —C(O)N(R$^{x4}$)NR$^{x2}$R$^{x3}$ in which R$^{x2}$, R$^{x3}$ and R$^{x4}$ have the aforementioned meanings can additionally be prepared by reacting compounds of the formula I in which X is COOH with hydrazine compounds of the formula NH(R$^{x4}$)NR$^{x2}$R$^{x3}$ or diamines of the formula NH(R$^{x4}$)—(C$_1$-C$_6$-alkylene)-NR$^{x2}$R$^{x3}$. The reaction can be carried out in analogy to step i) in Scheme 1.

The amino alcohols III can be obtained by purchase or can be prepared by processes disclosed in the literature (for amino hydroxy carboxylic acid derivatives, see, for example, S. L. Harbenson et al., J. Med. Chem. 1994, 37, 2918-2929 or J. P. Burkhardt et al., Tetrahedron Lett. 1988, 29, 3433-3436) or in analogy to the processes described in the preparation examples.

The carboxylic acid II can be prepared by hydrolyzing the carboxylic ester V with acids or bases under generally customary conditions. The hydrolysis preferably takes place with bases such as alkali metal or alkaline earth metal hydroxides, for example lithium hydroxide, sodium hydroxide or potassium hydroxide in aqueous medium or in a mixture of water and organic solvents, e.g. alcohols such as methanol or ethanol, ethers such as tetrahydrofuran or dioxane, at room temperature or elevated temperature such as 25-100° C.

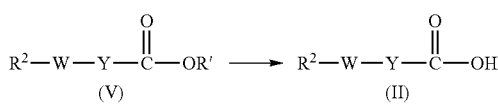

In formulae II and V, R$^2$, W and Y have the aforementioned meanings. In formula V, R' is alkyl, preferably C$_1$-C$_6$-alkyl.

The carboxylic ester of the formula V can advantageously be obtained by reacting the carboxylic ester of the general formula VI with an imidazole or pyrazole compound VII, see Scheme 2.

Scheme 2:

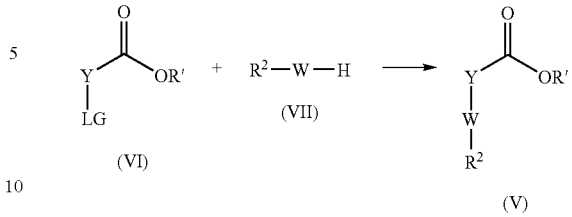

In scheme 2, LG represents a nucleophilically displaceable leaving group. Examples of suitable nucleophilically displaceable leaving groups are halogen, e.g. chlorine or bromine, or tosylate. R' is alkyl, preferably C$_1$-C$_6$-alkyl. R$^2$, Y and W have the aforementioned meanings.

As shown in Scheme 2, an ester VI is reacted with an appropriate imidazole or pyrazole compound of the formula VII. The reaction is ordinarily carried out under conventional conditions in the presence of a base in an inert solvent at elevated temperature. It may be advantageous where appropriate to carry out the reaction in the presence of catalytically active amounts of a transition metal, in particular of a metal of group 10 or 11 in the periodic table.

In the case where Y is a divalent heteroaromatic radical, in particular a divalent nitrogen-containing heteroaromatic radical, the reaction is preferably carried out at elevated temperature without diluent or in an inert solvent such as an ether, e.g. tetrahydrofuran or dioxane, carboxamides such as N,N-dimethylformamide, N,N-dimethylacetamide or N-methylpyrrolidone, or an aromatic hydrocarbon such as benzene, toluene or o-, m- or p-xylene. The reaction takes place in the presence of inorganic or organic bases and of a crown ether. Suitable inorganic bases are alkali metal or alkaline earth metal amides such as sodium amide, alkali metal or alkaline earth metal carbonates such as potassium carbonate or cesium carbonate or alkali metal hydrides such as sodium hydride. Suitable organic bases are tertiary amines, such as, for example, trimethylamine or triethylamine. A suitable crown ether is 18-crown-6. A Cu(I) salt such as, for example, CuI, CuCN, Cu$_2$O is added where appropriate as catalyst (see, for example, U.S. Pat. No. 4,826,835 and WO 88/00468).

In the case where Y is a divalent aromatic radical, the reaction of the carboxylic ester VI with the pyrazole or imidazole compound VII preferably takes place by transition metal-catalyzed N-arylation as described for example by H. J. Cristeau et al., Eur. J. Org. Chem. 2004, pp. 695-709, and S. L. Buchwald et al.; J. Org. Chem. 2004, 69, pages 5578-5587. The reaction frequently takes place in the presence of catalytically active amounts of a metal of group 10 in the periodic table, especially in the presence of a nickel(II) compound, Ni(0) compound, Pd(II) compound or Pd(0) compound. An example of a suitable method is the Buchwald cross-coupling.

The Buchwald cross-coupling normally takes place in the presence of a phosphorus-containing ligand, especially of a monodentate or bidentate phosphine ligand. Preferred ligands on the palladium are bulky, monodentate or bidentate phosphines such as triphenylphosphine, tri(o-tolyl)phosphine, tri(cyclohexyl)phosphine, BINAP (2,2'-bis-(diphenylphosphino)-1,1'-binaphthyl) or the Buchwald phosphines. The ligand may be present in the palladium compound or be added separately. Suitable palladium compounds include tris (dibenzylideneacetone)dipalladium(0), palladium(II) bis(o-tolyl)phosphine chloride and palladium(II) acetate. The Buchwald cross-coupling normally takes place in an organic solvent. Suitable organic solvents are aromatic hydrocarbons such as benzene or toluene, halogenated aromatic hydrocarbons such as chlorobenzene, halogenated hydrocarbons such as dichloromethane, trichloromethane, dichloroethane, ethers such as tetrahydrofuran, dioxane, ethylene glycol dimethyl ether, methyl tert-butyl ether, or amides such as dimethylformamide or N-methylpyrrolidone, and mixtures thereof. The Buchwald coupling reaction can be carried out under normal conditions or with use of microwaves.

The imidazole or pyrazole compounds VII can be purchased or can be prepared by conventional methods, which are briefly outlined below, from precursors which can be obtained by purchase.

A general overview of the preparation of imidazoles is to be found in W. M. Menge, Pharmacochemistry Library 1998, 30, pages 145-158. The imidazole compounds VII used are particularly advantageously prepared by the method described by Bredereck et al. (Chem. Ber. 1953, 86, pages 88-96) in which alpha-halo or alpha-hydroxy ketones are reacted with formamide—ordinarily with heating—to give the imidazoles VII.

General methods for preparing pyrazoles of the general formula VII are described for example in R. Fusco in "The Chemistry of Heterocyclic Compounds: Pyrazoles, Pyrazolines, Pyrazolidines, Indazoles and Condensed Rings", Wiley, R. H., editor; Wiley: New York, 1967; Vol. 22, pages 1-174; or J. Elguero, in "Comprehensive Heterocyclic Chemistry"; Potts, K. T., Ed.; Pergamon: Oxford 1984; Vol. 5, pages 291-298. One of the most commonly used methods is cyclocondensation of 1,3-dicarbonyl compounds or correspondingly reactive analogs with hydrazine or substituted hydrazine derivatives.

3-Aryl- or 3-hetaryl-substituted pyrazoles VII are particularly advantageously prepared by reacting 1-aryl- or 1-hetaryl-3-dimethylamino-2-propene compounds with hydrazine in analogy to the processes described for example in M. A. Halcrow et al.; J. Chem. Soc. Dalton Trans. 1997, pages 4025-4035. The 1-aryl- or 1-hetaryl-3-dimethylamino-2-propenes required as starting material can easily be prepared by condensing the analogous aromatic acetyl compounds with N,N-dimethylformamide dimethyl acetal (or analogously using the corresponding diethyl acetal). The reaction is normally carried out without diluent or in an inert solvent such as, for example, dimethylformamide or toluene, at elevated temperature. It is particularly advantageous to introduce the activation energy necessary for the reaction into the reaction mixture also by means of microwaves and to carry out the reaction under elevated pressure as described in A. K. Pleier, Synthesis 2001, 1, pages 55-62.

Analogous 4-substituted pyrazoles of the general formula VII are prepared for example starting from aryl- or hetarylacetic acids which are converted by means of the Vilsmeier reagent into the corresponding gamma-dimethylamino-2-propenals, with subsequent cyclization with hydrazine, see, for example, U.S. Pat. No. 4,888,352.

A further general possibility for preparing substituted pyrazoles of the formula VII is the Suzuki coupling of appropriate pyrazoleboronic acids or pyrazoleboronic esters as described for example in: N. Zhe et al.; J. Med. Chem. 2005, 48 (5), pages 1569-1609; Young et al.; J. Med. Chem. 2004, 47 (6), pp. 1547-1552; C. Slee et al.; Bioorg. Med. Chem. Lett. 2001, 9, pages 3243-3253. An appropriate alternative is also Stille coupling of halogenated pyrazole derivatives with appropriate tin organyls as described for example by J. Eluguero et al.; Synthesis 1997, 5, pp. 563-566.

The preparation of 1,4-dihydrobenzopyranopyrazoles can be performed according to the methods described by Chandrasekhar, S. et al.; Tetrahedron Letters 2001, 42(37), 6599-6601.

The reaction mixtures are worked up in a conventional way, e.g. by mixing with water, separating the phases and, where appropriate, purifying the crude products by chromatography. The intermediates and final products in some cases result in the form of colorless or pale brownish, viscous oils which are freed of volatiles or purified under reduced pressure and at moderately elevated temperature. If the intermediates and final products are obtained as solids, the purification can also take place by recrystallization or digestion.

If individual compounds I are not obtainable by the routes described above, they can be prepared by derivatization of other compounds I.

The compounds of the invention exhibit extremely low Ki values in relation to the inhibition of calpain and thus permit efficient inhibition of calpain, especially calpain I, at low serum levels. The compounds of the invention ordinarily exhibit Ki values in relation to the inhibition of calpain in vitro of <500 nM, in particular <100 nM and specifically $\leq$40 nM. The compounds of the invention are therefore particularly suitable for the treatment of disorders associated with an elevated calpain activity.

In addition, the compounds of the invention are selective calpain inhibitors, i.e. the inhibition of other cysteine proteases such as cathepsin B, cathepsin K, cathepsin L or cathepsin S takes place only at concentrations which are distinctly higher than the concentrations necessary for inhibition of calpain. Accordingly, the compounds of the invention ought to show distinctly fewer side effects than the prior art compounds which are comparatively unselective in relation to inhibition of calpain and likewise inhibit other cysteine proteases.

Compounds preferred according to the invention accordingly have a selectivity in relation to inhibition of cathepsin B, expressed in the form of the ratio of the Ki for inhibition of cathepsin B to the Ki for inhibition of calpain of $\geq$10, in particular $\geq$30.

Compounds preferred according to the invention accordingly have a selectivity in relation to inhibition of cathepsin K, expressed in the form of the ratio of the Ki for inhibition of cathepsin K to the Ki for inhibition of calpain of $\geq$10, in particular $\geq$30.

Compounds preferred according to the invention accordingly have a selectivity in relation to inhibition of cathepsin L, expressed in the form of the ratio of the Ki for inhibition of cathepsin L to the Ki for inhibition of calpain of $\geq$30, in particular $\geq$50.

Compounds preferred according to the invention accordingly have a selectivity in relation to inhibition of cathepsin S, expressed in the form of the ratio of the Ki for inhibition of cathepsin S to the Ki for inhibition of calpain of $\geq$50, in particular $\geq$100.

Owing to their inhibitory effect on calpain and their selectivity for calpain by comparison with other cysteine proteases, the compounds of the invention of the formula I, their tautomers and their pharmaceutically suitable salts are particularly suitable for the treatment of a disorder or of a condition which is associated with an elevated calpain activity as are described for example in the prior art cited at the outset.

Disorders associated with an elevated calpain activity are in particular neurodegenerative disorders, especially those neurodegenerative disorders occurring as a result of a chronic brain supply deficit, of an ischemia (stroke) or of a trauma such as brain trauma, and the neurodegenerative disorders Alzheimer's disease, Parkinson's disease, amyotrophic lateral sclerosis and Huntington's disease, also multiple sclerosis and the damage to the nervous system associated therewith, especially damage to the optic nerve (optic neuritis) and the nerves which control the movement of the eye. Accordingly, preferred embodiments of the invention relate to the treatment of neurodegenerative disorders, especially of the aforementioned neurodegenerative disorders in humans, and to the use of the compounds of the invention of the formula I, their tautomers and their pharmaceutically suitable salts for the manufacture of a medicament for the treatment of these disorders.

Disorders associated with an elevated calpain activity also include epilepsy. Accordingly, preferred embodiments of the invention relate to the treatment of epilepsy in humans, and to the use of the compounds of the invention of the formula I, their tautomers and their pharmaceutically suitable salts for the manufacture of a medicament for the treatment of epilepsy.

The disorders or conditions associated with an elevated calpain activity also include pain and painful conditions. Accordingly, preferred embodiments of the invention relate to the treatment of pain and painful conditions in mammals, especially in humans, and to the use of the compounds of the invention of the formula I, their tautomers and their pharmaceutically suitable salts for the manufacture of a medicament for the treatment of pain and painful conditions.

The disorders or conditions associated with an elevated calpain activity also include damage to the heart following cardiac ischemias, damage to the kidneys following renal ischemias, skeletal muscle damage, muscular dystrophies, damage arising through proliferation of smooth muscle cells, coronary vasospasms, cerebral vasospasms, macular degeneration, cataracts of the eyes, or restenosis of blood vessels following angioplasty. Accordingly, preferred embodiments of the invention relate to the treatment of diseases or conditions associated with damage to the heart following cardiac ischemias, damage to the kidneys following renal ischemias, skeletal muscle damage, muscular dystrophies, damage arising through proliferation of smooth muscle cells, coronary vasospasms, cerebral vasospasms, macular degeneration, cataracts of the eyes, or restenosis of blood vessels following angioplasty in mammals, especially in humans, and to the use of the compounds of the invention of the formula I, their tautomers, prodrugs and their pharmaceutically suitable salts for the manufacture of a medicament for the treatment of these disorders.

It has further emerged that inhibition of calpain brings about cytotoxic effects on tumor cells. Accordingly, the compounds of the invention are suitable for the chemotherapy of tumors and metastasis thereof. Preferred embodiments of the invention therefore relate to the use of the compounds of the invention of the formula I, their tautomers and their pharmaceutically suitable salts in the therapy of tumors and metastases, and to their use for the manufacture of a medicament for the therapy of tumors and metastases.

It has further been found that various impairments associated with an HIV disorder, especially nerve damage (HIV-induced neurotoxicity), are mediated by calpain and therefore inhibition of calpain allows such impairments to be treated or alleviated. Accordingly, the compounds of the invention of the formula I, their tautomers, their prodrugs and their pharmaceutically suitable salts are suitable for the treatment of HIV patients. Preferred embodiments of the invention therefore relate to the use of the compounds of the invention of the formula I, their tautomers and their pharmaceutically suitable salts for the treatment of HIV-infected patients, especially the treatment of those impairments caused by an HIV-induced neurotoxicity, and to their use for the manufacture of a medicament for the treatment of HIV patients.

It has further been found that the release of interleukin-I, TNF or beta-amyloid peptides (Aβ or Aβ-peptides) can be reduced or completely inhibited by calpain inhibitors. Accordingly, impairments or disorders associated with an elevated interleukin-I, TNF or Aβ level can be treated by using the compounds of the invention of the formula I, their tautomers and their pharmaceutically suitable salts. Preferred embodiments of the invention therefore relate to the use of the compounds of the invention of the formula I, their tautomers, their produgs and their pharmaceutically acceptable salts for the treatment of impairments or disorders associated with an elevated interleukin-I, TNF or Aβ level such as rheumatism, rheumatoid arthritis and to their use for the manufacture of a medicament for the treatment of such impairments or disorders.

The compounds of the general formula (I) are distinguished in particular also by a good metabolic stability. The metabolic stability of a compound can be measured for example by incubating a solution of this compound with liver microsomes from particular species (for example rat, dog or human) and determining the half-life of the compound under these conditions (R S Obach, Curr Opin Drug Discov Devel. 2001, 4, 36-44). It is possible to conclude from larger half-lives that the metabolic stability of the compound is improved. The stability in the presence of human liver microsomes is of particular interest because it makes it possible to predict the metabolic degradation of the compound in the human liver. Compounds with increased metabolic stability are therefore probably also degraded more slowly in the liver (measured in the liver microsome test). Slower metabolic degradation in the liver can lead to higher and/or longer-lasting concentrations (effective levels) of the compound in the body, so that the elimination half-life of the compounds of the invention is increased. Increased and/or longer-lasting effective levels may lead to a better efficacy of the compound in the treatment or prophylaxis of various calpain-dependent diseases. An improved metabolic stability may additionally lead to an increased bioavailability after oral administration, because the compound is subjected, after being absorbed in the intestine, to less metabolic degradation in the liver (termed the first pass effect). An increased oral bioavailability may, because the concentration (effective level) of the compound is increased, lead to a better efficacy of the compound after oral administration.

The compounds of the invention of the formula I are further distinguished by exhibiting an improved pharmacological activity, compared with the carboxamide compounds of the formula I disclosed in the prior art, in patients or relevant animal models allowing prognostic statements for use in treatment.

The present invention also relates to pharmaceutical compositions (i.e. medicaments) which comprise at least one compound of the invention of the formula I or a tautomer or a pharmaceutically suitable salt thereof and, where appropriate, one or more suitable drug carriers.

These drug carriers are chosen according to the pharmaceutical form and the desired mode of administration.

The compounds of the invention of the general formula I, their tautomers and the pharmaceutically suitable salts of these compounds can be used to manufacture pharmaceutical compositions for oral, sublingual, subcutaneous, intramuscular, intravenous, topical, intratracheal, intranasal, transdermal or rectal administration, and be administered to animals or humans in unit dose forms, mixed with conventional pharmaceutical carriers, for the prophylaxis or treatment of the above impairments or diseases.

Suitable unit dose forms include forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active basic ingredient may vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose can be administered 1 to 5 times a day, so that a daily dose of from 0.5 to 25 000 mg, preferably 1 to 5000 mg, is administered.

If a solid composition is prepared in the form of tablets, the main ingredient is mixed with a pharmaceutical carrier such as gelatin, starch, lactose, magnesium stearate, talc, silicon dioxide or the like.

The tablets may be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable coloring.

The water-dispersible powders or granules may comprise the active ingredients mixed with dispersants, wetting agents or suspending agents such as polyvinylpyrrolidones, and sweeteners or taste improvers.

Rectal administration is achieved by the use of suppositories which are prepared with binders which melt at the rectal temperature, for example cocoabutter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active basic ingredient may also be formulated as microcapsules or liposomes/centrosomes, if suitable with one or more carriers or additives.

In addition to the compounds of the general formula I, their tautomers or their pharmaceutically suitable salts, the compositions of the invention may comprise further active basic ingredients which may be beneficial for the treatment of the impairments or diseases indicated above.

The present invention thus further relates to pharmaceutical compositions in which a plurality of active basic ingredients are present together, where at least one thereof is a compound of the invention.

The following examples illustrate the invention without restricting it. Depending on the management of the reaction and working up, the compounds of the general formula I result as mixtures of carbonyl form and the corresponding hydrates. Conversion into the pure carbonyl compounds generally takes place by treating the substances with HCl in an inert solvent.

PREPARATION EXAMPLES

Example 1

N-(3-Amino-1-benzyl-2,3-dioxopropyl)-2-(4-phenyl-1H-imidazol-1-yl)nicotinamide 1.1 Ethyl 2-(4-phenyl-1H-imidazol-1-yl)pyridine-3-carboxylate A mixture of 5.0 g of ethyl 2-chloronicotinate (26.94 mmol), 3.4 g of 4-phenylimidazole (23.58 mmol), 7.6 g of $K_2CO_3$ and 80 mg of 18-crown-6 in 18 ml of N,N-dimethylformamide was heated in a microwave at 160° C. for about 1 hour. This was followed by concentrating, taking up the residue in dichloromethane, washing with water and sat. NaCl solution, drying over $MgSO_4$, filtering and evaporating. Chromatography on silica gel (eluent: $CH_2Cl_2$/methanol 2%-5%) resulted in 2 g of a dark oil, which was immediately reacted further; ESI-MS $[M+H]^+=294.15$.

1.2
2-(4-Phenyl-1H-imidazol-1-yl)pyridin-3-carboxylic acid 15 m of a 2N NaOH solution were added to a solution of 2.0 g of ethyl 2-(4-phenyl-1H-imidazol-1-yl)pyridine-3-carboxylate (6.82 mmol) in 30 ml of methanol, and the mixture was then stirred at room temperature for 2 hours. The reaction mixture was subsequently evaporated to dryness, mixed with 10 ml of $H_2O$ and neutralized by adding 2N HCl. Filtration with suction and drying the precipitate formed resulted in 1.3 g of the acid as brown amorphous solid.

ESI-MS $[M+H]^+=266.05$.
$^1$H-NMR (500 MHz DMSO) δ ppm: 13.99-13.45 (s broad, 1H), 8.74 (m, 1H), 8.37 (m, 1H), 8.08 (s, 1H), 8.03 (s, 1H), 7.86 (m, 1H), 7.84 (m, 1H), 7.62 (m, 1H), 7.39 (m, 2H), 7.25 (m, 1H).

1.3 N-[3-Amino-2-hydroxy-3-oxo-1-(phenylmethyl)propyl]-2-(4-phenyl-1H-imidazol-1-yl)pyridine-3-carboxamide 0.75 g of 1-ethyl-3-(3-dimethylaminopropyl)carbodiimide (EDC), 0.51 g of hydroxylbenzotriazole (HOBt) and 0.55 ml of triethylamine ($Et_3N$) were successively added to a solution of 1.0 g of 2-(4-phenyl-1H-imidazol-1-yl)pyridine-3-carboxylic acid (3.77 mmol) in 50 ml of dichloromethane at 0-4° C., and the mixture was stirred at 0-4° C. for 1 hour. 0.9 g of 3-amino-2-hydroxy-4-phenylbutanamide hydrochloride (3.9 mmol) and 0.55 ml of $Et_3N$ were then added and, after about 5 minutes, a pH of 8-9 was adjusted by adding 0.5 ml of $Et_3N$. The mixture was stirred at 0-4° C. for 1 hour and then at room temperature overnight. 50 ml of saturated $NaHCO_3$ solution were then added to the mixture, and the organic phase was separated off. Drying and evaporating the solvent resulted in 620 mg of a reddish oil, which was reacted further immediately without further purification.

ESI-MS $[M+H]^+=442.15$.

1.4 N-(3-Amino-1-benzyl-2,3-dioxopropyl)-2-(4-phenyl-1H-imidazol-1-yl)nicotinamide 2.7 g of EDC and 0.5 ml of dichloroacetic acid were added to 620 mg of N-[3-amino-2-hydroxy-3-oxo-1-(phenylmethyl)propyl]-2-(4-phenyl-1H-imidazol-1-yl)pyridine-3-carboxamide (1.45 mmol) in 15 ml of dry dimethyl sulfoxide, and the mixture was stirred at room temperature for about 1 hour. To work up the reaction mixture it was mixed with 40 ml of NaCl solution and sat. NaHCO$_3$ solution (1:1), and the resulting solid was filtered off with suction, dried and stirred with methyl tert-butyl ether. The residue obtained in this way was further purified by stirring with 2N HCl and then with 10 ml of 1:1 acetonitrile/water. The remaining residue was filtered off with suction and dried. 50 mg of the target compound were obtained as a pale amorphous solid in this way.

ESI-MS [M+H$_2$O+H]$^+$=458.15.

$^1$H-NMR (500 MHz DMSO) δ ppm: 9.51 (d, 1H), 8.72 (dd, 2H), 8.16 (s, 1H), 8.12 (s, 1H), 7.93 (m, 2H), 7.88 (m, 2H), 7.70 (dd, 1H), 7.85 (m, 2H), 7.38 (m, 1H), 7.27 (m, 4H), 7.19 (m, 1H), 6.54 (m, 1H), 3.24 (dd, 1H), 2.87 (dd, 1H).

Example 2

N-{1-[Amino(oxo)acetyl]pentyl}-2-(4-phenyl-1H-imidazol-1-yl)nicotinamide

2.1 N-[1-(2-Amino-1-hydroxy-2-oxoethyl)pentyl]-2-(4-phenyl-1H-imidazol-1-yl)pyridine-3-carboxamide Preparation took place in analogy to 1.3 using 0.23 g of 3-amino-2-hydroxyheptanamide hydrochloride (1.17 mmol). During the usual workup, the target product precipitated as a white solid from the aqueous phase. The solid was filtered off with suction and dried at 40° C. in a vacuum drying oven. 219 mg of the title compound were obtained.

ESI-MS [M+H]$^+$=408.15.

2.2 N-{1-[Amino(oxo)acetyl]pentyl}-2-(4-phenyl-1H-imidazol-1-yl)nicotinamide 200 mg of N-[1-(2-amino-1-hydroxy-2-oxoethyl)pentyl]-2-(4-phenyl-1H-imidazol-1-yl)pyridine-3-carboxamide (0.49 mmol) were oxidized in a manner analogous to Example 1.4. The crude product obtained after workup was purified by chromatography on silica gel (eluent: CH$_2$Cl$_2$/methanol 0%-7%). Evaporation of the solvent resulted in 37 mg of the title compound.

ESI-MS [M+H]$^+$=406.15.

$^1$H-NMR (500 MHz DMSO) δ ppm: 9.15 (d, 1H), 8.65 (d, 1H), 8.12 (s, 1H), 8.09 (s, 1H), 8.01 (dd, 1H), 7.95 (s, 1H), 7.84 (m, 3H), 7.56 (m, 1H), 7.39 (m, 2H), 7.24 (m, 1H), 5.16 (m, 1H), 1.77 and 1.50 (each m, H), 1.26 (m, 4H), 0.77 (m, 3H).

Example 3

N-{1-[Amino(oxo)acetyl]pentyl}-2-(4-phenyl-1H-pyrazol-1-yl)nicotinamide

3.1 Ethyl 2-(4-phenyl-1H-pyrazol-1-yl)pyridine-3-carboxylate

A mixture of 3.6 g of ethyl 2-chloronicotinate (19.4 mmol), 1.3 g of 4-phenylpyrazole (8.12 mmol), 4.4 g of K$_2$CO$_3$, 40 mg of 18-crown-6 and 30 mg of KI in 30 ml of N,N-dimethylformamide was stirred at 130° C. for 6 hours. For workup, H$_2$O was added and, after extraction with ethyl acetate, the organic phase was washed with H$_2$O and sat. NaCl solution. The crude product obtained after drying and concentration of the solution was purified by chromatography on silica gel (eluent: CH$_2$Cl$_2$/methanol 1-10%). In total, 1.9 g of an oil were obtained, which crystallized completely on standing in a refrigerator.

ESI-MS [M+H]$^+$=294.15.

3.2 2-(4-Phenyl-1H-pyrazol-1-yl)pyridine-3-carboxylic acid

Hydrolysis of 1.0 g of ethyl 2-(4-phenyl-1H-pyrazol-1-yl)pyridine-3-carboxylate (6.48 mmol) took place in analogy to 1.2. 0.8 g of the carboxylic acid was obtained as a white amorphous solid.

ESI-MS [M+H]$^+$=266.1

$^1$H-NMR (500 MHz DMSO) δ ppm: 8.64 (s, 1H), 8.32 (m, 1H), 8.06 (s, 1H), 7.77 (m, 1H), 7.67 (m, 2H), 7.40 (m, 1H), 7.32 (m, 1H), 7.24 (m, 1H).

3.3 N-[1-(2-Amino-1-hydroxy-2-oxoethyl)pentyl]-2-(4-phenyl-1H-pyrazol-1-yl)pyridine-3-carboxamide Preparation took place in analogy to 1.3 using 0.19 g of 3-amino-2-hydroxyheptanamide hydrochloride (1.0 mmol). Completion of the reaction was followed by concentration, addition of H$_2$O and filtration of the resulting precipitate with suction and drying. Crystallization of the crude product from ethanol afforded 290 mg of the title compound as a white amorphous solid.

ESI-MS [M+H]$^+$=408.3.

3.4 N-{1-[Amino(oxo)acetyl]pentyl}-2-(4-phenyl-1H-pyrazol-1-yl)nicotinamide 0.47 g of EDC and 0.08 ml of dichloroacetic acid were added to 100 mg of N-[1-(2-amino-1-hydroxy-2-oxoethyl)pentyl]-2-(4-phenyl-1H-pyrazol-1-yl)pyridine-3-carboxamide (0.25 mmol) in 4 ml of dimethyl sulfoxide, and the mixture was stirred at room temperature overnight. For workup, the reaction mixture was poured into H$_2$O, and the resulting precipitate was filtered off with suction and dried in a vacuum drying oven at 40° C. 77 mg of the title compound were obtained as an amorphous white solid.

ESI-MS [M+H]$^+$=406.2

$^1$H-NMR (500 MHz DMSO) δ ppm: 8.87 (d, 1H), 8.68 (d, 1H), 8.60 (dd, 1H), 8.16 (s, 1H), 8.02 (s, 1H), 7.87 (dd, 1H), 7.76 (m, 3H), 7.55 (dd, 1H), 7.41 (m, 2H), 7.27 (m, 1H), 5.11 (m, 1H), 1.76 (m, 1H), 1.51 (m, 1H), 1.35-1.25 (m, 4H), 0.85-0.82 (m, 3H).

Example 4

N-(3-Amino-1-benzyl-2,3-dioxopropyl)-2-(4-phenyl-1H-pyrazol-1-yl)nicotinamide

4.1 N-[3-Amino-2-hydroxy-3-oxo-1-(phenylmethyl)propyl]-2-(4-phenyl-1H-pyrazol-1-yl)pyridine-3-carboxamide 0.23 g of 3-amino-2-hydroxy-4-phenylbutanamide hydrochloride (1.0 mmol) was reacted with 2-(4-phenyl-1H-imidazol-1-yl)pyridine-3-carboxylic acid in analogy to Example 3.3, resulting in 280 mg of the title compound of a white amorphous solid.

ESI-MS [M+H]$^+$=442.4.

4.2 N-(3-Amino-1-benzyl-2,3-dioxopropyl)-2-(4-phenyl-1H-pyrazol-1-yl)nicotinamide 250 mg of N-[3-amino-2-hydroxy-3-oxo-1-(phenylmethyl)propyl]-2-(4-phenyl-1H-pyrazol-1-yl)pyridine-3-carboxamide (0.57 mmol) were oxidized in analogy to Example 3.4, resulting in 228 mg of the title compound as a white solid.
ESI-MS [M+H]$^+$=440.1.
$^1$H-NMR (500 MHz DMSO) δ ppm: 8.92 (d, 1H), 8.86 (s, 1H), 8.58 (dd, 1H), 8.05 (s, 2H), 7.82 (s, 1H), 7.75 (m, 3H), 7.49 (dd, 1H), 7.43 (m, 2H), 7.30 (m, 5H), 7.20 (m, 1H), 5.39 (m, 1H), 3.18 (dd, 1H), 2.91 (dd, 1H).

Example 5

N-(3-Amino-1-benzyl-2,3-dioxopropyl)-2-(3-phenyl-1H-pyrazol-1-yl)nicotinamide 5.1 Ethyl 2-(3-phenyl-1H-pyrazol-1-yl)pyridine-3-carboxylate Reaction of 4.3 g of 3-phenyl-1H-pyrazole (29.82 mmol) in a manner analogous to Example 3.1 and chromatography of the resulting crude product on silica gel (eluent: $CH_2Cl_2$) afforded 9.7 g of the title compound as a pale oil.
ESI-MS [M+H]$^+$=294.0.

5.2 2-(3-Phenyl-1H-pyrazol-1-yl)pyridine-3-carboxylic acid

Hydrolysis took place in analogy to Example 1.2. After the reaction was complete, the reaction mixture was extracted with ethyl acetate, and the aqueous phase was acidified with 2N HCl and extracted with dichloromethane. Washing with $H_2O$ and sat. NaCl solution, drying and evaporation afforded 5.1 g of the acid as a pale solid.
ESI-MS [M+H]$^+$=266.0.
$^1$H-NMR (500 MHz DMSO) δ ppm: 13.2 (s broad, 1H), 8.61 (m, 1H), 8.56 (m, 1H), 8.11 (m, 1H), 7.92 (m, 2H), 7.52-7.39 (m, 2H), 7.39 (m, 1H), 7.08 (m, 1H).

5.3 N-[1-(2-Amino-1-hydroxy-2-oxoethyl)pentyl]-2-(3-phenyl-1H-pyrazol-1-yl)pyridine-3-carboxamide Coupling and working up in a manner analogous to Example 3.3 afforded 5.1 g of the title compound as a white solid.
ESI-MS [M+H]$^+$=442.1.

5.4 N-(3-Amino-1-benzyl-2,3-dioxopropyl)-2-(3-phenyl-1H-pyrazol-1-yl)nicotinamide Oxidation of 5.1 g of N-[1-(2-amino-1-hydroxy-2-oxoethyl)pentyl]-2-(3-phenyl-1H-pyrazol-1-yl)pyridine-3-carboxamide (11.55 mmol) in a manner analogous to Example 3.4, and purification of the crude product by recrystallization from ethyl acetate afforded 3.5 g of the title compound as a white solid with a melting point of 190° C.
ESI-MS [M+H]$^+$=440.0.
$^1$H-NMR (500 MHz DMSO) δ ppm: 8.93 (d, 1H), 8.56 (dd, 1H), 8.49 (dd, 1H), 8.48 (m, 1H), 8.06 (s, 1H), 7.84 (s, 1H), 7.78 (m, 2H), 7.7.73 (dd, 1H), 7.48 (dd, 1H), 7.42-7.35 (m, 3H), 7.19 (m, 5H), 7.02 (d, 1H), 5.58 (m, 1H), 3.15 (dd, 1H), 2.81 (dd, 1H).

Example 6

N-{1-[Amino(oxo)acetyl]pentyl}-2-(3-phenyl-1H-pyrazol-1-yl)nicotinamide

Preparation in analogy to Example 5 by coupling 2-(3-phenyl-1H-pyrazol-1-yl)pyridine-3-carboxylic acid and 3-amino-2-hydroxyheptanamide hydrochloride and subsequent oxidation afforded 40 mg of the title compound as a white solid.
ESI-MS [M+H]$^+$=406.1
$^1$H-NMR (500 MHz DMSO) δ ppm: 8.73 (d, 1H), 8.58 (d, 1H), 8.52 (d, 1H), 8.02 (s, 1H), 7.90-7.85 (m, 3H), 7.79 (s, 1H), 7.51 (dd, 1H), 7.45 (m, 2H), 7.37 (m, 1H), 7.05 (m, 1H), 5.17 (m, 1H), 1.73 (m, 1H), 1.46 (m, 1H), 1.15 (m, 4H), 0.70 (m, 3H).

Example 7

N-{1-[Amino(oxo)acetyl]-3-methylbutyl}-2-(4-phenyl-1H-imidazol-1-yl)nicotinamide 7.1 N-[1-(2-Amino-1-hydroxy-2-oxoethyl)-3-methylbutyl]-2-(4-phenyl-1H-imidazol-1-yl)pyridine-3-carboxamide Coupling of 0.39 g of 3-amino-2-hydroxy-5-methylhexanamide hydrochloride (1.0 mmol) with 2-(4-phenyl-1H-imidazol-1-yl)pyridine-3-carboxylic acid in a manner analogous to Example 3.3 afforded 280 mg of the title compound as a white amorphous solid.
ESI-MS [M+H]$^+$=442.4.

7.2 N-{1-[Amino(oxo)acetyl]-3-methylbutyl}-2-(4-phenyl-1H-imidazol-1-yl)nicotinamide Oxidation of 200 mg of N-[3-amino-2-hydroxy-3-oxo-1-(phenylmethyl)propyl]-2-(4-phenyl-1H-pyrazol-1-yl)pyridine-3-carboxamide (0.49 mmol) afforded 102 mg of the title compound as a pale solid.
ESI-MS [M+H]$^+$=406.24.
$^1$H-NMR (500 MHz DMSO) δ ppm: 9.18 (d, 1H), 8.69 (d, 1H), 8.13 (m, 2H), 8.01 (dd, 1H), 7.95 (s, 1H), 7.85 (m, 3H), 7.61 (m, 1H), 7.41 (m, 2H), 7.27 (m, 1H), 5.25 (m, 1H), 1.65 (m, 1H), 1.53 (dd, 1H), 1.44 (dd, 1H).

The compounds of Examples 8 to 13 can be prepared in a manner analogous to the above examples.

Example 8

N-(3-Amino-1-benzyl-2,3-dioxopropyl)-2-[4-(4-fluorophenyl)-1H-imidazol-1-yl]nicotinamide ESI-MS [M+H]$^+$=458.15.
$^1$H-NMR (500 MHz DMSO) δ ppm: 9.34 (m, 1H), 8.63 (m, 1H), 8.16 (s, 1H), 8.03 (s, 1H), 7.91-7.75 (m, 5H), 7.56 (m, 1H), 7.31-7.20 (m, 7H), 5.50 (m, 1H), 3.22 (m overlapped by $H_2O$), 2.83 (dd, 1H).

Example 9

N-(3-Amino-1-benzyl-2,3-dioxopropyl)-2-[4-(4-chlorophenyl)-1H-imidazol-1-yl]nicotinamide ESI-MS [M+H]$^+$=474.15.
$^1$H-NMR (500 MHz DMSO) δ ppm: 9.38 (m, 1H), 8.64 (m, 1H), 8.16 (s, 1H), 8.05 (s, 1H), 7.94-7.91 (m, 2H), 7.83-7.81 (m, 2H), 7.76 (m, 1H), 7.56 (m, 1H), 7.45 (m, 2H), 7.31-7.21 (m, 5H), 5.45 (m, 1H), 3.23 (m overlapped by $H_2O$), 2.82 (dd, 1H).

Example 10

N-{1-[Amino(oxo)acetyl]pentyl}-2-[4-(4-chlorophenyl)-1H-imidazol-1-yl]nicotinamide ESI-MS [M+H]$^+$=440.2.
$^1$H-NMR (500 MHz DMSO) δ ppm: 9.20 (m, 1H), 8.69 (dd, 1H), 8.17 (s, 1H), 8.14 (m, 1H), 8.03 (m, 2H), 7.89 (m, 3H), 7.61 (dd, 1H), 7.48 (m, 1H), 7.46 (m, 1H), 5.18 (m, 1H), 1.78 and 1.52 (each dd, 1H), 1.26 (m, 4H), 0.79 (m, 3H).

Example 11

N-{1-[Amino(oxo)acetyl]pentyl}-2-[4-(4-fluorophenyl)-1H-imidazol-1-yl]nicotinamide ESI-MS [M+H]$^+$=424.2.
$^1$H-NMR (500 MHz DMSO) δ ppm: 9.17 (m, 1H), 8.68 (m, 1H), 8.13 (m, 1H), 8.11 (m, 1H), 8.03 (m, 1H), 7.97 (s, 1H), 7.91-7.86 (m, 3H), 7.60 (m, 1H), 7.24 (m 3H), 5.17 (m, 1H), 1.78 (m, 1H), 1.52 (m, 1H), 1.27 (m, 4H), 0.79 (m, 3H).

Example 12

N-{1-[Amino(oxo)acetyl]pentyl}-2-[4-(4-methoxyphenyl)-1H-imidazol-1-yl]nicotinamide ESI-MS [M+H]$^+$=436.25.
$^1$H-NMR (500 MHz DMSO) δ ppm: 9.19 (m, 1H), 8.66 (m, 1H), 8.11 (m, 2H), 8.01 (m, 1H), 7.85 (m, 2H), 7.71 (m, 2H), 7.58 (m, 1H), 6.99 (m, 2H), 5.19 (m, 1H), 3.79 (s, 3H), 1.79 (m, 1H), 1.52 (m, 1H), 1.29 (m, 4H), 0.80 (m, 3H).

Example 13

N-(3-Amino-1-benzyl-2,3-dioxopropyl)-2-[4-(4-methoxyphenyl)-1H-imidazol-1-yl]nicotinamide $^1$H-NMR (500 MHz DMSO) δ ppm: 9.45 (d, 1H), 8.66 (dd, 1H), 8.28 (s, 1H), 8.19 (s, 1H), 7.94 (s, 1H), 7.87 (s, 1H), 7.81 (m, 2H), 7.75 (m, 2H), 7.61 (m, 1H), 7.30-7.24 (m, 5H), 7.01 (d, 1H), 5.46 (m, 1H), 3.82 (s, 3H), 3.26 (dd, 1H), 2.85 (dd, 1H).

Example 14

N-(3-Amino-1-benzyl-2,3-dioxopropyl)-2-[4-(4-morpholin-4-ylphenyl)-1H-imidazol-1-yl]nicotinamide

14.1 4-[4-(1H-Imidazol-4-yl)phenyl]morpholine 3.0 g of 2-bromo-1-(4-morpholin-4-ylphenyl)ethanone and 8 ml of formamide were heated in a microwave at 180° C. for about 30 minutes. The mixture was then poured into 150 ml of H$_2$O, the pH was adjusted to 10-12 by adding 2N NaOH solution, and the resulting solid was filtered off with suction and dried, resulting in 2.2 g of the title compound.
ESI-MS [M+H]$^+$=230.1.

14.2 Ethyl 2-[4-(4-morpholin-4-ylphenyl)-1H-imidazol-1-yl]pyridine-3-carboxylate Starting from 0.9 g of 4-[4-(1H-imidazol-4-yl)phenyl] morpholine (3.93 mmol) and reaction in analogy to Example 3.2 resulted in 0.6 g of the title compound as a dark oil.
ESI-MS [M+H]$^+$=379.15.

Further reactions took place in a manner analogous to the above examples, resulting in 78 mg of N-(3-amino-1-benzyl-2,3-dioxopropyl)-2-[4-(4-morpholin-4-ylphenyl)-1H-imidazol-1-yl]nicotinamide.
ESI-MS [M+H$_2$O+H+]=543.2.

Example 15

N-{1-[Amino(oxo)acetyl]pentyl}-2-[4-(4-morpholin-4-ylphenyl)-1H-imidazol-1-yl]nicotinamide hydrochloride The title compound was prepared in a manner analogous to the above examples. ESI-MS [M+H]$^+$=491.29.

Example 16

N-(3-Amino-1-benzyl-2,3-dioxopropyl)-2-{4-[4-(diethylamino)phenyl]-1H-imidazol-1-yl}nicotinamide hydrochloride

16.1 N,N-Diethyl-4-(1H-imidazol-4-yl)aniline

Preparation took place in a manner analogous to Example 14.1. Chromatography on silica gel (eluent: CH$_2$Cl$_2$/methanol 2-7%) resulted in 1.1 g of the title compound as a dark solid.
ESI-MS [M+H]$^+$=216.15.

The title compound was prepared in a manner analogous to the above examples, resulting in 32 mg of N-(3-amino-1-benzyl-2,3-dioxopropyl)-2-{4-[4-(diethylamino)phenyl]-1H-imidazol-1-yl}nicotinamide hydrochloride.
$^1$H-NMR (500 MHz DMSO) δ ppm: 9.43 (s, 1H), 8.64 (s, 1H), 8.21 (s, 1H), 8.04 (s, 1H), 7.95 (s, 1H), 7.75 (d, 1H), 7.68-7.52 (m, 5H), 7.35-7.17 (m, 7H), 6.72 (s broad, 2H), 5.47 (m, 1H), 3.38 and 3.28 (overlapped by H$_2$O), 2.86 (dd, 1H), 1.14 (m, 6H).

Example 17

N-{1-[Amino(oxo)acetyl]pentyl}-2-{4-[4-(trifluoromethyl)phenyl]-1H-imidazol-1-yl}nicotinamide hydrochloride The title compound was prepared in a manner analogous to the above examples. ESI-MS [M+H]$^+$=474.21.
$^1$H-NMR (500 MHz DMSO) δ ppm: 9.24 (m, 1H), 8.74 (m, 1H), 8.63 (s, 1H), 8.31 (s, 1H), 8.15-8.12 (m, 4H), 7.88 (s, 1H), 7.90 (m, 2H), 7.71 (m, 1H), 6.13 (s broad, 5.17 (m, 1H), 1.78 (m, 1H), 1.52 (m, 1H), 1.25 (m, 4H), 0.77 (m, 3H).

Example 18

N-(3-Amino-1-benzyl-2,3-dioxopropyl)-2-{4-[4-(trifluoromethyl)phenyl]-1H-imidazol-1-yl}nicotinamide hydrochloride The title compound was prepared in a manner analogous to the above examples. ESI-MS [M+H]$^+$=508.26.
$^1$H-NMR (500 MHz DMSO) δ ppm: 9.46 (m, 1H), 8.69 (m, 1H), 8.37 (s, 1H), 8.20 (m, 2H), 8.07 (m, 2H), 7.95 (s, 1H), 7.86 (m, 3H), 7.65 (m, 1H), 7.28 (m, 4H), 7.21 (m, 1H), 5.47 (m, 1H), 5.27 (s broad), 3.26 and 2.86 (each dd, 1H).

Example 19

N-(3-Amino-1-benzyl-2,3-dioxopropyl)-2-[4-(2-chlorophenyl)-1H-imidazol-1-yl]nicotinamide hydrochloride The title compound was prepared in a manner analogous to the above examples. ESI-MS [M+H$_2$O+H+]=492.17.

$^1$H-NMR (500 MHz DMSO) δ ppm: 9.46 (m, 1H), 8.71 (m, 2H), 8.14 (s, 2H), 8.04 (d, 1H), 7.93 (dd, 1H), 7.69 (m, 1H), 7.58 (d, 1H), 7.49 (m, 1H), 7.42 (m, 1H), 7.24 (m, 5H), 7.14 (m, 1H), 5.45 (m, 1H), 3.23 and 2.84 (each dd, 1H).

Example 20

N-{1-[Amino(oxo)acetyl]pentyl}-2-[4-(2-chlorophenyl)-1H-imidazol-1-yl]nicotinamide hydrochloride The title compound was prepared in a manner analogous to the above examples. The crude product was purified by chromatography on silica gel (eluent: CH$_2$Cl$_2$/methanol 1-10%) and lyophilized after addition of 1 equivalent of HCl to afford 50 mg of the title compound as a white solid.

ESI-MS [M+H]$^+$=440.21.

$^1$H-NMR (500 MHz DMSO) δ ppm: 9.17 (d, 1H), 8.72 (m, 1H), 8.49 (s, 1H), 8.21 (s, 1H), 8.15 (m, 1H), 8.08 (m, 1H), 8.06 (m, 1H), 7.85 (s, 1H), 7.67 (dd, 1H), 7.56 (d, 1H), 7.46 (m, 1H), 7.36 (m, 1H), 5.16 (m, 1H), 4.09 (s broad), 1.75 and 1.49 (each m, 1H), 1.21 (m, 4H), 0.74 (m, 3H).

Example 21

N-{1-[Amino(oxo)acetyl]pentyl}-2-[4-(3-chlorophenyl)-1H-imidazol-1-yl]nicotinamide The title compound was prepared in a manner analogous to the above examples. ESI-MS [M+H]$^+$=440.21.

$^1$H-NMR (500 MHz DMSO) δ ppm: 9.16 (m, 1H), 8.69 (m, 1H), 8.14-8.03 (m, 4H), 7.91-7.82 (m, 3H), 7.62 (m 1H), 7.44 (m, 1H), 7.32 (m, 1H), 5.16 (m, 1H), 1.78 (m, 1H), 1.51 (m, 1H), 1.25 (m, 4H), 0.79 (m, 3H).

Example 22

N-(3-Amino-1-benzyl-2,3-dioxopropyl)-2-[4-(3-chlorophenyl)-1H-imidazol-1-yl]nicotinamide The title compound was prepared in a manner analogous to the above examples. ESI-MS [M+H$_3$O]$^+$=492.14.

$^1$H-NMR (500 MHz DMSO) δ ppm: 9.40 (dd, 1H), 8.66 (m, 1H), 8.16 (s, 1H), 8.04 (m, 2H), 7.95 (s, 1H), 7.89 (s, 1H), 7.78 (m, 2H), 7.59 (m, 1H), 7.45 (m, 1H), 7.33-7.25 (m, 5H), 7.22 (m, 1H), 5.46 (m, 1H), 3.26 (dd, overlapped by H$_2$O), 2.84 (dd, 1H).

Example 23

N-(3-Amino-1-benzyl-2,3-dioxopropyl)-5-chloro-2-(4-phenyl-1H-imidazol-1-yl)nicotinamide hydrochloride 5.4 g of methyl 2,5-dichloronicotinate (26.2 mmol) and 2.8 g of 4-phenylimidazole were reacted in a manner analogous to Example 3.1. Purification by chromatography resulted in 1.7 g of methyl 5-chloro-2-(4-phenyl-1H-imidazol-1-yl)pyridine-3-carboxylate as a dark oil.

ESI-MS [M+H]$^+$=314.05.

The title compound was prepared in a manner analogous to the above examples starting from methyl 5-chloro-2-(4-phenyl-1H-imidazol-1-yl)pyridine-3-carboxylate. 110 mg of the title compound were obtained as a pale solid.

ESI-MS [M+H$_2$O+H+]=492.11.

$^1$H-NMR (500 MHz DMSO) δ ppm: 9.54 (dd, 1H), 8.83 (s, 1H), 8.59 (s, 1H), 8.18 (s, 1H), 8.07 (s, 1H), 7.95 (m, 2H), 7.85 (m, 2H), 7.48 (m, 2H), 7.37 (m, 1H), 7.27 (m, 4H), 7.21 (m, 1H), 5.45 (m, 1H), 4.97 (s broad), 3.26 and 2.89 (each dd, 1H).

Example 24

N-{1-[Amino(oxo)acetyl]pentyl}-5-chloro-2-(4-phenyl-1H-imidazol-1-yl)nicotinamide hydrochloride The title compound was prepared in a manner analogous to the above examples. ESI-MS [M+H]$^+$=440.19.

$^1$H-NMR (500 MHz DMSO) δ ppm: 9.26 (m, 1H), 8.77 (m, 1H), 8.16 (m, 1H), 8.13 (m, 2H), 7.96 (s, 1H), 7.89-7.84 (m, 3H), 7.41 (m, 2H), 7.27 (m, 1H), 5.19 (m, 1H), 1.79 and 1.54 (each m, 1H), 1.28 (m, 4H), 0.80 (m, 3H).

Example 25

N-{1-[Amino(oxo)acetyl]-3-methylbutyl}-5-chloro-2-(4-phenyl-1H-imidazol-1-yl)nicotinamide The title compound was prepared in a manner analogous to the above examples. ESI-MS [M+H]$^+$=440.2.

$^1$H-NMR (500 MHz DMSO) δ ppm: 9.26 (m, 1H), 8.78 (m, 1H), 8.13 (m, 3H), 7.94 (s, 1H), 7.85 (m, 3H), 7.41 (m, 2H), 7.28 (m, 1H), 5.26 (m, 1H), 1.68 (m, 1H), 1.54 (m, 1H), 1.44 (m, 1H), 0.87 (m, 6H).

Example 26

N-(3-Amino-1-benzyl-2,3-dioxopropyl)-2-{4-[4-(morpholin-4-ylmethyl)phenyl]-1H-imidazol-1-yl}nicotinamide hydrochloride 26.1 1-[4-(Morpholin-4-ylmethyl)phenyl]ethanone 4.7 g of 1,4-dihydro-2,6-dimethyl-3,5-pyridinecarboxylate and 1.3 g of scandium triflate were added to 2.75 g of 4-acetylbenzaldehyde (18.56 mmol), 1.7 ml of morpholine and 3 g of 4 Å molecular sieves in 100 ml of tetrahydrofuran under argon, and the mixture was heated to reflux for 3 hours. The mixture was concentrated. The residue was mixed with ethyl acetate and washed with sat. NaHCO$_3$ solution and sat. NaCl solution. Drying and evaporation of the mixture resulted in a crude product which was purified by chromatography on silica gel (eluent: cyclohexane/ethyl acetate 40-80%). 1.85 g of a yellowish oil were obtained.

ESI-MS [M+H]$^+$=220.1.

26.2 4-{[4-(1H-Imidazol-4-yl)phenyl]methyl}morpholine 0.55 ml of bromine (dissolved in 5 ml of 47% HBr) was added dropwise to 1.76 g of 1-[4-(morpholin-4-ylmethyl)phenyl]ethanone (8.03 mmol) in 15 ml of 47% HBr at 5° C., and the mixture was stirred at room temperature for about 2 hours. Water was then added to the reaction mixture, and it was neutralized by adding NaHCO$_3$ and extracted with dichloromethane. The combined organic phases were washed with saturated NaCl solution, dried and evaporated. The resulting yellowish oil (2.7 g) was mixed with 8 ml of formamide and heated in a microwave at 185° C. for 30 minutes. The reaction mixture was worked up by diluting with H$_2$O, adjusting the pH to 11-12 by adding 2N NaOH, extracting with dichloromethane and washing the combined organic phases anew with saturated NaCl solution. Drying of the organic phase and evaporation of the solvent was followed by treating the remaining residue with methyl tert-butyl ether, resulting in 1.3 g of the title compound as a brown oil.

ESI-MS [M+H]$^+$=244.15.

The title compound was prepared in a manner analogous to the above examples. 115 mg of N-(3-amino-1-benzyl-2,3-dioxopropyl)-2-{4-[4-(morpholin-4-ylmethyl)phenyl]-1H-imidazol-1-yl}nicotinamide were obtained as hydrochloride.

ESI-MS [M+H]$^+$=541.1.

Example 27

N-(3-Amino-1-benzyl-2,3-dioxopropyl)-5-chloro-2-(3-phenyl-1H-pyrazol-1-yl)nicotinamide The title compound was prepared in a manner analogous to the above examples. ESI-MS [M+H]$^+$=474.2.

$^1$H-NMR (500 MHz DMSO) δ ppm: 9.02 (d, 1H), 8.64 (d, 1H), 8.48 (s, 1H), 8.10 (s, 1H), 7.88 (s, 1H), 7.75 (m, 2H), 7.66 (d, 1H), 7.38 (m, 3H), 7.21 (m, 6H), 5.59 (m, 1H), 3.20 (dd, 1H), 2.83 (dd, 1H).

Example 28

N-{1-[Amino(oxo)acetyl]pentyl}-5-chloro-2-(3-phenyl-1H-pyrazol-1-yl)nicotinamide The title compound was prepared in a manner analogous to the above examples. ESI-MS [M+H]$^+$=440.2.

$^1$H-NMR (500 MHz DMSO) δ ppm: 8.84 (dd, 1H), 8.67 (s, 1H), 8.52 (s, 1H), 8.05 (s, 1H), 7.94 (s, 1H), 7.84 (m, 3H), 7.45 (m, 2H), 7.39 (m, 1H), 7.08 (s, 1H), 5.19 (m, 1H), 1.75 (m, 1H), 1.49 (m, 1H), 1.17 (m, 4H), 0.71 (m, 3H).

Example 29

N-(3-Amino-1-benzyl-2,3-dioxopropyl)-2-[3-(4-morpholin-4-ylphenyl)-1H-pyrazol-1-yl]nicotinamide hydrochloride 29.1 4-[4-(1H-Pyrazol-3-yl)phenyl]morpholine A mixture of 2.05 g of 4-morpholinoacetophenone (10 mmol) and N,N-dimethylformamide dimethyl acetal was heated under reflux for 7 hours. The mixture was then mixed with 30 ml of methanol and, after addition of 0.57 ml of hydrazine hydrate, again heated under reflux for about 6 hours. The solid formed on cooling the mixture was filtered off with suction and thoroughly washed with methanol, resulting in 3.8 g of the title compound.

ESI-MS [M+H]$^+$=230.1.

The title compound was prepared in a manner analogous to the above examples. 82 mg of N-(3-amino-1-benzyl-2,3-dioxopropyl)-2-[3-(4-morpholin-4-ylphenyl)-1H-pyrazol-1-yl]nicotinamide hydrochloride were obtained.

ESI-MS [M+H]$^+$=525.3.

$^1$H-NMR (500 MHz DMSO) δ ppm: 8.93 (d, 1H), 8.54 (d, 1H), 8.45 (d, 1H), 8.08 (s, 1H), 7.86 (s, 1H), 7.70 (m, 3H), 7.46 (dd, 1H), 7.30 (m, 8H), 6.94 (d, 1H), 5.58 (m, 1H), 4.86 (s broad), 3.87 (m, 4H), 3.29 (m, 4H), 3.16 (dd, 1H), 2.81 (dd, 1H).

Example 30

N-{1-[Amino(oxo)acetyl]-3-methylbutyl}-2-(3-phenyl-1H-pyrazol-1-yl)nicotinamide

The title compound was prepared in a manner analogous to the above examples. ESI-MS [M+H]$^+$=406.02.

$^1$H-NMR (500 MHz DMSO) δ ppm: 8.73 (d, 1H), 8.58 (dd, 1H), 8.49 (d, 1H), 8.01 (s, 1H), 7.89 (dd, 1H), 7.85 (m, 2H), 7.78 (s broad, 1H), 7.51 (dd, 1H), 7.44 (m, 2H), 7.37 (m, 1H), 7.03 (d, 1H), 5.25 (m, 1H), 1.60 (m, 1H), 1.47 (m, 1H), 1.35 (m, 1H), 0.79 and 0.76 (each d, 3H).

Example 31

N-(3-Amino-1-benzyl-2,3-dioxopropyl)-5-chloro-2-[3-(4-morpholin-4-ylphenyl)-1H-pyrazol-1-yl]nicotinamide The title compound was prepared in a manner analogous to the above examples. ESI-MS [M+H]$^+$=559.2.

$^1$H-NMR (500 MHz DMSO) δ ppm: 8.96 (d, 1H), 8.57 (d, 1H), 8.38 (d, 1H), 8.08 (s, 1H), 7.87 (s, 1H), 7.59 (dd, 1H), 7.18 (m, 5H), 0.89 (m, 3H), 5.57 (m, 1H), 3.74 (m, 4H), 3.14 (m, 5H), 2.81 (dd, 1H).

Example 32

N-{1-[Amino(oxo)acetyl]-3-methylbutyl}-5-chloro-2-(3-phenyl-1H-pyrazol-1-yl)nicotinamide The title compound was prepared in a manner analogous to the above examples. ESI-MS [M+H+]=440.04.

$^1$H-NMR (500 MHz DMSO) δ ppm: 8.34 (d, 1H), 8.67 (s, 1H), 8.50 (s, 1H), 8.03 (s, 1H), 7.95 (s, 1H), 7.83 (m, 3H), 7.40-7.37 (3H), 7.07 (d, 1H), 5.25 (m, 1H), 1.62 (m, 1H), 1.51 (m, 1H), 1.41 (m, 1H), 0.80 (m, 6H).

Example 33

N-{1-[Amino(oxo)acetyl]pentyl}-2-[3-(4-morpholin-4-ylphenyl)-1H-pyrazol-1-yl]nicotinamide The title compound was prepared in a manner analogous to the above examples. ESI-MS [M+H+]=491.1.

$^1$H-NMR (500 MHz DMSO) δ ppm: 8.70 (d, 1H), 8.55 (d, 1H), 8.46 (d, 1H), 8.03 (s, 1H), 7.85 (d, 1H), 7.80 (s, 1H), 7.72 (m, 2H), 7.47 (dd, 1H), 7.01 (m, 2H), 6.93 (m, 1H), 5.18 (m, 1H), 3.85 (s broad, overlapped by H$_2$O), 3.19 (m, 4H), 1.72 (m, 1H), 1.47 (m, 1H), 1.25-1.15 (m, 4H), 0.82 (m, 3H).

Example 34

N-{1-[Amino(oxo)acetyl]-3-methylbutyl}-2-[3-(4-morpholin-4-ylphenyl)-1H-pyrazol-1-yl]nicotinamide The title compound was prepared in a manner analogous to the above examples. ESI-MS [M+H]$^+$=491.2.

$^1$H-NMR (500 MHz DMSO) δ ppm: 8.71 (d, 1H), 8.56 (d, 1H), 8.45 (d, 1H), 8.02 (s, 1H), 7.87 (d, 1H), 7.79 (s, 1H), 7.71

(m, 2H), 7.48 (dd, 1H), 7.02 (d, 1H), 6.92 (m, 1H), 5.28 (m, 1H), 3.78 (m broad, 4H), 3.20 (m, 4H), 1.63 (m, 1H), 1.48 (m, 1H), 1.39 (m, 1H), 0.81 (m, 6H).

Example 35

N-(3-Amino-1-benzyl-2,3-dioxopropyl)-2-(3-pyridin-2-yl-1H-pyrazol-1-yl)nicotinamide The title compound was prepared in a manner analogous to the above examples. $^1$H-NMR (500 MHz DMSO) δ ppm: 8.97 (d, 1H), 8.60 (m, 2H), 8.49 (m, 2H), 8.08 (s, 1H), 7.85 (s, 1H), 7.80-7.69 (m, 3H), 7.51 (m, 1H), 7.35 (m, 1H), 7.19-7.13 (m, 5H), 7.04 (m, 1H), 5.55 (m, 1H), 3.15 (m, 1H), 2.79 (m, 1H).

Example 36

N-{1-[Amino(oxo)acetyl]pentyl}-2-(3-pyridin-2-yl-1H-pyrazol-1-yl)nicotinamide

The title compound was prepared in a manner analogous to the above examples. ESI-MS [M+H]$^+$=407.2.

$^1$H-NMR (500 MHz DMSO) δ ppm: 8.73 (d, 1H), 8.62 (m, 2H), 8.53 (d, 1H), 8.03 (s, 1H), 7.90 (m, 3H), 7.79 (s, 1H), 7.54 (dd, 1H), 7.38 (m, 1H), 7.08 (d, 1H), 5.18 (m, 1H), 1.71 (m, 1H), 1.44 (m, 1H), 1.11 (m, 4H), 0.67 (m, 3H).

Example 37

N-{1-[Amino(oxo)acetyl]pentyl}-2-[3-(4-chlorophenyl)-1H-pyrazol-1-yl]nicotinamide The title compound was prepared in a manner analogous to the above examples. ESI-MS [M+H]$^+$=440.05.

$^1$H-NMR (500 MHz DMSO) δ ppm: 8.71 (d, 1H), 8.59 (d, 1H), 8.52 (s broad, 1H), 8.04 (s, 1H), 7.98-7.88 (m, 3H), 7.81 (s, 1H), 7.51 (m, 3H), 7.08 (m, 1H), 5.17 (m, 1H), 1.70 (m, 1H), 1.44 (m, 1H), 1.12 (m, 4H), 0.69 (m, 3H).

Example 38

N-(3-Amino-1-benzyl-2,3-dioxopropyl)-2-[3-(4-fluorophenyl)-1H-pyrazol-1-yl]nicotinamide The title compound was prepared in a manner analogous to the above examples. ESI-MS [M+H]$^+$=458.1.

$^1$H-NMR (500 MHz DMSO) δ ppm: 8.93 (d, 1H), 8.55 (dd, 1H), 8.47 (d, 1H), 8.09 (s, 1H), 7.87 (s, 1H), 7.78 (m, 2H), 7.71 (m, 1H), 7.48 (dd, 1H), 7.20-7.16 (m, 7H), 7.0 (m, 1H), 5.58 (m, 1H), 3.15 (m, 1H), 2.79 (m, 1H).

Example 39

N-(3-Amino-1-benzyl-2,3-dioxopropyl)-2-[3-(4-chlorophenyl)-1H-pyrazol-1-yl]nicotinamide The title compound was prepared in a manner analogous to the above examples. ESI-MS [M+H]$^+$=474.05.

$^1$H-NMR (500 MHz DMSO) δ ppm: 8.94 (dd, 1H), 8.57 (dd, 1H), 8.48 (d, 1H), 8.10 (s, 1H), 7.88 (s, 1H), 7.77 (m, 2H), 7.72 (dd, 1H), 7.48 (dd, 1H), 7.44 (m, 2H), 7.19 (m, 5H), 7.04 (m, 1H), 5.56 (m, 1H), 3.15 and 2.78 (each dd, 1H).

Example 40

N-[3-Amino-2,3-dioxo-1-(2-thienylmethyl)propyl]-2-(3-phenyl-1H-pyrazol-1-yl)pyridine-3-carboxamide

40.1 Phenylmethyl [2-hydroxy-1-(2-thienylmethyl)ethyl]carbamate 24.8 g of 3-(2-thienyl)alanine (144.8 mmol) were added in portions to 11.0 g of LiAlH$_4$ in 550 ml of tetrahydrofuran, heated to reflux. The mixture was then heated under reflux for 8 hours and subsequently stirred at room temperature overnight. 17.6 ml of 10% NaOH solution were added and then 22 ml of H$_2$O were slowly added dropwise, and the mixture was stirred for 5 minutes. Then, first 391 ml of 10% NaOH solution and subsequently, at −5° C., 22.2 g of benzyl chloroformate (130.32 mmol) were added, and the mixture was stirred at room temperature for 3 hours. For workup, the mixture was extracted with dichloromethane, the organic phase was dried, the solvent was evaporated and the remaining residue was filtered through silica gel (eluent: CH$_2$Cl$_2$/methanol 2.5%). 36.8 g of the title compound were obtained as a yellowish oil.
ESI-MS [M+H]$^+$=292.

40.2 Phenylmethyl [3-amino-2-hydroxy-3-oxo-1-(2-thienylmethyl)propyl]carbamate 40.2 g of pyridine-SO$_3$ complex were added in portions to a mixture of 36.8 g of phenylmethyl [2-hydroxy-1-(2-thienylmethyl)ethyl]carbamate (126.3 mmol) and 51.2 g of triethylamine in 220 ml of dimethyl sulfoxide at about 16° C., and the mixture was stirred at room temperature for 3 hours. It was then poured into ice-water (1.5 l) and extracted with ethyl acetate, and the organic phase was washed with 1N HCl and sat. NaCl solution, dried and evaporated. The resulting oil (38 g) was dissolved in 150 ml of tetrahydrofuran, and a solution of 44.4 g of NaCN in 225 ml of saturated NaHCO$_3$ solution was added dropwise. After 2 hours, the phases were separated, the aqueous phase was extracted with ethyl acetate, and the combined organic phases were washed with H$_2$O and saturated NaCl solution, dried and concentrated. The residue obtained in this way was again dissolved in 400 ml of tetrahydrofuran and, over the course of 30 minutes, 65 ml of conc. HCl and 150 ml of conc. H$_2$SO$_4$ were added dropwise in parallel while cooling in ice, and the mixture was stirred at room temperature. After the reaction was complete, the reaction mixture was poured into ice-water and extracted with ethyl acetate, and the organic phase was washed with 1N NaOH and sat. NaCl solution, dried and concentrated. The remaining oily residue was stirred with diethyl ether, and the resulting solid was filtered off with suction and dried, resulting in 16.3 g of the title compound as a whitish gray amorphous solid.
ESI-MS [M+H]$^+$=335.

40.3 3-Amino-2-hydroxy-4-(2-thienyl)butanamide 70 ml of 30% HBr in glacial acetic acid were added to 11 g of phenylmethyl [3-amino-2-hydroxy-3-oxo-1-(2-thienylmethyl)propyl]carbamate (29.66 mmol) in 30 ml of glacial acetic acid. After about 2 hours, the mixture was concentrated and the resulting residue was stirred firstly with cyclohexane and then with dichloromethane. 7.8 g of the title compound were obtained as hydrobromide.

ESI-MS [M+H]$^+$=201.

The title compound was prepared in a manner analogous to the above examples, resulting in 25 mg of N-[3-amino-2,3-dioxo-1-(2-thienylmethyl)propyl]-2-(3-phenyl-1H-pyrazol-1-yl)pyridine-3-carboxamide as a white solid.

ESI-MS [M+H]$^+$=446.05.

$^1$H-NMR (500 MHz DMSO) δ ppm: 9.01 (d, 1H), 8.59 (m, 1H), 8.50 (m, 1H), 8.05 (s, 1H), 7.84-7.78 (m, 4H), 7.50 (m, 1H), 7.41 (m, 2H), 7.36-7.31 (m, 2H), 7.02 (m, 1H), 6.84 (m, 2H), 5.52 (m, 1H), 3.38 and 3.12 (each dd, 1H).

Example 41

N-{1-[Amino(oxo)acetyl]pentyl}-2-[3-(4-fluorophenyl)-1H-pyrazol-1-yl]nicotinamide The title compound was prepared in a manner analogous to the above examples.

ESI-MS [M+H]$^+$=424.05.

$^1$H-NMR (500 MHz DMSO) δ ppm: 8.71 (d, 1H), 8.57 (d, 1H), 8.51 (m, 1H), 8.03 (s, 1H), 7.89 (m, 2H), 7.80 (s, 1H), 7.51 (m, 1H), 7.28 (m, 1H), 7.04 (s, 1H), 5.17 (m, 1H), 1.70 (m, 1H), 1.44 (m, 1H), 1.13 (m, 4H), 0.70 (m, 3H).

Example 42

N-(3-Amino-1-benzyl-2,3-dioxopropyl)-2-{3-[4-(diethylamino)phenyl]-1H-pyrazol-1-yl}nicotinamide The title compound was prepared in a manner analogous to the above examples. ESI-MS [M+H]$^+$=511.3.

$^1$H-NMR (500 MHz DMSO) δ ppm: 8.91 (d, 1H), 8.52 (d, 1H), 8.41 (d, 1H), 8.07 (s, 1H), 7.82 (s, 1H), 7.71 (d, 1H), 7.56 (m, 2H), 7.42 (dd, 1H), 7.21 (m, 5H), 6.82 (d, 1H), 6.66 and 6.63 (each s, 1H), 5.57 (m, 1H), 3.39 (m, 4H), 3.17 and 2.84 (each dd, 1H), 1.15 (m, 6H).

Example 43

N-(3-Amino-1-benzyl-2,3-dioxopropyl)-2-(3-{4-[(diethylamino)methyl]phenyl}-1H-pyrazol-1-yl)nicotinamide hydrochloride 43.1 1-{4-[(Diethylamino)methyl]phenyl}ethanone 5.3 g of diethylamine were added to 10 g of 4-[chloromethyl]benzonitrile (65.96 mmol), 18.24 g of K$_2$CO$_3$ and 1.1 g of KI in 150 ml of N,N-dimethylformamide at room temperature, and the mixture was stirred at room temperature until the reaction was complete. The mixture was then poured into ice-water and extracted with diethyl ether, and the organic phase was washed with saturated NaCl solution, dried and evaporated, resulting in 12.1 g of 4-[diethylaminomethyl]benzonitrile as an oil.

ESI-MS [M+H]$^+$=189.05.

A solution of 12.1 g of 4-[diethylaminomethyl]benzonitrile in 40 ml of toluene was added to a solution of methylmagnesium bromide (43 ml of a 3 M solution in diethyl ether) in 40 ml of toluene, and the mixture was heated to reflux. Completion of the reaction was followed by pouring into ice-water, extracting with methyl tert-butyl ether, adjusting the aqueous phase to pH 11-12 by adding NaOH, and renewed extracting with methyl tert-butyl ether. The organic phase was dried and the solvent was evaporated. 12.1 g of the title compound were obtained.

ESI-MS [M+H]$^+$=206.15.

It was possible in a manner analogous to the above examples to prepare N-(3-amino-1-benzyl-2,3-dioxopropyl)-2-(3-{4-[(diethylamino)methyl]phenyl}-1H-pyrazol-1-yl)nicotinamide hydrochloride.

ESI-MS [M+H]$^+$=525.35.

$^1$H-NMR (500 MHz DMSO) δ ppm: 10.02 (s broad, 1H), 8.95 (d, 1H), 8.51 (d, 1H), 8.05 (s, 1H), 7.86-7.81 (m, 3H), 7.76 (m, 1H), 7.61 (m, 2H), 7.52 (m, 1H), 7.19-7.12 (m, 5H), 7.07 8m, 1H), 5.53 (m, 1H), 4.35 (d, 2H), 3.10 (m, 5H), 2.80 (dd, 1H), 1.29 (m, 6H).

It was possible to prepare the compounds of Examples 44 to 105 in a manner analogous to the above examples.

Example 44

N-{1-[Amino(oxo)acetyl]pentyl}-2-(3-{4-[(diethylamino)methyl]phenyl}-1H-pyrazol-1-yl)nicotinamide

ESI-MS [M+H]$^+$=491.35.

Example 45

N-{1-[Amino(oxo)acetyl]pentyl}-2-{3-[4-(morpholin-4-ylmethyl)phenyl]-1H-pyrazol-1-yl}nicotinamide

ESI-MS [M+H]$^+$=505.15.

$^1$H-NMR (500 MHz DMSO) δ ppm: 8.72 (d, 1H), 8.58 (d, 1H), 8.51 (m, 1H), 8.02 (s, 1H), 7.88 (d, 1H), 7.82-7.78 (m, 3H), 7.50 (dd, 1H), 7.38-7.36 (m, 2H), 7.02 (m, 1H), 5.16 (m, 1H), 3.61 (m, 4H), 3.52 (m, 2H), 2.40 (m, 4H), 1.71 and 1.43 (each m, 1H), 1.26-1.11 (m, 4H), 0.69 (m, 1H).

Example 46

N-(3-Amino-1-benzyl-2,3-dioxopropyl)-2-{3-[4-(morpholin-4-ylmethyl)phenyl]-1H-pyrazol-1-yl}nicotinamide

ESI-MS [M+H]$^+$=539.35

$^1$H-NMR (500 MHz DMSO) δ ppm: 8.92 (d, 1H), 8.56 (dd, 1H), 8.47 (d, 1H), 8.05 (s, 1H), 7.83 (s, 1H), 7.73 (m, 3H), 7.47 (dd, 1H), 7.33 (s, 1H), 7.31 (s, 1H), 7.17 (m, 5H), 6.98 (d, 1H), 5.56 (m, 1H), 3.61 (m, 4H), 3.51 (s, 2H), 3.12 (m, 1H), 2.82 (m, 1H), 2.39 (m, 4H).

Example 47

N-{1-[Amino(oxo)acetyl]pentyl}-2-{3-[4-(diethylamino)phenyl]-1H-pyrazol-1-yl}nicotinamide

ESI-MS [M+H]$^+$=477.15

$^1$H-NMR (500 MHz DMSO) δ ppm: 8.71 (d, 1H), 8.54 (d, 1H), 8.44 (m, 1H), 8.03 (s, 1H), 7.84 (d, 1H), 7.78 (s, 1H), 7.63 (m, 1H), 7.44 (m, 1H), 6.84 (s, 1H), 6.69 (m, 2H), 5.18 (m, 1H), 3.40 (m, 4H), 1.74 and 1.50 (each m, 1H), 1.30-1.12 (m, 10H), 0.75 (m, 3H).

Example 48

N-(3-Amino-1-benzyl-2,3-dioxopropyl)-2-[3-(4-methoxyphenyl)-1H-pyrazol-1-yl]nicotinamide ESI-MS [M+H]$^+$=470.45.
$^1$H-NMR (500 MHz DMSO) δ ppm: 8.92 (d, 1H), 8.54 (dd, 1H), 8.44 (d, 1H), 8.08 (s, 1H), 7.86 (s, 1H), 7.72-7.68 (m, 3H), 7.45 (dd, 1H), 7.21 (m, 5H), 6.96 (s, 1H), 6.93 (m, 2H), 5.59 (m, 1H), 3.82 (s, 3H), 3.16 and 2.81 (each dd, 1H).

Example 49

N-{1-[Amino(oxo)acetyl]pentyl}-2-[3-(4-methoxyphenyl)-1H-pyrazol-1-yl]nicotinamide ESI-MS [M+H]$^+$=436.45.
$^1$H-NMR (500 MHz DMSO) δ ppm: 8.72 (d, 1H), 8.56 (d, 1H), 8.47 (d, 1H), 8.03 (s, 1H), 7.87 (dd, 1H), 7.79-7.70 (m, 3H), 7.49 (m, 1H), 7.01 (s, 1H), 6.99 (s, 1H), 6.96 (dd, 1H), 5.18 (m, 1H), 3.83 (s, 3H), 1.73 and 1.47 (each m, 1H), 1.17 (m, 4H), 0.72 (m, 3H).

Example 50

N-[3-Amino-1-(4-chlorobenzyl)-2,3-dioxopropyl]-2-(3-phenyl-1H-pyrazol-1-yl)nicotinamide ESI-MS [M+H]$^+$=474.13.
$^1$H-NMR (500 MHz DMSO) δ ppm: 8.57 (dd, 1H), 8.48 (d, 1H), 8.07 (s, 1H), 7.86 (s, 1H), 7.78 (dd, 1H), 7.74 (m, 2H), 7.49 (dd, 1H), 7.41-7.30 (m, 3H), 7.18 (m, 4H), 7.0 (m, 1H), 5.50 (m, 1H), 3.12 and 2.77 (each m, 1H).

3-Amino-4-(4-chlorophenyl)-2-hydroxybutanamide was prepared in a manner analogous to the preparation of 3-amino-2-hydroxy-4-(2-thienyl)butanamide in Example 40.

Example 51

N-(3-Amino-1-benzyl-2,3-dioxopropyl)-5-fluoro-2-(3-phenyl-1H-pyrazol-1-yl)nicotinamide ESI-MS [M+H]$^+$=458.6.
$^1$H-NMR (500 MHz DMSO) δ ppm: 9.01 (d, 1H), 8.62 (d, 1H), 8.42 (d, 1H), 8.08 (s, 1H), 7.87 (s, 1H), 7.77 (s, 1H), 7.75 (s, 1H), 7.58 (dd, 1H), 7.42-7.32 (m, 3H), 7.23-7.17 (m, 5H), 7.02 (d, 1H), 5.58 (m, 1H), 3.17 and 2.83 (each dd, 1H).

Example 52

N-(3-Amino-1-benzyl-2,3-dioxopropyl)-2-{3-[3-(morpholin-4-ylmethyl)phenyl]-1H-pyrazol-1-yl}nicotinamide hydrochloride ESI-MS [M+H]$^+$=539.35.
$^1$H-NMR (500 MHz DMSO) δ ppm: 10.89 (s, broad, 1H), 8.96 (d, 1H), 8.58 (m, 1H), 8.49 (d, 1H), 8.08 (s, 2H), 7.84 (m, 2H), 7.76 (dd, 1H), 7.58 (m, 1H), 7.52-7.48 (m, 2H), 7.15 (5H), 7.03 (d, 1H), 5.52 (m, 1H), 4.38 (s broad, 2H), 3.95 and 3.77 (each m, 2H), 3.26 (dd, 1H), 3.10 (m, 4H), 2.80 (dd, 1H).

Example 53

N-{1-[Amino(oxo)acetyl]pentyl}-2-{3-[3-(morpholin-4-ylmethyl)phenyl]-1H-pyrazol-1-yl}nicotinamide hydrochloride ESI-MS [M+H]$^+$=505.35.
$^1$H-NMR (500 MHz DMSO) δ ppm: 11.03 (s broad, 1H), 8.72 (d, 1H), 8.60 (dd, 1H), 8.54 (d, 1H), 8.13 (s, 1H), 8.05 (s, 1H), 7.95-7.89 (m, 2H), 7.81 (m, 1H), 7.62 (m, 1H), 7.54 (m, 2H), 7.06 (d, 1H), 5.16 (m, 1H), 4.43 (s, 2H), 3.96 and 3.81 (each m, 2H), 3.3 (m, overlapped by H$_2$O), 3.15 (m, 2H), 1.67 and 1.43 (each m, 1H), 1.14 (m, 4H), 0.68 (m, 3H).

Example 54

N-(3-Amino-1-benzyl-2,3-dioxopropyl)-2-[3-(2-chlorophenyl)-1H-pyrazol-1-yl]nicotinamide ESI-MS [M+H]$^+$=474.06.
$^1$H-NMR (400 MHz DMSO) δ ppm: 8.94 (d, 1H), 8.57 (d, 1H), 8.50 (d, 1H), 7.98 (s, 1H), 7.80 (s, 1H), 7.70 (dd, 2H), 7.47-7.54 (m, 2H), 7.30-7.37 (m, 2H), 7.13 (s, 5H), 7.02 (s, 1H), 5.48-5.53 (m, 1H), 3.11 (dd, 1H), 2.77 (dd, 1H).

Example 55

N-(3-Amino-1-benzyl-2,3-dioxopropyl)-2-[3-(2-thienyl)-1H-pyrazol-1-yl]nicotinamide ESI-MS [M+H]$^+$=446.0.
$^1$H-NMR (400 MHz DMSO) δ ppm: 8.94 (d, 0.5H), 8.58 (s, 1H), 8.43 (s, 1H), 8.04 (s, 0.5H), 7.75-7.86 (m, 2H), 7.46-7.52 (m, 3H), 7.22-7.264 (m, 5H), 7.12 (s, 1H), 6.89 (s, 0.5H), 6.70 (s, 0.5H), 6.39 (s, 0.5H), 6.11 (s, 0.5H) 5.50-5.56 (m, 0.5H), 4.46-4.52 (m, 0.5H), 3.18 (dd, 0.5H), 3.06 (dd, 0.5H), 2.85-2.92 (m, 0.5H), 2.71-2.77 (m, 0.5H).

The compound is in the form of a mixture of carbonyl and hydrate forms.

Example 56

N-{1-[Amino(oxo)acetyl]pentyl}-2-(3-pyridin-4-yl-1H-pyrazol-1-yl)nicotinamide

ESI-MS [M+H]$^+$=407.15.
$^1$H-NMR (500 MHz DMSO) δ ppm: 8.75 (d, 1H), 8.65-8.58 (m, 3H), 8.03 (s, 1H), 7.93 (m, 1H), 7.80 (m, 3H), 7.56 (dd, 1H), 7.22 (d, 1H), 5.17 (m, 1H), 1.71 and 1.43 (each m, 1H), 1.12 (m, 4H), 0.69 (m, 3H).

Example 57

N-[3-Amino-2,3-dioxo-1-(2-thienylmethyl)propyl]-2-[3-(4-fluorophenyl)-1H-pyrazol-1-yl]nicotinamide ESI-MS [M+H]$^+$=464.45.
$^1$H-NMR (500 MHz DMSO) δ ppm: 8.75 (d, 1H), 8.65-8.58 (m, 3H), 8.03 (s, 1H), 7.93 (m, 1H), 7.80 (m, 3H), 7.56 (dd, 1H), 7.22 (d, 1H), 5.17 (m, 1H), 1.71 and 1.43 (each m, 1H), 1.12 (m, 4H), 0.69 (m, 3H).

Example 58

N-(3-Amino-1-benzyl-2,3-dioxopropyl)-2-[3-(3-morpholin-4-ylphenyl)-1H-pyrazol-1-yl]nicotinamide ESI-MS [M+H]$^+$=525.25.
$^1$H-NMR (500 MHz DMSO) δ ppm: 8.90 (d, 1H), 8.56 (dd, 1H), 8.47 (d, 1H), 8.02 (s, 1H), 7.81 (s, 1H), 7.75 (dd, 1H), 7.48 (m, 2H), 7.29 (m, 2H), 7.12 (m, 5H), 7.03 (d, 1H), 6.99 (m, 1H), 5.50 (m, 1H), 3.80 (m, 4H), 3.21 (m, 4H), 3.13 and 2.80 (each dd, 1H).

Example 59

N-{1-[Amino(oxo)acetyl]pentyl}-2-[3-(3-morpholin-4-ylphenyl)-1H-pyrazol-1-yl]nicotinamide ESI-MS [M+H]$^+$=491.25.
$^1$H-NMR (500 MHz DMSO) δ ppm: 8.68 (d, 1H), 5.57 (d, 1H), 8.51 (m, 1H), 8.00 (s, 1H), 7.86 (m, 1H), 7.78 (d, 1H), 7.50 (m, 1H), 7.44 (s, 1H), 7.31 (m, 2H), 7.04 (m, 1H), 6.95 (d, 1H), 5.14 (m, 1H), 3.81 (m, 4H), 3.20 (m, 4H), 1.67 (m, 1H), 1.45 (m, 1H), 1.14 (m, 4H), 0.67 (m, 3H).

Example 60

N-(3-Amino-1-benzyl-2,3-dioxopropyl)-2-{3-[4-(trifluoromethyl)phenyl]-1H-pyrazol-1-yl}nicotinamide ESI-MS [M+H]$^+$=508.0.
$^1$H-NMR (400 MHz DMSO) δ ppm: 8.95 (d, 1H), 8.57 (d, 1H), 8.51 (d, 1H), 8.10 (s, 1H), 7.94 (d, 2H), 7.86 (s, 1H), 7.74 (d, 1H), 7.71 (d, 2H), 7.50 (dd, 1H), 7.14-7.16 (m, 4H), 7.11-7.13 (m, 2H), 5.51-5.56 (m, 1H), 3.11 (dd, 1H), 2.75 (dd, 1H).

Example 61

N-(3-Amino-1-benzyl-2,3-dioxopropyl)-2-(5-methyl-3-phenyl-1H-pyrazol-1-yl)nicotinamide ESI-MS [M+H]$^+$=454.1
$^1$H-NMR (400 MHz DMSO) δ ppm: 8.83 (d, 1H), 8.58 (d, 1H), 7.96 (s, 1H), 7.85 (d, 1H), 7.74 (s, 1H), 7.66 (d, 2H), 7.50-7.54 (m, 1H), 7.34 (dd, 2H), 7.27 (dd, 1H), 7.10-7.17 (m, 3H), 7.06 (d, 2H), 6.64 (s, 1H), 5.26-5.31 (m, 1H), 3.02 (dd, 1H), 2.67 (dd, 1H), 2.49 (s, 3H).

Example 62

N-(3-Amino-1-benzyl-2,3-dioxopropyl)-2-[3-(4-cyanophenyl)-1H-pyrazol-1-yl]nicotinamide ESI-MS [M+H]$^+$=465.1.
$^1$H-NMR (400 MHz DMSO) δ ppm: 8.96 (d, 1H), 8.57 (s, 1H), 8.51 (s, 1H), 8.09 (s, 1H), 7.82-7.92 (m, 5H), 7.72 (d, 1H), 7.50 (dd, 1H), 7.17 (s, 5H), 7.14 (s, 1H), 5.51-5.56 (m, 1H), 3.12 (dd, 1H), 2.74 (dd, 1H)

Example 63

N-(3-Amino-1-benzyl-2,3-dioxopropyl)-2-(4,5-dihydro-2H-benzo[g]indazol-2-yl)nicotinamide ESI-MS [M+H]$^+$=466.09
$^1$H-NMR (400 MHz DMSO) δ ppm: 8.94 (d, 1H), 8.51 (d, 1H), 8.23 (s, 1H), 8.05 (s, 1H), 7.63 (s, 1H), 7.70 (d, 1H), 7.48 (d, 1H), 7.41 (dd, 1H), 7.28 (dd, 1H), 7.13-7.24 (m, 7H), 5.50-5.55 (m, 1H), 3.16 (dd, 1H), 2.90 (t, 2H), 2.80 (dd, 1H), 2.73-2.79 (m, 2H).

Example 64

N-(3-Amino-1-benzyl-2,3-dioxopropyl)-2-[3-(4-piperidin-1-ylphenyl)-1H-pyrazol-1-yl]nicotinamide ESI-MS [M+H]$^+$=523.18.
$^1$H-NMR (500 MHz DMSO) δ ppm: 8.91 (d, 1H), 8.53 (d, 1H), 8.42 (s, 1H), 8.08 (s, 1H), 7.85 (s, 1H), 7.70 (d, 1H), 7.60 (m, 2H), 7.43 (m, 1H), 7.20 (m, 5H), 6.91 (m, 3H), 5.58 (m, 1H), 3.23 (m, 4H), 3.15 (m overlapped, 1H), 1.66-1.60 (m, 6H).

Example 65

N-(3-Amino-1-benzyl-2,3-dioxopropyl)-2-(3-pyridin-4-yl-1H-pyrazol-1-yl)nicotinamide ESI-MS [M+H]$^+$=441.16.
$^1$H-NMR (500 MHz DMSO) δ ppm: 8.98 (m, 1H), 8.62-8.53 (m, 4H), 8.09 (s, 1H), 7.87 (m, 1H), 7.75 (m, 1H), 7.67 (m, 2H), 7.54 (m, 1H), 7.18 (m, 6H), 5.56 (m, 1H), 3.15 and 2.78 (each m, 1H).

Example 66

N-[3-Amino-1-(cyclohexylmethyl)-2,3-dioxopropyl]-2-(3-phenyl-1H-pyrazol-1-yl)nicotinamide ESI-MS [M+H]$^+$=446.15.
$^1$H-NMR (500 MHz DMSO) δ ppm: 8.77 (d, 1H), 8.59 (m, 1H), 8.51 (d, 1H), 7.96 (s, 1H), 7.87 (m, 3H), 7.76 (s, 1H), 7.51 (dd, 1H), 7.43 (m, 2H), 7.37 (m, 1H), 7.05 (m, 1H), 5.22 (m, 1H), 1.65 (m, 1H), 1.54-1.24 (m, 7H), 1.01 (m, 2H), 0.89-0.68 (m, 3H).

Example 67

N-[3-Amino-1-(4-chlorobenzyl)-2,3-dioxopropyl]-2-[3-(4-fluorophenyl)-1H-pyrazol-1-yl]nicotinamide ESI-MS [M+H]$^+$=492.09.
$^1$H-NMR (500 MHz DMSO) δ ppm: 8.91 (d, 1H), 8.57 (d, 1H), 8.48 (s, 1H), 8.09 (s, 1H), 7.88 (s, 1H), 7.74 (m, 3H), 7.50 (m, 1H), 7.19 (m, 6H), 6.98 (m, 1H), 5.48 (m, 1H), 3.12 (m, 1H), 2.75 (m, 1H).

Example 68

N-(3-Amino-1-benzyl-2,3-dioxopropyl)-2-{3-[4-(4-methylpiperazin-1-yl)phenyl]-1H-pyrazol-1-yl}nicotinamide ESI-MS [M+H]$^+$=538.24.
$^1$H-NMR (500 MHz DMSO) δ ppm: 8.91 (d, 1H), 8.54 (m, 1H), 8.42 (m, 1H), 8.08 (s, 1H), 7.86 (s, 1H), 7.69 (dd, 1H), 7.61 (m, 2H), 7.44 (m, 1H), 7.20 (m, 5H), 6.92 (m, 3H), 5.58 (m, 1H), 3.20 (m, 5H), 2.81 (m, 1H), 2.49 (m overlapped by DMSO), 2.26 (s, 3H).

Example 69

N-(3-Amino-1-benzyl-2,3-dioxopropyl)-2-[3-(4-pyrrolidin-1-ylphenyl)-1H-pyrazol-1-yl]nicotinamide ESI-MS [M+H]$^+$=509.25.
$^1$H-NMR (500 MHz DMSO) δ ppm: 8.91 (d, 1H), 8.51 (m, 1H), 8.40 (d, 1H), 8.07 (s, 1H), 7.84 8s, 1H), 7.69 (m, 1H), 7.58 (m, 2H), 7.41 (m, 1H), 7.22 (m, 5H), 6.83 (m, 1H), 6.54 (m, 2H), 5.59 (m, 1H), 3.29 (m overlapped by H$_2$O), 3.10 and 2.83 (each dd, 1H), 2.01 (m, 4H).

Example 70

N-(3-Amino-1-benzyl-2,3-dioxopropyl)-2-[3-(3-chlorophenyl)-1H-pyrazol-1-yl]nicotinamide ESI-MS [M+H]$^+$=474.05.
$^1$H-NMR (500 MHz DMSO) δ ppm: 8.91 (d, 1H), 8.58 (d, 1H), 8.50 (d, 1H), 8.01 (s, 1H), 7.84 (s, 1H), 7.81 (s, 1H), 7.73 (m, 2H), 7.49 (dd, 1H), 7.41 (m, 2H), 7.16 (m, 5H), 7.09 (m, 1H), 5.51 (m, 1H), 3.15 and 2.80 (each dd, 1H).

Example 71

N-(3-Amino-1-benzyl-2,3-dioxopropyl)-2-[3-(2-chloro-4-fluorophenyl)-1H-pyrazol-1-yl]nicotinamide ESI-MS [M+H]$^+$=492.05
$^1$H-NMR (500 MHz DMSO) δ ppm: 8.93 (d, 1H), 8.58 (d, 1H), 8.52 (d, 1H), 8.06 (s, 1H), 7.84 (s, 1H), 7.74 (d, 1H), 7.67 (dd, 1H), 7.51 (m, 2H), 7.19 (dd, 1H), 7.15 (m, 5H), 7.01 (d, 1H), 5.51 (m, 1H), 3.12 (dd, 1H), 2.78 (dd, 1H).

Example 72

N-(3-Amino-1-benzyl-2,3-dioxopropyl)-2-{3-[2-(trifluoromethyl)phenyl]-1H-pyrazol-1-yl}nicotinamide ESI-MS [M+H]$^+$=508.06.
$^1$H-NMR (400 MHz DMSO) δ ppm: 8.94 (d, 1H), 8.57 (d, 1H), 8.50 (d, 1H), 7.98 (s, 1H), 7.75-7.83 (m, 3H), 7.46-7.74 (m, 4H), 7.09 (s, 5H), 6.67 (s, 1H), 5.40-5.45 (m, 1H), 3.08 (dd, 1H), 2.74-2.80 (dd, 1H).

Example 73

N-[1-Benzyl-3-(ethylamino)-2,3-dioxopropyl]-2-(3-phenyl-1H-pyrazol-1-yl)nicotinamide ESI-MS [M+H]$^+$=468.10
$^1$H-NMR (400 MHz DMSO) δ ppm: 8.92 (d, 1H), 8.70 (t, 1H), 8.54 (dd, 1H), 8.47 (d, 1H), 7.75 (d, 2H), 7.71 (d, 1H), 7.76 (dd, 1H), 7.31-7.39 (m, 3H), 7.13-7.21 (m, 5H), 6.99 (d, 1H), 5.56-5.61 (m, 1H), 3.10-3.20 (m, 3H), 2.76-2.81 (dd, 1H), 1.05 (t, 3H).

Example 74

N-(3-Amino-1-benzyl-2,3-dioxopropyl)-2-[3-(3-pyrrolidin-1-ylphenyl)-1H-pyrazol-1-yl]nicotinamide

ESI-MS [M+H]$^+$=509.15.

Example 75

N-(3-Amino-1-benzyl-2,3-dioxopropyl)-2-[3-(2,3-dihydrobenzo[b]furan-5-yl)-1H-pyrazol-1-yl]nicotinamide ESI-MS [M+H]$^+$=482.1.
$^1$H-NMR (400 MHz DMSO) δ ppm: 8.87 (d, 1H), 8.52 (d, 1H), 8.44 (d, 1H), 8.01 (s, 1H), 7.81 (s, 1H), 7.65 (s, 1H), 7.51 (d, 1H), 7.41 (dd, 1H), 7.15-7.21 (m, 6H), 6.88 (d, 1H), 6.75 (d, 1H), 5.56-5.62 (m, 1H), 4.55 (t, 2H), 3.11-3.20 (m, 3H), 2.81 (dd, 1H).

Example 76

N-(3-Amino-1-benzyl-2,3-dioxopropyl)-2-[3-(2-fluorophenyl)-1H-pyrazol-1-yl]nicotinamide ESI-MS [M+H]$^+$=458.07.
$^1$H-NMR (400 MHz DMSO) δ ppm: 8.91 (d, 1H), 8.57 (d, 1H), 8.50 (d, 1H), 8.04 (s, 1H), 7.82 (s, 1H), 7.78 (d, 1H), 7.74 (d, 1H), 7.49 (dd, 1H), 7.39 (dd, 1H), 7.39 (dd, 1H), 7.19 (dd, 1H), 7.15 (s, 5H), 6.85 (dd, 1H), 5.50-5.56 (m, 1H), 3.12 (dd, 1H), 2.76 (dd, 1H)

Example 77

N-(3-Amino-1-benzyl-2,3-dioxopropyl)-2-(1H-indazol-1-yl)nicotinamide 77.1 Ethyl 2-(1H-indazol-1-yl)pyridine-3-carboxylate and ethyl 2-(2H-indazol-2-yl)pyridine-3-carboxylate Reaction of 4.7 g of ethyl 2-chloronicotinate (25.39 mmol) with 2.5 g of indazole (21.16 mmol) afforded a mixture of the isomers which were separated by chromatography on silica gel (eluent: cyclohexane/ethyl acetate 5-40%).
Fraction 1: ethyl 2-(1H-indazol-1-yl)pyridine-3-carboxylate about 80%, contaminated with fraction 2.
$^1$H-NMR (500 MHz DMSO) δ ppm: 8.74 (d, 1H), 8.41 (s, 1H), 8.36 (d, 1H), 8.23 (d, 1H), 8.18 (d, 1H), 7.61 (m, 2H), 7.36 (m, 1H), 4.23 (q, 2H), 1.12 (t, 3H).
Fraction 2: ethyl 2-(2H-indazol-2-yl)pyridine-3-carboxylate
$^1$H-NMR (500 MHz DMSO) δ ppm: 9.11 (s, 1H), 8.75 (d, 1H), 8.24 (d, 1H), 7.83 (d, 1H), 7.67 (m, 2H), 7.36 (m, 1h), 7.15 (m, 1H), 4.26 (q, 2H), 1.05 (t, 3H).

N-(3-Amino-1-benzyl-2,3-dioxopropyl)-2-(1H-indazol-1-yl)nicotinamide

ESI-MS [M+H]$^+$=414.05.
$^1$H-NMR (500 MHz DMSO) δ ppm: 8.93 (d, 1H), 8.64 (dd, 1H), 8.30 (dd, 1H), 8.13 (s, 1H), 8.05 (s, 1H), 7.86 (m, 1H), 7.80 (m, 2H), 7.53 (m, 1H), 7.48 (m, 1H), 7.34 (m, 1H), 7.26 (m, 5H), 5.36 (m, 1H), 3.15 and 2.19 (each dd, 1H).

Example 78

N-(3-Amino-1-benzyl-2,3-dioxopropyl)-2-(2H-indazol-2-yl)nicotinamide

ESI-MS [M+H+]=414.05.
$^1$H-NMR (500 MHz DMSO) δ ppm: 9.07 (d, 1H), 8.98 (s, 1H), 8.67 (m, 1H), 8.05 (s, 1H), 7.86-7.79 (m, 3H), 7.62 (m, 1H), 7.52 (d, 1H), 7.32-7.19 (m, 6H), 7.12 (m, 1H), 5.41 (m 1H), 3.18 and 2.92 (each dd, 1H).

Example 79

N-(3-Amino-1-benzyl-2,3-dioxopropyl)-2-[3-(2,4-dichlorophenyl)-1H-pyrazol-1-yl]nicotinamide ESI-MS [M+H]$^+$=508.03
$^1$H-NMR (400 MHz DMSO) δ ppm: 8.93 (d, 1H), 8.57 (d, 1H), 8.51 (d, 1H), 8.06 (s, 1H), 7.84 (s, 1H), 7.74 (d, 1H), 7.68 (s, 1H), 7.65 (d, 1H), 7.49 (dd, 1H), 7.36 (d, 1H), 7.13 (s, 5H), 7.03 (s, 1H), 5.46-5.51 (m, 1H), 3.09 (dd, 1H), 2.75 (dd, 1H).

Example 80

N-[3-Amino-1-(4-methoxybenzyl)-2,3-dioxopropyl]-2-(3-phenyl-1H-pyrazol-1-yl)nicotinamide ESI-MS [M+H]$^+$=470.25.
$^1$H-NMR (500 MHz DMSO) δ ppm: 8.89 (m, 1H), 8.50 (m, 2H), 8.49 (s, 1H), 8.04 (s, 1H), 7.80-7.58 (m, 4H), 7.49 (m, 1H), 7.40-7.37 (m, 3H), 7.09 (m, 2H), 7.01 (m, 1H), 6.75 (m, 1H), 5.52 (m, 1H), 3.69 (s, 3H), 3.06 and 2.76 (each dd, 1H).

Example 81

N-[3-Amino-1-(4-methoxybenzyl)-2,3-dioxopropyl]-2-[3-(4-fluorophenyl)-1H-pyrazol-1-yl]nicotinamide ESI-MS [M+H]$^+$=488.25.
$^1$H-NMR (500 MHz DMSO) δ ppm: 8.89 (dd, 1H), 8.56 (dd, 1H), 8.47 (s, 1H), 8.07 (s, 1H), 7.86 (s, 1H), 7.76 (m, 3H), 7.48 (dd, 1H), 7.21 (m, 2H), 7.10 (m, 2H), 7.0 (m, 1H), 6.75 (m, 2H), 5.51 (m, 1H), 3.70 (s, 3H), 3.07 and 2.73 (each dd, 1H).

Example 82

N-(3-Amino-1-benzyl-2,3-dioxopropyl)-5-cyano-2-(3-phenyl-1H-pyrazol-1-yl)nicotinamide ESI-MS [M+H]$^+$=465.3.
$^1$H-NMR (500 MHz DMSO) δ ppm: 9.03 (s, 1H), 8.99 (d, 1H), 8.63 (s, 1H), 8.09 (s, 1H), 8.05 (s, 1H), 7.89 (s, 1H), 7.87 (m, 2H), 7.34 (m, 3H), 7.18 (m, 5H), 6.91 (m, 1H), 5.67 (m, 1H), 3.20 (dd, 1H), 2.86 (dd, 1H).

Example 83

N-(3-Amino-1-benzyl-2,3-dioxopropyl)-2-{3-[3-(trifluoromethyl)phenyl]-1H-pyrazol-1-yl}nicotinamide ESI-MS [M+H]$^+$=508.05.
$^1$H-NMR (400 MHz DMSO) δ ppm: 8.91 (d, 1H), 8.57 (d, 1H), 8.51 (d, 1H), 8.49 (s, 1H), 8.03 (s, 1H), 8.00 (d, 1H), 7.80 (s, 1H), 7.76 (d, 1H), 7.68 (d, 1H), 7.61 (dd, 1H), 7.50 (dd, 1H), 7.16 (dd, 1H), 7.09 (s, 5H), 5.42-5.47 (m, 1H), 3.11 (dd, 1H), 2.75 (dd, 1H).

Example 84

N-(3-Amino-1-benzyl-2,3-dioxopropyl)-2-(4-methyl-3-phenyl-1H-pyrazol-1-yl)nicotinamide ESI-MS [M+H]$^+$=454.08.
$^1$H-NMR (400 MHz DMSO) δ ppm: 8.88 (d, 1H), 8.52 (d, 1H), 8.32 (s, 1H), 8.01 (s, 1H), 7.80 (s, 1H), 7.69 (d, 1H), 7.64 (d, 2H), 7.33-7.43 (m, 4H), 7.15 (s, 5H), 5.50-5.55 (m, 1H), 3.12 (dd, 1H), 2.79 (dd, 1H), 2.29 (s, 3H).

Example 85

N-[3-Amino-2,3-dioxo-1-(phenyl methyl)propyl]-2-[3-(2,6-difluorophenyl)-1H-pyrazol-1-yl]pyridine-3-carboxamide ESI-MS [M+H]$^+$=476.05.
$^1$H-NMR (400 MHz DMSO) δ ppm: 8.81 (d, 1H), 8.58 (d, 1H), 8.49 (d, 1H), 7.91 (s, 1H), 7.78 (d, 1H), 7.73 (s, 1H), 7.51 (dd, 1H), 7.41-7.47 (m, 1H), 7.15 (d, 2H), 7.11 (s, 5H), 6.77 (s, 1H), 5.36-5.41 (m, 1H), 3.09 (dd, 1H), 2.78 (dd, 1H).

Example 86

N-[3-Amino-2,3-dioxo-1-(phenylmethyl)propyl]-2-(4-methyl-3-phenyl-1H-pyrazol-1-yl)pyridine-3-carboxamide ESI-MS [M+H]$^+$=454.07.
$^1$H-NMR (400 MHz DMSO) δ ppm: 8.91 (d, 1H), 8.58 (s, 1H), 8.52 (d, 1H), 8.02 (s, 1H), 7.79 (s, 1H), 7.70 (d, 1H), 7.54 (d, 2H), 7.40-7.45 (m, 3H), 7.23-7.32 (m, 5H), 7.19 (dd, 1H), 5.39-5.44 (m, 1H), 3.17 (dd, 1H), 2.90 (dd, 1H), 2.23 (s, 3H).

Example 87

N-[3-Amino-2,3-dioxo-1-(phenylmethyl)propyl]-2-{3-[4-(1-methylethyl)phenyl]-1H-pyrazol-1-yl}pyridine-3-carboxamide ESI-MS [M+H]$^+$=482.09
$^1$H-NMR (500 MHz DMSO) δ ppm: 8.92 (m, 1H), 8.56 (m, 1H), 8.46 (m, 1H), 8.05 (s, 1H), 7.83 (s, 1H), 7.73 (m, 1H), 7.68 (m, 2H), 7.46 (m, 1H), 7.25 (m, 2H), 7.18 (m, 5H), 6.95 (m, 1H), 5.56 (m, 1H), 3.15 (dd, 1H), 2.94 (m, 1H), 2.82 (dd, 1H), 1.26 (d, 6H).

Example 88

N-[3-Amino-2,3-dioxo-1-(pyridin-3-ylmethyl)propyl]-2-(3-phenyl-1H-pyrazol-1-yl)pyridine-3-carboxamide hydrochloride ESI-MS [M+H]$^+$=441.15.
$^1$H-NMR (500 MHz DMSO) δ ppm: 9.16 (d, 1H), 8.69 (s, 1H), 8.58 (m, 2H), 8.46 (d, 1H), 8.31 (d, 1H), 8.16 (s, 1H), 7.95 (s, 1H), 7.85 (dd, 1H), 7.69 (dd, 1H), 7.62 (m, 2H), 7.49 (dd, 1H), 7.35 (m, 3H), 6.98 (d, 1H), 5.39 (m, 1H), 3.36 and 3.03 (each dd, 1H).

Example 89

N-[3-Amino-2,3-dioxo-1-(phenylmethyl)propyl]-2-[3-(3,5-dichlorophenyl)-1H-pyrazol-1-yl]pyridine-3-carboxamide ESI-MS [M+H+]=581.09.
$^1$H-NMR (500 MHz DMSO) δ ppm: 8.90 (d, 1H), 8.59 (m, 1H), 8.51 (m, 1H), 7.94 (s, 1H), 7.76 (m, 4H), 7.55 (s, 1H), 7.52 (m, 1H), 7.17-7.05 (m, 6H), 7.49 (m, 1H), 3.15 and 2.79 (each dd, 1H).

Example 90

N-[3-Amino-2,3-dioxo-1-(phenylmethyl)propyl]-2-{3-[2-(methyloxy)phenyl]-1H-pyrazol-1-yl}pyridine-3-carboxamide ESI-MS [M+H]$^+$=470.13.
$^1$H-NMR (400 MHz DMSO) δ ppm: 8.90 (d, 1H), 8.54 (d, 1H), 8.44 (s, 1H), 8.02 (s, 1H), 7.80 (s, 1H), 7.73 (dd, 2H), 7.44 (t, 1H), 7.32 (t, 1H), 7.15 (m, 5H), 7.10 (d, 1H), 6.96 (d, 1H), 6.92 (t, 1H), 5.52-5.57 (m, 1H), 3.89 (s, 3H), 3.12 (dd, 1H), 2.79 (dd, 1H).

Example 91

N-[3-Amino-2,3-dioxo-1-(phenylmethyl)propyl]-2-[3-(3,5-difluorophenyl)-1H-pyrazol-1-yl]pyridine-3-carboxamide ESI-MS [M+H]$^+$=476.16.
$^1$H-NMR (500 MHz DMSO) δ ppm: 8.91 (d, 1H), 8.58 (m, 1H), 8.51 (d, 1H), 7.95 (s, 1H), 7.80 (s, 1H), 7.76 (dd, 1H), 7.51 (dd, 1H), 7.45 (m, 2H), 7.14 (m, 7H), 5.47 (m, 1H), 3.14 and 2.77 (each dd, 1H).

Example 92

N-(3-Amino-1-{[4-(methyloxy)phenyl]methyl}-2,3-dioxopropyl)-2-[3-(2-fluorophenyl)-1H-pyrazol-1-yl]pyridine-3-carboxamide ESI-MS [M+H]$^+$=488.15.
$^1$H-NMR (500 MHz DMSO) δ ppm: 3.86 (d, 1H), 3.58 (m, 1H), 8.51 (m, 1H), 8.02 (s, 1H), 7.78 (m, 3H), 7.51 (m 1H), 7.41 (m, 1H), 7.29 (m, 1H), 7.20 (m, 1H), 7.05 (m, 2H), 6.86 (s, 1H), 6.71 (m, 2H), 5.47 (m, 1H), 3.68 (s, 3H), 3.04 and 2.72 (each dd, 1H).

Example 93

N-[3-Amino-2,3-dioxo-1-(phenylmethyl)propyl]-2-[3-(2-methylphenyl)-1H-pyrazol-1-yl]pyridine-3-carboxamide ESI-MS [M+H]$^+$=454.10.
$^1$H-NMR (400 MHz DMSO) δ ppm: 8.87 (d, 1H), 8.56 (d, 1H), 8.49 (d, 1H), 7.97 (s, 1H), 7.77 (m, 2H), 7.54 (d, 1H), 7.47 (t, 1H), 7.22 (m, 3H), 7.11 (m, 5H), 6.81 (m, 1H), 5.48-5.42 (m, 1H), 3.09 (dd, 1H), 2.77 (dd, 1H), 2.36 (s, 3H).

Example 94

N-[3-Amino-2,3-dioxo-1-(phenylmethyl)propyl]-2-[3-(2,4-difluorophenyl)-1H-pyrazol-1-yl]pyridine-3-carboxamide ESI-MS [M+H]$^+$=476.05.
$^1$H-NMR (400 MHz DMSO) δ ppm: 8.89 (d, 1H), 8.56 (d, 1H), 8.49 (d, 1H), 8.06 (s, 1H), 7.84 (s, 1H), 7.76 (dd, 1H), 7.73 (dd, 1H), 7.49 (dd, 1H), 7.33 (dd, 1H), 7.15 (s, 5H), 7.06 (dd, 1H), 6.81 (dd, 1H), 5.48-5.53 (m, 1H), 3.11 (dd, 1H), 2.73 (dd, 1H).

Example 95

N-[3-Amino-2,3-dioxo-1-(phenylmethyl)propyl]-2-[3-(2,6-dichlorophenyl)-1H-pyrazol-1-yl]pyridine-3-carboxamide ESI-MS [M+H]$^+$=508.05.
$^1$H-NMR (400 MHz DMSO) δ ppm: 8.92 (d, 1H), 8.57 (d, 1H), 8.51 (d, 1H), 8.50 (s, 1H), 7.85 (s, 1H), 7.78 (d, 1H), 7.67 (s, 1H), 7.47-7.53 (m, 3H), 7.40 (dd, 1H), 7.50 (dd, 1H), 7.08 (s, 5H), 6.60 (s, 1H), 5.22-5.27 (m, 1H), 3.09 (dd, 1H), 2.85 (dd, 1H).

Example 96

N-[3-Amino-2,3-dioxo-1-(phenylmethyl)propyl]-2-(3-{3-[(phenylmethyl)oxy]phenyl}-1H-pyrazol-1-yl)pyridine-3-carboxamide ESI-MS [M+H]$^+$=546.17.
$^1$H-NMR (400 MHz DMSO) δ ppm: 8.88 (d, 1H), 8.54-8.56 (m, 1H), 8.45 (d, 1H), 7.97 (s, 1H), 7.73-7.78 (m, 2H), 7.45-7.50 (m, 4H), 7.27-7.41 (m, 5H), 7.10-7.20 (m, 6H), 6.97-7.01 (d, 1H), 5.49-5.54 (m, 1H), 5.15 (s, 2H), 3.12 (dd, 1H), 2.80 (dd, 1H).

Example 97

N-(3-Amino-1-{[4-(methyloxy)phenyl]methyl}-2,3-dioxopropyl)-2-[3-(2,4-difluorophenyl)-1H-pyrazol-1-yl]pyridine-3-carboxamide ESI-MS [M+H]$^+$=506.15.
$^1$H-NMR (500 MHz DMSO) δ ppm: 8.85 (d, 1H), 8.58 (dd, 1H), 8.51 (m, 1H), 8.05 (s, 1H), 7.84 (s, 1H), 7.77 (m, 2H), 7.51 (dd, 1H), 7.33 (m, 1H), 7.06 (m, 3H), 6.83 (m, 1H), 6.72 (s, 1H), 6.70 (s, 1H), 5.46 (m, 1H), 3.69 (s, 3H), 3.04 and 2.70 (each dd, 1H).

Example 98

N-(3-Amino-1-{[4-(methyloxy)phenyl]methyl}-2,3-dioxopropyl)-2-[3-(2,4-dichlorophenyl)-1H-pyrazol-1-yl]pyridine-3-carboxamide ESI-MS [M+H]$^+$=538.05.
$^1$H-NMR (500 MHz DMSO) δ ppm: 8.87 (d, 1H), 8.60 (m, 1H), 8.53 (d, 1H), 8.04 (s, 1H), 7.83 (s, 1H), 7.80 (dd, 1H), 7.69 (m, 1H), 7.62 (d, 1H), 7.53 (dd, 1H), 7.36 (dd, 1H), 7.04 (m, 3H), 6.69 (s, 1H), 6.67 (s, 1H), 5.44 (m, 1H), 3.68 (s, 3H), 3.03 and 2.70 (each dd, 1H).

Example 99

N-[3-Amino-2,3-dioxo-1-(phenylmethyl)propyl]-2-[3-(2-chloro-4-morpholin-4-ylphenyl)-1H-pyrazol-1-yl]pyridine-3-carboxamide ESI-MS [M+H]$^+$=559.15.
$^1$H-NMR (500 MHz DMSO) δ ppm: 8.90 (d, 1H), 8.56 (m, 1H), 8.48 (m, 1H), 8.05 (s, 1H), 7.83 (s, 1H), 7.72 (m, 1H), 7.56 (m, 1H), 7.47 (dd, 1H), 7.17 (m, 5H), 7.04 (d, 1H), 6.95 (d, 1H), 6.87 (dd, 1H), 5.56 (m, 1H), 3.77 (m, 4H), 3.20 (m, 4H), 3.15 and 2.81 (each dd, 1H).

Example 100

N-[3-Amino-2,3-dioxo-1-(phenylmethyl)propyl]-2-chromeno[4,3-c]pyrazol-2(4H)-ylpyridine-3-carboxamide ESI-MS [M+H]$^+$=468.1.
$^1$H-NMR (400 MHz DMSO) δ ppm: 8.97 (d, 1H), 8.54 (d, 1H), 8.27 (s, 1H), 8.05 (s, 1H), 7.83 (s, 1H), 7.74 (d, 1H), 7.46 (dd, 1H), 7.40 (d, 1H), 7.24 (s, 5H), 7.18 (dd, 1H), 6.97 dd, 2H), 5.43-5.54 (m, 1H), 5.31 (s, 2H), 3.16 (dd, 1H), 2.82 (dd, 1H).

Example 101

N-[3-Amino-2,3-dioxo-1-(phenylmethyl)propyl]-2-{3-[4-(1H-imidazol-1-yl)phenyl]-1H-pyrazol-1-yl}pyridine-3-carboxamide ESI-MS [M+H]$^+$=506.1.
$^1$H-NMR (400 MHz DMSO) δ ppm: 8.94 (d, 1H), 8.55 (d, 1H), 8.48 (d, 1H), 8.33 (s, 1H), 8.08 (s, 1H), 7.88 (s, 2H), 7.86

(s, 1H), 7.80 (s, 1H), 7.65-7.71 (m, 3H), 7.47 (dd, 1H), 7.13-7.19 (m, 6H), 7.06 (d, 1H), 5.56-5.60 (m, 1H), 3.14 (dd, 1H), 2.77 (dd, 1H).

Example 102

N-[3-Amino-2,3-dioxo-1-(phenylmethyl)propyl]-2-[3-(2-fluoro-4-morpholin-4-ylphenyl)-1H-pyrazol-1-yl]pyridine-3-carboxamide ESI-MS [M+H]$^+$=543.2.
$^1$H-NMR (500 MHz DMSO) δ ppm: 8.99 (d, 1H), 8.55 (m, 1H), 8.48 (m, 1H), 8.17 (s, 1H), 7.93 (s, 1H), 7.71 (m, 1H), 7.62 (m, 1H), 7.48 (m, 1H), 7.20 (m, 5H), 6.84-6.75 (m, 3H), 5.59 (m, 1H), 3.77 (m, 4H), 3.22-3.15 (m, 5H), 2.78 (dd, 1H).

Example 103

N-[3-Amino-2,3-dioxo-1-(phenylmethyl)propyl]-2-[3-(5-chloro-2-thienyl)-1H-pyrazol-1-yl]pyridine-3-carboxamide ESI-MS [M+H]$^+$=480.5.
$^1$H-NMR (500 MHz DMSO) δ ppm: 8.91 (d, 1H), 8.55 (d, 1H), 8.45 (d, 1H), 8.01 (s, 1H), 7.80 (m, 1H), 7.77 (s, 1H), 7.49 (dd, 1H), 7.35 (m, 1H), 7.34 (m, 5H), 7.21 (d, 1H), 6.91 (d, 1H), 5.51 (m, 1H), 3.17 and 2.86 (each dd, 1H).

Example 104

N-[3-Amino-2,3-dioxo-1-(phenylmethyl)propyl]-2-[4-(2-fluorophenyl)-1H-pyrazol-1-yl]pyridine-3-carboxamide 4-(2-Fluorophenyl)-1H-pyrazole 11.08 ml of N,N-dimethylformamide was slowly added dropwise to 11.03 ml of POCl$_3$ were at 0-5° C. while stirring and, after about 5 minutes a solution of 2-fluorophenylacetic acid (6 g, 38.9 mmol) in 20 ml of N,N-dimethylformamide was added dropwise. The mixture was then heated at 70° C. for about 17 hours. The mixture was subsequently quenched with ice-water and the mixture was made alkaline by adding NaOH. The resulting solid was filtered off, the solution was extracted with dichloromethane, and the organic phase was dried and concentrated. The oil obtained in this way was directly dissolved in 50 ml of ethanol. 7.3 ml of hydrazine hydrate were added, and the reaction mixture was heated at 55° C. for 3 hours. After the reaction was complete, the solvent was evaporated and the remaining solid was stirred with water and then dried. 2.65 g of 4-(2-fluorophenyl)-1H-pyrazole were obtained.
ESI-MS [M+H]$^+$=163.1.
$^1$H-NMR (500 MHz DMSO) δ ppm: 13.07 (s, 1H), 8.10 (s broad, 2H), 7.73 (m, 1H), 7.24 (m, 3H).
The 4-(2-fluorophenyl)-1H-pyrazole obtained in this way was then reacted in a manner analogous to the above examples to give N-[3-amino-2,3-dioxo-1-(phenylmethyl)propyl]-2-[4-(2-fluorophenyl)-1H-pyrazol-1-yl]pyridine-3-carboxamide.
ESI-MS [M+H]$^+$=458.2.
$^1$H-NMR (500 MHz DMSO) δ ppm: 8.91 (d, 1H), 8.79 (s broad, 1H), 8.59 (d, 1H), 8.05 (m, 2H), 7.88 (m, 1H), 7.81 (s, 1H), 7.76 (d, 1H), 7.51 (m, 1H), 7.35-7.20 (m, 7H), 7.18 (m, 1H), 5.34 (m, 1H), 3.18 and 2.90 (each dd, 1H).

Example 105

N-[(1S)-1-Formyl-2-phenylethyl]-2-(3-phenyl-1H-pyrazol-1-yl)pyridine-3-carboxamide N-[(1S)-2-Hydroxy-1-(phenylmethyl)ethyl]-2-(3-phenyl-1H-pyrazol-1-yl)pyridine-3-carboxamide Coupling of 1.0 g of 2-(3-phenyl-1H-pyrazol-1-yl)pyridine-3-carboxylic acid (3.77 mmol) with 0.63 g of L-phenylalaninol afforded 1.14 g of N-[(1S)-2-hydroxy-1-(phenylmethyl)ethyl]-2-(3-phenyl-1H-pyrazol-1-yl)pyridine-3-carboxamide as a white solid.
ESI-MS [M+H]$^+$=399.2.
$^1$H-NMR (500 MHz DMSO) δ ppm: 8.54 (dd, 1H), 8.45 (d, 1H), 8.30 (d, 1H), 7.91 (s, 1H), 7.89 (s, 1H), 7.69 (d, 1H), 7.42 (m, 3H), 7.35 (m, 1H), 7.28 (m, 2H), 7.20 (m, 3H), 7.01 (1H), 4.70 (t, 1H), 4.09 (m, 1H), 3.49 (m, 1H), 3.35 (m, overlapped by H$_2$O), 2.91 and 2.71 (each dd, 1H).
Oxidation of N-[(1S)-2-hydroxy-1-(phenylmethyl)ethyl]-2-(3-phenyl-1H-pyrazol-1-yl)pyridine-3-carboxamide in a manner analogous to the above examples and subsequent treatment of the resulting crude product with HCl in dioxane and stirring the resulting residue with ether afforded 71 mg of the title compound as a white solid.
ESI-MS [M+H]+
$^1$H-NMR (500 MHz DMSO) δ ppm: 9.58 (s, 1H), 8.99 (d, 1H), 8.58 (dd, 1H), 8.51 (d, 1H), 7.83 (m, 2H), 7.80 (m, 1H), 7.48 (dd, 1H), 7.43 (m, 2H), 7.37 (m, 1H), 7.27-7.19 (m, 5H), 7.05 (d, 1H), 4.48 (m, 1H), 3.13 and 2.87 (each dd, 1H).

Example 106

N-[3-Amino-2,3-dioxo-1-(phenylmethyl)propyl]-2-(3-phenyl-1H-pyrazol-1-yl)benzamide ESI-MS [M+H]$^+$=439.
$^1$H-NMR (400 MHz DMSO) δ ppm: 9.01 (d, 1H), 8.07 (s, 1H), 7.8 (s, 1H), 7.82 (d, 1H), 7.73 (d, 2H), 7.70 (d, 1H), 7.59 (dd, 1H), 7.39-7.47 (m, 3H), 7.34 (dd, 2H), 7.23-7.28 (m, 5H), 6.81 (d, 1H), 5.35-5.41 (m, 1H), 3.18 (dd, 1H), 2.78 (dd, 1H).
The compounds of Examples 107 and 108 can be prepared in a manner analogous to the Example 5 using (3S)-amino-2-(R/S)-hydroxy-4-phenyl-butyramide (e.g. prepared according to WO 98/29401 or DE 19642591):

Example 107

N-[(1S)-3-Amino-2,3-dioxo-1-(phenylmethyl)propyl]-2-(3-phenyl-1H-pyrazol-1-yl)pyridine-3-carboxamide ESI-MS [M+H]$^+$=440.1;
$[α]_D^{20}$: +71° (c: 1% in DMF; freshly prepared solution)

Example 108

N-[(1S)-3-Amino-2,3-dioxo-1-(phenylmethyl)propyl]-2-[3-(4-fluorophenyl)-1H-pyrazol-1-yl]pyridine-3-carboxamide ESI-MS [M+H]$^+$=458.2;
$[α]_D^{20}$: +62.5° (c: 1% in dimethylformamide (DMF); freshly prepared solution)

The following examples were prepared in a manner analogous to the above examples

Example 109

N-[3-Amino-2,3-dioxo-1-(phenylmethyl)propyl]-2-[3-(3-chloro-2-thienyl)-1H-pyrazol-1-yl]pyridine-3-carboxamide

ESI-MS [M+H]$^+$=480.2

Example 110

N-[3-Amino-2,3-dioxo-1-(phenylmethyl)propyl]-2-(3-naphthalen-1-yl-1H-pyrazol-1-yl)pyridine-3-carboxamide ESI-MS [M+H]$^+$=490.0
$^1$H-NMR (400 MHz DMSO) δ ppm: 8.90 (d, 1H), 8.75 (d, 1H), 8.60 (s, 1H), 8.59 (d, 1H), 7.75 (dd, 3H), 7.81 (d, 1H), 7.75 (d, 1H), 7.74 (s, 1H), 7.48-7.63 (m, 4H), 6.91-6.96 (m, 2H), 6.82-6.88 (m, 4H), 5.47-5.53 (m, 1H), 3.02 (dd, 1H), 2.70 (dd, 1H).

Example 111

N-(3-Amino-1-{[4-(methyloxy)phenyl]methyl}-2,3-dioxopropyl)-2-[3-(2-chloro-4-fluorophenyl)-1H-pyrazol-1-yl]pyridine-3-carboxamide

ESI-MS [M+H]$^+$=522.1

Example 112

N-[3-Amino-2,3-dioxo-1-(phenylmethyl)propyl]-2-[3-(2,5-dichlorophenyl)-1H-pyrazol-1-yl]pyridine-3-carboxamide ESI-MS [M+H]$^+$=508.1.
$^1$H-NMR (400 MHz DMSO) δ ppm: 8.88 (d, 1H), 8.59 (d, 1H), 8.52 (d, 1H), 7.94 (s, 1H), 7.79 (d, 1H), 7.76 (s, 1H), 7.64 (d, 1H), 7.50-7.56 (m, 2H), 7.42 (dd, 1H), 7.02-7.10 (m, 6H), 5.35-5.41 (m, 1H), 3.13 (dd, 1H), 2.77 (dd, 1H).

Example 113

N-[3-Amino-2,3-dioxo-1-({4-[(phenylmethyl)oxy]phenyl}methyl)propyl]-2-[3-(2,4-dichlorophenyl)-1H-pyrazol-1-yl]pyridine-3-carboxamide ESI-MS [M+H]$^+$=615.2
$^1$H-NMR (400 MHz DMSO) δ ppm: 8.87 (d, 1H), 8.57 (dd, 1H), 8.51 (d, 1H), 8.04 (s, 1H), 7.83 (s, 1H), 7.77 (dd, 1H), 7.65 (d, 1H), 7.59 (d, 1H), 7.50 (dd, 1H), 7.30-7.43 (m, 6H), 7.04 (d, 2H), 7.02 (s, 1H), 6.75 (d, 2H), 5.39-5.45 (m, 1H), 4.97 (s, 2H), 3.01 (dd, 1H), 2.68 (dd, 1H).

Example 114

N-{-3-Amino-1-[(4-fluorophenyl)methyl]-2,3-dioxopropyl}-2-[3-(2,4-dichlorophenyl)-1H-pyrazol-1-yl]pyridine-3-carboxamide ESI-MS [M+H]$^+$=526.1
$^1$H-NMR (400 MHz DMSO) δ ppm: 8.91 (d, 1H), 8.58 (dd, 1H), 8.52 (d, 1H), 8.05 (s, 1H), 7.85 (s, 1H), 7.78 (d, 1H), 7.67 (d, 1H), 7.59 (d, 1H), 7.51 (dd, 1H), 7.35 (dd, 1H), 7.13 (dd, 2H), 7.03 (d, 1H), 6.90 (dd, 2H), 5.38-5.44 (m, 1H), 3.06 (dd, 1H), 2.72 (dd, 1H).

Example 115

N-[3-Amino-2,3-dioxo-1-(phenylmethyl)propyl]-2-[3-(2,3-dichlorophenyl)-1H-pyrazol-1-yl]pyridine-3-carboxamide ESI-MS [M+H]$^+$=508.1
$^1$H-NMR (400 MHz DMSO) δ ppm: 8.92 (d, 1H), 8.58 (dd, 1H), 8.53 (d, 1H), 8.01 (s, 1H), 7.79 (s, 1H), 7.76 (dd, 1H), 7.64 (dd, 1H), 7.56 (dd, 1H), 7.50 (dd, 1H), 7.33 (dd, 1H), 7.12 (s, 5H), 7.02 (d, 1H), 5.44-5.50 (m, 1H), 3.09 (dd, 1H), 2.76 (dd, 1H).

Example 116

N-[3-Amino-2,3-dioxo-1-(phenylmethyl)propyl]-2-[3-(2,4,6-trifluorophenyl)-1H-pyrazol-1-yl]pyridine-3-carboxamide

ESI-MS [M+H]$^+$=494.04

Example 117

N-[3-Amino-2,3-dioxo-1-(phenylmethyl)propyl]-2-{3-[2,4-bis(methyloxy)phenyl]-1H-pyrazol-1-yl}pyridine-3-carboxamide ESI-MS [M+H]$^+$=500.2
$^1$H-NMR (400 MHz DMSO) δ ppm: 8.88 (d, 1H), 8.52 (dd, 1H), 8.41 (d, 1H), 8.04 (s, 1H), 7.82 (s, 1H), 7.67 (t, 2H), 7.41 (dd, 1H), 7.17 (s, 5H), 6.88 (d, 1H), 6.63 (d, 1H), 6.49 (dd, 1H), 5.54-5.59 (m, 1H), 3.87 (s, 3H), 3.80 (s, 3H), 3.16 (dd, 1H), 2.79 (dd, 1H).

Example 118

N-[3-Amino-2,3-dioxo-1-(phenylmethyl)propyl]-2-[3-(2,2-difluoro-1,3-benzodioxol-5-yl)-1H-pyrazol-1-yl]pyridine-3-carboxamide

ESI-MS [M+H]$^+$=520.1

Example 119

N-[3-Amino-2,3-dioxo-1-(phenylmethyl)propyl]-2-[3-(2,2-difluoro-1,3-benzodioxol-4-yl)-1H-pyrazol-1-yl]pyridine-3-carboxamide

ESI-MS [M+H]$^+$=520.1

Example 120

N-[3-Amino-2,3-dioxo-1-(phenylmethyl)propyl]-2-[3-(2,3-dichloro-6-fluorophenyl)-1H-pyrazol-1-yl]pyridine-3-carboxamide ESI-MS [M+H]$^+$=526.1
$^1$H-NMR (400 MHz DMSO) δ ppm: 8.96 (d, 1H), 8.58 (d, 1H), 8.54 (d, 1H), 7.86 (s, 1H), 7.79 (d, 1H), 7.69 (s, 1H), 7.45-7.58 (m, 3H), 7.03-7.13 (m, 5H), 6.64 (d, 1H), 5.21-5.27 (m, 1H), 3.08 (dd, 1H), 2.84 (dd, 1H).

Example 121

N-[3-Amino-2,3-dioxo-1-(phenylmethyl)propyl]-2-{3-[3,5-dimethyl-2-(methyloxy)phenyl]-1H-pyrazol-1-yl}pyridine-3-carboxamide

ESI-MS [M+H]$^+$=498.02

Example 122

N-{3-Amino-1-[(4-bromophenyl)methyl]-2,3-dioxopropyl}-2-(3-phenyl-1H-pyrazol-1-yl)pyridine-3-carboxamide

ESI-MS [M+H]$^+$=518.1

Example 123

N-{3-Amino-1-[(4-fluorophenyl)methyl]-2,3-dioxopropyl}-2-(3-phenyl-1H-pyrazol-1-yl)pyridine-3-carboxamide

ESI-MS [M+H]$^+$=458.1

Example 124

N-[3-Amino-2,3-dioxo-1-(phenylmethyl)propyl]-2-(3-{2-[(trifluoromethyl)oxy]phenyl}-1H-pyrazol-1-yl)pyridine-3-carboxamide

ESI-MS [M+H]$^+$=524.2

Example 125

N-[3-Amino-2,3-dioxo-1-(phenylmethyl)propyl]-2-{3-[4-fluoro-2-(methyloxy)phenyl]-1H-pyrazol-1-yl}pyridine-3-carboxamide

ESI-MS [M+H]$^+$=488.1.

Example 126

N-(3-Amino-1-{[4-(methyloxy)phenyl]methyl}-2,3-dioxopropyl)-2-{3-[3-(trifluoromethyl)phenyl]-1H-pyrazol-1-yl}pyridine-3-carboxamide

ESI-MS [M+H]$^+$=537.5

Example 127

N-[3-Amino-2,3-dioxo-1-({4-[(phenylmethyl)oxy]phenyl}methyl)propyl]-2-(3-phenyl-1H-pyrazol-1-yl)pyridine-3-carboxamide

ESI-MS [M+H]$^+$=546.3

Example 128

N-[3-Amino-2,3-dioxo-1-(phenylmethyl)propyl]-5-phenyl-2-(3-phenyl-1H-pyrazol-1-yl)pyridine-3-carboxamide

ESI-MS [M+H]$^+$=516.25.

Example 129

N-[3-Amino-2,3-dioxo-1-(phenylmethyl)propyl]-2-[3-(1,3-benzoxazol-5-yl)-1H-pyrazol-1-yl]pyridine-3-carboxamide

ESI-MS [M+H$_2$O+H]+=499.1

Example 130

N-[3-Amino-2,3-dioxo-1-(phenylmethyl)propyl]-2-{3-[5-fluoro-2-(methyloxy)phenyl]-1H-pyrazol-1-yl}pyridine-3-carboxamide

ESI-MS [M+H]$^+$=488.1

Example 131

N-[3-Amino-2,3-dioxo-1-(phenylmethyl)propyl]-2-{3-[5-chloro-2-(methyloxy)phenyl]-1H-pyrazol-1-yl}pyridine-3-carboxamide

ESI-MS [M+H]$^+$=504.1

Example 132

N-[3-Amino-2,3-dioxo-1-({4-[(trifluoromethyl)oxy]phenyl}methyl)propyl]-2-[3-(4-fluorophenyl)-1H-pyrazol-1-yl]pyridine-3-carboxamide

ESI-MS [M+H]$^+$=542.1

Example 133

N-[3-Amino-2,3-dioxo-1-({4-[(trifluoromethyl)oxy]phenyl}methyl)propyl]-2-(3-phenyl-1H-pyrazol-1-yl)pyridine-3-carboxamide

ESI-MS [M+H]$^+$=524.1

Example 134

N-[3-Amino-2,3-dioxo-1-({4-[(trifluoromethyl)oxy]phenyl}methyl)propyl]-2-{3-[3-(trifluoromethyl)phenyl]-1H-pyrazol-1-yl}pyridine-3-carboxamide

ESI-MS [M+H]$^+$=592.1.

Example 135

N-(3-Amino-1-{[4-(methyloxy)phenyl]methyl}-2,3-dioxopropyl)-2-(3-naphthalen-1-yl-1H-pyrazol-1-yl)pyridine-3-carboxamide

ESI-MS [M+H]$^+$=520.2

Example 136

N-(3-Amino-1-{[4-(methyloxy)phenyl]methyl}-2,3-dioxopropyl)-2-{3-[4-fluoro-2-(methyloxy)phenyl]-1H-pyrazol-1-yl}pyridine-3-carboxamide

ESI-MS [M+H]$^+$=518.2

Example 137

N-(3-Amino-1-{[4-(methyloxy)phenyl]methyl}-2,3-dioxopropyl)-2-[3-(2,2-difluoro-1,3-benzodioxol-5-yl)-1H-pyrazol-1-yl]pyridine-3-carboxamide

ESI-MS [M+H]$^+$=550.1

Example 138

N-[3-Amino-2,3-dioxo-1-({4-[(trifluoromethyl)oxy]phenyl}methyl)propyl]-2-(3-naphthalen-1-yl-1H-pyrazol-1-yl)pyridine-3-carboxamide

ESI-MS [M+H]$^+$=573.5

Example 139

N-[3-Amino-2,3-dioxo-1-(phenylmethyl)propyl]-2-{3-[4-chloro-2-(methyloxy)phenyl]-1H-pyrazol-1-yl}pyridine-3-carboxamide

ESI-MS [M+H]$^+$=504.1

Example 140

N-[3-Amino-2,3-dioxo-1-(phenylmethyl)propyl]-2-(8-chlorochromeno[4,3-c]pyrazol-2(4H)-yl)pyridine-3-carboxamide

ESI-MS [M+H]$^+$=502.2

Example 141

N-[3-Amino-2,3-dioxo-1-(phenylmethyl)propyl]-2-(4,5-dihydro-2H-[1]benzoxepino[5,4-c]pyrazol-2-yl)pyridine-3-carboxamide

ESI-MS [M+H]$^+$=482.1

Example 142

N-[3-Amino-2,3-dioxo-1-(phenylmethyl)propyl]-2-[7-(methyloxy)chromeno[4,3-c]pyrazol-2(4H)-yl]pyridine-3-carboxamide

ESI-MS [M+H]$^+$=498.1

Example 143

N-[3-Amino-2,3-dioxo-1-(phenylmethyl)propyl]-2-(8-chloro-9-methylchromeno[4,3-c]pyrazol-2(4H)-yl)pyridine-3-carboxamide

ESI-MS [M+H]$^+$=516.2

Example 144

N-[3-Amino-2,3-dioxo-1-(phenylmethyl)propyl]-2-[8-(1-methylethyl)chromeno[4,3-c]pyrazol-2(4H)-yl]pyridine-3-carboxamide

ESI-MS [M+H]$^+$=510.2

Example 145

N-[3-Amino-2,3-dioxo-1-(phenylmethyl)propyl]-2-[3-(2-chloro-3-fluorophenyl)-1H-pyrazol-1-yl]pyridine-3-carboxamide

ESI-MS [M+H]$^+$=492.1

Example 146

N-[3-Amino-2,3-dioxo-1-(phenylmethyl)propyl]-2-[3-(4-fluoronaphthalen-1-yl)-1H-pyrazol-1-yl]pyridine-3-carboxamide

ESI-MS [M+H]$^+$=508.1

Example 147

N-{3-Amino-1-[(4-fluorophenyl)methyl]-2,3-dioxopropyl}-2-{3-[3-(trifluoromethyl)phenyl]-1H-pyrazol-1-yl}pyridine-3-carboxamide

ESI-MS [M+H]$^+$=526.2

Example 148

N-[3-Amino-2,3-dioxo-1-(phenylmethyl)propyl]-2-{4-[(diethylamino)methyl]-3-(4-fluorophenyl)-1H-pyrazol-1-yl}pyridine-3-carboxamide methanesulfonate ESI-MS [M+H]$^+$=543.20 (free base)

Example 149

N-[3-Amino-2,3-dioxo-1-(phenylmethyl)propyl]-2-[3-(4-fluorophenyl)-4-(morpholin-4-ylmethyl)-1H-pyrazol-1-yl]pyridine-3-carboxamide methanesulfonate ESI-MS [M+H]$^+$=557.2 (free base)

Example 150

N-[3-Amino-2,3-dioxo-1-(phenylmethyl)propyl]-2-{3-[4-fluoro-2-(morpholin-4-ylmethyl)phenyl]-1H-pyrazol-1-yl}pyridine-3-carboxamide methanesulfonate ESI-MS [M+H]$^+$=557.2 (free base)

Example 151

N-[3-Amino-2,3-dioxo-1-(phenylmethyl)propyl]-2-{3-[2,5-bis(methyloxy)phenyl]-1H-pyrazol-1-yl}pyridine-3-carboxamide

ESI-MS [M+H]$^+$=500.1

Example 152

N-{3-Amino-1-[(4-fluorophenyl)methyl]-2,3-dioxopropyl}-2-(3-{2-[(trifluoromethyl)oxy]phenyl}-1H-pyrazol-1-yl)pyridine-3-carboxamide

ESI-MS [M+H]$^+$=542.1

Example 153

N-(3-Aamino-1-{[4-(methyloxy)phenyl]methyl}-2,3-dioxopropyl)-2-[3-(2,3-dichlorophenyl)-1H-pyrazol-1-yl]pyridine-3-carboxamide

ESI-MS [M+H]$^+$=538.2

Example 154

N-{3-Amino-1-[(4-fluorophenyl)methyl]-2,3-dioxopropyl}-2-[3-(2-chloro-3-fluorophenyl)-1H-pyrazol-1-yl]pyridine-3-carboxamide

ESI-MS [M+H]$^+$=511.1

Example 155

N-[3-Amino-2,3-dioxo-1-(phenylmethyl)propyl]-2-{3-[2-chloro-3-(trifluoromethyl)phenyl]-1H-pyrazol-1-yl}pyridine-3-carboxamide

ESI-MS [M+H]$^+$=542.2

Example 156

N-[3-Amino-2,3-dioxo-1-(phenylmethyl)propyl]-2-(3-isoquinolin-5-yl-1H-pyrazol-1-yl)pyridine-3-carboxamide

ESI-MS [M+H]$^+$=491.1

Example 157

N-(3-Amino-1-{[4-(methyloxy)phenyl]methyl}-2,3-dioxopropyl)-2-[3-(2-chloro-3-fluorophenyl)-1H-pyrazol-1-yl]pyridine-3-carboxamide

ESI-MS [M+H]$^+$=522.2

Example 158

N-[3-Amino-2,3-dioxo-1-(phenylmethyl)propyl]-5-[(methylsulfonyl)amino]-2-(3-phenyl-1H-pyrazol-1-yl)pyridine-3-carboxamide

ESI-MS [M+H]$^+$=533.2

Example 159

N-{3-Amino-1-[(4-fluorophenyl)methyl]-2,3-dioxopropyl}-2-[3-(2,3-dichlorophenyl)-1H-pyrazol-1-yl]pyridine-3-carboxamide

ESI-MS [M+H]$^+$=526.2

Example 160

N-[3-amino-2,3-dioxo-1-(phenylmethyl)propyl]-2-(3-quinolin-8-yl-1H-pyrazol-1-yl)pyridine-3-carboxamide

ESI-MS [M+H]$^+$=491.1

Example 161

N-{3-Amino-1-[(4-fluorophenyl)methyl]-2,3-dioxopropyl}-2-[3-(2,3-dichlorophenyl)-1H-pyrazol-1-yl]pyridine-3-carboxamide

ESI-MS [M+H]$^+$=607.2

Example 162

N-{3-Amino-1-[(3-fluorophenyl)methyl]-2,3-dioxopropyl}-2-(3-{2-[(trifluoromethyl)oxy]phenyl}-1H-pyrazol-1-yl)pyridine-3-carboxamide

ESI-MS [M+H]$^+$=542.2

Example 163

N-[3-Amino-2,3-dioxo-1-(phenylmethyl)propyl]-2-{3-[2-(morpholin-4-ylmethyl)-5-(trifluoromethyl)phenyl]-1H-pyrazol-1-yl}pyridine-3-carboxamide

ESI-MS [M+H]$^+$=607.25

Example 164

N-[3-Amino-2,3-dioxo-1-(phenylmethyl)propyl]-2-[3-(2,3-dihydro-1-benzofuran-7-yl)-1H-pyrazol-1-yl]pyridine-3-carboxamide

ESI-MS [M+H]$^+$=482.1

Example 165

N-[3-Amino-2,3-dioxo-1-(phenylmethyl)propyl]-2-[3-(4-fluorophenyl)-4-(2-morpholin-4-ylethyl)-1H-pyrazol-1-yl]pyridine-3-carboxamide

ESI-MS [M+H]$^+$=571.2

Example 166

N-[3-Amino-2,3-dioxo-1-(phenylmethyl)propyl]-2-(3-{2-[(difluoromethyl)oxy]phenyl}-1H-pyrazol-1-yl)pyridine-3-carboxamide

ESI-MS [M+H]$^+$=506.1

Example 167

N-[3-Amino-2,3-dioxo-1-(phenylmethyl)propyl]-2-(3-{2-[(diethylamino)methyl]-4-fluorophenyl}-1H-pyrazol-1-yl)pyridine-3-carboxamide

ESI-MS [M+H]$^+$=543.25

Example 168

N-[3-Amino-2,3-dioxo-1-(phenylmethyl)propyl]-2-(3-{3-[(trifluoromethyl)oxy]phenyl}-1H-pyrazol-1-yl)pyridine-3-carboxamide

ESI-MS [M+H]$^+$=524.15

Example 169

N-[3-Amino-2,3-dioxo-1-(phenylmethyl)propyl]-2-[3-(4-fluorophenyl)-4-(pyrrolidin-1-ylmethyl)-1H-pyrazol-1-yl]pyridine-3-carboxamide

ESI-MS [M+H]$^+$=541.25

Example 170

N-[3-Amino-2,3-dioxo-1-(phenylmethyl)propyl]-2-{3-(4-fluorophenyl)-4-[(methyloxy)methyl]-1H-pyrazol-1-yl}pyridine-3-carboxamide

ESI-MS [M+H]$^+$=502.2

Example 171

N-{3-Amino-1-[(4-bromophenyl)methyl]-2,3-dioxo-propyl}-2-[3-(4-fluorophenyl)-1H-pyrazol-1-yl]pyridine-3-carboxamide

ESI-MS [M+H]$^+$=536.1

Example 172

N-[3-Amino-2,3-dioxo-1-(phenylmethyl)propyl]-5-(dimethylamino)-2-(3-phenyl-1H-pyrazol-1-yl)pyridine-3-carboxamide

ESI-MS [M+H]$^+$=483.25

Example 173

N-[3-Amino-2,3-dioxo-1-(phenylmethyl)propyl]-2-thiochromeno[4,3-c]pyrazol-2(4H)-ylpyridine-3-carboxamide

ESI-MS [M+H]$^+$=484.2

Example 174

N-[3-Amino-2,3-dioxo-1-(phenylmethyl)propyl]-2-(5,5-dioxidothiochromeno[4,3-c]pyrazol-2(4H)-yl)pyridine-3-carboxamide

ESI-MS [M+H]$^+$=516.2

Example 175

N-[3-Amino-2,3-dioxo-1-(phenylmethyl)propyl]-2-(6-chlorochromeno[4,3-c]pyrazol-2(4H)-yl)pyridine-3-carboxamide

ESI-MS [M+H]$^+$=502.3

Example 176

N-[3-Amino-2,3-dioxo-1-(phenylmethyl)propyl]-2-{4-[(dimethylamino)methyl]-3-[3-(trifluoromethyl)phenyl]-1H-pyrazol-1-yl}pyridine-3-carboxamide

ESI-MS [M+H]$^+$=565.2

Example 177

N-[3-Amino-2,3-dioxo-1-(phenylmethyl)propyl]-2-{4-(morpholin-4-ylmethyl)-3-[3-(trifluoromethyl)phenyl]-1H-pyrazol-1-yl}pyridine-3-carboxamide

ESI-MS [M+H]$^+$=607.25

Example 178

N-[3-Amino-2,3-dioxo-1-(phenylmethyl)propyl]-2-{4-(pyrrolidin-1-ylmethyl)-3-[3-(trifluoromethyl)phenyl]-1H-pyrazol-1-yl}pyridine-3-carboxamide

ESI-MS [M+H]$^+$=591.25

Example 179

N-[3-Amino-2,3-dioxo-1-(phenylmethyl)propyl]-2-{3-(4-fluorophenyl)-4-[(phenyloxy)methyl]-1H-pyrazol-1-yl}pyridine-3-carboxamide

ESI-MS [M+H]$^+$=564.15

Example 180

N-[3-Amino-2,3-dioxo-1-(phenylmethyl)propyl]-2-(3-{2-[(diethylamino)methyl]-3-(trifluoromethyl)phenyl}-1H-pyrazol-1-yl)pyridine-3-carboxamide

ESI-MS [M+H]$^+$=593.15

Example 181

N-[3-Amino-2,3-dioxo-1-(phenylmethyl)propyl]-2-(8-fluorochromeno[4,3-c]pyrazol-2(4H)-yl)pyridine-3-carboxamide

ESI-MS [M+H]$^+$=486.2

Example 182

N-[3-Amino-2,3-dioxo-1-(phenylmethyl)propyl]-2-[6-(ethyloxy)chromeno[4,3-c]pyrazol-2(4H)-yl]pyridine-3-carboxamide

ESI-MS [M+H]$^+$=512.3

Example 183

N-[3-Aamino-2,3-dioxo-1-(phenylmethyl)propyl]-2-[8-(methyloxy)chromeno[4,3-c]pyrazol-2(4H)-yl]pyridine-3-carboxamide

ESI-MS [M+H]$^+$=498.2

Example 184

N-[3-Amino-2,3-dioxo-1-(phenylmethyl)propyl]-2-[4-chloro-3-(4-fluorophenyl)-1H-pyrazol-1-yl]pyridine-3-carboxamide

ESI-MS [M+H]$^+$=492.1

Example 185

N-[3-Amino-2,3-dioxo-1-(phenylmethyl)propyl]-2-[4-(dimethylamino)-3-(4-fluorophenyl)-1H-pyrazol-1-yl]pyridine-3-carboxamide

ESI-MS [M+H]$^+$=483.55

Example 186

N-[3-Amino-2,3-dioxo-1-(phenylmethyl)propyl]-2-(8-methylchromeno[4,3-c]pyrazol-2(4H)-yl)pyridine-3-carboxamide

ESI-MS [M+H]$^+$=482.1

Example 187

N-[3-Amino-2,3-dioxo-1-(phenylmethyl)propyl]-2-[3-(4-fluorophenyl)-4-{[(methylsulfonyl)amino]methyl}-1H-pyrazol-1-yl]pyridine-3-carboxamide

ESI-MS [M+H]$^+$=565.15.

Example 188

N-[3-Amino-2,3-dioxo-1-(phenylmethyl)propyl]-5-cyano-2-[3-(2-fluorophenyl)-1H-pyrazol-1-yl]pyridine-3-carboxamide

ESI-MS [M+H]$^+$=483.15

Example 189

Ethyl-3-[({2-[3-(4-fluorophenyl)-1H-pyrazol-1-yl]pyridin-3-yl}carbonyl)amino]-2-oxo-4-phenylbutanoate Ethyl-3-amino-2-hydroxy-4-phenylbutanoate was prepared according to WO 2005/124673. The title compound was prepared in a manner analogous to the above Examples.

ESI-MS [M+H]$^+$=487.14

Example 190

2-[3-(4-Fluorophenyl)-1H-pyrazol-1-yl]-N-[3-(methylamino)-2,3-dioxo-1-(phenylmethyl)propyl]pyridine-3-carboxamide

ESI-MS [M+H]$^+$=472.15

Example 191

2-[3-(5-Fluoropyridin-2-yl)-1H-pyrazol-1-yl]-N-[3-(methylamino)-2,3-dioxo-1-(phenylmethyl)propyl]pyridine-3-carboxamide

ESI-MS [M+H]$^+$=459.1

The 3-alkyl- and 3-cycloalkyl-1H-pyrazole used in the following examples were prepared in a manner analogous to the method described above for 3-isopropyl-1H-pyrazol (Trofimenko et al.; Inorganic Chemistry 1989, 28(6), 1091-1101).

Example 192

N-[3-Amino-2,3-dioxo-1-(phenylmethyl)propyl]-2-(3-cyclohexyl-1H-pyrazol-1-yl)pyridine-3-carboxamide

ESI-MS [M+H]$^+$=446.2

Example 193

N-[3-Amino-2,3-dioxo-1-(phenylmethyl)propyl]-2-(3-tricyclo[3.3.1.1$^{3,7}$]dec-1-yl-1H-pyrazol-1-yl)pyridine-3-carboxamide

ESI-MS [M+H]$^+$=498.2

Example 194

N-[3-Amino-2,3-dioxo-1-(phenylmethyl)propyl]-2-[3-(2,2-dimethylpropyl)-1H-pyrazol-1-yl]pyridine-3-carboxamide

ESI-MS [M+H]$^+$=434.2

Example 195

N-[3-Amino-2,3-dioxo-1-(phenylmethyl)propyl]-2-[3-(1,1-dimethylethyl)-1H-pyrazol-1-yl]pyridine-3-carboxamide

ESI-MS [M+H]$^+$=420.2

Biological Investigation of Inhibition of Calpain and Cathepsins

The following solutions and buffers were employed:

HBS (for 40 ml): 800 µl 1M HEPES; 2.16 ml 100 mM KCl; 4.8 ml 1M NaCl; 3.59 ml 5% glucose; 60 µl 1M MgSO$_4$; 400 µl 100 mM Na pyruvate, 28.19 ml water; pH 7.2-7.5.

lysis buffer (for 20 ml): 400 µl 1M Tris pH 8.2; 2.74 ml 1M NaCl; 520 µl 0.5M EDTA; 2 ml 10% triton X-100; 0.8 ml (=1:25) CompletePlus (1 tablet/2 ml H$_2$O); 200 µl 100 mM Pefabloc; 13.34 ml water, pH 8.2.

TBST (10×) (for 1 l): 100 mM Tris (12.1 g); 1.5M NaCl (87 g); 1% Tween 20 (10 g), adjusted to pH 8.

I Enzyme inhibition in vitro:

Testing for blockade of the corresponding enzymic activities was carried out by means of kinetic fluorescence assays (excitation 390 nm, emission 460 nm).

Apparent Ki values were calculated from the experimentally determined IC$_{50}$ values by the Cheng-Prussoff relation assuming a reversible competitive enzyme inhibition. The Km values of the substrates used under the assay conditions indicated above were: 90 µM (Z-Phe-Arg-AMC, cathepsin B), 10 µM (Z-Gly-Pro-Arg-AMC, cathepsin K), 2 µM (Z-Phe-Arg-AMC, cathepsin L), and 30 µM (Z-Val-Val-Arg-AMC, cathepsin S).

The indicated Ki values are averages of the inhibition constants calculated on the basis of 2 to 4 independent dose-effect plots.

The following assays were used:

1. Calpain I:
   20 nM calpain-I—isolated from human erythrocytes (Calbiochem #208713), 100 µM Suc-Leu-Tyr-AMC (Bachem #I-1355) as substrate in buffer with 62 mM imidazole, 0.3 mM CaCl₂, 0.10% CHAPS, 0.05% BSA, 1 mM DTT at pH 7.3 and room temperature.

2. Cathepsin B:
   0.25 nM cathepsin B—isolated from human liver (Calbiochem #219362), 100 μM Z-Phe-Arg-AMC (Bachem #I-1160) as substrate 50 mM MES, 2 mM EDTA, 0.05% Brij 35, 2.5 mM L-cysteine, pH 6.0, room temperature.

3. Cathepsin K:
   3 nM cathepsin K—activated from recombinant human procathepsin K from *E. coli* (Calbiochem #342001), 10 μM Z-Gly-Pro-Arg-AMC (Biomol #P-142) as substrate in 50 mM MES, 2 mM EDTA, 0.05% Brij 35, 2.5 mM L-cysteine, pH 6.0, room temperature.

4. Cathepsin L:
   1 nM cathepsin L—isolated from human liver (Calbiochem #219402), 2 μM Z-Phe-Arg-AMC (Bachem #I-1160) as substrate in 50 mM MES, 2 mM EDTA, 0.05% Brij 35, 2.5 mM L-cysteine, pH 6.0, room temperature.

5. Cathepsin S:
   0.5 nM recombinant human cathepsin S from *E. coli* (Calbiochem #219343), 20 μM Z-Val-Val-Arg-AMC (Bachem #I-1540) as substrate in 50 mM MES, 2 mM EDTA, 0.05% Brij 35, 2.5 mM L-cysteine, pH 6.0, room temperature.

The results of the in vitro determination are indicated in Table 1. The following abbreviations are used in Table 1:

The "Calpain activity" column, ++ stands for a calpain Ki (Ki(calpain)) of ≦40 nM and + means: 40 nM<Ki (Calpain)≦100 nM.

The "Sel. cat. B" column indicates the Ki(cathepsin B)/Ki(calpain) ratio. In this connection, ++ means a Ki(cathepsin B)/Ki(calpain) ratio of ≧30 and + means 10≦Ki(cathepsin B)/Ki(calpain)<30.

The "Sel. cat. K" column indicates the Ki(cathepsin K)/Ki(calpain) ratio. In this connection, ++ means a Ki(cathepsin K)/Ki(calpain) ratio of ≧30 and + means 10≦Ki(cathepsin K)/Ki(calpain)<30.

The "Sel. cat. L" column indicates the Ki(cathepsin L)/Ki(calpain) ratio. In this connection, ++ means a Ki(cathepsin L)/Ki(calpain) ratio of ≧50 and + means 30≦Ki(cathepsin L)/Ki(calpain)<50.

The "Sel. cat. S" column indicates the Ki(cathepsin S)/Ki(calpain) ratio. In this connection, ++ means a Ki(cathepsin S)/Ki(calpain) ratio of ≧100 and + means 50≦Ki(cathepsin S)/Ki(calpain)<100.

TABLE 1

| Example | Calpain activity | Sel cat. B | Sel cat. K | Sel cat. L | Sel cat. S |
|---|---|---|---|---|---|
| 2 | ++ | | | ++ | |
| 4 | ++ | | | | |
| 5 | ++ | + | + | ++ | ++ |
| 6 | ++ | | | | + |
| 9 | ++ | | | + | ++ |
| 10 | ++ | | | | |
| 12 | ++ | | | | |
| 13 | + | | | ++ | + |
| 14 | + | | | | ++ |
| 15 | ++ | | | ++ | + |
| 16 | + | | | + | + |
| 17 | ++ | | | ++ | + |
| 18 | ++ | | | + | ++ |
| 19 | ++ | | | | |
| 20 | ++ | | | | |
| 21 | ++ | | | | |
| 22 | ++ | | | + | ++ |
| 23 | ++ | | | + | |
| 24 | ++ | | | + | |
| 25 | ++ | | | | |
| 26 | ++ | | | | ++ |
| 27 | ++ | ++ | + | + | |
| 28 | ++ | + | | | |
| 29 | ++ | | + | ++ | ++ |
| 31 | ++ | ++ | + | + | |
| 32 | ++ | + | | | |
| 33 | ++ | + | | | + |
| 35 | + | + | + | ++ | ++ |
| 38 | + | + | + | ++ | ++ |
| 39 | + | | | ++ | ++ |
| 40 | ++ | + | | ++ | ++ |
| 42 | ++ | | | | ++ |
| 43 | + | | | | ++ |
| 44 | ++ | | | | + |
| 45 | ++ | | | | + |
| 46 | + | | | | ++ |
| 47 | ++ | | | | ++ |
| 48 | + | + | + | ++ | ++ |
| 49 | + | | | + | ++ |
| 50 | + | + | + | + | + |
| 52 | + | | | | ++ |
| 54 | + | ++ | ++ | ++ | ++ |
| 55 | ++ | + | + | ++ | ++ |
| 57 | + | | | ++ | ++ |
| 58 | ++ | + | + | ++ | ++ |
| 59 | ++ | | | ++ | + |
| 60 | + | + | + | ++ | + |
| 61 | | + | | | ++ |
| 62 | + | | | ++ | ++ |
| 63 | ++ | + | + | ++ | ++ |
| 64 | ++ | + | | | ++ |
| 65 | | | | | ++ |
| 66 | ++ | | + | + | ++ |
| 67 | + | + | + | ++ | ++ |
| 68 | + | | + | | ++ |
| 69 | + | + | + | ++ | ++ |
| 70 | ++ | + | + | ++ | ++ |
| 71 | + | ++ | ++ | ++ | ++ |
| 72 | + | + | + | + | ++ |
| 74 | ++ | ++ | ++ | | |
| 75 | + | | + | ++ | ++ |
| 76 | ++ | ++ | + | ++ | ++ |
| 77 | ++ | | | | |
| 78 | + | | | ++ | + |
| 79 | + | ++ | ++ | ++ | ++ |
| 80 | + | ++ | + | ++ | ++ |
| 81 | ++ | + | + | ++ | ++ |
| 82 | + | ++ | ++ | ++ | |
| 83 | ++ | + | + | ++ | ++ |
| 84 | ++ | + | | ++ | ++ |
| 85 | ++ | + | ++ | ++ | ++ |
| 86 | ++ | | | ++ | |
| 87 | ++ | ++ | ++ | ++ | ++ |
| 88 | + | + | ++ | ++ | ++ |
| 89 | + | + | + | ++ | ++ |
| 90 | ++ | ++ | + | ++ | ++ |
| 91 | ++ | ++ | + | ++ | ++ |
| 92 | + | ++ | + | ++ | ++ |
| 93 | ++ | ++ | + | ++ | ++ |
| 94 | + | ++ | + | ++ | ++ |
| 95 | ++ | ++ | ++ | ++ | ++ |
| 96 | ++ | ++ | ++ | ++ | ++ |
| 97 | ++ | ++ | + | ++ | ++ |
| 98 | ++ | ++ | ++ | ++ | ++ |
| 99 | ++ | ++ | ++ | ++ | ++ |
| 100 | ++ | + | ++ | ++ | ++ |
| 101 | ++ | | | | ++ |
| 102 | ++ | + | ++ | ++ | ++ |
| 103 | ++ | + | + | ++ | ++ |
| 104 | ++ | | | | + |
| 105 | ++ | ++ | | ++ | ++ |
| 106 | ++ | | | + | ++ |
| 107 | ++ | + | + | ++ | ++ |
| 109 | ++ | ++ | ++ | ++ | ++ |

TABLE 1-continued

| Example | Calpain activity | Sel cat. B | Sel cat. K | Sel cat. L | Sel cat. S |
|---|---|---|---|---|---|
| 110 | ++ | ++ | ++ | ++ | ++ |
| 111 | ++ | ++ | ++ | ++ | ++ |
| 112 | ++ | ++ | ++ | ++ | ++ |
| 114 | + | ++ | ++ | ++ | ++ |
| 115 | ++ | ++ | ++ | ++ | ++ |
| 116 | ++ | ++ | + | ++ | ++ |
| 117 | ++ | ++ | ++ | ++ | ++ |
| 118 | ++ | ++ | + | ++ | ++ |
| 119 | ++ | ++ | ++ | ++ | ++ |
| 120 | ++ | ++ | ++ | + | ++ |
| 121 | ++ | ++ | ++ | ++ | ++ |
| 122 | ++ | ++ |  | ++ | ++ |
| 123 | ++ | ++ | ++ | ++ | ++ |
| 124 | ++ | ++ | ++ | ++ | ++ |
| 125 | ++ | ++ | ++ | ++ | ++ |
| 126 | ++ | ++ | ++ | ++ | ++ |
| 127 | ++ | ++ | ++ | ++ | ++ |
| 129 | + |  |  |  | ++ |
| 130 | ++ | ++ | ++ | ++ | ++ |
| 131 | ++ | ++ | ++ | ++ | ++ |
| 132 | + | + | ++ | ++ | ++ |
| 133 | + | ++ | ++ | ++ | ++ |
| 134 |  | ++ | ++ | + | + |
| 135 | ++ | ++ | ++ | ++ | ++ |
| 136 | ++ | ++ | ++ | ++ | ++ |
| 137 | + | + | + | ++ | ++ |
| 138 |  | ++ | ++ | ++ | ++ |
| 139 | + | + | ++ | ++ | ++ |
| 140 | ++ | + | ++ | ++ | ++ |
| 141 | + |  |  | ++ | ++ |
| 142 | ++ | + | + | ++ | ++ |
| 143 | + | ++ | ++ | ++ | ++ |
| 144 | ++ | + |  | ++ | ++ |
| 151 | + | ++ | ++ | ++ |  |
| 152 | ++ | ++ | ++ | ++ | ++ |
| 153 | ++ | ++ | ++ | ++ | ++ |
| 154 |  | ++ | ++ | ++ | ++ |
| 155 | + | ++ | ++ | ++ | ++ |
| 156 |  | + |  | + | ++ |
| 157 | ++ | ++ | ++ | ++ | ++ |
| 158 | + | ++ | ++ | ++ | ++ |
| 160 | + | ++ | ++ | ++ | ++ |
| 161 |  | + |  | + | ++ |
| 162 | + | ++ | ++ | ++ | ++ |
| 163 | + | + | + | + | ++ |
| 164 | ++ | + | ++ | ++ | ++ |
| 165 | + |  |  |  | ++ |
| 166 | ++ | + | ++ | ++ | ++ |
| 168 | ++ | + | + | ++ | ++ |
| 170 | + |  |  | + |  |
| 173 | ++ | + | + | ++ | ++ |
| 174 | ++ | + | + | ++ | ++ |
| 175 | ++ | ++ | ++ | ++ | ++ |
| 176 |  |  |  |  | ++ |
| 177 | + |  |  |  | ++ |
| 178 | + |  |  |  | ++ |
| 179 |  |  |  | + | ++ |
| 183 | ++ | + | + | ++ | ++ |
| 184 | + | + | + | ++ | ++ |
| 187 | + |  |  | + | ++ |
| 188 | + |  | ++ | ++ |  |
| 192 | + |  | + | ++ | ++ |
| 193 | ++ | ++ | ++ | ++ | ++ |

II Spectrin molt-4 assay to determine cellular calpain inhibition:

The assay design and procedure were as disclosed by Chatterjee; BMC 1998, 6, pp. 509-522; the $EC_{50}$ values are calculated from the percentage degradation of spectrin as a function of the dose.

Cell culture conditions: the molt-4 cells are maintained in RPMI 1640+Glutamax™ I medium (Gibco) with 10% FCS and 50 µg/ml gentamicin at 37° C., 5% $CO_2$ and split 1:15 twice a week.

Preparation of the molt-4 cells: the cells are washed, counted and taken up in a concentration of $2\times10^7$ cells/ml in HBS buffer.

Dilution of the inhibitor substances: all the inhibitors are dissolved in a concentration of $10^{-2}$ M in DMSO. The stock solution is then diluted 1:15 in DMSO (=$6.67\times10^{-4}$ M). Thereafter the stock solution diluted 1:15 is diluted 1:4 in DMSO in two steps (=$1.67\times10^{-4}$ M and $4.17\times10^{-5}$ M). Thereafter, these three solutions are further diluted 1:50 in HBS buffer to give solutions having a concentration of $1.33\times10^{-5}$ M, $3.36\times10^{-6}$ M and $8.34\times10^{-7}$ M.

Test mixture: for each mixture, $10^6$ cells (see above) are introduced into a 1.5 ml Eppendorf tube. To these are added in each case 150 µl of the diluted substances (final conc. $10^{-5}$ M; $2.5\times10^{-6}$ M and $6.25\times10^{-7}$ M) and thoroughly mixed. A negative control and a positive control are used as controls. In this case, initially only 150 µl of HBS buffer is pipetted onto the cells. All the mixtures are incubated at 37° C., 5% $CO_2$ in an incubator for 10 min. Thereafter, except for the negative control, in each case $CaCl_2$ (final conc. mM) and ionomycin (final conc. 5 µM) are added, thoroughly mixed and incubated at 37° C., 5% $CO_2$ in an incubator for 30 min. Then centrifuge at 700 g for 5 min. The supernatants are discarded and the pellets are taken up in 20 µl of lysis buffer. The mixtures are subsequently placed on ice for 30-60 min and then centrifuged at 15000 g for 15 min. The supernatants are removed and put into new Eppendorf tubes. The protein determination is then carried out thereon, e.g. with a MicroBCA assay (Pierce).

SDS-PAGE electrophoresis: 10 µg of total protein from each mixture are put into a new Eppendorf tube and, after pipetting in the same volume of 2× Tris-glycine SDS sample buffer (Invitrogen) and ⅒ volume of 1M DTT, thoroughly mixed and heated at 95° C. for 15 min. The solutions are briefly centrifuged and loaded onto a 6% SDS gel (Invitrogen). The gel is run at 100V with 1× Tris-glycine laemmli buffer (Biomol) until the lower band of the marker has reached the base of the gel.

Western blotting: the gel is removed from the apparatus and blotted onto nitrocellulose in 1× Tris-glycine transfer buffer (Invitrogen)+20% methanol with 1.5 A/cm² in a FastBlot chamber (Biometra) for 30 min. The nitrocellulose filter is removed, briefly washed in TBST buffer and blocked in TBST/5% milk powder for 1 h at RT (room temperature). The blocked nitrocellulose is then incubated with an anti-spectrin Ab (Chemicon) (1:10000 in TBST/5% milk powder) at RT for 3 h or at 4° C. overnight. The nitrocellulose is washed 3× in TBST buffer. It is then incubated with anti-mouse IgG (POD) antibody (Sigma) (1:10000 in TBST/5% milk powder) at room temperature for 1 h.

The nitrocellulose is then washed 5× in TBST buffer. In the next step, 5 ml of prepared solution of the SuperSignal® West Pico chemiluminescence substrate (Pierce) are put on the filter and incubated for 5 min. The nitrocellulose is then taken out of the solution, gently dabbed dry and inserted into a development folder film (Tropix). A digital image analysis system (VersaDoc, Biorad) is used to record and quantify the ECL (QuantitylOne), and the percentage degradation of spectrin is calculated from the data. Graph-pad prism is used to fit the percentage spectrum degradation as a function of the dose to a sigmoidal dose-effect plot (top fixed at 100% and bottom at 0%), and the EC 50% is calculated.

We claim:
1. A carboxamide compound of the formula I-A' or I-A''',

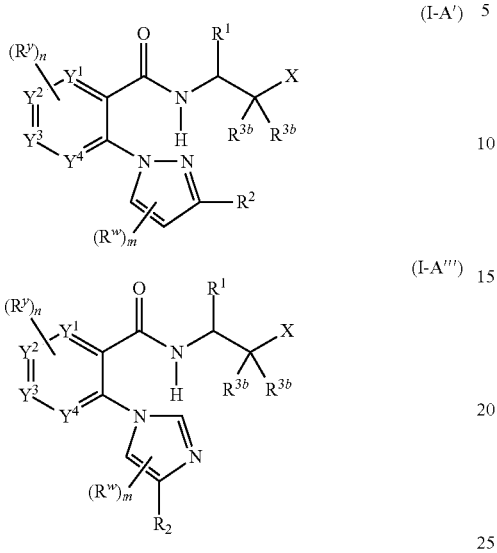

in which
n is 0, 1 or 2,
m is 0, 1 or 2,
one of the variables $Y^1, Y^2, Y^3$ and $Y^4$ is a nitrogen atom, and the remaining variables $Y^1, Y^2, Y^3$ and $Y^4$ are CH,
$R^1$ is hydrogen, $C_1$-$C_{10}$-alkyl, $C_2$-$C_{10}$-alkenyl, $C_2$-$C_{10}$-alkynyl, where the last 3 radicals mentioned may be partly or completely halogenated and/or have 1, 2 or 3 substituents $R^{1a}$,
$C_3$-$C_7$-cycloalkyl, $C_3$-$C_7$-cycloalkyl-$C_1$-$C_4$-alkyl, where a cycloalkyl in the last two radicals mentioned may additionally have 1,2,3 or 4 identical or different $R^{1b}$ radicals, may have a $CH_2$ group replaced by O, NH, or S, or may have two adjacent C atoms form a double bond,
aryl, hetaryl, aryl-$C_1$-$C_6$-alkyl, aryl-$C_2$-$C_6$-alkenyl, hetaryl-$C_1$-$C_4$-alkyl or hetaryl-$C_2$-$C_6$-alkenyl, where aryl and hetaryl in the last 6 radicals mentioned may be unsubstituted or carry 1, 2, 3 or 4 identical or different radicals $R^{1c}$; where
$R^{1a}$ is selected independently of one another from OH, SH, COOH, CN, $OCH_2COOH$, $C_1$-$C_6$-alkoxy, $C_1$-$C_6$-haloalkoxy, $C_3$-$C_7$-cycloalkoxy, $C_1$-$C_6$-alkylthio, $C_1$-$C_6$-haloalkylthio, $COOR^{a1}$, $CONR^{a2}R^{a3}$, $SO_2NR^{a2}R^{a3}$, $-NR^{a2}-SO_2-R_{a4}$, $NR^{a2}-CO-R^{a5}$, $SO_2-R^{a4}$, and $NR^{a6}R^{a7}$,
$R^{1b}$ is selected independently of one another from OH, SH, COOH, CN, $OCH_2COOH$; halogen, phenyl which optionally has 1, 2 or 3 substituents $R^{1d}$, $C_1$-$C_6$-alkyl, $C_1$-$C_6$-alkoxy, $C_1$-$C_6$-alkylthio, where the alkyl moieties in the last 3 substituents mentioned may be partly or completely halogenated and/or have 1, 2 or 3 substituents $R^{1a}$, $COOR^{b1}$, $CONR^{b2}R^{b3}$, $SO_2NR^{b2}R^{b3}$, $NR^{b2}-SO_2-R^{b4}$, $NR^{b2}-CO-R^{b5}$, $SO_2-R^{b4}$, and $NR^{b6}R^{b7}$, where
in addition two $R^{1b}$ radicals may together form a $C_1$-$C_4$-alkylene group, or 2 $R^{1b}$ radicals bonded to adjacent C atoms of cycloalkyl may form together with the carbon atoms to which they are bonded a benzene ring, $R^{1c}$ is selected independently of one another from OH, SH, halogen, $NO_2$, $NH_2$, CN, $CF_3$, $CHF_2$, $CH_2F$, $O-CF_3$, $O-CHF_2$, $O-CH_2F$, COOH, $OCH_2COOH$, $C1$-$C_6$-alkyl, $C_1$-$C_6$-alkoxy, $C_1$-$C_6$-alkoxy-$C_1$-$C_4$-alkyl, $C_1$-$C_6$-alkylthio, where the alkyl moieties in the last 4 substituents mentioned may be partly or completely halogenated and/or have 1, 2 or 3 substituents $R^{1a}$,
$C_3$-$C_7$-cycloalkyl, $C_3$-$C_7$-cycloalkyl-$C_1$-$C_4$-alkyl, $C_3$-$C_7$-cycloalkoxy, where the cycloalkyl moiety of the last three radicals mentioned may have 1, 2, 3 or 4 $R^{1b}$ radicals,
aryl, hetaryl, O-aryl, $O-CH_2$-aryl, where the last three radicals mentioned are unsubstituted in the aryl moiety or may carry 1, 2, 3 or 4 $R^{1d}$ radicals,
$COOR^{c1}$, $CONR^{c2}RO^{c3}$, $SO_2NR^{c2}R^{c3}$, $NR^{c2}-SO_2-R^{c4}$, $NR^{c2}-CO-R^{c5}$, $SO_2-R^{c4}$,
$-(CH_2)_p-NR^{c6}R^{c7}$ with p=0, 1, 2, 3, 4, 5 or 6 and $O-(CH_2)_q-NR^{c6}R^{c7}$ with q=2, 3, 4, 5 or 6; where
$R^{a1}$, $R^{b1}$ and $R^{c1}$ are independently of one another H, $C_1$-$C_6$-alkyl, $C_1$-$C_6$-haloalkyl, $C_1$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$,
$R^{a2}$, $R^{b2}$ and $R^{c2}$ are independently of one another H, $C_1$-$C_6$-alkyl, $C_1$-$C_6$-haloalkyl, $C,$-$C_6$-alkyl which has 1, 2 or 3 substituents $R^{1a}$, or $C_2$-$C_6$-alkenyl, $C_2$-$C_6$-alkynyl, $C_3$-$C_7$-cycloalkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, and
$R^{a3}$, $R^{b3}$ and $R^{c3}$ are independently of one another H, $C_1$-$C_6$-alkyl, $C_1$-$C_6$-haloalkyl, $C_1$-$C_6$-alkyl which has 1, 2 or 3 substituents $R^{1a}$, $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, or the two radicals $R^{a2}$ and $R^{a3}$, or $R^{b2}$ and $R^{b3}$ or $R^{c2}$ and $R^{c3}$ form together with the N atom a 3 to 7-membered, optionally substituted nitrogen heterocycle which may optionally have 1, 2 or 3 further different or identical heteroatoms from the group of O, N, S as ring members,
$R^{a4}$, $R^{b4}$ and $R^{c4}$ are independently of one another $C_1$-$C_6$-alkyl, $C_1$-$C_6$-haloalkyl, $C_1$-$C_6$-alkyl which has 1, 2 or 3 substituents $R^{1a}$, $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, aryl-$C_1$-$C_4$-alkyl, hetaryl or hetaryl-$C_1$-$C_4$-alkyl, where aryl and hetaryl in the last 4 radicals mentioned are unsubstituted or have 1, 2 or 3 substituents $R^{1d}$, and
$R^{a5}$, $R^{b5}$ and $R^{c5}$ have independently of one another one of the meanings mentioned for $R^{a1}$, $R^{b1}$, and $R^{c1}$;
$R^{a6}$, $R^{b6}$ and $R^{c6}$ are independently of one another H, $C_1$-$C_6$-alkyl, $C_1$-$C_6$-alkoxy, $C_1$-$C_6$-haloalkyl, $C_1$-$C_6$-alkyl which has 1, 2 or 3 substituents $R^{1a}$, $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, $CO-C_1$-$C_6$-alkyl, $CO-O-C,$-$C_6$-alkyl, $SO_2-C_1$-$C_6$-alkyl, aryl, hetaryl, O-aryl, OCH$_2$-aryl, aryl-C$_1$-Ca-alkyl, hetaryl-C$_1$-C$_4$-alkyl, CO-aryl, CO-hetaryl, CO-(aryl-C$_1$-C$_4$-alkyl), CO-(hetaryl-C$_1$-C$_4$-alkyl), CO—O-aryl, CO—O-hetaryl, CO—O-(aryl-C$_1$-C$_4$-alkyl), CO—O-(hetaryl-C$_1$-C$_4$-alkyl), SO$_2$-aryl, SO$_2$-hetaryl, SO$_2$-(aryl-C$_1$-C$_4$-alkyl) or SO$_2$-(hetaryl-C$_1$-C$_4$-alkyl), where aryl and hetaryl in the last 18 radicals mentioned are unsubstituted or have 1, 2 or 3 substituents R$^{1d}$, and R$^{a7}$, R$^{b7}$ and R$^{c7}$ are independently of one another H, C$_1$-C$_6$-alkyl, C$_1$-C$_6$-haloalkyl, C$_1$-C$_6$-alkyl which has 1, 2 or 3 substituents R$^{1a}$, or C$_2$-C$_6$-alkenyl, C$_2$-C$_6$-alkynyl, C$_3$-C$_7$-cycloalkyl, C$_3$-C$_7$-hetercycloalkyl-C$_1$-C$_4$-alkyl, C$_1$-C$_6$-alkoxy-C$_1$-C$_4$-alkyl, aryl, aryl-C$_1$-C$_4$-alkyl, hetaryl or hetaryl-C$_1$-C$_4$-alkyl, where aryl and hetaryl in the last 4 radicals mentioned are unsubstituted or have 1, 2 or 3 substituents R$^{1d}$, or the two radicals R$^{a6}$ and R$^{a7}$, or R$^{b6}$ and R$^{b7}$ or R$^{c6}$ and R$^{c7}$ form together with the N atom a 3 to 7-membered, optionally substituted nitrogen heterocycle which may optionally have 1, 2 or 3 further different or identical heteroatoms from the group of O, N and S as ring members, or two radicals R$^{1b}$ and R$^{1c}$ bonded to adjacent C atoms form together with the C atoms to which they are bonded a 4, 5, 6 or 7-membered, optionally substituted carbocycle or an optionally substituted heterocycle which has 1, 2 or 3 different or identical heteroatoms from the group of O, N and S as ring members;

R$^{1d}$ is selected from halogen, OH, SH, NO$_2$, COOH, C(O)NH$_2$, CHO, CN, NH$_2$, OCH$_2$COOH, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, CO—C$_1$-C$_6$-alkyl, CO—O—C$_1$-C$_6$-alkyl, NH—C$_1$-C$_6$-alkyl, NHCHO, NH—C(O)C$_1$-C$_6$-alkyl, and SO$_2$—C$_1$-C$_6$-alkyl;

R$^2$ is hydrogen, C$_1$-C$_{10}$-alkyl, C$_1$-C$_{10}$-alkoxy, C$_2$-C$_{10}$-alkenyl, C$_2$-C-alkynyl, where the last 4 radicals mentioned may be partly or completely halogenated and/or have 1, 2 or 3 substituents R$^{2a}$, C$_3$-C$_7$-cycloalkyl, C$_3$-C$_7$-cycloalkyl-C$_1$-C$_4$-alkyl, where cycloalkyl in the last two radicals mentioned may additionally have 1,2,3, or 4 identical or different R$^{2b}$ radicals, may have a CH$_2$ group replaced by O, NH, or S, or may have two adjacent C atoms form a double bond, aryl, O-aryl, O—CH$_2$-aryl, hetaryl, aryl-C$_1$-C$_6$-alkyl, aryl-C$_2$-C$_6$-alkenyl, hetaryl-C$_1$-C$_4$-alkyl or hetaryl-C$_2$-C$_6$-alkenyl, where aryl and hetaryl in the last 8 radicals mentioned may be unsubstituted or carry 1, 2, 3 or 4 identical or different R$^{2c}$ radicals; where R$^{2a}$ has one of the meanings indicated for R$^{1a}$,
R$^{2b}$ has one of the meanings indicated for R$^{1b}$, and
R$^{2c}$ has one of the meanings indicated for R$^{1c}$;

R$^{3a}$ and R$^{3b}$ are independently of one another hydroxy or C$_1$-C$_4$-alkoxy, or together with the carbon atom to which they are bonded are C=O; or R$^{3a}$ and R$^{3b}$ together form a group O-Alk-O, S-Alk-O or S-Alk-S, where Alk is linear C$_2$-C$_5$-alkanediyl, which may be unsubstituted or substituted with 1, 2, 3 or 4 radicals selected from C$_1$-C$_4$-alkyl and halogen; or R$^{3a}$ and R$^{3b}$ together with the carbon atom to which they are bonded form a group C=NR$^3$, where R$^3$ is selected from H, C$_1$-C$_6$-alkyl, C$_1$-C$_6$-alkoxy, C$_2$-C$_6$-alkenyl, C$_3$-C$_6$-cycloalkyl, C$_3$-C$_6$-cycloalkyl-C$_1$-C$_4$-alkyl, C$_2$-C$_6$-alkenyloxy, C$_3$-C$_6$-cycloalkoxy and C$_3$-C$_6$-cycloalkyl-C$_1$-C$_4$-alkyloxy;

X is hydrogen or a radical of the formulae C(=O)—O—R$^{x1}$, C(=O)—NR$^{x2}$R$^{x3}$, C(=O)—N(R$^{x4}$)—(C$_1$-C$_6$-alkylene)-NR$^{x2}$R$^{x3}$ or C(=O)—N(R$^{x4}$)NR$^{x2}$R$^{x3}$, in which R$^{x1}$ is hydrogen, C$_1$-C$_6$-alkyl, C$_1$-C$_6$-haloalkyl, C$_1$-C$_6$-alkyl which has 1, 2 or 3 substituents R$^{xa}$, or C$_2$-C$_6$-alkenyl, C$_2$-C$_6$-alkynyl, C$_3$-C$_7$-cycloalkyl, C$_3$-C$_7$-cycloalkyl-C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, where alkyl, alkenyl, alkoxy, alkynyl, cycloalkyl, heterocycloalkyl in the last 6 radicals mentioned are unsubstituted or have 1, 2 or 3 substituents R$^{xa}$, aryl, aryl-C$_1$-C$_4$-alkyl, hetaryl or hetaryl-C$_1$-C$_4$-alkyl, where aryl and hetaryl in the last 4 radicals mentioned are unsubstituted or have 1, 2 or 3 substituents R$^{xd}$, R$^{x2}$ is H, OH, CN, C$_1$-C$_6$-alkyl, C$_1$-C$_6$-haloalkyl, C$_1$-C$_6$-alkyl which has 1, 2 or 3 substituents R$^{xa}$, C$_2$-C$_6$-alkenyl, C$_2$-C$_6$-alkynyl, C$_3$-C$_7$-cycloalkyl, C$_3$-C$_7$-cycloalkyl -C$_1$-C$_4$-alkyl, C$_3$-C$_7$-heterocycloalkyl-C$_1$-C$_4$-alkyl, C$_1$-C$_6$-alkoxy-C$_1$-C$_4$-alkyl, CO—C$_1$-C$_6$-alkyl, CO—O—C$_1$-C$_6$-alkyl, SO$_2$—Ci-C$_6$-alkyl, O—C$_1$-C$_6$-alkyl, where alkyl, alkoxy, alkenyl, alkynyl, cycloalkyl, heterocycloalkyl in the last 10 radicals mentioned are unsubstituted or have 1, 2 or 3 substituents R$^{xa}$, aryl, O-aryl, O—CH$_2$-aryl, hetaryl, O—CH$_2$-hetaryl, aryl-C$_1$-C$_4$-alkyl, hetaryl-C$_1$-C$_4$-alkyl, CO-aryl, CO-hetaryl, CO-(aryl-C$_1$-C$_4$-alkyl), CO-(hetaryl-C$_1$-C$_4$-alkyl), CO—O-aryl, CO—O-hetaryl, CO—O-(aryl-C$_1$-C$_4$-alkyl), CO—O-(hetaryl-C$_1$-C$_4$-alkyl), SO$_2$-aryl, SO$_2$-hetaryl, SO$_2$-(aryl-C$_1$-C$_4$-alkyl) or SO$_2$-(hetaryl-C$_1$-C$_4$-alkyl), where aryl and hetaryl in the last 19 radicals mentioned are unsubstituted or have 1, 2 or 3 substituents R$^{xd}$, and R$^{x3}$ is H, C$_1$-C$_6$-alkyl, C$_1$-C$_6$-haloalkyl, C$_1$-C$_6$-alkyl which has 1, 2 or 3 substituents R$^{xa}$, C$_2$-C$_6$-alkenyl, C$_2$-C$_6$-alkynyl, C$_3$-C$_1$-cycloalkyl, C$_3$-C$_7$-cycloalkyl-C$_1$-Ca-alkyl, C$_3$-C$_7$-heterocycloalkyl-C$_1$-C$_4$-alkyl, C$_1$-C$_6$-alkoxy-C$_1$-C$_4$-alkyl, where alkyl, alkenyl, alkoxy, alkynyl, cycloalkyl, heterocycloalkyl in the last 6 radicals mentioned are unsubstituted or have 1, 2 or 3 substituents R$^{xa}$, aryl, aryl-C$_1$-C$_4$-alkyl, hetaryl or hetaryl-C$_1$-C$_4$-alkyl, where aryl and hetaryl in the last 4 radicals mentioned are unsubstituted or have 1, 2 or 3 substituents R$^{xd}$, or the two radicals R$^4$ and R$^{x3}$ form together with the N atom a 3 to 7-membered nitrogen heterocycle which may optionally have 1, 2 or 3 further different or identical heteroatoms from the group of O, N and S as ring members, and which may have 1, 2 or 3 substituents R$^{xb}$, R$^{x4}$ is H, OH, CN, C$_1$-C$_6$-alkyl, C$_1$-C$_6$-haloalkyl, C$_1$-C$_6$-alkyl which has 1, 2 or 3 substituents R$^{xa}$, or C$_2$-C$_6$-alkenyl, C$_2$-C$_6$-alkynyl, C$_3$-C$_7$-cycloalkyl, C$_3$-C$_7$-heterocycloalkyl-C$_1$-C$_4$-alkyl, C$_1$-C$_6$-alkoxy-C$_1$-Ca-alkyl, CO—C$_1$-C$_6$-alkyl, CO—O—C$_1$-C$_6$-alkyl, SO$_2$—C$_1$-C$_6$-alkyl, where alkyl, alkenyl, alkoxy, alkynyl, cycloalkyl, heterocycloalkyl in the last 9 radicals mentioned are unsubstituted or have 1, 2 or 3 substituents R$^{xa}$, aryl, O-aryl, O—CH$_2$-aryl, hetaryl, aryl-C$_1$-C$_4$-alkyl, hetaryl-C$_1$-C$_4$-alkyl, CO-aryl, CO-hetaryl, CO-(aryl-C$_1$-C$_4$-alkyl), CO-(hetaryl-C$_1$-C$_4$-alkyl), CO—O-aryl, CO—O-hetaryl, CO—O-(aryl-C$_1$-C$_4$-alkyl), CO—O-(hetaryl-C$_1$-C$_4$-alkyl), SO$_2$-aryl, SO$_2$-hetaryl, SO$_2$-(aryl-C$_1$-C$_4$-alkyl) or SO$_2$-(hetaryl-C$_1$-C$_4$-alkyl), where aryl and hetaryl in the last 18 radicals mentioned are unsubstituted or have 1, 2 or 3 substituents R$^{xd}$, and where $R^{xa}$ has one of the meanings indicated for $R^{1a}$, $R^{xb}$ has one of the meanings indicated for $R^{1b}$, and $R^{xd}$ has one of the meanings indicated for $R^{1d}$;

$R^y$ is selected independently of one another from OH, SH, halogen, $NO_2$, $NH_2$, CN, $CF_3$, $CHF_2$, $CH_2F$, O—$CF_3$, O—$CHF_2$, O—$CH_2F$, COOH, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the last 4 radicals mentioned may be partly or completely halogenated and/or have 1, 2 or 3 substituents $R^{ya}$, $C_3$-$C_7$-cycloalkyl, $C_3$-$C_7$-cycloalkyl-$C_1$-$C_4$-alkyl, $C_3$-$C_7$-cycloalkyl-O, where the cycloalkyl moiety in the last three radicals mentioned may have 1, 2, 3 or 4 $R^{yb}$ radicals, aryl, O-aryl, $CH_2$-aryl, O—$CH_2$-aryl, where the last 4 radicals mentioned are unsubstituted in the aryl moiety or may carry 1, 2, 3 or 4 radicals $R^{yd}$, $COOR^{y1}$, $CONR^{y2}R^{y3}$, $SO_2NR^{y2}R^{y3}$, —NH—$SO_2$—$R^{y4}$, NH—CO—$R^{y5}$, $SO_2$—$R^{y4}$, —$(CH_2)_p$—$NR^{y6}R^{y7}$ with p=0, 1, 2, 3, 4, 5 or 6 and O—$(CH_2)_q$—$NR^{y6}R^{y7}$ with q=2, 3, 4, 5 or 6;

or two $R^y$ radicals bonded to adjacent C atoms form together with the C atoms to which they are bonded a 4, 5, 6 or 7-membered, optionally substituted carbocycle or heterocycle which has 1, 2 or 3 different or identical heteroatoms from the group of O, N, S as ring members, where $R^{ya}$ has one of the meanings indicated for $R^{1a}$, $R^{yb}$ has one of the meanings indicated for $R^{1b}$, $R^{yd}$ has one of the meanings indicated for $R^{1d}$, $R^{y1}$ has one of the meanings indicated for $R^{c1}$, $R^{y2}$ has one of the meanings indicated for $R^{c2}$, $R^{y3}$ has one of the meanings indicated for $R^{c3}$, $R^{y4}$ has one of the meanings indicated for $R^{c4}$, $R^{y5}$ has one of the meanings indicated for $R^{c5}$, $R^{y6}$ has one of the meanings indicated for $R^{c6}$, and $R^{y7}$ has one of the meanings indicated for $R^{c7}$;

$R^w$ is selected from OH, SH, halogen, $NO_2$, $NH_2$, CN, $CF_3$, $CHF_2$, $CH_2F$, O—$CF_3$, O—$CHF_2$, O—$CH_2F$, COOH, $OCH_2COOH$, $C_1$-$C_6$-alkyl, $C_1$-$C_6$-alkoxy, $C_1$-$C_6$-alkoxy-$C_1$-$C_4$-alkyl, $C_1$-$C_6$-alkylthio, where the last 4 radicals mentioned may be partly or completely halogenated and/or have 1, 2 or 3 substituents $R^{wa}$, $C_3$-$C_7$-cycloalkyl, $C_3$-$C_7$-cycloalkyl-$C_1$-$C_4$-alkyl, $C_3$-$C_7$-cycloalkoxy, where the cycloalkyl moiety of the last three radicals mentioned may have 1, 2, 3 or 4 radicals $R^{wb}$, aryl, O-aryl, O—$CH_2$-aryl, hetaryl, where the last four radicals mentioned are unsubstituted in the aryl moiety or may carry 1, 2, 3 or 4 radicals $R^{wd}$, $COOR^{w1}$, $CONR^{w2}R^{w3}$, $SO_2NR^{w2}R^{w3}$, $NR^{w2}$—$SO_2$—$R^{w4}$, $NR^{w2}$—CO—$R^{w5}$, $SO_2$—$R^{w4}$, —$(CH_2)_p$—$NR^{w6}R^{w7}$ with p=0, 1, 2, 3, 4, 5 or 6 and O—$(CH_2)_q$—$NR^{w6}R^{w7}$ with q=2, 3, 4, 5 or 6;

or two $R^w$ radicals bonded to adjacent C atoms form together with the C atoms to which they are bonded a 4, 5, 6 or 7-membered, optionally substituted carbocycle or an optionally substituted heterocycle which has 1, 2 or 3 different or identical heteroatoms from the group of O, N, S as ring members, where $R^{wa}$ has one of the meanings indicated for $R^{1a}$, $R^{wb}$ has one of the meanings indicated for $R^{1b}$, $R^{wd}$ has one of the meanings indicated for $R^{1d}$, $R^{w1}$ has one of the meanings indicated for $R^{c1}$, $R^{w2}$ has one of the meanings indicated for $R^{c2}$, $R^{w3}$ has one of the meanings indicated for $R^{c3}$, $R^{w4}$ has one of the meanings indicated for $R^{c4}$, $R^{w5}$ has one of the meanings indicated for $R^{c5}$, $R^{w6}$ has one of the meanings indicated for $R^{c6}$, $R^{w7}$ has one of the meanings indicated for $R^{c7}$, where aryl means a mono-, bi- or tricyclic aromatic hydrocarbon radical;

or a tautomer thereof or a pharmaceutically suitable salt thereof.

2. The carboxamide compound as claimed in claim 1, in which m is 0 or 1 and, when m=1, $R^w$ is selected from OH, F, Cl, CN, $CF_3$, $C_1$-$C_6$-alkyl which is unsubstituted or may have 1, 2 or 3 substituents $R^{wa}$, or $C_1$-$C_6$-haloalkyl, $C_1$-$C_6$-alkoxy, $C_1$-$C_6$-haloalkoxy and $C_3$-$C_7$-cycloalkyl.

3. The carboxamide compound as claimed in claim 1, in which X is a C(=O)—$NR^{x2}R^{x3}$ radical.

4. The carboxamide compound as claimed in claim 3, in which $R^{x2}$ is H, OH, CN, $C_1$-$C_6$-alkyl, $C_1$-$C_6$-haloalkyl, $C_1$-$C_6$-alkyl which has 1, 2 or 3 substituents $R^{xa}$, $C_2$-$C_6$-alkenyl, $C_2$-$C_6$-alkynyl, $C_3$-$C_7$-cycloalkyl, $C_3$-$C_7$-cycloalkyl-$C_1$-$C_4$-alkyl, $C_3$-$C_7$-heterocycloalkyl-$C_1$-$C_4$-alkyl, $C_1$-$C_6$-alkoxy-$C_1$-$C_4$-alkyl, aryl, hetaryl, aryl-$C_1$-$C_4$-alkyl or hetaryl-$C_1$-$C_4$-alkyl, where aryl and hetaryl in the last 4 radicals mentioned are unsubstituted or have 1, 2 or 3 substituents $R^{xd}$, and $R^{x3}$ is H, $C_1$-$C_6$-alkyl, $C_1$-$C_6$-haloalkyl or $C_1$-$C_6$-alkyl which has 1, 2 or 3 substituents $R^{xa}$, or $NR^{x2}R^{x3}$ is:

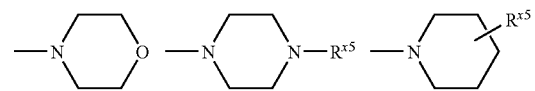

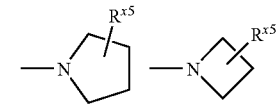

in which $R^{x5}$ is hydrogen or has the meaning indicated in claim 1 for $R^{xb}$.

5. The carboxamide compound as claimed in claim 4, in which X is C(O)—$NH_2$.

6. The carboxamide compound as claimed in claim 1, in which $R^1$ is selected from $C_1$-$C_{10}$-alkyl which may be partly or completely halogenated and/or have 1, 2 or 3 substituents $R^{1a}$, $C_3$-$C_7$-cycloalkyl-$C_1$-$C_4$-alkyl, where the cycloalkyl moiety may have 1, 2, 3 or 4 radicals $R^{1b}$, phenyl-$C_1$-$C_4$-alkyl and hetaryl-$C_1$-$C_4$-alkyl, where phenyl and hetaryl in the last 2 radicals mentioned may be unsubstituted or carry 1, 2, 3 or 4 identical or different radicals $R^{1c}$.

7. The carboxamide compound as claimed in claim 1, in which $R^2$ is different from hydrogen.

8. The carboxamide compound as claimed in claim 7, in which $R^2$ is selected from:

$C_1$-$C_{10}$-alkyl which may be partly or completely halogenated and/or have 1, 2 or 3 substituents $R^{2a}$, aryl, hetaryl, aryl-$C_1$-$C_6$-alkyl, aryl-$C_2$-$C_6$-alkenyl and hetaryl-$C_1$-$C_4$-alkyl, where aryl and hetaryl in the last 5 radicals mentioned may be unsubstituted or carry 1, 2, 3 or 4 identical or different radicals $R^{2c}$.

9. The carboxamide compound as claimed in claim 8, in which $R^2$ is selected from aryl and hetaryl, where aryl and hetaryl may be unsubstituted or carry 1, 2, 3 or 4 identical or different radicals $R^{2c}$.

10. The carboxamide compound as claimed in claim 1, in which $R^y$ is selected from OH, F, Cl, $NH_2$, CN, $CF_3$, —$CHF_2$, O—$CF_3$, O—$CHF_2$, O—$CH_2F$, $C_1$-$C_6$-alkyl, $C_3$-$C_7$-cycloalkyl, $C_1$-$C_6$-alkylamino, $C_1$-$C_6$-dialkylamino, pyrrolidinyl, piperidinyl, morpholinyl, imidazolyl, $C_1$-$C_4$-alkoxy, $C_1$-$C_4$-alkoxy-$C_1$-$C_4$-alkyl, $CONR^{y2}R^{y3}$, $SO_2NR^{y2}R^{y3}$, —NH—$SO_2$—$R^{y4}$, —$(CH_2)_p$—$NR^{y6}R^{y7}$, NH—CO—$R^{y5}$, in which p is 1, 2, 3, 4, or 5, and $R^{y2}$, $R^{y3}$, $R^{y4}$, $R^{y5}$, $R^{y6}$, $R^{y7}$ are H or $C_1$-$C_6$-alkyl, phenyl, benzyl and O-benzyl, where the phenyl ring in the last 3 groups mentioned may have 1, 2 or 3 substituents selected from halogen, OH, SH, $NO_2$, COOH, $C(O)NH_2$, CHO, CN, $NH_2$, $OCH_2COOH$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, CO—$C_1$-$C_6$-alkyl, CO—O—$C_1$-$C_6$-alkyl, NH—$C_1$-$C_6$-alkyl, NHCHO, NH—C(O)$C_1$-$C_6$-alkyl, and $SO_2$—$C_1$-$C_6$-alkyl.

11. The carboxamide compound as claimed in claim 1, which corresponds to the formulae I-A.a'

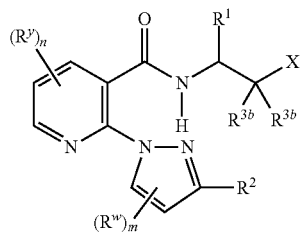

(I-A.a')

in which m, $R^1$, $R^{3a}$, $R^{3b}$, $R^2$, $R^y$, and $R^w$ have the aforementioned meanings, n is 0, 1 or 2, or a tautomer thereof or a pharmaceutically suitable salt thereof.

12. The carboxamide compound as claimed in claim 1, which has the S configuration at the carbon atom carrying the group $R^1$.

13. A pharmaceutical composition comprising at least one carboxamide compound as claimed in claim 1, or a tautomer or pharmaceutically suitable salt thereof and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,436,034 B2 | Page 1 of 1 |
| APPLICATION NO. | : 11/990652 | |
| DATED | : May 7, 2013 | |
| INVENTOR(S) | : Kling et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 96 days.

Signed and Sealed this
Twenty-third Day of December, 2014

Michelle K. Lee
*Deputy Director of the United States Patent and Trademark Office*